US012799205B2

(12) United States Patent

Luo et al.

(10) Patent No.: US 12,799,205 B2

(45) Date of Patent: Nov. 17, 2026

(54) COMBINATION THERAPIES FOR TREATING CANCER

(71) Applicants: ADAGENE INC., Grand Cayman (KY); Peter Peizhi Luo, Suzhou (CN)

(72) Inventors: Peter Peizhi Luo, Morgan Hill, CA (US); Guizhong Liu, Suzhou (CN)

(73) Assignee: ADAGENE INC., Grand Cayman (KY)

( * ) Notice: Subject to any disclaimer, the term of this patent is extended or adjusted under 35 U.S.C. 154(b) by 470 days.

(21) Appl. No.: 18/554,870

(22) PCT Filed: Apr. 11, 2022

(86) PCT No.: PCT/CN2022/086143

§ 371 (c)(1),
(2) Date: Oct. 11, 2023

(87) PCT Pub. No.: WO2022/218264

PCT Pub. Date: Oct. 20, 2022

(65) Prior Publication Data

US 2024/0209092 A1 Jun. 27, 2024

Related U.S. Application Data

(60) Provisional application No. 63/300,567, filed on Jan. 18, 2022, provisional application No. 63/173,479, filed on Apr. 11, 2021.

(51) Int. Cl.
*A61K 39/395* (2006.01)
*A61K 31/337* (2006.01)
(Continued)

(52) U.S. Cl.
CPC ........ *C07K 16/2818* (2013.01); *A61K 31/337* (2013.01); *A61K 31/502* (2013.01);
(Continued)

(58) Field of Classification Search
CPC .................................................. A61K 39/3955
See application file for complete search history.

(56) References Cited

U.S. PATENT DOCUMENTS

| | | | |
|---|---|---|---|
| 4,399,216 | A | 8/1983 | Axel et al. |
| 4,634,665 | A | 1/1987 | Axel et al. |

(Continued)

FOREIGN PATENT DOCUMENTS

| | | | |
|---|---|---|---|
| AU | 2013202755 A1 | 5/2013 | |
| AU | 2010203353 B2 | 6/2016 | |

(Continued)

OTHER PUBLICATIONS

Adagene, (Apr. 13, 2021). "Adagene Presents Preclinical Data from Lead SAFEbody™ Program, ADG126, at the American Association for Cancer Research (AACR) Annual Meeting 2021," available online at <https://investor.adagene.com/news-releases/news-release-details/adagene-presents-preclinical-data-lead-safebodytm-program-adg126/>, 2 pages.

(Continued)

*Primary Examiner* — Prema M Mertz
(74) *Attorney, Agent, or Firm* — Morrison & Foerster LLP

(57) ABSTRACT

Provided herein are compositions and methods for treating cancers using anti-cytotoxic T-lymphocyte-associated protein 4 (CTLA4) antibodies, such as activatable anti-CTLA4 antibodies. In some embodiments, combination therapies including an anti-CT-LA4 antibody and an immune checkpoint inhibitor, an anti-CD137 antibody, a vascular endothelial growth factor (VEGF) inhibitor, a chemotherapeutic agent, or a poly ADP ribose polymerase (PARP) inhibitor are provided.

18 Claims, 51 Drawing Sheets

Specification includes a Sequence Listing.

(51) Int. Cl.
*A61K 31/502* (2006.01)
*A61K 31/7048* (2006.01)
*A61P 35/00* (2006.01)
*C07K 16/28* (2006.01)
*A61K 39/00* (2006.01)

(52) U.S. Cl.
CPC ...... *A61K 31/7048* (2013.01); *A61K 39/3955* (2013.01); *A61P 35/00* (2018.01); *C07K 16/2878* (2013.01); *A61K 2039/545* (2013.01); *C07K 2317/24* (2013.01); *C07K 2319/30* (2013.01)

(56) References Cited

U.S. PATENT DOCUMENTS

| | | | |
|---|---|---|---|
| 4,816,567 | A | 3/1989 | Cabilly et al. |
| 5,179,017 | A | 1/1993 | Axel et al. |
| 5,500,362 | A | 3/1996 | Robinson et al. |
| 5,677,425 | A | 10/1997 | Axel et al. |
| 5,821,337 | A | 10/1998 | Carter et al. |
| 5,994,619 | A | 11/1999 | Axel et al. |
| 6,172,197 | B1 | 1/2001 | McCafferty et al. |
| 6,194,551 | B1 | 2/2001 | Idusogie et al. |
| 6,291,158 | B1 | 9/2001 | Bodmer et al. |
| 6,582,915 | B1 | 6/2003 | Stice et al. |
| 6,593,081 | B1 | 7/2003 | McCafferty et al. |
| 6,696,245 | B2 | 2/2004 | Winter et al. |
| 6,737,056 | B1 | 5/2004 | Presta |
| 6,765,087 | B1 | 7/2004 | Casterman et al. |
| 6,838,254 | B1 | 1/2005 | Hamers et al. |
| 6,933,368 | B2 | 8/2005 | Co et al. |
| 7,332,582 | B2 | 2/2008 | Hardy et al. |
| 7,488,802 | B2 | 2/2009 | Collins et al. |
| 7,521,051 | B2 | 4/2009 | Collins et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 8,354,509 | B2 | 1/2013 | Carven et al. |
| 8,383,796 | B2 | 2/2013 | Korman et al. |
| 8,609,089 | B2 | 12/2013 | Langermann et al. |
| 8,735,553 | B1 | 5/2014 | Li et al. |
| 9,683,048 | B2 | 6/2017 | Freeman et al. |
| 10,066,013 | B2 | 9/2018 | Chen et al. |
| 10,357,571 | B2 | 7/2019 | Williams et al. |
| 11,078,281 | B2 | 8/2021 | Wang et al. |
| 11,359,016 | B2 | 6/2022 | Luo et al. |
| 11,692,036 | B2 | 7/2023 | Luo et al. |
| 2006/0153808 | A1 | 7/2006 | Cristofanilli et al. |
| 2007/0117809 | A1 | 5/2007 | Fridman |
| 2007/0160619 | A1 | 7/2007 | Nichol et al. |
| 2009/0304719 | A1 | 12/2009 | Daughtery et al. |
| 2010/0189651 | A1 | 7/2010 | Stagliano et al. |
| 2011/0271358 | A1 | 11/2011 | Freeman et al. |
| 2013/0034559 | A1 | 2/2013 | Queva et al. |
| 2015/0079109 | A1 | 3/2015 | Li et al. |
| 2016/0258025 | A1 | 9/2016 | Klinger et al. |
| 2016/0311903 | A1 | 10/2016 | West et al. |
| 2018/0117147 | A1 | 5/2018 | Graziano et al. |
| 2019/0055314 | A1 | 2/2019 | Luo et al. |
| 2019/0169245 | A1 | 6/2019 | Williams et al. |
| 2019/0241662 | A1 | 8/2019 | Luo et al. |
| 2020/0123621 | A1 | 4/2020 | Bachireddy |
| 2021/0020264 | A1 | 1/2021 | Stroh et al. |
| 2021/0047409 | A1 | 2/2021 | Lala et al. |
| 2021/0206855 | A1 | 7/2021 | Luo et al. |
| 2024/0141046 | A1 | 5/2024 | Luo et al. |
| 2024/0209091 | A1 | 6/2024 | Luo et al. |
| 2025/0326847 | A1 | 10/2025 | Luo et al. |

FOREIGN PATENT DOCUMENTS

| | | | |
|---|---|---|---|
| CN | 101146553 | A | 3/2008 |
| CN | 102482347 | A | 5/2012 |
| CN | 105296433 | A | 2/2016 |
| CN | 107840887 | A | 3/2018 |
| CN | 108271359 | A | 7/2018 |
| CN | 112352000 | A | 2/2021 |
| CN | 115768525 | A | 3/2023 |
| EP | 368684 | B1 | 3/1994 |
| EP | 338841 | A1 | 3/1995 |
| EP | 616640 | B1 | 9/2004 |
| JP | 2009518446 | A | 5/2009 |
| JP | 2010536370 | A | 12/2010 |
| JP | 2012514982 | A | 7/2012 |
| JP | 2015509952 | A | 4/2015 |
| JP | 2016538240 | A | 12/2016 |
| KR | 1020170036092 | A | 3/2017 |
| WO | WO-1987004462 | A1 | 7/1987 |
| WO | WO-1989001036 | A1 | 2/1989 |
| WO | WO-1999051642 | A1 | 10/1999 |
| WO | WO-2002053596 | A2 | 7/2002 |
| WO | WO-2002055106 | A2 | 7/2002 |
| WO | WO-2003002609 | A2 | 1/2003 |
| WO | WO-2003015711 | A2 | 2/2003 |
| WO | WO-2003040170 | A2 | 5/2003 |
| WO | WO-2003048731 | A2 | 6/2003 |
| WO | WO-2004003019 | A3 | 1/2004 |
| WO | WO-2004004771 | A1 | 1/2004 |
| WO | WO-2004016805 | A2 | 2/2004 |
| WO | WO-2004056875 | A1 | 7/2004 |
| WO | WO-2004058821 | A2 | 7/2004 |
| WO | WO-2004072286 | A1 | 8/2004 |
| WO | WO-2004081026 | A2 | 9/2004 |
| WO | WO-2004101790 | A1 | 11/2004 |
| WO | WO-2005035572 | A2 | 4/2005 |
| WO | WO-2006066568 | A2 | 6/2006 |
| WO | WO-2006079372 | A1 | 8/2006 |
| WO | WO-2006101692 | A1 | 9/2006 |
| WO | WO-2006121168 | A1 | 11/2006 |
| WO | WO-2006129163 | A1 | 12/2006 |
| WO | WO-2007005874 | A2 | 1/2007 |
| WO | WO-2007059782 | A1 | 5/2007 |
| WO | WO-2008156712 | A1 | 12/2008 |
| WO | WO-2009022215 | A1 | 2/2009 |
| WO | WO-2009025846 | A2 | 2/2009 |
| WO | WO-2009079335 | A1 | 6/2009 |
| WO | WO-2009101611 | A1 | 8/2009 |
| WO | WO-2009114335 | A2 | 9/2009 |
| WO | WO-2010027827 | A2 | 3/2010 |
| WO | WO-2010077634 | A1 | 7/2010 |
| WO | WO-2011066342 | A2 | 6/2011 |
| WO | WO-2011066389 | A1 | 6/2011 |
| WO | WO-2014179664 | A2 | 11/2014 |
| WO | WO-2014194302 | A2 | 12/2014 |
| WO | WO-2015085847 | A1 | 6/2015 |
| WO | WO-2015112800 | A1 | 7/2015 |
| WO | WO-2015112900 | A1 | 7/2015 |
| WO | WO-2016118629 | A1 | 7/2016 |
| WO | WO-2016130898 | A2 | 8/2016 |
| WO | WO-2016130986 | A1 | 8/2016 |
| WO | WO-2016196237 | A1 | 12/2016 |
| WO | WO-2017011580 | A2 | 1/2017 |
| WO | WO-2017106372 | A1 | 6/2017 |
| WO | WO-2017194265 | A1 | 11/2017 |
| WO | WO-2018202649 | A1 | 11/2018 |
| WO | WO-2018209701 | A1 | 11/2018 |
| WO | WO-2018213732 | A1 | 11/2018 |
| WO | WO-2019036842 | A1 | 2/2019 |
| WO | WO-2019036855 | A1 | 2/2019 |
| WO | WO-2019036856 | A1 | 2/2019 |
| WO | WO-2019037711 | A1 | 2/2019 |
| WO | WO-2019149281 | A1 | 8/2019 |
| WO | WO-2019149282 | A1 | 8/2019 |
| WO | WO-2020139920 | A2 | 7/2020 |
| WO | WO-2020149026 | A1 | 7/2020 |
| WO | WO-2020198672 | A1 | 10/2020 |
| WO | WO-2021228178 | A1 | 11/2021 |
| WO | WO-2022171192 | A1 | 8/2022 |

(56) References Cited

FOREIGN PATENT DOCUMENTS

| | | | |
|---|---|---|---|
| WO | WO-2022212286 | A1 | 10/2022 |
| WO | WO-2022218264 | A1 | 10/2022 |

OTHER PUBLICATIONS

Adagene, (Apr. 18, 2023). “Adagene Presents Clinical Data for Anti-CTLA-4 SAFEbody® ADG126 Reinforcing Best-in-Class Safety Profile at Repeat Doses and Showing Early Efficacy Profile in Advanced/Metastatic Solid Tumors,” available online at <https://investor.adagene.com/news-releases/news-release-details/adagene-presents-clinical-data-anti-ctla-4-safebodyr-adg126/>, 2 pages.

Adagene, (Apr. 23, 2025). “Adagene Announces Upcoming Poster Presentation on Masked Anti-CTLA-4 SAFEbody® ADG126 (Muzastotug) at American Society of Clinical Oncology (ASCO) Annual Meeting,” available online at <https://investor.adagene.com/node/8076/pdf>, 1 page.

Adagene, (Dec. 16, 2022). “Adagene Announces Clinical Trial Collaboration to Evaluate Anti-CTLA-4 SAFEbody® ADG126 in Combination with Roche’s Standard-of-Care for First-Line Advanced Liver Cancer,” available online at <https://investor.adagene.com/news-releases/news-release-details/adagene-announces-clinical-trial-collaboration-evaluate-anti>, 2 pages.

Adagene, (Feb. 9, 2024). “Adagene Announces Progress and Expansion of Clinical Collaboration Program for Masked, Anti-CTLA-4 SAFEbody® ADG126 (muzastotug) in Combination with KEYTRUDA® (pembrolizumab) to Demonstrate Further Efficacy in Patients with Metastatic Microsatellite-stable (MSS) Colorectal Cancer (CRC),” available online at <https://investor.adagene.com/news-releases/news-release-details/adagene-announces-progress-and-expansion-clinical-collaboration/>, 2 pages.

Adagene, (Jan. 27, 2022). “Adagene Announces First Patient Dosed with Novel, Proprietary Combination of Anti-CD137 Agonist, ADG106, and Anti-CTLA-4 Monoclonal Antibody, ADG116,” available online at <https://investor.adagene.com/news-releases/news-release-details/adagene-announces-first-patient-dosed-novel-proprietary/>, 2 pages.

Adagene, (Jan. 27, 2025). “Adagene Announces Updated Data from Phase 1b/2 Study of Muzastotug in Combination with KEYTRUDA® (pembrolizumab) in Colorectal Cancer at ASCO Gastrointestinal Cancers Symposium,” available online at <https://investor.adagene.com/news-releases/news-release-details/adagene-announces-updated-data-phase-1b2-study-muzastotug/>, 2 pages.

Adagene, (Jan. 4, 2024). “Adagene To Present Interim Results of Masked anti-CTLA-4 SAFEbody® ADG126 (muzastotug) in Combination with Pembrolizumab in MSS CRC at ASCO-GI Symposium,” available online at <https://www.theglobeandmail.com/investing/markets/stocks/ADAG/pressreleases/23112344/adagene-to-present-interim-results-of-masked-anti-ctla-4-safebody-adg 126-muzastotug-in-combination-with-pembrolizumab-in-mss-crc-at-asco-gi-symposium/>, 1 page.

Adagene, (Jan. 9, 2023). “Adagene Announces Interim Data Demonstrating Safety and Confirmed Clinical Responses of Anti-CTLA-4 SAFEbody® ADG126 up to 10 mg/kg with Repeat Cycles in Combination with Anti-PD-1 Therapy from Dose Escalation Portion of Phase 1b/2 Trial,” available online at <https://investor.adagene.com/news-releases/news-release-details/adagene-announces-interim-data-demonstrating-safety-and>, 1 page.

Adagene, (Jan. 21, 2025). “Adagene to Announce Updated Data from Phase 1b/2 Study of Muzastotug in Combination with KEYTRUDA® (pembrolizumab) in Colorectal Cancer at ASCO Gastrointestinal Cancers Symposium,” available online at <https://investor.adagene.com/news-releases/news-release-details/adagene-announce-updated-data-phase-1b2-study-muzastotug/>, 2 pages.

Adagene, (Jul. 12, 2024). “Adagene Announces Poster Presentation on Masked Anti-CTLA-4 SAFEbody® ADG126 (muzastotug) in Combination with Pembrolizumab in MSS CRC at Upcoming European Society for Medical Oncology (ESMO) Congress in September,” available online at <https://investor.adagene.com/news-releases/news-release-details/adagene-announces-poster-presentation-masked-anti-ctla-4>, 1 page.

Adagene, (Jul. 22, 2021). “Adagene Announces Clinical Trial Collaboration With Merck to Advance Two Anti-CTLA-4 Monoclonal Antibody Programs (ADG116 and ADG126) in Combination Therapy with KEYTRUDA® (pembrolizumab),” available online at <https://investor.adagene.com/news-releases/news-release-details/adagene-announces-clinical-trial-collaboration-merck-advance-two>, 2 pages.

Adagene, (Mar. 14, 2023). “Adagene Announces Poster Presentations on Anti-CTLA-4 SAFEbody®, ADG126, at Upcoming American Association for Cancer Research (AACR) Annual Meeting in April,” available online at <https://investor.adagene.com/news-releases/news-release-details/adagene-announces-poster-presentation-optimal-dose-selection/>, 1 page.

Adagene, (Mar. 16, 2022). “Adagene Announces FDA Clearance to Proceed with Phase 1b/2 Trial of Anti-CTLA-4 ADG126 SAFEbody® in Combination Therapy With Anti-PD-1 Antibody Pembrolizumab,” available online at <https://investor.adagene.com/news-releases/news-release-details/adagene-announces-fda-clearance-proceed-phase-1b2-trial-anti/>, 1 page.

Adagene, (Mar. 29, 2021). “Adagene Announces Clinical Advancement for ADG116,” available online at <https://investor.adagene.com/news-releases/news-release-details/adagene-announces-clinical-advancement-adg116>, 2 pages.

Adagene, (May 22, 2025). “Adagene Announces Updated Data from Phase 1b/2 Study of Muzastotug (ADG126) in Combination with KEYTRUDA® (pembrolizumab) in Colorectal Cancer at the American Society of Clinical Oncology (ASCO) Annual Meeting,” available online at <https://investor.adagene.com/news-releases/news-release-details/adagene-announces-updated-data-phase-1b2-study-muzastotug-adg126>, 2 pages.

Adagene, (Nov. 22, 2021). “Adagene Announces Poster Presentations of Clinical Data for Two Novel Antibody Programs at ESMO Immuno-Oncology Congress 2021,” available online at <https://www.biospace.com/adagene-announces-poster-presentations-of-clinical-data-for-two-novel-antibody-programs-at-esmo-immuno-oncology-congress-2021>, 2 page.

Adagene, (Nov. 3, 2023). “Adagene Presents Data Demonstrating the Best-in-Class Therapeutic Index for Masked Anti-CTLA-4 SAFEbody® ADG126 at SITC 2023,” available online at <https://investor.adagene.com/node/7591/pdf>, 2 pages.

Adagene, (Nov. 7, 2024). “Adagene Presents Two Posters with New Insights on Increased Therapeutic Index for Masked Anti-CTLA-4 SAFEbody® ADG126 (Muzastotug) and Data Reinforcing Clinical Safety and Efficacy for ADG126 as Monotherapy and in Combination with Anti-PD-1 Therapy at Society for Immunotherapy of Cancer (SITC) 39th Annual Meeting,” available online at <https://investor.adagene.com/news-releases/news-release-details/adagene-presents-two-posters-new-insights-increased-therapeutic/>, 3 pages.

Adagene, (Oct. 11, 2022). “Adagene Announces Poster Presentations on Anti-CTLA-4 NEObody™, ADG116, at Upcoming Society for Immunotherapy of Cancer’s (SITC) Annual Meeting in November,” available online at <https://investor.adagene.com/news-releases/news-release-details/adagene-announces-poster-presentations-anti-ctla-4-neobodytm/>, 2 page.

Adagene, (Oct. 12, 2023). “Adagene Announces Poster Presentation on Optimal Dose Selection for Masked Anti-CTLA-4 SAFEbody® ADG126 at Upcoming Society for Immunotherapy of Cancer (SITC) 38th Annual Meeting,” available online at <https://investor.adagene.com/news-releases/news-release-details/adagene-announces-poster-presentation-optimal-dose-selection/>, 1 page.

Adagene, (Oct. 9, 2024). “Adagene Announces Upcoming Poster Presentations on Masked Anti-CTLA-4 SAFEbody® ADG126 (Muzastotug) at Society for Immunotherapy of Cancer (SITC) 39th Annual Meeting,” available online at <https://investor.adagene.com/news-releases/news-release-details/adagene-announces-upcoming-poster-presentations-masked-anti-ctla/>, 2 pages.

Adagene, (Sep. 10, 2022). “Adagene Presents Interim Monotherapy Data at ESMO 2022 Showing Compelling Safety, Anti-Tumor Activity and Pharmacokinetics of Masked, Anti-CTLA-4 SAFEbody® ADG126 in Patients with Advanced Tumors,” available online at

(56) References Cited

OTHER PUBLICATIONS

<https://investor.adagene.com/news-releases/news-release-details/adagene-presents-interim-monotherapy-data-esmo-2022-showing/>, 2 pages.
Adagene, (Sep. 16, 2024). "Adagene Presents Results at ESMO Congress that Show Best-in-Class Therapeutic Potential for Anti-CTLA-4 SAFEbody® ADG126 (Muzastotug) in Combination with KEYTRUDA® (Pembrolizumab) in Advanced/Metastatic Microsatellite-stable (MSS) Colorectal Cancer (CRC)," available online at <https://investor.adagene.com/news-releases/news-release-details/adagene-presents-results-esmo-congress-show-best-class-8>, 3 pages.
Adagene, (Sep. 5, 2025). "Adagene's ADG126 to be Highlighted in Two Presentations at the 2025 Chinese Society of Clinical Oncology (CSCO) Meeting in Jinan, China," available online at <https://investor.adagene.com/news-releases/news-release-details/adagenes-adg126-be-highlighted-two-presentations-2025-chinese>, 2 pages.
Ariyapperuma et al., (2023). "Poster: Interim Results of a Phase 1b/2 Study of ADG126 (a Masked anti-CTLA-4 SAFEbody®) Monotherapy and in Combination with Toripalimab (an anti-PD-1 Antibody) in Patients (pts) with Advanced / Metastatic Solid Tumors," AACR 2023, Abstract No. CT227, 1 page.
Fakih et al., (2026). "Poster: Ph1b evaluation of ADG126 (muzastotug, an anti-CTLA-4 masking antibody) pembrolizumab (Pembro) IO doublet in combination with fruquintinib (Fruq) in advanced and metastatic microsatellite stable colorectal cancer," AACR 2026, Abstract No. CT083, 1 page.
Li et al., (2023). "Poster CT233: Initial Results of a Phase 1b/2 Study of ADG126 (a Masked Anti CTLA 4 SAFEbody® ) in Combination with Pembrolizumab (an Anti PD 1 Antibody) in Patients with Advanced/Metastatic Solid Tumors," AACR 2023, 1 page.
Li et al., (2024). "Poster 127: Results of a Phase 1b/2 Study of ADG126 (a Masked Anti-CTLA-4 SAFEbody®) in Combination with Pembrolizumab (Pembro) in Patients with Metastatic Microsatellite-stable (MSS) Colorectal Cancer (CRC)," ASCO GI 2024, 1 page.
Li et al., (2024). "Poster 578P: Increased Therapeutic Index of Muzastotug (ADG126), a Masked Anti-CTLA-4 Antibody, in Combination with Pembrolizumab (Pembro) Enables Significant Clinical Benefits and Supports Further Clinical Development in Patients with Metastatic MSS CRC," ESMO 2024, Abstract No. 6055, 1 page.
Li et al., (2024). "Poster: Phase 1b/2, Multicenter Dose Escalation and Expansion Study of Muzastotug (ADG126, a Masked Anti-CTLA-4 SAFEbody®) in Combination with Pembrolizumab in Advanced/Metastatic MSS CRC," SITC 2024, Abstract No. 744, 1 page.
Li et al., (2025). "Poster 248: Safety and Efficacy of ADG126 (an Anti-CTLA-4 Masking Antibody) in Combination with Pembrolizumab: Updated Results of Phase 1b/2 Study in Advanced MSS CRC,"ASCO 2025, Abstract No. 3579, 1 page.
Li et al., (2025). "Poster: Update of Phase 1b/2 Study of Muzastotug (ADG126, an Anti-CTLA-4 SAFEbody®) in Combination with Pembrolizumab in Advanced/Metastatic MSS CRC," ASCO GI 2025, Abstract No. 129, 1 page.
Li et al., (2026). "Poster: Results from the phase 1b/2 Morpheus Liver study in patients with unresectable locally advanced or metastatic hepatocellular carcinoma (HCC): muzastotug (ADG126: masked anti-CTLA-4 Ab) combination arm," AACR 2026, Abstract No. CTO54, 1 page.
Li, (2025). "2025 ASCO Data Presentation: Safety and Efficacy of ADG126 (an Anti-CTLA-4 Masking Antibody) in Combination with Pembrolizumab: Updated Results of Phase 1b/2 Study in Advanced MSS CRC," ASCO 2025, 16 pages.
Liu et al., (2019). "Poster P788: Development of a novel antagonist anti-CTLA-4 antibody for cancer immunotherapy," SITC 2019, 1 page.
Liu et al., (2021). "Poster: A Novel Anti-CTLA-4 Checkpoint Inhibitor Prodrug to Address On-target Off-tumor Toxicity for Cancer Immunotherapy," 2021 AACR Annual Conference, Abstract No. 1853, 1 page.
Park et al., (2022). "Poster: A Phase 1b/2 Study of a Novel Anti-CTLA-4 NEObodyTM ADG116 Monotherapy and in Combination with Toripalimab (TORI; Anti-PD-1 Antibody) in Patients with Advanced / Metastatic Solid Tumors," SITC 2022, Abstract No. 753, 1 page.
Richardson et al., (2021). "Poster: Phase 1 dose-finding study of a novel anti-CTLA-4 antibody ADG116 as monotherapy in patients with advanced solid tumors," ESMO IO 2021, Abstract No. 394, 1 page.
Richardson et al., (2022). "Abstract e17601: Phase 1 study of ADG126, a novel masked anti-CTLA-4 SAFEbody, that combines tumor-localized activation with strong Treg depletion and soft ligand blocking in patients with advanced solid tumors," Gynelogical Cancer, 40(suppl 16):e17601, 1 page.
Richardson et al., (2022). "Poster 741P: Phase 1 Results Demonstrate Highly Differentiated Safety and PK Profile of ADG126, a Masked anti-CTLA-4 SAFEbody® in Patients with Advanced Solid Tumors," ESMO 2022, 1 page.
Tolcher et al., (2022). "Poster 773: A Phase 1b/2, Open-Label, Dose Escalation and Expansion Study of an Anti-CTLA-4 NEOBodyTM ADG116 in Combination with Pembrolizumab (Anti-PD-1 Antibody) in Patients with Advanced/Metastatic Solid Tumors: A Preliminary Update," SITC 2022, 1 page.
Zheng et al., (2023). "Poster 847: Optimal Dose Selection of ADG126 (Masked Anti-CTLA-4 SAFEbody®) with Significantly Widened Therapeutic Index Compared to Ipilimumab in Combination with anti-PD-1 Antibodies Informed by QSP Modeling," SITC 2023, 1 page.
Zheng et al., (2024). "Poster: Deciphering Improved Clinical Therapeutic Index (TI) of Muzastotug (ADG126), a Masked Anti-CTLA-4 SAFEbody® over its Unmasked Form (ADG116) as Monotherapy or in Combination with anti-PD-1 Therapy (Toripalimab)," SITC 2024, Abstract No. 506, 1 page.
ClinicalTrials.gov, (2021). "NCT04645069, Record History, ver 3," available online at <https://clinicaltrials.gov/study/NCT04645069?tab=history&a=3#version-content-panel>, 13 pages.
ClinicalTrials.org, (2020). "A Phase 1b/2 Study of ADG116, ADG116 Combined With Anti-PD-1 Antibody or Anti-CD137 Antibody in Solid Tumors Patients, NCT04501276," Available online at <https://clinicaltrials.gov/study/NCT04501276?term=NCT04501276&rank=1&tab=history&a=2#version-content-panel> obtained on May 21, 2021, 15 pages.
Committee for Medicinal Products for Human Use (CHMP). Assessment Report For Yervoy (ipilirnumab). CHMP assessment report EMNCHMP/557664/2011. May 19, 2011(May 19, 2011) pp. 1-71.
Extended European Search Report and Written Opinion received for European Patent Application No. 22787490.6 mailed on Feb. 3, 2025, 10 pages.
Fairfax et al., (2020). "Peripheral CD8+ T cell characteristics associated with durable responses to immune checkpoint blockade in patients with metastatic melanoma," Nat Med, 26(2):193-199, 31 pages.
He et al., (2017). "Study on the mechanism of action of CTLA-4 therapeutic antibody Ipilimumab," Compilation of abstracts of the 12th National Immunology Academic Conference, pp. 322-323. English Abstract Only.
Ingram et al. (2018). "Anti-CTLA-4 therapy requires an Fc domain for efficacy," Proc Natl Acad Sci USA. 115(15):3912-3917.
Keler et al., (2003). "Activity and Safety of CTLA-4 Blockade Combined with Vaccines in Cynomolgus macaques," The Journal of Immunology, 171:6251-59.
Korman et al., (2017). "Abstract SY09-01: Next generation anti-CTLA-4 antibodies," Cancer Res, 77(13_Supplement):SY09-01, 2 pages.
Lin et al., (2011). "Improved affinity of a chicken single-chain antibody to avian infectious bronchitis virus by site-directed mutagenesis of complementarity-determining region H3," African Journal of Biotechnology, 10(79):18294-18302.
Liu et al., (2019). "P788: Development of ADG116, a novel antagonist anti-CTLA-4 human antibody for cancer immunotherapy," Journal of Immuno Therapy of Cancer, 7(suppl 1):283, pp. 151-152.
Mariuzza, (1987). "The Structural Basis Of Antigen-Antibody Recognition," Annu. Rev. Biophys. Biophys. Chem., 16:139-159.

(56) References Cited

OTHER PUBLICATIONS

McCarthy et al., (2001). "Altering the fine specificity of an anti-Legionella single chain antibody by a single amino acid insertion," J. Immunol. Methods, 251(1-2):137-149.

Patnaik et al., (2021). "135P First-in-human phase I trial of SRF617, a potent inhibitor of CD39 activity, as monotherapy or in combination, in patients(pts) with advanced solid tumors," Annals Of Oncology, 32:S1435-S1436.

Perets et al., (2020). "Safety and efficacy of quavonlimab, a novel anti-CTLA-4 antibody (MK-1308), in combination with pembrolizumab in #rst-line advanced non-small-cell lung cancer," Annals of Oncology, 32(3):395-403.

Ramagopal et al., (2017). "Structural basis for cancer immunotherapy by the first-in-class checkpoint inhibitor ipilimumab," Proc Natl Acad Sci USA 114(21): 4223-4232.

Ribas et al., (2007). "Tremelimumab (CP-675, 206), a Cytotoxic T 1-61 Lymphocyte-Associated Antigen 4 Blocking Monoclonal Antibody in Clinical Development for Patients with Cancer," The Oncologist, 12:873-883.

Richardson et al. (2021). "137P Phase I dose-finding study of a novel anti-CTLA-4 antibody ADG116 as monotherapy in patients with advanced solid tumors," Annals of Oncology 32(7): S1436-S1437.

Sharma et al., (2015). "The future of immune checkpoint therapy," Science, 348(6230):56-61.

Simpson et al., (2013). "Fc-dependent depletion of tumor-infiltrating regulatory T cells co-defines the efficacy of anti-CTLA-4 therapy against melanoma," J Exp Med, 210(9):1695-1710.

Ternyila, (2020). "FDA Approves Every-6-Week Pembrolizurnab Dosage," available online <https://www.targetedonccom/view/fda-approves-every-6-week-pembrolizumab-dosage>, 2 pages.

US Food & Drug Administration, (2020). "FDA approves new dosing regimen for pembrolizumab," available online at <https://www.fda.gov/drugs/resources-information-approved-drugs/fda-approves-new-dosing-regimen-pembrolizumab>, 2 pages.

Xu et al., (2012). "Preparation and characterization of a chimeric anti-human CTLA-4 monoclonal antibody," Current Immunology, 5(32):359-364. English Abstract Only.

Zimmer et al., (2017). "Ipilimumab alone or in combination with nivolumab after progression on anti-PD-1 therapy in advanced melanoma," Eur J Cancer, 75:47-55.

Ahmadzadeh et al., (2009). "Tumor antigen-specific CD8 T cells infiltrating the tumor express high levels of PD-1 and are functionally impaired," Blood, 114:1537-1544.

Andria et al., (1990). "Diverse VH and VL genes are used to produce antibodies against a defined protein epitope," J. Immunol., 144:2614-2619.

Angal et al., (1993). "A single amino acid substitution abolishes the heterogeneity of chimeric mouse/human (IgG4) antibody," Mol. Imunol., 30:105-108.

Boder and Wittrup, (1997). "Yeast surface display for screening combinatorial polypeptide libraries," Nat Biotechnol, 15(6):553-7.

Chester et al., (2018). "Immunotherapy targeting 4-1 BB: mechanistic rationale, clinical results, and future strategies," Blood, 131(1):49-57.

Chichili et al., (2013). "Linkers in the structural biology of protein-protein interactions," Prot. Sci., 22:153-167.

Clackson et al., (1991). "Making antibody fragments using phage display libraries," Nature, 352:624-628.

ClinicalTrials.org, (2025). "ADG126 in Combination With Pembrolizumab in Patients With Advanced/Metastatic Solid Tumors, NCT05405595," Available online at <https://www.clinicaltrials.gov/study/NCT05405595>, 18 pages.

Desnoyers et al., (2013). "Tumor-Specific Activation of an EGFR-Targeting Probody Enhances Therapeutic Index," Sci. Transl. Med., 5(207):e144, 25 pages.

Dong et al., (2002). "Tumor-associated B7-H1 promotes T-cell apoptosis: a potential mechanism of immune evasion," Nat Med., 8(8):793-800.

Feldhaus et al., (2003). "Flow cytometric isolation of human antibodies from a non-immune *Saccharomyces cerevisiae* surface display library," Nat Biotechnol, 21(2):163-170.

Ferrara et al., (2018). "Anti-CTLA-4 immunotherapy does not deplete FOXP3+ regulatory T cells (Tregs) in human cancers—Letter," Clin. Cancer Res, 25(11):3468.

Gao et al., (2009). "Overexpression of PD-L1 significantly associates with tumor aggressiveness and postoperative recurrence in human hepatocellular carcinoma," Clinical Cancer Research, 15:971-979.

Gerspach et al., (2006). "Target-selective activation of a TNF prodrug by urokinase-type plasminogen activator (uPA) mediated proteolytic processing at the cell surface," Cancer Immunol Immunother, 55(12):1590-1600.

Ghebeh et al., (2006). "The B7-H1 (PD-L1) T lymphocyte-inhibitory molecule is expressed in breast cancer patients with infiltrating ductal carcinoma: correlation with important high-risk prognostic factors," Neoplasia, 8:190-198.

Ghebeh et al., (2008). "Foxp3+ Tregs and B7-H1+/PD-1+ T lymphocytes co-infiltrate the tumor tissues of high-risk breast cancer patients: implication for immunotherapy," BMC Cancer, 8:57, 12 pages.

Green et al., (1994). "Antigen-specific human monoclonal antibodies from mice engineered with human Ig heavy and light chain YACs," Nature Genetics, 7:13-21.

Ha et al., (2019). "Differential control of human Treg and effector T cells in tumor immunity by Fc-engineered anti-CTLA-4 antibody," PNAS, 116(2):609-618.

Hamanishi et al., (2007). "Programmed cell death 1 ligand 1 and tumor-infiltrating CDS+ T lymphocytes are prognostic factors of human ovarian cancer," Proc. Natl. Acad. Sci. USA, 104:3360-3365.

He et al., (2017). "Remarkably similar CTLA-4 binding properties of therapeutic ipilimumab and tremelimumab antibodies," Oncotarget 8:67129-67139.

Hino et al., (2010). "Tumor cell expression of programmed cell death-1 is a prognostic factor for malignant melanoma," Cancer, 116(7):1757-66.

Holliger et al., (1993). "Diabodies: small bivalent and bispecific antibody fragments," Proc. Natl. Acad. Sci. USA, 90(14):6444-6448.

Inman et al., (2007). "PD-L1 (B7-H1) expression by urothelial carcinoma of the bladder and ECG-induced granulomata: associations with localized stage progression," Cancer, 109:1499-1505.

Jiang et al., (2004). "Tumor imaging by means of proteolytic activation of cell-penetrating peptides," Proc Natl Acad Sci USA 101(51):17867-72.

Kaufman and Sharp, (1982). "Amplification and expression of sequences cotransfected with a modular dihydrofolate reductase complementary DNA gene," J Mol. Biol., 159(4):601-621.

Ke et al., (1997). "Optimal Subsite Occupancy and Design of a Selective Inhibitor of Urokinase," J Biol Chem 272(33):20456-62.

Knappik et al., (2000). "Fully Synthetic Human Combinatorial Antibody Libraries (HuCAL) Based on Modular Consensus Frameworks and CD Rs Randomized with Trinucleotides," J. Mol. Biol., 296(1):57-86.

Kohler and Milstein, (1975). "Continuous cultures of fused cells secreting antibody of predefined specificity," Nature 256:495.

Kranz et al., (1981). "Restricted reassociation of heavy and light chains from hapten-specific monoclonal antibodies," Proc. Natl. Acad. Sci. USA, 78(9):5807-5811.

Kumar et al., (2021). "Beyond the single average tumor: understanding IO combinations using a clinical QSP model that incorporates heterogeneity in patient response," CPT Pharmacomet Syst Pharmacol, 10:684-695.

Lee et al., (2016). "Structural basis of checkpoint blockade by monoclonal antibodies in cancer immunotherapy," Nat Commun 7(13354):1-10.

Marks et al., (1991). "By-passing immunization. Human antibodies from V-gene libraries displayed on phage," J. Mol. Biol., 222:581-597.

McCafferty et al., (1990). "Phage antibodies: filamentous phage displaying antibody variable domains," Nature, 348(6301):552-554.

(56) References Cited

OTHER PUBLICATIONS

Nakanishi et al., (2007). "Overexpression of B7-H1 (PD-L1) significantly associates with tumor grade and postoperative prognosis in human urothelial cancers," Cancer Immunol Immunother, 56:1173-1182.

Nomi et al., (2007). "Clinical significance and therapeutic potential of the programmed death-1 ligand/programmed death-I pathway in human pancreatic cancer," Clinical Cancer Research, 13:2151-2157.

Ohigashi et al., (2005). "Clinical significance of programmed death-1 ligand-1 and programmed death-1 ligand-2 expression in human esophageal cancer," Clin. Cancer Research, 11:2947-2953.

Park et al., (2023). "Abstract 105: Fecal microbiota transplantation combined with anti-PD-1 inhibitor for unresectable or metastatic solid cancers refractory to anti-PD-1 inhibitor," Journal of Clinical Oncology, 41(16_suppl).

Poljak (1994). "Production and structure of diabodies," Structure, 2(12):1121-1123.

Presta, (2005). "Selection, design, and engineering of therapeutic antibodies," J. Allergy Clin. Immunol., 116:731-6.

Schuurman et.al., (2001). "The inter-heavy chain disulfide bonds of IgG4 are in equilibrium with intra-chain disulfide bonds," Mol. Immunol., 38:1-8.

Schwartz et al., (2001). "Structural basis for co-stimulation by the human CTLA-4/B7-2 complex," Nature 410(6828): 604-608.

Sharma et al., (2019; epub 2018). "Anti-CTLA-4 Immunotherapy Does Not Deplete FOXP3+ Regulatory T Cells (Tregs) in Human Cancers," Clin. Cancer Res., 25:1233-1238.

Sharpe et al., (2007). "The function of programmed cell death 1 and its ligands in regulating autoimmunity and infection," Nature Immunology, 8:239-245.

Shimauchi et al., (2007). "Augmented expression of programmed death-1 in both neoplasmatic and non-neoplastic CD4+ T-cells in adult T-cell Leukemia/ Lymphoma," Int. J. Cancer, 121:2585-2590.

Stamper et al., (2001). "Crystal structure of the B7-1/CTLA-4 complex that inhibits human immune responses," Nature 410(6828): 608-611.

Takebe et al. (1988). "SR alpha promoter: an efficient and versatile mammalian cDNA expression system composed of the simian virus 40 early promoter and the R-U5 segment of human T-cell leukemia virus type 1 long terminal repeat," Mol. Cell. Biol., 8(1):466-472.

Tang et al., (2018). "Class 2 CRISPR/Cas: an expanding biotechnology toolbox for and beyond genome editing," Cell Biosci, 8:59, 13 pages.

Thompson et al., (2006). "Significance of B7-H1 overexpression in kidney cancer," Clinical Genitourinary Cancer, 5:206-211.

Thompson et al., (2007). "PD-1 is expressed by tumor infiltrating cells and is associated with poor outcome for patients with renal carcinoma," Clinical Cancer Research, 15:1757-1761.

Urlaub and Chasin (1980). "Isolation of Chinese hamster cell mutants deficient in dihydrofolate reductase activity," Proc. Natl. Acad. Sci. USA, 77(7):4216-4220.

WHO Drug Information, (2013). "International Nonproprietary Names for Pharmaceutical Substances (INN): Iambrolizumab," WHO Drug Information, 27(2):161-162.

WHO Drug Information, (2013). "International Nonproprietary Names for Pharmaceutical Substances (INN): nivolumab," WHO Drug Information, 27(1):68-69.

Wolchok et al., (2017). "Overall Survival with Combined Nivolumab and Ipilimumab in Advanced Melanoma," N Engl J Med, 377(14):1345-1356.

Yang et al., (2008). "PD-L1: PD-1 interaction contributes to the functional suppression of T-cell responses to human uveal melanoma cells in vitro," Invest Ophthalmol Vis Sci., 49(6):2518-2525.

Zhou et al., (2019). "Is protein context responsible for peptide-mediated interactions," Mol. Omics, 15:280-295.

Abhinandan et al., (2008). "Analysis and improvements to Kabat and structurally correct numbering of antibody variable domains," Mol Immunol, 45:3832-3839.

Adolf-Bryfogle et al., (2015). "PylgClassify: a database of antibody CDR structural classifications," Nucleic Acids Res, 43:D432-D438.

Al-Lazikani et al., (1997). "Standard conformations for the canonical structures of immunoglobulins," J. Rol. Biol., 273:927-948.

Allen, (2002). "Ligand-targeted therapeutics in anticancer therapy," Nat. Rev. Cancer, 2:750-763.

Altschul et al., (1990). "Basic Local Alignment Search Tool," J. Mol Biol., 215:403-410.

Altschul et al., (1997). "Gapped BLAST and PSI-BLAST: a new generation of protein database search programs," Nucleic Acids Res., 25:3389-3402.

Bird et al., (1988). "Single-chain antigen-binding proteins," Science, 242(4877):423-426.

Broll et al., (2001). "CD137 Expression in Tumor Vessel Walls: High Correlation With Malignant Tumors," Amer. J. Clin. Pathol., 115(4):543-549.

Chen et al., (1999). "Selection and Analysis of an Optimized Anti-VEGF Antibody: Crystal Structure of an Affinity-matured Fab in Complex with Antigen", J. Mol. Biol., 293:865-881.

Cheuk et al., (2004). "Role of 4-1BB:4-1BB ligand in cancer immunotherapy," Cancer Gene Therapy, 11(3):215-226.

Chothia et al., (1987). "Canonical structures for the hypervariable regions of immunoglobulins," J. Mol. Biol., 196:901-917.

Clynes et al., (1998). "Fc receptors are required in passive and active immunity to melanoma," Proc. Natl. Acad. Sci. USA, 95:652-656.

Cox et al., (1994). "A directory of human germ-line V kappa segments reveals a strong bias in their usage," Eur. J Immunol., 24(4):827-836.

Drenkard, (2007). "CD137 is expressed on blood vessel walls at sites of Inflammation and enhances monocyte migratory activity," FASEB Journal, 21: 456-463.

Ehrenmann et al., (2009). "IMGT/3Dstructure-DB and IMGT/DomainGapAlign: a database and a tool for immunoglobulins or antibodies, T cell receptors, MHC, IgSF and MhcSF," Nucleic Acids Res., 38:D301-D307.

Flatman et al., (2007). "Process analytics for purification of monoclonal antibodies," J Chromatogr B Analyt Technol Biomed Life Sci, 848(1):79-87.

Gazzano-Santoro et al., (1997). "A non-radioactive complement-dependent cytotoxicity assay for anti-CD20 monoclonal antibody," J. Immunol. Methods, 202:163-71.

Hack et al., (2020). "Augmenting Anticancer Immunity Through Combined Targeting of Angiogenic and PD-1/PD-L1 Pathways: Challenges and Opportunities," Frontiers In Immunology, 11:598877, 24 pages.

Honegger et al., (2001)."Yet another numbering scheme for immunoglobulin variable domains: an automatic modeling and analysis tool," Mol Biol., 309:657-670.

Hurwitz et al., (1998). "CTLA-4 blockade synergizes with tumor-derived granulocyte- macrophage colony-stimulating factor for treatment of an experimental mammary carcinoma," Proc Natl Acad Sci USA 95 (17):10067-71.

Huston et al., (1988). "Protein engineering of antibody binding sites: recovery of specific activity in an anti-digoxin single-chain Fv analogue produced in *Escherichia coli*," PNAS USA, 85:5879-5883.

Idusogie et al., (2000). "Mapping of the C1q binding site on rituxan, a chimeric antibody with a human IgG1 Fc," J. Immunol, 164:4178-4184.

International Search Report and Written Opinion received for International Patent Application No. PCT/CN2022/086143 mailed on Jul. 12, 2022, 16 pages.

Jenkins et al., (2020). "Abstract 587: Tumor-Activated Fc-Engineered Anti-Ctla-4 Monoclonal Antibody, Xtxi0i, Demonstrates Tumor-Selective Pd And Efficacy In Preclinical Models," J Immunother Cancer, 8(3):A351.

Kabat et al., (1977). "Unusual distributions of amino acids in complementarity-determining (hypervariable) segments of heavy and light chains of immunoglobulins and their possible roles in specificity of antibody-combining sites," J. Biol. Chem., 252:6609-6616.

(56) References Cited

OTHER PUBLICATIONS

Kwon et al., (1997). "Manipulation of T cell costimulatory and inhibitory signals for immunotherapy of prostate cancer," Proc Natl Acad Sci USA, 94(15):8099-103.
Lefranc et al., (2003). "IMGT unique numbering for immunoglobulin and T cell receptor variable domains and Ig superfamily V-like domains," Dev. Comp. Immunol., 27:55-77.
MacCallum et al., (1996). "Antibody-antigen interactions: contact analysis and binding site topography," Journal of Molecular Biology, 262:732-745.
Olofsson et al., (2008). "CD137 is expressed in human atherosclerosis and promotes development of plaque inflammation in hypercholesterolemic mice," Circulation, 117(10):1292-1301.
Pastan et al., (2002). "Immunotoxins in cancer therapy," Curr. Opin. Investig. Drugs, 3(7):1089-1091. Abstract Only.
Payne, (2003). "Progress in immunoconjugate cancer therapeutics," Cancer Cell, (3)3:207-212.
Pearson, (1990). "Rapid and Sesitive Sequence Comparison with FASTP and FASTA," Methods Enzyntol., 183:63-98.
Pearson, (2000). "Flexible Sequence Similarity Searching with the FASTA3 Program Package," Methods MoL Biol., 132:185-219.
Ravetch et al., (1991). "Fc receptors," Annu. Rev. Immunol, 9:457-92.
Rowshanravan et al., (2018). "CTLA4: a moving target in immunotherapy," Blood, 131:58-67.
Saito et al., (2003). "Drug delivery strategy utilizing conjugation via reversible disulfide linkages: role and site of cellular reducing activities," Adv. Drug Deliv. Rev., 55(2): 199-215.
Seaman et al., (2007). "Genes that distinguish physiological and pathological angiogenesis," Cancer Cell, 11(6): 539-554.
Senter et al., (2001). "Selective activation of anticancer prodrugs by monoclonal antibody-enzyme conjugates," Adv. Drug Deliv. Rev., 53:247-264.
Tomlinson et al., (1992). "The repertoire of human germline VH sequences reveals about fifty groups of VH segments with different hypervariable loops," J Mol. Biol., 227(3):776-798.
Trail et al., (2003). "Monoclonal antibody drug immunoconjugates for targeted treatment of cancer," Cancer Immunol. Immunother., 52(5):328-337.
Wang et al., (2009). "Immune regulation by 4-1BB and 4-1BBL: complexities and challenges," Immunological Reviews, 229(1):192-215.
Ward et al., (1989). "Binding activities of a repertoire of single immunoglobulin variable domains secreted from *Escherichia coli*," Nature, 341:544-546.
Yang et al., (1997). "Enhanced induction of antitumor T-cell responses by cytotoxic T lymphocyte-associated molecule-4 blockade: the effect is manifested only at the restricted tumor-bearing stages," Cancer Res 57(18):4036-41.

| Test Antibody | Tumor volume (mm³) (14th day after administration) | TGI[b] (%) | p value[c] One-way ANOVA |
|---|---|---|---|
| IgG1 Isotype Control (2 mg/kg) | 2000 ± 200 (n=8) | -- | -- |
| TY21580 (2 mg/kg) | 984 ± 169 (n=8) | 51 | 0.0036 |
| TY22404 (2 mg/kg) | 1667 ± 277 (n=8) | 18 | 0.6460 |
| 2E5 (10 mg/kg) | 596 ± 259 (n=8) | 69 | 0.0001 |
| TY21580 (2 mg/kg) + 2E5 (10 mg/kg) | 179 ± 109 (n=8) | 92 | 0.0001 |
| TY22404 (2mg/kg) + 2E5 (10 mg/kg) | 215 ± 113 (n=8) | 91 | 0.0001 |

Dosing: BIW; *i.p.*
n=8/group

| Treatment | Tumor Size ($mm^3$)[a] on Day 27 (Mean± SEM) | TGI | *P* value (*vs* isotype Ctrl) |
|---|---|---|---|
| Isotype control (5 mg/kg) | 2819±228 (n=8) | -- | -- |
| TY22404 (5 mg/kg) | 648±193 (n=8) | 77 | 0.0001 |
| ADG106 (5 mg/kg) | 2260±289 (n=8) | 21 | 0.1686 |
| TY22404 (5 mg/kg) + ADG106 (5 mg/kg) | 163±61 (n=8) | 94 | 0.0001 |

*Progressed on anti-PD-1 or anti-PD-L1 therapy, but naïve to anti-CTLA4 therapy

2nd line who progressed on anti-PD-1 or anti-PD-L1 therapy, but naïve to anti-CTLA4 therapy

- The 20 mg/kg cohort is being opened

| AE (PT) | 0.1mg/kg (n=3) | | | 0.3mg/kg(n=3) | | | 1mg/kg(n=4) | | | 3mg/kg(n=3) | | | 10mg/kg(n=3) | | | Total(n=16) | | |
|---|---|---|---|---|---|---|---|---|---|---|---|---|---|---|---|---|---|---|
| | All G | G1/2 | G3/4 | All G | G1/2 | G3/4 | All G | G1/2 | G3/4 | All G | G1/2 | G3/4 | All G | G1/2 | G3/4 | All G | G1/2 | G3/4 |
| Fatigue | 0 | 0 | 0 | 1 | 0 | 1 | 1 | 1 | 0 | 2 | 2 | 0 | 0 | 0 | 0 | 4 (25%) | 3 | 1 |
| Pruritus | 0 | 0 | 0 | 0 | 0 | 0 | 1 | 1 | 0 | 1 | 1 | 0 | 0 | 0 | 0 | 2 (13%) | 2 | 0 |
| Diarrhea | 0 | 0 | 0 | 1 | 1 | 0 | 0 | 0 | 0 | 0 | 0 | 0 | 0 | 0 | 0 | 1 (6%) | 1 | 0 |
| Hypothermia | 0 | 0 | 0 | 0 | 0 | 0 | 1 | 1 | 0 | 0 | 0 | 0 | 0 | 0 | 0 | 1 (6%) | 1 | 0 |
| Nausea | 0 | 0 | 0 | 0 | 0 | 0 | 0 | 0 | 0 | 1 | 1 | 0 | 0 | 0 | 0 | 1 (6%) | 1 | 0 |
| Headache | 0 | 0 | 0 | 0 | 0 | 0 | 0 | 0 | 0 | 1 | 1 | 0 | 0 | 0 | 0 | 1 (6%) | 1 | 0 |
| Rash | 0 | 0 | 0 | 0 | 0 | 0 | 0 | 0 | 0 | 1 | 1 | 0 | 0 | 0 | 0 | 1 (6%) | 1 | 0 |

FIG. 31

Subject ID: 6103-005

Tumor type: Ovarian Cancer

Dose Level: 1 mg/kg

Prior therapies: 5 lines, no prior IO treatment

Dose cycle: 7

CA-125: 303 U/ml at baseline and 70 U/ml at the end of C7 (77% reduction from baseline)

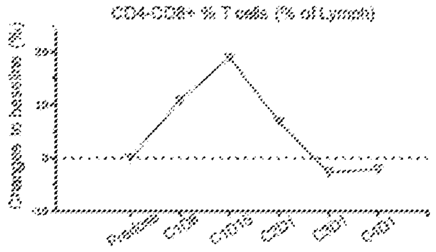

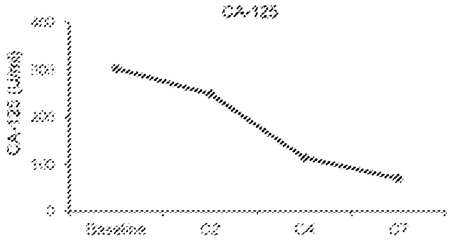

| | | Baseline (07 AUG 2021) | End of C2 | End of C4 | End of C7 |
|---|---|---|---|---|---|
| Target Lesion | TL1- Lymph Node | 17 mm | 13 mm | 12 mm | 12 mm |
| | TL2 -Lymph Node | 15 mm | 15 mm | 14 mm | 13 mm |
| | **Sum (% change from baseline)** | 32 mm | 28 mm (-13%) | 26 mm (-19%) | 25 mm (-22%) |
| Non-Target Lesion | | Present | Present | Present | Present |
| New Lesion | | NA | No | No | No |
| Overall Response | | NA | SD | SD | SD |
| CA-125, U/ml (% change from Baseline) | | 303 | 249 (-18%) | 114 (-62%) | 70 (-77%) |

FIG. 32A

Patient ID: 5101-101
Indication: Uveal Melanoma
Dose Level: 10 mg/kg
Prior anti-tumor treatment: 3 lines of therapy including Nivo + Ipi followed by Nivo
Dosing cycle: 3

| Baseline | | | End of C2 |
|---|---|---|---|
| Target Lesion | TL1- Liver | 14 mm | 10 mm |
| | TL2 -Liver | 15 mm | 12 mm |
| | Sum (percent change) | 29 mm | 22 mm (SD, -24%) |
| Non-Target Lesion | N/A | | N/A |
| New Lesion | No | | No |
| Overall Response | | | SD |

SEQUENCE LISTING

```
<160> NUMBER OF SEQ ID NOS: 328

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Phe or Tyr
<220> FEATURE:
<221> NAME/KEY: VARIANT
<222> LOCATION: 5
<223> OTHER INFORMATION: Xaa = Asp or Gly
<220> FEATURE:
<221> NAME/KEY: VARIANT
<222> LOCATION: 7
<223> OTHER INFORMATION: Xaa = Ala, Gly or Trp

<400> SEQUENCE: 1

Xaa Thr Phe Ser Xaa Tyr Xaa Ile His Trp Val
1               5                   10


<210> SEQ ID NO 2
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser or Thr
<220> FEATURE:
<221> NAME/KEY: VARIANT
<222> LOCATION: 7, 8
<223> OTHER INFORMATION: Xaa = His or Tyr
<220> FEATURE:
<221> NAME/KEY: VARIANT
<222> LOCATION: 10
<223> OTHER INFORMATION: Xaa = Ala, Asp, or Ser

<400> SEQUENCE: 2

Tyr Ser Ile Xaa Ser Gly Xaa Xaa Trp Xaa Trp Ile
1               5                   10


<210> SEQ ID NO 3
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 11
<223> OTHER INFORMATION: Xaa = Gly or Ser

<400> SEQUENCE: 3

Phe Ser Leu Ser Thr Gly Gly Val Ala Val Xaa Trp Ile
1               5                   10


<210> SEQ ID NO 4
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
```

```
<223> OTHER INFORMATION: Xaa = Asp or Glu
<220> FEATURE:
<221> NAME/KEY: VARIANT
<222> LOCATION: 5
<223> OTHER INFORMATION: Xaa = Ser or Tyr
<220> FEATURE:
<221> NAME/KEY: VARIANT
<222> LOCATION: 14
<223> OTHER INFORMATION: Xaa = Pro or Gln

<400> SEQUENCE: 4

Ile Gly Xaa Ile Xaa His Ser Gly Ser Thr Tyr Tyr Ser Xaa Ser Leu
1               5                   10                  15

Lys Ser Arg Val
            20


<210> SEQ ID NO 5
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ile or Trp
<220> FEATURE:
<221> NAME/KEY: VARIANT
<222> LOCATION: 8, 10
<223> OTHER INFORMATION: Xaa = Gly or Ser
<220> FEATURE:
<221> NAME/KEY: VARIANT
<222> LOCATION: 12
<223> OTHER INFORMATION: Xaa = Lys or Asn

<400> SEQUENCE: 5

Ile Gly Xaa Ile Ser Pro Ser Xaa Gly Xaa Thr Xaa Tyr Ala Gln Lys
1               5                   10                  15

Phe Gln Gly Arg Val
            20


<210> SEQ ID NO 6
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ala, Gly, or Ser
<220> FEATURE:
<221> NAME/KEY: VARIANT
<222> LOCATION: 7
<223> OTHER INFORMATION: Xaa = Ser or Tyr
<220> FEATURE:
<221> NAME/KEY: VARIANT
<222> LOCATION: 9
<223> OTHER INFORMATION: Xaa = Gly or Ser
<220> FEATURE:
<221> NAME/KEY: VARIANT
<222> LOCATION: 10
<223> OTHER INFORMATION: Xaa = Ser or Thr

<400> SEQUENCE: 6

Val Ser Xaa Ile Ser Gly Xaa Gly Xaa Xaa Thr Tyr Tyr Ala Asp Ser
1               5                   10                  15

Val Lys Gly Arg Phe
            20
```

```
<210> SEQ ID NO 7
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Gly, Arg, or Ser
<220> FEATURE:
<221> NAME/KEY: VARIANT
<222> LOCATION: 4
<223> OTHER INFORMATION: Xaa = Ala, Ile, or Tyr
<220> FEATURE:
<221> NAME/KEY: VARIANT
<222> LOCATION: 5
<223> OTHER INFORMATION: Xaa = Asp, Val, or Tyr
<220> FEATURE:
<221> NAME/KEY: VARIANT
<222> LOCATION: 6
<223> OTHER INFORMATION: Xaa = Ala, Glu, or Tyr
<220> FEATURE:
<221> NAME/KEY: VARIANT
<222> LOCATION: 9
<223> OTHER INFORMATION: Xaa = Ile or Tyr

<400> SEQUENCE: 7

Ala Arg Xaa Xaa Xaa Xaa Phe Asp Xaa
1               5


<210> SEQ ID NO 8
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Asp or Leu
<220> FEATURE:
<221> NAME/KEY: VARIANT
<222> LOCATION: 5
<223> OTHER INFORMATION: Xaa = Phe or Tyr
<220> FEATURE:
<221> NAME/KEY: VARIANT
<222> LOCATION: 10
<223> OTHER INFORMATION: Xaa = Val or Tyr

<400> SEQUENCE: 8

Ala Arg Xaa Gly Xaa Gly Tyr Phe Asp Xaa
1               5                   10


<210> SEQ ID NO 9
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Leu or Arg
<220> FEATURE:
<221> NAME/KEY: VARIANT
<222> LOCATION: 4
<223> OTHER INFORMATION: Xaa = Ile or Pro
<220> FEATURE:
<221> NAME/KEY: VARIANT
<222> LOCATION: 5
<223> OTHER INFORMATION: Xaa = Ala or Tyr
<220> FEATURE:
<221> NAME/KEY: VARIANT
<222> LOCATION: 6
```

<223> OTHER INFORMATION: Xaa = Ser or Thr
<220> FEATURE:
<221> NAME/KEY: VARIANT
<222> LOCATION: 8
<223> OTHER INFORMATION: Xaa = Thr or Tyr
<220> FEATURE:
<221> NAME/KEY: VARIANT
<222> LOCATION: 9
<223> OTHER INFORMATION: Xaa = Ala or Tyr

<400> SEQUENCE: 9

Ala Arg Xaa Xaa Xaa Xaa Ala Xaa Xaa Phe Asp Tyr
1 5 10

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ile or Val
<220> FEATURE:
<221> NAME/KEY: VARIANT
<222> LOCATION: 5
<223> OTHER INFORMATION: Xaa = Ala or His
<220> FEATURE:
<221> NAME/KEY: VARIANT
<222> LOCATION: 6
<223> OTHER INFORMATION: Xaa = Pro or Ser
<220> FEATURE:
<221> NAME/KEY: VARIANT
<222> LOCATION: 13
<223> OTHER INFORMATION: Xaa = Asp or Tyr
<220> FEATURE:
<221> NAME/KEY: VARIANT
<222> LOCATION: 17
<223> OTHER INFORMATION: Xaa = Phe or Val

<400> SEQUENCE: 10

Ala Arg Asp Xaa Xaa Xaa Gly Ser Ser Gly Tyr Tyr Xaa Gly Phe Asp
1 5 10 15

Xaa

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5, 7
<223> OTHER INFORMATION: Xaa = Gly or Ser
<220> FEATURE:
<221> NAME/KEY: VARIANT
<222> LOCATION: 6
<223> OTHER INFORMATION: Xaa = Ile or Val
<220> FEATURE:
<221> NAME/KEY: VARIANT
<222> LOCATION: 9
<223> OTHER INFORMATION: Xaa = Ser or Tyr
<220> FEATURE:
<221> NAME/KEY: VARIANT
<222> LOCATION: 11
<223> OTHER INFORMATION: Xaa = Ala or Asn

<400> SEQUENCE: 11

Arg Ala Ser Gln Xaa Xaa Xaa Ser Xaa Leu Xaa
1 5 10

<210> SEQ ID NO 12
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Thr
<220> FEATURE:
<221> NAME/KEY: VARIANT
<222> LOCATION: 7
<223> OTHER INFORMATION: Xaa = Phe, Arg, or Ser
<220> FEATURE:
<221> NAME/KEY: VARIANT
<222> LOCATION: 8
<223> OTHER INFORMATION: Xaa = Gly or Ser
<220> FEATURE:
<221> NAME/KEY: VARIANT
<222> LOCATION: 10
<223> OTHER INFORMATION: Xaa = Phe or Tyr

<400> SEQUENCE: 12

```
Arg Ala Ser Gln Xaa Val Xaa Xaa Arg Xaa Leu Ala
1               5                   10
```

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Glu or Gln
<220> FEATURE:
<221> NAME/KEY: VARIANT
<222> LOCATION: 9
<223> OTHER INFORMATION: Xaa = Asp, Phe, His, or Tyr
<220> FEATURE:
<221> NAME/KEY: VARIANT
<222> LOCATION: 11
<223> OTHER INFORMATION: Xaa = Phe, Ile, or Lys
<220> FEATURE:
<221> NAME/KEY: VARIANT
<222> LOCATION: 15
<223> OTHER INFORMATION: Xaa = Ala, Asp, or His

<400> SEQUENCE: 13

```
Arg Ala Ser Xaa Ser Val Asp Phe Xaa Gly Xaa Ser Phe Leu Xaa
1               5                   10                  15
```

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ala or Asp
<220> FEATURE:
<221> NAME/KEY: VARIANT
<222> LOCATION: 4
<223> OTHER INFORMATION: Xaa = Asn, Ser or Thr
<220> FEATURE:
<221> NAME/KEY: VARIANT
<222> LOCATION: 5
<223> OTHER INFORMATION: Xaa = Leu or Arg
<220> FEATURE:
<221> NAME/KEY: VARIANT -continued
<222> LOCATION: 6
<223> OTHER INFORMATION: Xaa = Ala, Glu, or Gln
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 9
<223> OTHER INFORMATION: Xaa = Ile or Val

<400> SEQUENCE: 14

Xaa Ala Ser Xaa Xaa Xaa Xaa Gly Xaa
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Glu, Gln, or Val
<220> FEATURE:
<221> NAME/KEY: VARIANT
<222> LOCATION: 4
<223> OTHER INFORMATION: Xaa = His or Gln
<220> FEATURE:
<221> NAME/KEY: VARIANT
<222> LOCATION: 5
<223> OTHER INFORMATION: Xaa = Ala, Gly, His, Arg, or Ser
<220> FEATURE:
<221> NAME/KEY: VARIANT
<222> LOCATION: 6
<223> OTHER INFORMATION: Xaa = Asp, Leu, Ser, or Tyr
<220> FEATURE:
<221> NAME/KEY: VARIANT
<222> LOCATION: 7
<223> OTHER INFORMATION: Xaa = Glu, Gly, Pro, Gln, or Ser
<220> FEATURE:
<221> NAME/KEY: VARIANT
<222> LOCATION: 8
<223> OTHER INFORMATION: Xaa = Leu, Thr, Val, or Trp
<220> FEATURE:
<221> NAME/KEY: VARIANT
<222> LOCATION: 10
<223> OTHER INFORMATION: Xaa = Phe, Leu, Pro, Trp, or Tyr

<400> SEQUENCE: 15

Tyr Cys Xaa Xaa Xaa Xaa Xaa Xaa Pro Xaa Thr
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Tyr
<220> FEATURE:
<221> NAME/KEY: VARIANT
<222> LOCATION: 6
<223> OTHER INFORMATION: Xaa = Asp or Tyr
<220> FEATURE:
<221> NAME/KEY: VARIANT
<222> LOCATION: 7
<223> OTHER INFORMATION: Xaa = Gln or Tyr

<400> SEQUENCE: 16

-continued

Tyr Cys Gln Gln Xaa Xaa Xaa Trp Pro Pro Trp Thr
1 5 10

<210> SEQ ID NO 17
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = His or Gln
<220> FEATURE:
<221> NAME/KEY: VARIANT
<222> LOCATION: 6
<223> OTHER INFORMATION: Xaa = Thr or Val
<220> FEATURE:
<221> NAME/KEY: VARIANT
<222> LOCATION: 11
<223> OTHER INFORMATION: Xaa = Glu or Val

<400> SEQUENCE: 17

Tyr Cys Gln Xaa Tyr Xaa Ser Ser Pro Pro Xaa Tyr Thr
1 5 10

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Phe Thr Phe Ser Asp Tyr Ala Ile His Trp Val
1 5 10

<210> SEQ ID NO 19
<211> LENGTH: 12
<212> TYPE: PRT
<213> ORGANISM: Artificial Sequence
<220> FEATURE:
<223> OTHER INFORMATION: Synthetic Construct

<400> SEQUENCE: 19

Tyr Ser Ile Thr Ser Gly Tyr Tyr Trp Ala Trp Ile
1 5 10

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Phe Thr Phe Ser Asp Tyr Gly Ile His Trp Val
1 5 10

<210> SEQ ID NO 21
<211> LENGTH: 12
<212> TYPE: PRT
<213> ORGANISM: Artificial Sequence
<220> FEATURE:
<223> OTHER INFORMATION: Synthetic Construct

<400> SEQUENCE: 21

Tyr Ser Ile Ser Ser Gly Tyr His Trp Asp Trp Ile
1 5 10

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

Phe Thr Phe Ser Asp Tyr Trp Ile His Trp Val
1 5 10

<210> SEQ ID NO 23
<211> LENGTH: 12
<212> TYPE: PRT
<213> ORGANISM: Artificial Sequence
<220> FEATURE:
<223> OTHER INFORMATION: Synthetic Construct

<400> SEQUENCE: 23

Tyr Ser Ile Ser Ser Gly Tyr His Trp Ser Trp Ile
1 5 10

<210> SEQ ID NO 24
<211> LENGTH: 13
<212> TYPE: PRT
<213> ORGANISM: Artificial Sequence
<220> FEATURE:
<223> OTHER INFORMATION: Synthetic Construct

<400> SEQUENCE: 24

Phe Ser Leu Ser Thr Gly Gly Val Ala Val Ser Trp Ile
1 5 10

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

Phe Ser Leu Ser Thr Gly Gly Val Ala Val Gly Trp Ile
1 5 10

<210> SEQ ID NO 26
<211> LENGTH: 11
<212> TYPE: PRT
<213> ORGANISM: Artificial Sequence
<220> FEATURE:
<223> OTHER INFORMATION: Synthetic Construct

<400> SEQUENCE: 26

Phe Thr Phe Ser Gly Tyr Ala Ile His Trp Val
1 5 10

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Tyr Thr Phe Ser Gly Tyr Gly Ile His Trp Val
1 5 10

-continued

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Tyr Thr Phe Ser Gly Tyr Ala Ile His Trp Val
1 5 10

<210> SEQ ID NO 29
<211> LENGTH: 12
<212> TYPE: PRT
<213> ORGANISM: Artificial Sequence
<220> FEATURE:
<223> OTHER INFORMATION: Synthetic Construct

<400> SEQUENCE: 29

Tyr Ser Ile Thr Ser Gly His Tyr Trp Ser Trp Ile
1 5 10

<210> SEQ ID NO 30
<211> LENGTH: 21
<212> TYPE: PRT
<213> ORGANISM: Artificial Sequence
<220> FEATURE:
<223> OTHER INFORMATION: Synthetic Construct

<400> SEQUENCE: 30

Ile Gly Ile Ile Ser Pro Ser Ser Gly Ser Thr Asn Tyr Ala Gln Lys
1 5 10 15

Phe Gln Gly Arg Val
20

<210> SEQ ID NO 31
<211> LENGTH: 21
<212> TYPE: PRT
<213> ORGANISM: Artificial Sequence
<220> FEATURE:
<223> OTHER INFORMATION: Synthetic Construct

<400> SEQUENCE: 31

Val Ser Ser Ile Ser Gly Ser Gly Ser Thr Thr Tyr Tyr Ala Asp Ser
1 5 10 15

Val Lys Gly Arg Phe
20

<210> SEQ ID NO 32
<211> LENGTH: 20
<212> TYPE: PRT
<213> ORGANISM: Artificial Sequence
<220> FEATURE:
<223> OTHER INFORMATION: Synthetic Construct

<400> SEQUENCE: 32

Ile Gly Glu Ile Tyr His Ser Gly Ser Thr Tyr Tyr Ser Pro Ser Leu
1 5 10 15

Lys Ser Arg Val
20

<210> SEQ ID NO 33
<211> LENGTH: 21
<212> TYPE: PRT
<213> ORGANISM: Artificial Sequence
<220> FEATURE:
<223> OTHER INFORMATION: Synthetic Construct

<400> SEQUENCE: 33

Val Ser Gly Ile Ser Gly Tyr Gly Gly Ser Thr Tyr Tyr Ala Asp Ser
1 5 10 15

Val Lys Gly Arg Phe
20

<210> SEQ ID NO 34
<211> LENGTH: 21
<212> TYPE: PRT
<213> ORGANISM: Artificial Sequence
<220> FEATURE:
<223> OTHER INFORMATION: Synthetic Construct

<400> SEQUENCE: 34

Ile Gly Trp Ile Ser Pro Ser Gly Gly Gly Thr Lys Tyr Ala Gln Lys
1 5 10 15

Phe Gln Gly Arg Val
20

<210> SEQ ID NO 35
<211> LENGTH: 20
<212> TYPE: PRT
<213> ORGANISM: Artificial Sequence
<220> FEATURE:
<223> OTHER INFORMATION: Synthetic Construct

<400> SEQUENCE: 35

Leu Ala Arg Ile Asp Trp Asp Asp Asp Lys Tyr Tyr Ser Thr Ser Leu
1 5 10 15

Lys Ser Arg Leu
20

<210> SEQ ID NO 36
<211> LENGTH: 21
<212> TYPE: PRT
<213> ORGANISM: Artificial Sequence
<220> FEATURE:
<223> OTHER INFORMATION: Synthetic Construct

<400> SEQUENCE: 36

Val Ser Ala Ile Ser Gly Tyr Gly Ser Thr Thr Tyr Tyr Ala Asp Ser
1 5 10 15

Val Lys Gly Arg Phe
20

<210> SEQ ID NO 37
<211> LENGTH: 21
<212> TYPE: PRT
<213> ORGANISM: Artificial Sequence
<220> FEATURE:
<223> OTHER INFORMATION: Synthetic Construct

<400> SEQUENCE: 37

Ile Gly Ile Ile Ser Pro Ser Gly Gly Gly Thr Lys Tyr Ala Gln Lys
1 5 10 15

Phe Gln Gly Arg Val
20

<210> SEQ ID NO 38
<211> LENGTH: 21
<212> TYPE: PRT

<213> ORGANISM: Artificial Sequence
<220> FEATURE:
<223> OTHER INFORMATION: Synthetic Construct

<400> SEQUENCE: 38

Ile Gly Ile Ile Ser Pro Ser Gly Gly Ser Thr Lys Tyr Ala Gln Lys
1 5 10 15

Phe Gln Gly Arg Val
20

<210> SEQ ID NO 39
<211> LENGTH: 20
<212> TYPE: PRT
<213> ORGANISM: Artificial Sequence
<220> FEATURE:
<223> OTHER INFORMATION: Synthetic Construct

<400> SEQUENCE: 39

Ile Gly Asp Ile Ser His Ser Gly Ser Thr Tyr Tyr Ser Gln Ser Leu
1 5 10 15

Lys Ser Arg Val
20

<210> SEQ ID NO 40
<211> LENGTH: 17
<212> TYPE: PRT
<213> ORGANISM: Artificial Sequence
<220> FEATURE:
<223> OTHER INFORMATION: Synthetic Construct

<400> SEQUENCE: 40

Ala Arg Asp Ile His Ser Gly Ser Ser Gly Tyr Tyr Tyr Gly Phe Asp
1 5 10 15

Val

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Ala Arg Asp Gly Phe Gly Tyr Phe Asp Tyr
1 5 10

<210> SEQ ID NO 42
<211> LENGTH: 17
<212> TYPE: PRT
<213> ORGANISM: Artificial Sequence
<220> FEATURE:
<223> OTHER INFORMATION: Synthetic Construct

<400> SEQUENCE: 42

Ala Arg Asp Val Ala Pro Gly Ser Ser Gly Tyr Tyr Asp Gly Phe Asp
1 5 10 15

Phe

<210> SEQ ID NO 43
<211> LENGTH: 13
<212> TYPE: PRT
<213> ORGANISM: Artificial Sequence
<220> FEATURE:
<223> OTHER INFORMATION: Synthetic Construct

<400> SEQUENCE: 43

Ala Arg His Ser Tyr Tyr Gly Ser Gly Asn Phe Asp Tyr
1 5 10

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Ala Arg Gly Ala Tyr Glu Phe Asp Tyr
1 5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Ala Arg Ser Tyr Val Tyr Phe Asp Tyr
1 5

<210> SEQ ID NO 46
<211> LENGTH: 12
<212> TYPE: PRT
<213> ORGANISM: Artificial Sequence
<220> FEATURE:
<223> OTHER INFORMATION: Synthetic Construct

<400> SEQUENCE: 46

Ala Arg Arg Ile Ala Thr Ala Thr Tyr Phe Asp Tyr
1 5 10

<210> SEQ ID NO 47
<211> LENGTH: 12
<212> TYPE: PRT
<213> ORGANISM: Artificial Sequence
<220> FEATURE:
<223> OTHER INFORMATION: Synthetic Construct

<400> SEQUENCE: 47

Ala Arg Leu Pro Tyr Ser Ala Tyr Ala Phe Asp Tyr
1 5 10

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Ala Arg His Pro Phe Ala Tyr
1 5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Ala Arg Arg Ile Asp Ala Phe Asp Ile
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Ala Arg Leu Tyr Asp Val Ala Tyr
1               5

<210> SEQ ID NO 51
<211> LENGTH: 10
<212> TYPE: PRT
<213> ORGANISM: Artificial Sequence
<220> FEATURE:
<223> OTHER INFORMATION: Synthetic Construct

<400> SEQUENCE: 51

Ala Arg Leu Gly Tyr Gly Tyr Phe Asp Val
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct

<400> SEQUENCE: 52

Ala Arg Gly Ser Arg Thr Gly Tyr Phe Asp Tyr
1               5                   10

<210> SEQ ID NO 53
<211> LENGTH: 15
<212> TYPE: PRT
<213> ORGANISM: Artificial Sequence
<220> FEATURE:
<223> OTHER INFORMATION: Synthetic Construct

<400> SEQUENCE: 53

Arg Ala Ser Glu Ser Val Asp Phe Phe Gly Ile Ser Phe Leu Ala
1               5                   10                  15

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Ser Ala Ser Ser Ser Val Ser Tyr Val Tyr
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic Construct

<400> SEQUENCE: 55

-continued

```
Arg Ala Ser Gln Gly Ile Gly Ser Ser Leu Ala
1               5                   10


<210> SEQ ID NO 56
<211> LENGTH: 15
<212> TYPE: PRT
<213> ORGANISM: Artificial Sequence
<220> FEATURE:
<223> OTHER INFORMATION: Synthetic Construct

<400> SEQUENCE: 56

Arg Ala Ser Glu Ser Val Asp Phe Phe Gly Lys Ser Phe Leu His
1               5                   10                  15


<210> SEQ ID NO 57
<211> LENGTH: 12
<212> TYPE: PRT
<213> ORGANISM: Artificial Sequence
<220> FEATURE:
<223> OTHER INFORMATION: Synthetic Construct

<400> SEQUENCE: 57

Arg Ala Ser Gln Ser Val Ser Ser Arg Phe Leu Ala
1               5                   10


<210> SEQ ID NO 58
<211> LENGTH: 12
<212> TYPE: PRT
<213> ORGANISM: Artificial Sequence
<220> FEATURE:
<223> OTHER INFORMATION: Synthetic Construct

<400> SEQUENCE: 58

Arg Ala Ser Gln Ser Val Arg Gly Arg Phe Leu Ala
1               5                   10


<210> SEQ ID NO 59
<211> LENGTH: 12
<212> TYPE: PRT
<213> ORGANISM: Artificial Sequence
<220> FEATURE:
<223> OTHER INFORMATION: Synthetic Construct

<400> SEQUENCE: 59

Arg Ala Ser Gln Thr Val Phe Ser Arg Tyr Leu Ala
1               5                   10


<210> SEQ ID NO 60
<211> LENGTH: 11
<212> TYPE: PRT
<213> ORGANISM: Artificial Sequence
<220> FEATURE:
<223> OTHER INFORMATION: Synthetic Construct

<400> SEQUENCE: 60

Arg Ala Ser Gln Gly Val Ser Ser Tyr Leu Ala
1               5                   10


<210> SEQ ID NO 61
<211> LENGTH: 15
<212> TYPE: PRT
<213> ORGANISM: Artificial Sequence
<220> FEATURE:
<223> OTHER INFORMATION: Synthetic Construct

<400> SEQUENCE: 61

Arg Ala Ser Gln Ser Val Asp Phe Tyr Gly Ile Ser Phe Leu Asp
```

1 5 10 15

<210> SEQ ID NO 62
<211> LENGTH: 15
<212> TYPE: PRT
<213> ORGANISM: Artificial Sequence
<220> FEATURE:
<223> OTHER INFORMATION: Synthetic Construct

<400> SEQUENCE: 62

Arg Ala Ser Gln Ser Val Asp Phe Asp Gly Phe Ser Phe Leu His
1 5 10 15

<210> SEQ ID NO 63
<211> LENGTH: 15
<212> TYPE: PRT
<213> ORGANISM: Artificial Sequence
<220> FEATURE:
<223> OTHER INFORMATION: Synthetic Construct

<400> SEQUENCE: 63

Arg Ala Ser Gln Ser Val Asp Phe His Gly Lys Ser Phe Leu His
1 5 10 15

<210> SEQ ID NO 64
<211> LENGTH: 15
<212> TYPE: PRT
<213> ORGANISM: Artificial Sequence
<220> FEATURE:
<223> OTHER INFORMATION: Synthetic Construct

<400> SEQUENCE: 64

Arg Ala Ser Gln Ser Val Asp Phe Tyr Gly Ile Ser Phe Leu His
1 5 10 15

<210> SEQ ID NO 65
<211> LENGTH: 11
<212> TYPE: PRT
<213> ORGANISM: Artificial Sequence
<220> FEATURE:
<223> OTHER INFORMATION: Synthetic Construct

<400> SEQUENCE: 65

Arg Ala Ser Gln Ser Ile Ser Ser Tyr Leu Asn
1 5 10

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Asp Ala Ser Asn Arg Ala Thr Gly Ile
1 5

<210> SEQ ID NO 67
<211> LENGTH: 9
<212> TYPE: PRT
<213> ORGANISM: Artificial Sequence
<220> FEATURE:
<223> OTHER INFORMATION: Synthetic Construct

<400> SEQUENCE: 67

Asp Ala Ser Ser Leu Glu Ser Gly Val
1 5

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

Asp Ala Ser Asn Leu Glu Thr Gly Val
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic Construct

<400> SEQUENCE: 69

Ala Ala Ser Thr Leu Gln Ser Gly Val
1               5

<210> SEQ ID NO 70
<211> LENGTH: 13
<212> TYPE: PRT
<213> ORGANISM: Artificial Sequence
<220> FEATURE:
<223> OTHER INFORMATION: Synthetic Construct

<400> SEQUENCE: 70

Tyr Cys Gln His Tyr Thr Ser Ser Pro Pro Val Tyr Thr
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic Construct

<400> SEQUENCE: 71

Tyr Cys Val Gln Gly Leu Gln Thr Pro Trp Thr
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic Construct

<400> SEQUENCE: 72

Tyr Cys Gln Gln Tyr Asp Gln Trp Pro Pro Trp Thr
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic Construct

<400> SEQUENCE: 73

Tyr Cys Gln Gln Ser Tyr Ser Trp Pro Pro Thr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic Construct

<400> SEQUENCE: 74

Tyr Cys Gln Gln Ser Tyr Pro Thr Pro Leu Thr
1 5 10

<210> SEQ ID NO 75
<211> LENGTH: 11
<212> TYPE: PRT
<213> ORGANISM: Artificial Sequence
<220> FEATURE:
<223> OTHER INFORMATION: Synthetic Construct

<400> SEQUENCE: 75

Tyr Cys Gln Gln Ser Ser Ser Trp Pro Pro Thr
1 5 10

<210> SEQ ID NO 76
<211> LENGTH: 12
<212> TYPE: PRT
<213> ORGANISM: Artificial Sequence
<220> FEATURE:
<223> OTHER INFORMATION: Synthetic Construct

<400> SEQUENCE: 76

Tyr Cys Gln Gln Ser Tyr Tyr Trp Pro Pro Trp Thr
1 5 10

<210> SEQ ID NO 77
<211> LENGTH: 11
<212> TYPE: PRT
<213> ORGANISM: Artificial Sequence
<220> FEATURE:
<223> OTHER INFORMATION: Synthetic Construct

<400> SEQUENCE: 77

Tyr Cys Gln His His Tyr Gly Thr Pro Leu Thr
1 5 10

<210> SEQ ID NO 78
<211> LENGTH: 13
<212> TYPE: PRT
<213> ORGANISM: Artificial Sequence
<220> FEATURE:
<223> OTHER INFORMATION: Synthetic Construct

<400> SEQUENCE: 78

Tyr Cys Gln Gln Tyr Val Ser Ser Pro Pro Glu Tyr Thr
1 5 10

<210> SEQ ID NO 79
<211> LENGTH: 11
<212> TYPE: PRT
<213> ORGANISM: Artificial Sequence
<220> FEATURE:
<223> OTHER INFORMATION: Synthetic Construct

<400> SEQUENCE: 79

Tyr Cys Gln Gln Arg Asp Ser Trp Pro Tyr Thr
1 5 10

-continued

<210> SEQ ID NO 80
<211> LENGTH: 11
<212> TYPE: PRT
<213> ORGANISM: Artificial Sequence
<220> FEATURE:
<223> OTHER INFORMATION: Synthetic Construct

<400> SEQUENCE: 80

Tyr Cys Glu Gln Ser Leu Glu Val Pro Phe Thr
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic Construct

<400> SEQUENCE: 81

Tyr Cys Val Gln Ala Leu Gln Leu Pro Leu Thr
1               5                   10

<210> SEQ ID NO 82
<211> LENGTH: 124
<212> TYPE: PRT
<213> ORGANISM: Artificial Sequence
<220> FEATURE:
<223> OTHER INFORMATION: Synthetic Construct

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Ile His Trp Val Arg Gln Ala Pro Gly Lys Gly Leu Glu Trp Ile
        35                  40                  45

Gly Ile Ile Ser Pro Ser Ser Gly Ser Thr Asn Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Asp Ile His Ser Gly Ser Ser Gly Tyr Tyr Tyr Gly Phe Asp
            100                 105                 110

Val Trp Gly Gln Gly Thr Leu Val Thr Val Ser Ser
        115                 120

<210> SEQ ID NO 83
<211> LENGTH: 118
<212> TYPE: PRT
<213> ORGANISM: Artificial Sequence
<220> FEATURE:
<223> OTHER INFORMATION: Synthetic Construct

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

Tyr Tyr Trp Ala Trp Ile Arg Gln Ala Pro Gly Lys Gly Leu Glu Trp
        35                  40                  45

Val Ser Ser Ile Ser Gly Ser Gly Ser Thr Thr Tyr Tyr Ala Asp Ser

```
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Asp Gly Phe Gly Tyr Phe Asp Tyr Trp Gly Gln Gly Thr
            100                 105                 110

Leu Val Thr Val Ser Ser
        115


<210> SEQ ID NO 84
<211> LENGTH: 123
<212> TYPE: PRT
<213> ORGANISM: Artificial Sequence
<220> FEATURE:
<223> OTHER INFORMATION: Synthetic Construct

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Ile
        35                  40                  45

Gly Glu Ile Tyr His Ser Gly Ser Thr Tyr Tyr Ser Pro Ser Leu Lys
    50                  55                  60

Ser Arg Val Thr Ile Ser Arg Asp Asn Ser Lys Asn Thr Leu Tyr Leu
65                  70                  75                  80

Gln Leu Asn Ser Leu Arg Ala Glu Asp Thr Ala Val Tyr Tyr Cys Ala
                85                  90                  95

Arg Asp Val Ala Pro Gly Ser Ser Gly Tyr Tyr Asp Gly Phe Asp Phe
            100                 105                 110

Trp Gly Gln Gly Thr Leu Val Thr Val Ser Ser
        115                 120


<210> SEQ ID NO 85
<211> LENGTH: 121
<212> TYPE: PRT
<213> ORGANISM: Artificial Sequence
<220> FEATURE:
<223> OTHER INFORMATION: Synthetic Construct

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Asp Trp Ile Arg Gln Ala Pro Gly Lys Gly Leu Glu Trp
        35                  40                  45

Val Ser Gly Ile Ser Gly Tyr Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg His Ser Tyr Tyr Gly Ser Gly Asn Phe Asp Tyr Trp Gly
            100                 105                 110
```

```
Gln Gly Thr Leu Val Thr Val Ser Ser
        115                 120


<210> SEQ ID NO 86
<211> LENGTH: 116
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Ile His Trp Val Arg Gln Ala Pro Gly Lys Gly Leu Glu Trp Ile
        35                  40                  45

Gly Trp Ile Ser Pro Ser Gly Gly Gly Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Gly Ala Tyr Glu Phe Asp Tyr Trp Gly Gln Gly Thr Leu Val
            100                 105                 110

Thr Val Ser Ser
        115


<210> SEQ ID NO 87
<211> LENGTH: 116
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Ser Trp Ile Arg Gln Ala Pro Gly Lys Gly Leu Glu Trp
        35                  40                  45

Leu Ala Arg Ile Asp Trp Asp Asp Asp Lys Tyr Tyr Ser Thr Ser Leu
    50                  55                  60

Lys Ser Arg Leu Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Tyr Val Tyr Phe Asp Tyr Trp Gly Gln Gly Thr Leu Val
            100                 105                 110

Thr Val Ser Ser
        115


<210> SEQ ID NO 88
<211> LENGTH: 120
<212> TYPE: PRT
<213> ORGANISM: Artificial Sequence
<220> FEATURE:
<223> OTHER INFORMATION: Synthetic Construct
```

<400> SEQUENCE: 88

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Ala Val Ser Trp Ile Arg Gln Ala Pro Gly Lys Gly Leu Glu
        35                  40                  45

Trp Ile Gly Glu Ile Tyr His Ser Gly Ser Thr Tyr Tyr Ser Pro Ser
    50                  55                  60

Leu Lys Ser Arg Val Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Arg Ile Ala Thr Ala Thr Tyr Phe Asp Tyr Trp Gly Gln
            100                 105                 110

Gly Thr Leu Val Thr Val Ser Ser
        115                 120
```

<210> SEQ ID NO 89
<211> LENGTH: 121
<212> TYPE: PRT
<213> ORGANISM: Artificial Sequence
<220> FEATURE:
<223> OTHER INFORMATION: Synthetic Construct

<400> SEQUENCE: 89

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Ala Val Gly Trp Ile Arg Gln Ala Pro Gly Lys Gly Leu Glu
        35                  40                  45

Trp Val Ser Ala Ile Ser Gly Tyr Gly Ser Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Leu Pro Tyr Ser Ala Tyr Ala Phe Asp Tyr Trp Gly
            100                 105                 110

Gln Gly Thr Leu Val Thr Val Ser Ser
        115                 120
```

<210> SEQ ID NO 90
<211> LENGTH: 114
<212> TYPE: PRT
<213> ORGANISM: Artificial Sequence
<220> FEATURE:
<223> OTHER INFORMATION: Synthetic Construct

<400> SEQUENCE: 90

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Ile His Trp Val Arg Gln Ala Pro Gly Lys Gly Leu Glu Trp Ile
        35                  40                  45
```

-continued

Gly Ile Ile Ser Pro Ser Gly Gly Gly Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg His Pro Phe Ala Tyr Trp Gly Gln Gly Thr Leu Val Thr Val
            100                 105                 110

Ser Ser

<210> SEQ ID NO 91
<211> LENGTH: 115
<212> TYPE: PRT
<213> ORGANISM: Artificial Sequence
<220> FEATURE:
<223> OTHER INFORMATION: Synthetic Construct

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Gly Tyr
            20                  25                  30

Gly Ile His Trp Val Arg Gln Ala Pro Gly Lys Gly Leu Glu Trp Ile
        35                  40                  45

Gly Glu Ile Tyr His Ser Gly Ser Thr Tyr Tyr Ser Pro Ser Leu Lys
    50                  55                  60

Ser Arg Val Thr Ile Ser Arg Asp Asn Ser Lys Asn Thr Leu Tyr Leu
65                  70                  75                  80

Gln Leu Asn Ser Leu Arg Ala Glu Asp Thr Ala Val Tyr Tyr Cys Ala
                85                  90                  95

Arg Arg Ile Asp Ala Phe Asp Ile Trp Gly Gln Gly Thr Leu Val Thr
            100                 105                 110

Val Ser Ser
        115

<210> SEQ ID NO 92
<211> LENGTH: 115
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Gly Tyr
            20                  25                  30

Ala Ile His Trp Val Arg Gln Ala Pro Gly Lys Gly Leu Glu Trp Ile
        35                  40                  45

Gly Ile Ile Ser Pro Ser Gly Gly Gly Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Leu Tyr Asp Val Ala Tyr Trp Gly Gln Gly Thr Leu Val Thr
            100                 105                 110

Val Ser Ser
115

<210> SEQ ID NO 93
<211> LENGTH: 117
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Ala Ile His Trp Val Arg Gln Ala Pro Gly Lys Gly Leu Glu Trp Ile
35 40 45

Gly Ile Ile Ser Pro Ser Gly Gly Ser Thr Lys Tyr Ala Gln Lys Phe
50 55 60

Gln Gly Arg Val Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg Leu Gly Tyr Gly Tyr Phe Asp Val Trp Gly Gln Gly Thr Leu
100 105 110

Val Thr Val Ser Ser
115

<210> SEQ ID NO 94
<211> LENGTH: 118
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Ile Thr Ser Gly
20 25 30

His Tyr Trp Ser Trp Ile Arg Gln Ala Pro Gly Lys Gly Leu Glu Trp
35 40 45

Ile Gly Asp Ile Ser His Ser Gly Ser Thr Tyr Tyr Ser Gln Ser Leu
50 55 60

Lys Ser Arg Val Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg Gly Ser Arg Thr Gly Tyr Phe Asp Tyr Trp Gly Gln Gly Thr
100 105 110

Leu Val Thr Val Ser Ser
115

<210> SEQ ID NO 95
<211> LENGTH: 114
<212> TYPE: PRT
<213> ORGANISM: Artificial Sequence
<220> FEATURE:
<223> OTHER INFORMATION: Synthetic Construct

<400> SEQUENCE: 95

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Phe
            20                  25                  30

Gly Ile Ser Phe Leu Ala Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Tyr Thr
                85                  90                  95

Ser Ser Pro Pro Val Tyr Thr Phe Gly Gln Gly Thr Lys Val Glu Ile
            100                 105                 110

Lys Arg

<210> SEQ ID NO 96
<211> LENGTH: 107
<212> TYPE: PRT
<213> ORGANISM: Artificial Sequence
<220> FEATURE:
<223> OTHER INFORMATION: Synthetic Construct

<400> SEQUENCE: 96

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Val
            20                  25                  30

Tyr Trp Tyr Gln Gln Lys Pro Gly Lys Ala Pro Lys Leu Leu Ile Tyr
        35                  40                  45

Asp Ala Ser Ser Leu Glu Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Val Gln Gly Leu Gln Thr Pro Trp Thr
                85                  90                  95

Phe Gly Gln Gly Thr Lys Val Glu Ile Lys Arg
            100                 105

<210> SEQ ID NO 97
<211> LENGTH: 109
<212> TYPE: PRT
<213> ORGANISM: Artificial Sequence
<220> FEATURE:
<223> OTHER INFORMATION: Synthetic Construct

<400> SEQUENCE: 97

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ser
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro

-continued

```
65                  70                  75                  80

Glu Asp Phe Ala Thr Tyr Tyr Cys Gln Gln Tyr Asp Gln Trp Pro Pro
                85                  90                  95

Trp Thr Phe Gly Gln Gly Thr Lys Val Glu Ile Lys Arg
            100                 105


<210> SEQ ID NO 98
<211> LENGTH: 112
<212> TYPE: PRT
<213> ORGANISM: Artificial Sequence
<220> FEATURE:
<223> OTHER INFORMATION: Synthetic Construct

<400> SEQUENCE: 98

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Phe
            20                  25                  30

Gly Lys Ser Phe Leu His Trp Tyr Gln Gln Lys Pro Gly Lys Ala Pro
        35                  40                  45

Lys Leu Leu Ile Tyr Asp Ala Ser Asn Leu Glu Thr Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Tyr
                85                  90                  95

Ser Trp Pro Pro Thr Phe Gly Gln Gly Thr Lys Val Glu Ile Lys Arg
            100                 105                 110


<210> SEQ ID NO 99
<211> LENGTH: 109
<212> TYPE: PRT
<213> ORGANISM: Artificial Sequence
<220> FEATURE:
<223> OTHER INFORMATION: Synthetic Construct

<400> SEQUENCE: 99

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Arg
            20                  25                  30

Phe Leu Ala Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Pro Thr Pro
                85                  90                  95

Leu Thr Phe Gly Gln Gly Thr Lys Val Glu Ile Lys Arg
            100                 105


<210> SEQ ID NO 100
<211> LENGTH: 109
<212> TYPE: PRT
<213> ORGANISM: Artificial Sequence
<220> FEATURE:
<223> OTHER INFORMATION: Synthetic Construct

<400> SEQUENCE: 100
```

-continued

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Arg Gly Arg
            20                  25                  30

Phe Leu Ala Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Ser Ser Trp Pro
                85                  90                  95

Pro Thr Phe Gly Gln Gly Thr Lys Val Glu Ile Lys Arg
            100                 105
```

<210> SEQ ID NO 101
<211> LENGTH: 110
<212> TYPE: PRT
<213> ORGANISM: Artificial Sequence
<220> FEATURE:
<223> OTHER INFORMATION: Synthetic Construct

<400> SEQUENCE: 101

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Thr Val Phe Ser Arg
            20                  25                  30

Tyr Leu Ala Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Tyr Trp Pro
                85                  90                  95

Pro Trp Thr Phe Gly Gln Gly Thr Lys Val Glu Ile Lys Arg
            100                 105                 110
```

<210> SEQ ID NO 102
<211> LENGTH: 108
<212> TYPE: PRT
<213> ORGANISM: Artificial Sequence
<220> FEATURE:
<223> OTHER INFORMATION: Synthetic Construct

<400> SEQUENCE: 102

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
```

```
                85                  90                  95

Thr Phe Gly Gln Gly Thr Lys Val Glu Ile Lys Arg
            100                 105


<210> SEQ ID NO 103
<211> LENGTH: 114
<212> TYPE: PRT
<213> ORGANISM: Artificial Sequence
<220> FEATURE:
<223> OTHER INFORMATION: Synthetic Construct

<400> SEQUENCE: 103

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Ile Ser Phe Leu Asp Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Val
                85                  90                  95

Ser Ser Pro Pro Glu Tyr Thr Phe Gly Gln Gly Thr Lys Val Glu Ile
            100                 105                 110

Lys Arg


<210> SEQ ID NO 104
<211> LENGTH: 112
<212> TYPE: PRT
<213> ORGANISM: Artificial Sequence
<220> FEATURE:
<223> OTHER INFORMATION: Synthetic Construct

<400> SEQUENCE: 104

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Asp
            20                  25                  30

Gly Phe Ser Phe Leu His Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Arg Asp
                85                  90                  95

Ser Trp Pro Tyr Thr Phe Gly Gln Gly Thr Lys Val Glu Ile Lys Arg
            100                 105                 110


<210> SEQ ID NO 105
<211> LENGTH: 112
<212> TYPE: PRT
<213> ORGANISM: Artificial Sequence
<220> FEATURE:
<223> OTHER INFORMATION: Synthetic Construct

<400> SEQUENCE: 105
```

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Val Asp Phe His
20 25 30

Gly Lys Ser Phe Leu His Trp Tyr Gln Gln Lys Pro Gly Lys Ala Pro
35 40 45

Lys Leu Leu Ile Tyr Asp Ala Ser Ser Leu Glu Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Glu Gln Ser Leu
85 90 95

Glu Val Pro Phe Thr Phe Gly Gln Gly Thr Lys Val Glu Ile Lys Arg
100 105 110

<210> SEQ ID NO 106
<211> LENGTH: 112
<212> TYPE: PRT
<213> ORGANISM: Artificial Sequence
<220> FEATURE:
<223> OTHER INFORMATION: Synthetic Construct

<400> SEQUENCE: 106

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Val Asp Phe Tyr
20 25 30

Gly Ile Ser Phe Leu His Trp Tyr Gln Gln Lys Pro Gly Lys Ala Pro
35 40 45

Lys Leu Leu Ile Tyr Asp Ala Ser Ser Leu Glu Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Val Gln Ala Leu
85 90 95

Gln Leu Pro Leu Thr Phe Gly Gln Gly Thr Lys Val Glu Ile Lys Arg
100 105 110

<210> SEQ ID NO 107
<211> LENGTH: 108
<212> TYPE: PRT
<213> ORGANISM: Artificial Sequence
<220> FEATURE:
<223> OTHER INFORMATION: Synthetic Construct

<400> SEQUENCE: 107

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His His Tyr Gly Thr Pro Leu
85 90 95

Thr Phe Gly Gln Gly Thr Lys Val Glu Ile Lys Arg
100 105

<210> SEQ ID NO 108
<211> LENGTH: 372
<212> TYPE: DNA
<213> ORGANISM: Artificial Sequence
<220> FEATURE:
<223> OTHER INFORMATION: Synthetic Construct

<400> SEQUENCE: 108
gaggttcagc tggtggagtc tggcggtggc ctggtgcagc cagggggctc actccgtttg 60
tcctgtgcag cttccggatt caccttctcc gactacgcta ttcactgggt gcgtcaggcc 120
ccgggtaagg gactcgagtg gatcggtatc atctccccat ctagcggttc tactaactac 180
gcccagaagt tccagggtcg tgtgactata agtcgcgaca attcgaaaaa cacactgtac 240
ctacaactga acagcttaag agctgaggac actgccgtct attattgcgc cagagacatt 300
cactctggtt cttctggtta ctactacggt ttcgacgtct ggggtcaagg aacactagtc 360
accgtctcct cg 372

<210> SEQ ID NO 109
<211> LENGTH: 354
<212> TYPE: DNA
<213> ORGANISM: Artificial Sequence
<220> FEATURE:
<223> OTHER INFORMATION: Synthetic Construct

<400> SEQUENCE: 109
gaggttcagc tggtggagtc tggcggtggc ctggtgcagc cagggggctc actccgtttg 60
tcctgtgcag cttccggata ctctatcacc tctggttact actgggcctg gattcgtcag 120
gccccgggta agggcctcga gtgggtgtct tccatctctg gttccggttc tactacctac 180
tacgccgact ctgtcaaggg ccgtttcact ataagtcgcg acaattcgaa aaacacactg 240
tacctacaac tgaacagctt aagagctgag gacactgccg tctattattg cgccagagat 300
ggtttcggct acttcgacta ctggggtcaa ggaacactag tcaccgtctc ctcg 354

<210> SEQ ID NO 110
<211> LENGTH: 369
<212> TYPE: DNA
<213> ORGANISM: Artificial Sequence
<220> FEATURE:
<223> OTHER INFORMATION: Synthetic Construct

<400> SEQUENCE: 110
gaggttcagc tggtggagtc tggcggtggc ctggtgcagc cagggggctc actccgtttg 60
tcctgtgcag cttccggatt caccttctcc gactacggta ttcactgggt gcgtcaggcc 120
ccgggtaagg gcctcgagtg gatcggtgaa atctaccact ctggttctac ctactactct 180
ccatctctga agtctcgtgt gactataagt cgcgacaatt cgaaaaacac actgtaccta 240
caactgaaca gcttaagagc tgaggacact gccgtctatt attgcgccag agacgttgcc 300
cctggttctt ctggttacta cgacggtttc gacttctggg gtcaaggaac actagtcacc 360
gtctcctcg 369

<210> SEQ ID NO 111
<211> LENGTH: 363
<212> TYPE: DNA
<213> ORGANISM: Artificial Sequence
<220> FEATURE:
<223> OTHER INFORMATION: Synthetic Construct

<400> SEQUENCE: 111
gaggttcagc tggtggagtc tggcggtggc ctggtgcagc caggggggctc actccgtttg 60 tcctgtgcag cttccggata ctctatctcc tctggttacc actgggactg gattcgtcag 120
gccccgggta agggcctcga gtgggtgtct ggtatctctg gttacggtgg ttctacctac 180
tacgccgact ctgtcaaggg ccgtttcact ataagtcgcg acaattcgaa aaacacactg 240
tacctacaac tgaacagctt aagagctgag gacactgccg tctattattg cgccagacac 300
agttattacg gttccggtaa tttcgactac tggggtcaag gaacactagt caccgtctcc 360
tcg 363

<210> SEQ ID NO 112
<211> LENGTH: 348
<212> TYPE: DNA
<213> ORGANISM: Artificial Sequence
<220> FEATURE:
<223> OTHER INFORMATION: Synthetic Construct

<400> SEQUENCE: 112
gaggttcagc tggtggagtc tggcggtggc ctggtgcagc caggggggctc actccgtttg 60 tcctgtgcag cttccggatt caccttctcc gactactgga ttcactgggt gcgtcaggcc 120
ccgggtaagg gcctcgagtg gatcggttgg atctccccat ctggcggtgg tactaagtac 180
gcccagaagt tccagggtcg tgtgactata agtcgcgaca attcgaaaaa cacactgtac 240
ctacaactga acagcttaag agctgaggac actgccgtct attattgcgc cagaggggct 300
tacgaatttg actactgggg tcaaggaaca ctagtcaccg tctcctcg 348

<210> SEQ ID NO 113
<211> LENGTH: 348
<212> TYPE: DNA
<213> ORGANISM: Artificial Sequence
<220> FEATURE:
<223> OTHER INFORMATION: Synthetic Construct

<400> SEQUENCE: 113
gaggttcagc tggtggagtc tggcggtggc ctggtgcagc caggggggctc actccgtttg 60 tcctgtgcag cttccggata ctctatctcc tctggttacc actggagctg gattcgtcag 120
gccccgggta agggcctcga gtggctggcc cggatcgact gggacgatga caagtactac 180
tctacctctc tgaagtctcg tctgactata agtcgcgaca attcgaaaaa cacactgtac 240
ctacaactga acagcttaag agctgaggac actgccgtct attattgcgc cagatcgtac 300
gtgtacttcg actactgggg tcaaggaaca ctagtcaccg tctcctcg 348

<210> SEQ ID NO 114
<211> LENGTH: 360
<212> TYPE: DNA
<213> ORGANISM: Artificial Sequence
<220> FEATURE:
<223> OTHER INFORMATION: Synthetic Construct

<400> SEQUENCE: 114
gaggttcagc tggtggagtc tggcggtggc ctggtgcagc caggggggctc actccgtttg 60 tcctgtgcag cttccggatt ctctctgtct accggcggtg tggctgtgag ctggattcgt 120
caggccccgg gtaagggcct cgagtggatc ggtgaaatct accactctgg ttctacctac 180
tactctccat ctctgaagtc tcgtgtgact ataagtcgcg acaattcgaa aaacacactg 240
tacctacaac tgaacagctt aagagctgag gacactgccg tctattattg cgcccgtcgt 300
atcgccaccg ctacttactt cgactactgg ggtcaaggaa cactagtcac cgtctcctcg 360

<210> SEQ ID NO 115
<211> LENGTH: 363
<212> TYPE: DNA
<213> ORGANISM: Artificial Sequence
<220> FEATURE:
<223> OTHER INFORMATION: Synthetic Construct

<400> SEQUENCE: 115
gaggttcagc tggtggagtc tggcggtggc ctggtgcagc caggggggctc actccgtttg 60 tcctgtgcag cttccggatt ctctctgtct accggcggtg tggctgtggg ctggattcgt 120
caggccccgg gtaagggcct cgagtgggtg tctgctatct ctggttacgg ttctactacc 180
tactacgccg actctgtcaa gggccgtttc actataagtc gcgacaattc gaaaaacaca 240
ctgtacctac aactgaacag cttaagagct gaggacactg ccgtctatta ttgcgccaga 300
ttgccatact ccgcctacgc tttcgactac tggggtcaag gaacactagt caccgtctcc 360
tcg 363

<210> SEQ ID NO 116
<211> LENGTH: 342
<212> TYPE: DNA
<213> ORGANISM: Artificial Sequence
<220> FEATURE:
<223> OTHER INFORMATION: Synthetic Construct

<400> SEQUENCE: 116
gaggttcagc tggtggagtc tggcggtggc ctggtgcagc caggggggctc actccgtttg 60 tcctgtgcag cttccggatt caccttctcc ggctacgcta ttcactgggt gcgtcaggcc 120
ccgggtaagg gcctcgagtg gatcggtatc atctccccat ctggcggtgg tactaagtac 180
gcccagaagt tccagggtcg tgtgactata agtcgcgaca attcgaaaaa cacactgtac 240
ctacaactga acagcttaag agctgaggac actgccgtct attattgcgc cagacaccca 300
ttcgcctact ggggtcaagg aacactagtc accgtctcct cg 342

<210> SEQ ID NO 117
<211> LENGTH: 345
<212> TYPE: DNA
<213> ORGANISM: Artificial Sequence
<220> FEATURE:
<223> OTHER INFORMATION: Synthetic Construct

<400> SEQUENCE: 117
gaggttcagc tggtggagtc tggcggtggc ctggtgcagc caggggggctc actccgtttg 60 tcctgtgcag cttccggata caccttctcc ggctacggta ttcactgggt gcgtcaggcc 120
ccgggtaagg gcctcgagtg gatcggtgaa atctaccact ctggttctac ctactactct 180
ccatctctga agtctcgtgt gactataagt cgcgacaatt cgaaaaacac actgtaccta 240
caactgaaca gcttaagagc tgaggacact gccgtctatt attgcgccag aagaattgac 300
gccttcgaca tctggggtca aggaacacta gtcaccgtct cctcg 345

<210> SEQ ID NO 118
<211> LENGTH: 345
<212> TYPE: DNA
<213> ORGANISM: Artificial Sequence
<220> FEATURE:
<223> OTHER INFORMATION: Synthetic Construct

<400> SEQUENCE: 118
gaggttcagc tggtggagtc tggcggtggc ctggtgcagc caggggggctc actccgtttg 60 tcctgtgcag cttccggata caccttctcc ggctacgcta ttcactgggt gcgtcaggcc 120
ccgggtaagg gcctcgagtg gatcggtatc atctccccat ctggcggtgg tactaagtac 180
gcccagaagt tccagggtcg tgtgactata agtcgcgaca attcgaaaaa cacactgtac 240
ctacaactga acagcttaag agctgaggac actgccgtct attattgcgc cagactctat 300
gacgttgcct actggggtca aggaacacta gtcaccgtct cctcg 345

<210> SEQ ID NO 119
<211> LENGTH: 351
<212> TYPE: DNA
<213> ORGANISM: Artificial Sequence
<220> FEATURE:
<223> OTHER INFORMATION: Synthetic Construct

<400> SEQUENCE: 119
gaggttcagc tggtggagtc tggcggtggc ctggtgcagc caggggggctc actccgtttg 60 tcctgtgcag cttccggatt caccttctcc gactacgcta ttcactgggt gcgtcaggcc 120
ccgggtaagg gcctcgagtg gatcggtatc atctccccat ctggcggttc tactaagtac 180
gcccagaagt tccagggtcg tgtgactata agtcgcgaca attcgaaaaa cacactgtac 240
ctacaactga acagcttaag agctgaggac actgccgtct attattgcgc cagactcggt 300
tacgggtact tcgacgtctg ggtcaagga acactagtca ccgtctcctc g 351

<210> SEQ ID NO 120
<211> LENGTH: 354
<212> TYPE: DNA
<213> ORGANISM: Artificial Sequence
<220> FEATURE:
<223> OTHER INFORMATION: Synthetic Construct

<400> SEQUENCE: 120
gaggttcagc tggtggagtc tggcggtggc ctggtgcagc caggggggctc actccgtttg 60 tcctgtgcag cttccggata ctctatcacc tctggtcact actggagctg gattcgtcag 120
gccccgggta agggcctcga gtggatcggt gacatctccc actctggttc tacctactac 180
tctcaatctc tgaagtctcg tgtgactata agtcgcgaca attcgaaaaa cacactgtac 240
ctacaactga acagcttaag agctgaggac actgccgtct attattgcgc gcgtggtagt 300
aggaccggct acttcgacta ttggggtcaa ggaacactag tcaccgtctc ctcg 354

<210> SEQ ID NO 121
<211> LENGTH: 342
<212> TYPE: DNA
<213> ORGANISM: Artificial Sequence
<220> FEATURE:
<223> OTHER INFORMATION: Synthetic Construct

<400> SEQUENCE: 121
gatatccagt tgacccagtc cccgagttcc ctgtccgcct ctgtgggcga tcgggtcacc 60
atcacctgcc gtgcctctga gtctgtggac ttcttcggta tctctttcct ggcctggtat 120
caacagaaac caggaaaagc tccgaagctt ctgatctacg acgcctctaa ccgtgccacc 180
ggtatcccat ctcgcttctc tggatccggt tccgggacgg atttcactct gaccatcagc 240
agtctgcagc cggaagactt cgcaacttat tactgccagc actacacctc ttcgccacca 300
gtgtacacct tcggacaggg taccaaggtg gagatcaaac ga 342

<210> SEQ ID NO 122
<211> LENGTH: 321
<212> TYPE: DNA
<213> ORGANISM: Artificial Sequence
<220> FEATURE:
<223> OTHER INFORMATION: Synthetic Construct

<400> SEQUENCE: 122
gatatccagt tgacccagtc cccgagttcc ctgtccgcct ctgtgggcga tcgggtcacc 60
atcacctgct ctgcctcttc tagcgtgagc tacgtgtact ggtatcaaca gaaaccagga 120
aaagctccga agcttctgat ctacgacgcc tcttctctgg aatctggtgt gccatctcgc 180
ttctctggat ccggttccgg gacggatttc actctgacca tcagcagtct gcagccggaa 240
gacttcgcaa cttattactg cgtgcagggt cttcagaccc cttggacctt cggacagggt 300
accaaggtgg agatcaaacg a 321

<210> SEQ ID NO 123
<211> LENGTH: 327
<212> TYPE: DNA
<213> ORGANISM: Artificial Sequence
<220> FEATURE:
<223> OTHER INFORMATION: Synthetic Construct

<400> SEQUENCE: 123
gatatccagt tgacccagtc cccgagttcc ctgtccgcct ctgtgggcga tcgggtcacc 60
atcacctgcc gtgcctctca gggtattggc tcttccctgg cttggtatca acagaaacca 120
ggaaaagctc cgaagcttct gatctacgac gcctctaacc gtgccaccgg tatcccatct 180
cgcttctctg gatccggttc cgggacggat ttcactctga ccatcagcag tctgcagccg 240
gaagacttcg caacttatta ctgccagcag tacgaccaat ggccaccttg gaccttcgga 300
cagggtacca aggtggagat caaacga 327

<210> SEQ ID NO 124
<211> LENGTH: 336
<212> TYPE: DNA
<213> ORGANISM: Artificial Sequence
<220> FEATURE:
<223> OTHER INFORMATION: Synthetic Construct

<400> SEQUENCE: 124
gatatccagt tgacccagtc cccgagttcc ctgtccgcct ctgtgggcga tcgggtcacc 60
atcacctgcc gtgcctctga gtctgtggac ttcttcggta agtctttcct gcactggtat 120
caacagaaac caggaaaagc tccgaagctt ctgatctacg acgcctctaa cctggaaacc 180
ggtgtgccat ctcgcttctc tggatccggt tccgggacgg atttcactct gaccatcagc 240
agtctgcagc cggaagactt cgcaacttat tactgccagc agtcctactc ctggcctccg 300
accttcggac agggtaccaa ggtggagatc aaacga 336

<210> SEQ ID NO 125
<211> LENGTH: 327
<212> TYPE: DNA
<213> ORGANISM: Artificial Sequence
<220> FEATURE:
<223> OTHER INFORMATION: Synthetic Construct

<400> SEQUENCE: 125

-continued

```
gatatccagt tgacccagtc cccgagttcc ctgtccgcct ctgtgggcga tcgggtcacc      60

atcacctgcc gtgcctctca gtctgtgagc agccgtttcc tggcctggta tcaacagaaa     120

ccaggaaaag ctccgaagct tctgatctac gacgcctcta accgtgccac cggtatccca     180

tctcgcttct ctggatccgg ttccgggacg gatttcactc tgaccatcag cagtctgcag     240

ccggaagact tcgcaactta ttactgccag cagtcctacc ccacccctct taccttcgga     300

cagggtacca aggtggagat caaacga                                         327
```

<210> SEQ ID NO 126
<211> LENGTH: 327
<212> TYPE: DNA
<213> ORGANISM: Artificial Sequence
<220> FEATURE:
<223> OTHER INFORMATION: Synthetic Construct

<400> SEQUENCE: 126

```
gatatccagt tgacccagtc cccgagttcc ctgtccgcct ctgtgggcga tcgggtcacc      60

atcacctgcc gtgcctctca gtctgtgcgc ggccgtttcc tggcctggta tcaacagaaa     120

ccaggaaaag ctccgaagct tctgatctac gacgcctcta accgtgccac cggtatccca     180

tctcgcttct ctggatccgg ttccgggacg gatttcactc tgaccatcag cagtctgcag     240

ccggaagact tcgcaactta ttactgccag cagtcctcct cctggcctcc gaccttcgga     300

cagggtacca aggtggagat caaacga                                         327
```

<210> SEQ ID NO 127
<211> LENGTH: 330
<212> TYPE: DNA
<213> ORGANISM: Artificial Sequence
<220> FEATURE:
<223> OTHER INFORMATION: Synthetic Construct

<400> SEQUENCE: 127

```
gatatccagt tgacccagtc cccgagttcc ctgtccgcct ctgtgggcga tcgggtcacc      60

atcacctgcc gtgcctctca gaccgtgttc tctcgttacc tggcttggta tcaacagaaa     120

ccaggaaaag ctccgaagct tctgatctac gacgcctcta accgtgccac cggtatccca     180

tctcgcttct ctggatccgg ttccgggacg gatttcactc tgaccatcag cagtctgcag     240

ccggaagact tcgcaactta ttactgccag cagtcctact actggccacc ttggaccttc     300

ggacagggta ccaaggtgga gatcaaacga                                      330
```

<210> SEQ ID NO 128
<211> LENGTH: 324
<212> TYPE: DNA
<213> ORGANISM: Artificial Sequence
<220> FEATURE:
<223> OTHER INFORMATION: Synthetic Construct

<400> SEQUENCE: 128

```
gatatccagt tgacccagtc cccgagttcc ctgtccgcct ctgtgggcga tcgggtcacc      60

atcacctgcc gtgcctctca gggtgtgtct tcttacctgg cctggtatca acagaaacca     120

ggaaaagctc cgaagcttct gatctacgcc gcctctacct tgcagtctgg tgtgccatct     180

cgcttctctg gatccggttc cgggacggat ttcactctga ccatcagcag tctgcagccg     240

gaagacttcg caacttacta ctgccagcac cactacggca ccccactgac cttcggtcag     300

ggtaccaagg tggagatcaa acga                                            324
```

<210> SEQ ID NO 129
<211> LENGTH: 342
<212> TYPE: DNA
<213> ORGANISM: Artificial Sequence
<220> FEATURE:
<223> OTHER INFORMATION: Synthetic Construct

<400> SEQUENCE: 129
gatatccagt tgacccagtc cccgagttcc ctgtccgcct ctgtgggcga tcgggtcacc 60
atcacctgcc gtgcctctca gtctgtggac ttctacggta tctctttcct ggactggtat 120
caacagaaac caggaaaagc tccgaagctt ctgatctacg acgcctctaa ccgtgccacc 180
ggtatcccat ctcgcttctc tggatccggt tccgggacgg atttcactct gaccatcagc 240
agtctgcagc cggaagactt cgcaacttat tactgccagc agtacgtctc ttcgccacca 300
gagtacacct tcggacaggg taccaaggtg gagatcaaac ga 342

<210> SEQ ID NO 130
<211> LENGTH: 336
<212> TYPE: DNA
<213> ORGANISM: Artificial Sequence
<220> FEATURE:
<223> OTHER INFORMATION: Synthetic Construct

<400> SEQUENCE: 130
gatatccagt tgacccagtc cccgagttcc ctgtccgcct ctgtgggcga tcgggtcacc 60
atcacctgcc gtgcctctca gtctgtggac ttcgacggtt tctctttcct gcactggtat 120
caacagaaac caggaaaagc tccgaagctt ctgatctacg acgcctcttc tctggaatct 180
ggtgtgccat ctcgcttctc tggatccggt tccgggacgg atttcactct gaccatcagc 240
agtctgcagc cggaagactt cgcaacttat tactgccagc agcgtgactc ctggccttac 300
accttcggac agggtaccaa ggtggagatc aaacga 336

<210> SEQ ID NO 131
<211> LENGTH: 336
<212> TYPE: DNA
<213> ORGANISM: Artificial Sequence
<220> FEATURE:
<223> OTHER INFORMATION: Synthetic Construct

<400> SEQUENCE: 131
gatatccagt tgacccagtc cccgagttcc ctgtccgcct ctgtgggcga tcgggtcacc 60
atcacctgcc gtgcctctca gtctgtggac ttccacggta agtctttcct gcactggtat 120
caacagaaac caggaaaagc tccgaagctt ctgatctacg acgcctcttc tctggaatct 180
ggtgtgccat ctcgcttctc tggatccggt tccgggacgg atttcactct gaccatcagc 240
agtctgcagc cggaagactt cgcaacttat tactgcgagc aatccctgga agtcccattc 300
accttcggac agggtaccaa ggtggagatc aaacga 336

<210> SEQ ID NO 132
<211> LENGTH: 336
<212> TYPE: DNA
<213> ORGANISM: Artificial Sequence
<220> FEATURE:
<223> OTHER INFORMATION: Synthetic Construct

<400> SEQUENCE: 132
gatatccagt tgacccagtc cccgagttcc ctgtccgcct ctgtgggcga tcgggtcacc 60
atcacctgcc gtgcctctca gtctgtggac ttctacggta tctctttcct gcactggtat 120
caacagaaac caggaaaagc tccgaagctt ctgatctacg acgcctcttc tctggaatct 180
ggtgtgccat ctcgcttctc tggatccggt tccgggacgg atttcactct gaccatcagc 240
agtctgcagc cggaagactt cgcaacttat tactgcgtgc aggctcttca gttgcctctt 300
accttcggac agggtaccaa ggtggagatc aaacga 336

<210> SEQ ID NO 133
<211> LENGTH: 324
<212> TYPE: DNA
<213> ORGANISM: Artificial Sequence
<220> FEATURE:
<223> OTHER INFORMATION: Synthetic Construct

<400> SEQUENCE: 133
gatatccagt tgacccagtc cccgagttcc ctgtccgcct ctgtgggcga tcgggtcacc 60
atcacctgcc gtgcctctca gtctatctct tcttacctga actggtatca acagaaacca 120
ggaaaagctc cgaagcttct gatctacgac gcctctaacc tggaaaccgg tgtgccatct 180
cgcttctctg gatccggttc cgggacggat ttcactctga ccatcagcag tctgcagccg 240
gaagacttcg caacttacta ctgccagcac cactacggca ccccactgac cttcggtcag 300
ggtaccaagg tggagatcaa acga 324

<210> SEQ ID NO 134
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Present in repeats of at least two and up to ten
<220> FEATURE:
<221> NAME/KEY: VARIANT
<222> LOCATION: 3
<223> OTHER INFORMATION: Present in repeats of at least three and up to ten
<220> FEATURE:
<221> NAME/KEY: VARIANT
<222> LOCATION: 1, 3
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr
<220> FEATURE:
<221> NAME/KEY: VARIANT
<222> LOCATION: 5
<223> OTHER INFORMATION: Present in repeats of at least one and up to ten
<220> FEATURE:
<221> NAME/KEY: VARIANT
<222> LOCATION: 5
<223> OTHER INFORMATION: Xaa = Asp, Ala, Tyr, Ser, Thr, Asn, Ile, Leu, Phe, Val, His, or Pro

<400> SEQUENCE: 134

Xaa Cys Xaa Cys Xaa
1               5

<210> SEQ ID NO 135
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1

<223> OTHER INFORMATION: Present in repeats of at least two and up to
      ten
<220> FEATURE:
<221> NAME/KEY: VARIANT
<222> LOCATION: 3
<223> OTHER INFORMATION: Present in repeats of at least three and up to
      ten
<220> FEATURE:
<221> NAME/KEY: VARIANT
<222> LOCATION: 5
<223> OTHER INFORMATION: Present in repeats of at least one and up to
      ten
<220> FEATURE:
<221> NAME/KEY: VARIANT
<222> LOCATION: 1, 3, 5
<223> OTHER INFORMATION: Xaa = Asp, Ala, Tyr, Ser, Thr, Asn, Ile, Leu,
      Phe, Val, His, or Pro

<400> SEQUENCE: 135

Xaa Cys Xaa Cys Xaa
1               5

<210> SEQ ID NO 136
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3
<223> OTHER INFORMATION: Present in repeats of at least two and up to
      ten
<220> FEATURE:
<221> NAME/KEY: misc_feature
<222> LOCATION: 7, 8, 9
<223> OTHER INFORMATION: Present in repeats of at least three and up to
      ten
<220> FEATURE:
<221> NAME/KEY: misc_feature
<222> LOCATION: 13, 14, 15
<223> OTHER INFORMATION: Present in repeats of at least one and up to
      ten
<220> FEATURE:
<221> NAME/KEY: misc_feature
<222> LOCATION: 1, 2, 7, 8, 13
<223> OTHER INFORMATION: n = A,T,C or G
<220> FEATURE:
<221> NAME/KEY: misc_feature
<222> LOCATION: 3, 9
<223> OTHER INFORMATION: n = T or G
<220> FEATURE:
<221> NAME/KEY: misc_feature
<222> LOCATION: 6, 12
<223> OTHER INFORMATION: n = T or C
<220> FEATURE:
<221> NAME/KEY: misc_feature
<222> LOCATION: 14
<223> OTHER INFORMATION: n = A,T, or C

<400> SEQUENCE: 136
nnntgnnnnt gnnnc                                                        15

<210> SEQ ID NO 137
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 15, 16
<223> OTHER INFORMATION: Xaa = Asp, Ala, Tyr, Ser, Thr, Asn, Ile, Leu,
      Phe, Val, His, or Pro
<220> FEATURE:

-continued

```
<221> NAME/KEY: VARIANT
<222> LOCATION: 8, 9, 10, 11, 12, 13
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 137

Xaa Xaa Xaa Xaa Xaa Xaa Cys Xaa Xaa Xaa Xaa Xaa Xaa Cys Xaa Xaa
1               5                   10                  15


<210> SEQ ID NO 138
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 17, 18
<223> OTHER INFORMATION: Xaa = Asp, Ala, Tyr, Ser, Thr, Asn, Ile, Leu,
      Phe, Val, His, or Pro
<220> FEATURE:
<221> NAME/KEY: VARIANT
<222> LOCATION: 8, 9, 10, 11, 12, 13, 14, 15
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 138

Xaa Xaa Xaa Xaa Xaa Xaa Cys Xaa Xaa Xaa Xaa Xaa Xaa Xaa Xaa Cys
1               5                   10                  15

Xaa Xaa


<210> SEQ ID NO 139
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 8, 9, 10, 11, 12, 13, 15, 16
<223> OTHER INFORMATION: Xaa = Asp, Ala, Tyr, Ser, Thr, Asn, Ile, Leu,
      Phe, Val, His, or Pro

<400> SEQUENCE: 139

Xaa Xaa Xaa Xaa Xaa Xaa Cys Xaa Xaa Xaa Xaa Xaa Xaa Cys Xaa Xaa
1               5                   10                  15


<210> SEQ ID NO 140
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 8, 9, 10, 11, 12, 13, 14, 15, 17, 18
<223> OTHER INFORMATION: Xaa = Asp, Ala, Tyr, Ser, Thr, Asn, Ile, Leu,
      Phe, Val, His, or Pro

<400> SEQUENCE: 140

Xaa Xaa Xaa Xaa Xaa Xaa Cys Xaa Xaa Xaa Xaa Xaa Xaa Xaa Xaa Cys
1               5                   10                  15

Xaa Xaa


<210> SEQ ID NO 141
<211> LENGTH: 16
<212> TYPE: PRT
<213> ORGANISM: Artificial Sequence
<220> FEATURE:
```

<223> OTHER INFORMATION: Synthetic Construct

<400> SEQUENCE: 141

Asn Phe Val Ala Asp Ser Cys Pro Asp His Pro Tyr Pro Cys Ser Ala
1 5 10 15

<210> SEQ ID NO 142
<211> LENGTH: 16
<212> TYPE: PRT
<213> ORGANISM: Artificial Sequence
<220> FEATURE:
<223> OTHER INFORMATION: Synthetic Construct

<400> SEQUENCE: 142

Ile Val His His Ser Asp Cys Asp Ala Phe Tyr Pro Tyr Cys Asp Ser
1 5 10 15

<210> SEQ ID NO 143
<211> LENGTH: 16
<212> TYPE: PRT
<213> ORGANISM: Artificial Sequence
<220> FEATURE:
<223> OTHER INFORMATION: Synthetic Construct

<400> SEQUENCE: 143

Tyr Ser Ala Tyr Pro Ala Cys Asp Ser His Tyr Pro Tyr Cys Asn Ser
1 5 10 15

<210> SEQ ID NO 144
<211> LENGTH: 16
<212> TYPE: PRT
<213> ORGANISM: Artificial Sequence
<220> FEATURE:
<223> OTHER INFORMATION: Synthetic Construct

<400> SEQUENCE: 144

Pro Asn Pro Ser Ser Asp Cys Val Pro Tyr Tyr Tyr Ala Cys Ala Tyr
1 5 10 15

<210> SEQ ID NO 145
<211> LENGTH: 16
<212> TYPE: PRT
<213> ORGANISM: Artificial Sequence
<220> FEATURE:
<223> OTHER INFORMATION: Synthetic Construct

<400> SEQUENCE: 145

Tyr Ser Ala Tyr Pro Ala Cys Asp Ser His Tyr Pro Tyr Cys Gln Ser
1 5 10 15

<210> SEQ ID NO 146
<211> LENGTH: 16
<212> TYPE: PRT
<213> ORGANISM: Artificial Sequence
<220> FEATURE:
<223> OTHER INFORMATION: Synthetic Construct

<400> SEQUENCE: 146

Pro Gln Pro Ser Ser Asp Cys Val Pro Tyr Tyr Tyr Ala Cys Ala Tyr
1 5 10 15

<210> SEQ ID NO 147
<211> LENGTH: 16
<212> TYPE: PRT
<213> ORGANISM: Artificial Sequence
<220> FEATURE:
<223> OTHER INFORMATION: Synthetic Construct

<400> SEQUENCE: 147

Pro Asn Pro Ala Ser Asp Cys Val Pro Tyr Tyr Tyr Ala Cys Ala Tyr
1               5                   10                  15

<210> SEQ ID NO 148
<211> LENGTH: 5
<212> TYPE: PRT
<213> ORGANISM: Artificial Sequence
<220> FEATURE:
<223> OTHER INFORMATION: Synthetic Construct

<400> SEQUENCE: 148

Glu Val Gly Ser Tyr
1               5

<210> SEQ ID NO 149
<211> LENGTH: 5
<212> TYPE: PRT
<213> ORGANISM: Artificial Sequence
<220> FEATURE:
<223> OTHER INFORMATION: Synthetic Construct

<400> SEQUENCE: 149

Ser Gly Arg Ser Ala
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic Construct

<400> SEQUENCE: 150

Pro Leu Gly Leu Ala Gly
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic Construct

<400> SEQUENCE: 151

Glu Asn Leu Tyr Phe Gln Gly
1               5

<210> SEQ ID NO 152
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 13, 14, 15, 16, 17, 18, 20, 21
<223> OTHER INFORMATION: Xaa = Asp, Ala, Tyr, Ser, Thr, Asn, Ile, Leu,
      Phe, Val, His, or Pro

<400> SEQUENCE: 152

Glu Val Gly Ser Tyr Xaa Xaa Xaa Xaa Xaa Xaa Cys Xaa Xaa Xaa Xaa
1               5                   10                  15

Xaa Xaa Cys Xaa Xaa Ser Gly Arg Ser Ala
            20                  25

```
<210> SEQ ID NO 153
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 20, 21
<223> OTHER INFORMATION: Xaa = Asp, Ala, Tyr, Ser, Thr, Asn, Ile, Leu,
      Phe, Val, His, or Pro
<220> FEATURE:
<221> NAME/KEY: VARIANT
<222> LOCATION: 13, 14, 15, 16, 17, 18
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 153

Glu Val Gly Ser Tyr Xaa Xaa Xaa Xaa Xaa Xaa Cys Xaa Xaa Xaa Xaa
1               5                   10                  15

Xaa Xaa Cys Xaa Xaa Ser Gly Arg Ser Ala
            20                  25


<210> SEQ ID NO 154
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 13, 14, 15, 16, 17, 18, 19, 20, 22,
      23
<223> OTHER INFORMATION: Xaa = Asp, Ala, Tyr, Ser, Thr, Asn, Ile, Leu,
      Phe, Val, His, or Pro

<400> SEQUENCE: 154

Glu Val Gly Ser Tyr Xaa Xaa Xaa Xaa Xaa Xaa Cys Xaa Xaa Xaa Xaa
1               5                   10                  15

Xaa Xaa Xaa Xaa Cys Xaa Xaa Ser Gly Arg Ser Ala
            20                  25


<210> SEQ ID NO 155
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 22, 23
<223> OTHER INFORMATION: Xaa = Asp, Ala, Tyr, Ser, Thr, Asn, Ile, Leu,
      Phe, Val, His, or Pro
<220> FEATURE:
<221> NAME/KEY: VARIANT
<222> LOCATION: 13, 14, 15, 16, 17, 18, 19, 20
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 155

Glu Val Gly Ser Tyr Xaa Xaa Xaa Xaa Xaa Xaa Cys Xaa Xaa Xaa Xaa
1               5                   10                  15

Xaa Xaa Xaa Xaa Cys Xaa Xaa Ser Gly Arg Ser Ala
            20                  25


<210> SEQ ID NO 156
<211> LENGTH: 5
<212> TYPE: PRT
<213> ORGANISM: Artificial Sequence
```

-continued

<220> FEATURE:
<223> OTHER INFORMATION: Synthetic Construct

<400> SEQUENCE: 156

Gly Gly Gly Gly Ser
1               5

<210> SEQ ID NO 157
<211> LENGTH: 4
<212> TYPE: PRT
<213> ORGANISM: Artificial Sequence
<220> FEATURE:
<223> OTHER INFORMATION: Synthetic Construct

<400> SEQUENCE: 157

Ser Gly Gly Ser
1

<210> SEQ ID NO 158
<211> LENGTH: 4
<212> TYPE: PRT
<213> ORGANISM: Artificial Sequence
<220> FEATURE:
<223> OTHER INFORMATION: Synthetic Construct

<400> SEQUENCE: 158

Gly Gly Ser Gly
1

<210> SEQ ID NO 159
<211> LENGTH: 5
<212> TYPE: PRT
<213> ORGANISM: Artificial Sequence
<220> FEATURE:
<223> OTHER INFORMATION: Synthetic Construct

<400> SEQUENCE: 159

Gly Gly Ser Gly Gly
1               5

<210> SEQ ID NO 160
<211> LENGTH: 5
<212> TYPE: PRT
<213> ORGANISM: Artificial Sequence
<220> FEATURE:
<223> OTHER INFORMATION: Synthetic Construct

<400> SEQUENCE: 160

Gly Ser Gly Ser Gly
1               5

<210> SEQ ID NO 161
<211> LENGTH: 5
<212> TYPE: PRT
<213> ORGANISM: Artificial Sequence
<220> FEATURE:
<223> OTHER INFORMATION: Synthetic Construct

<400> SEQUENCE: 161

Gly Ser Gly Gly Gly
1               5

<210> SEQ ID NO 162
<211> LENGTH: 5
<212> TYPE: PRT
<213> ORGANISM: Artificial Sequence
<220> FEATURE:

<223> OTHER INFORMATION: Synthetic Construct

<400> SEQUENCE: 162

Gly Gly Gly Ser Gly
1 5

<210> SEQ ID NO 163
<211> LENGTH: 5
<212> TYPE: PRT
<213> ORGANISM: Artificial Sequence
<220> FEATURE:
<223> OTHER INFORMATION: Synthetic Construct

<400> SEQUENCE: 163

Gly Ser Ser Ser Gly
1 5

<210> SEQ ID NO 164
<211> LENGTH: 42
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Ala, Asp, Ile, Asn, Pro, or Tyr
<220> FEATURE:
<221> NAME/KEY: VARIANT
<222> LOCATION: 7
<223> OTHER INFORMATION: Xaa = Ala, Phe, Asn, Ser, or Val
<220> FEATURE:
<221> NAME/KEY: VARIANT
<222> LOCATION: 8
<223> OTHER INFORMATION: Xaa = Ala, His, Leu, Pro, Ser, Val, or Tyr
<220> FEATURE:
<221> NAME/KEY: VARIANT
<222> LOCATION: 9
<223> OTHER INFORMATION: Xaa = Ala, His, Ser, or Tyr
<220> FEATURE:
<221> NAME/KEY: VARIANT
<222> LOCATION: 10
<223> OTHER INFORMATION: Xaa = Ala, Asp, Pro, Ser, Val, or Tyr
<220> FEATURE:
<221> NAME/KEY: VARIANT
<222> LOCATION: 11
<223> OTHER INFORMATION: Xaa = Ala, Asp, Leu, Ser, or Tyr
<220> FEATURE:
<221> NAME/KEY: VARIANT
<222> LOCATION: 13
<223> OTHER INFORMATION: Xaa = Asp, Pro, or Val
<220> FEATURE:
<221> NAME/KEY: VARIANT
<222> LOCATION: 14
<223> OTHER INFORMATION: Xaa = Ala, Asp, His, Pro, Ser, or Thr
<220> FEATURE:
<221> NAME/KEY: VARIANT
<222> LOCATION: 15
<223> OTHER INFORMATION: Xaa = Ala, Asp, Phe, His, Pro, or Tyr
<220> FEATURE:
<221> NAME/KEY: VARIANT
<222> LOCATION: 16
<223> OTHER INFORMATION: Xaa = Leu, Pro, or Tyr
<220> FEATURE:
<221> NAME/KEY: VARIANT
<222> LOCATION: 17
<223> OTHER INFORMATION: Xaa = Phe, Pro, or Tyr
<220> FEATURE:
<221> NAME/KEY: VARIANT
<222> LOCATION: 18
<223> OTHER INFORMATION: Xaa = Ala, Pro, Ser, or Tyr
<220> FEATURE:
<221> NAME/KEY: VARIANT
<222> LOCATION: 20
<223> OTHER INFORMATION: Xaa = Ala, Asp, Asn, Ser, Thr, or Tyr
<220> FEATURE:
<221> NAME/KEY: VARIANT
<222> LOCATION: 21
<223> OTHER INFORMATION: Xaa = Ala, Ser, or Tyr

<400> SEQUENCE: 164

```
Glu Val Gly Ser Tyr Xaa Xaa Xaa Xaa Xaa Xaa Cys Xaa Xaa Xaa Xaa
1               5                   10                  15

Xaa Xaa Cys Xaa Xaa Ser Gly Arg Ser Ala Gly Gly Gly Gly Thr Glu
            20                  25                  30

Asn Leu Tyr Phe Gln Gly Ser Gly Gly Ser
        35                  40
```

<210> SEQ ID NO 165
<211> LENGTH: 42
<212> TYPE: PRT
<213> ORGANISM: Artificial Sequence
<220> FEATURE:
<223> OTHER INFORMATION: Synthetic Construct

<400> SEQUENCE: 165

```
Glu Val Gly Ser Tyr Asp Ala Leu His Tyr Ala Cys Pro Pro Asp Tyr
1               5                   10                  15

Tyr Ala Cys Tyr Tyr Ser Gly Arg Ser Ala Gly Gly Gly Gly Thr Glu
            20                  25                  30

Asn Leu Tyr Phe Gln Gly Ser Gly Gly Ser
        35                  40
```

<210> SEQ ID NO 166
<211> LENGTH: 42
<212> TYPE: PRT
<213> ORGANISM: Artificial Sequence
<220> FEATURE:
<223> OTHER INFORMATION: Synthetic Construct

<400> SEQUENCE: 166

```
Glu Val Gly Ser Tyr Asn Ser Tyr His Ala Tyr Cys Pro His Pro Leu
1               5                   10                  15

Tyr Pro Cys Thr Ala Ser Gly Arg Ser Ala Gly Gly Gly Gly Thr Glu
            20                  25                  30

Asn Leu Tyr Phe Gln Gly Ser Gly Gly Ser
        35                  40
```

<210> SEQ ID NO 167
<211> LENGTH: 42
<212> TYPE: PRT
<213> ORGANISM: Artificial Sequence
<220> FEATURE:
<223> OTHER INFORMATION: Synthetic Construct

<400> SEQUENCE: 167

```
Glu Val Gly Ser Tyr Ala Ser Ser Ala Val Leu Cys Val Thr Ala Tyr
1               5                   10                  15

Phe Ser Cys Asn Ser Ser Gly Arg Ser Ala Gly Gly Gly Gly Thr Glu
            20                  25                  30

Asn Leu Tyr Phe Gln Gly Ser Gly Gly Ser
        35                  40
```

<210> SEQ ID NO 168
<211> LENGTH: 41
<212> TYPE: PRT
<213> ORGANISM: Artificial Sequence
<220> FEATURE:

<223> OTHER INFORMATION: Synthetic Construct

<400> SEQUENCE: 168

Glu Val Gly Ser Tyr Asn Phe Val Ala Asp Ser Cys Pro Asp His Pro
1 5 10 15

Tyr Pro Cys Ser Ala Ser Gly Arg Ser Ala Gly Gly Gly Gly Ser Pro
20 25 30

Leu Gly Leu Ala Gly Ser Gly Gly Ser
35 40

<210> SEQ ID NO 169
<211> LENGTH: 42
<212> TYPE: PRT
<213> ORGANISM: Artificial Sequence
<220> FEATURE:
<223> OTHER INFORMATION: Synthetic Construct

<400> SEQUENCE: 169

Glu Val Gly Ser Tyr Asn Phe Val Ala Asp Ser Cys Pro Asp His Pro
1 5 10 15

Tyr Pro Cys Ser Ala Ser Gly Arg Ser Ala Gly Gly Gly Gly Thr Glu
20 25 30

Asn Leu Tyr Phe Gln Gly Ser Gly Gly Ser
35 40

<210> SEQ ID NO 170
<211> LENGTH: 41
<212> TYPE: PRT
<213> ORGANISM: Artificial Sequence
<220> FEATURE:
<223> OTHER INFORMATION: Synthetic Construct

<400> SEQUENCE: 170

Glu Val Gly Ser Tyr Ile Val His His Ser Asp Cys Asp Ala Phe Tyr
1 5 10 15

Pro Tyr Cys Asp Ser Ser Gly Arg Ser Ala Gly Gly Gly Gly Ser Pro
20 25 30

Leu Gly Leu Ala Gly Ser Gly Gly Ser
35 40

<210> SEQ ID NO 171
<211> LENGTH: 42
<212> TYPE: PRT
<213> ORGANISM: Artificial Sequence
<220> FEATURE:
<223> OTHER INFORMATION: Synthetic Construct

<400> SEQUENCE: 171

Glu Val Gly Ser Tyr Ile Val His His Ser Asp Cys Asp Ala Phe Tyr
1 5 10 15

Pro Tyr Cys Asp Ser Ser Gly Arg Ser Ala Gly Gly Gly Gly Thr Glu
20 25 30

Asn Leu Tyr Phe Gln Gly Ser Gly Gly Ser
35 40

<210> SEQ ID NO 172
<211> LENGTH: 41
<212> TYPE: PRT
<213> ORGANISM: Artificial Sequence
<220> FEATURE:
<223> OTHER INFORMATION: Synthetic Construct

<400> SEQUENCE: 172

```
Glu Val Gly Ser Tyr Tyr Ser Ala Tyr Pro Ala Cys Asp Ser His Tyr
1               5                   10                  15

Pro Tyr Cys Asn Ser Ser Gly Arg Ser Ala Gly Gly Gly Gly Ser Pro
            20                  25                  30

Leu Gly Leu Ala Gly Ser Gly Gly Ser
        35                  40


<210> SEQ ID NO 173
<211> LENGTH: 42
<212> TYPE: PRT
<213> ORGANISM: Artificial Sequence
<220> FEATURE:
<223> OTHER INFORMATION: Synthetic Construct

<400> SEQUENCE: 173

Glu Val Gly Ser Tyr Tyr Ser Ala Tyr Pro Ala Cys Asp Ser His Tyr
1               5                   10                  15

Pro Tyr Cys Asn Ser Ser Gly Arg Ser Ala Gly Gly Gly Gly Thr Glu
            20                  25                  30

Asn Leu Tyr Phe Gln Gly Ser Gly Gly Ser
        35                  40


<210> SEQ ID NO 174
<211> LENGTH: 41
<212> TYPE: PRT
<213> ORGANISM: Artificial Sequence
<220> FEATURE:
<223> OTHER INFORMATION: Synthetic Construct

<400> SEQUENCE: 174

Glu Val Gly Ser Tyr Pro Asn Pro Ser Ser Asp Cys Val Pro Tyr Tyr
1               5                   10                  15

Tyr Ala Cys Ala Tyr Ser Gly Arg Ser Ala Gly Gly Gly Gly Ser Pro
            20                  25                  30

Leu Gly Leu Ala Gly Ser Gly Gly Ser
        35                  40


<210> SEQ ID NO 175
<211> LENGTH: 42
<212> TYPE: PRT
<213> ORGANISM: Artificial Sequence
<220> FEATURE:
<223> OTHER INFORMATION: Synthetic Construct

<400> SEQUENCE: 175

Glu Val Gly Ser Tyr Pro Asn Pro Ser Ser Asp Cys Val Pro Tyr Tyr
1               5                   10                  15

Tyr Ala Cys Ala Tyr Ser Gly Arg Ser Ala Gly Gly Gly Gly Thr Glu
            20                  25                  30

Asn Leu Tyr Phe Gln Gly Ser Gly Gly Ser
        35                  40


<210> SEQ ID NO 176
<211> LENGTH: 41
<212> TYPE: PRT
<213> ORGANISM: Artificial Sequence
<220> FEATURE:
<223> OTHER INFORMATION: Synthetic Construct

<400> SEQUENCE: 176

Glu Val Gly Ser Tyr Tyr Ser Ala Tyr Pro Ala Cys Asp Ser His Tyr
1               5                   10                  15
```

```
Pro Tyr Cys Gln Ser Ser Gly Arg Ser Ala Gly Gly Gly Gly Ser Pro
            20                  25                  30

Leu Gly Leu Ala Gly Ser Gly Gly Ser
        35                  40


<210> SEQ ID NO 177
<211> LENGTH: 41
<212> TYPE: PRT
<213> ORGANISM: Artificial Sequence
<220> FEATURE:
<223> OTHER INFORMATION: Synthetic Construct

<400> SEQUENCE: 177

Glu Val Gly Ser Tyr Tyr Ser Ala Tyr Pro Ala Cys Asp Ser His Tyr
1               5                   10                  15

Pro Tyr Cys Asn Ser Ala Gly Arg Ser Ala Gly Gly Gly Gly Ser Pro
            20                  25                  30

Leu Gly Leu Ala Gly Ser Gly Gly Ser
        35                  40


<210> SEQ ID NO 178
<211> LENGTH: 41
<212> TYPE: PRT
<213> ORGANISM: Artificial Sequence
<220> FEATURE:
<223> OTHER INFORMATION: Synthetic Construct

<400> SEQUENCE: 178

Glu Val Gly Ser Tyr Pro Gln Pro Ser Ser Asp Cys Val Pro Tyr Tyr
1               5                   10                  15

Tyr Ala Cys Ala Tyr Ser Gly Arg Ser Ala Gly Gly Gly Gly Ser Pro
            20                  25                  30

Leu Gly Leu Ala Gly Ser Gly Gly Ser
        35                  40


<210> SEQ ID NO 179
<211> LENGTH: 41
<212> TYPE: PRT
<213> ORGANISM: Artificial Sequence
<220> FEATURE:
<223> OTHER INFORMATION: Synthetic Construct

<400> SEQUENCE: 179

Glu Val Gly Ser Tyr Pro Asn Pro Ala Ser Asp Cys Val Pro Tyr Tyr
1               5                   10                  15

Tyr Ala Cys Ala Tyr Ser Gly Arg Ser Ala Gly Gly Gly Gly Ser Pro
            20                  25                  30

Leu Gly Leu Ala Gly Ser Gly Gly Ser
        35                  40


<210> SEQ ID NO 180
<211> LENGTH: 20
<212> TYPE: PRT
<213> ORGANISM: Artificial Sequence
<220> FEATURE:
<223> OTHER INFORMATION: Synthetic Construct

<400> SEQUENCE: 180

Ser Gly Arg Ser Ala Gly Gly Gly Gly Ser Pro Leu Gly Leu Ala Gly
1               5                   10                  15

Ser Gly Gly Ser
            20
```

<210> SEQ ID NO 181
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Present in repeats of at least two and up to ten
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr

<400> SEQUENCE: 181

```
Xaa Cys Pro Asp His Pro Tyr Pro Cys Xaa Xaa
1               5                   10
```

<210> SEQ ID NO 182
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Present in repeats of at least two and up to ten
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr

<400> SEQUENCE: 182

```
Xaa Cys Asp Ala Phe Tyr Pro Tyr Cys Xaa Xaa
1               5                   10
```

<210> SEQ ID NO 183
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Present in repeats of at least two and up to ten
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr

<400> SEQUENCE: 183

```
Xaa Cys Asp Ser His Tyr Pro Tyr Cys Xaa Xaa
1               5                   10
```

<210> SEQ ID NO 184
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT

```
<222> LOCATION: 1
<223> OTHER INFORMATION: Present in repeats of at least two and up to
      ten
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 184

Xaa Cys Val Pro Tyr Tyr Tyr Ala Cys Xaa Xaa
1               5                   10


<210> SEQ ID NO 185

<400> SEQUENCE: 185

000


<210> SEQ ID NO 186

<400> SEQUENCE: 186

000


<210> SEQ ID NO 187

<400> SEQUENCE: 187

000


<210> SEQ ID NO 188

<400> SEQUENCE: 188

000


<210> SEQ ID NO 189
<211> LENGTH: 21
<212> TYPE: PRT
<213> ORGANISM: Artificial Sequence
<220> FEATURE:
<223> OTHER INFORMATION: Synthetic Construct

<400> SEQUENCE: 189

Glu Val Gly Ser Tyr Asn Phe Val Ala Asp Ser Cys Pro Asp His Pro
1               5                   10                  15

Tyr Pro Cys Ser Ala
            20


<210> SEQ ID NO 190
<211> LENGTH: 21
<212> TYPE: PRT
<213> ORGANISM: Artificial Sequence
<220> FEATURE:
<223> OTHER INFORMATION: Synthetic Construct

<400> SEQUENCE: 190

Glu Val Gly Ser Tyr Ile Val His His Ser Asp Cys Asp Ala Phe Tyr
1               5                   10                  15

Pro Tyr Cys Asp Ser
            20


<210> SEQ ID NO 191
<211> LENGTH: 21
<212> TYPE: PRT
<213> ORGANISM: Artificial Sequence
```

-continued

<220> FEATURE:
<223> OTHER INFORMATION: Synthetic Construct

<400> SEQUENCE: 191

Glu Val Gly Ser Tyr Tyr Ser Ala Tyr Pro Ala Cys Asp Ser His Tyr
1 5 10 15

Pro Tyr Cys Asn Ser
20

<210> SEQ ID NO 192
<211> LENGTH: 21
<212> TYPE: PRT
<213> ORGANISM: Artificial Sequence
<220> FEATURE:
<223> OTHER INFORMATION: Synthetic Construct

<400> SEQUENCE: 192

Glu Val Gly Ser Tyr Pro Asn Pro Ser Ser Asp Cys Val Pro Tyr Tyr
1 5 10 15

Tyr Ala Cys Ala Tyr
20

<210> SEQ ID NO 193
<211> LENGTH: 21
<212> TYPE: PRT
<213> ORGANISM: Artificial Sequence
<220> FEATURE:
<223> OTHER INFORMATION: Synthetic Construct

<400> SEQUENCE: 193

Glu Val Gly Ser Tyr Tyr Ser Ala Tyr Pro Ala Cys Asp Ser His Tyr
1 5 10 15

Pro Tyr Cys Gln Ser
20

<210> SEQ ID NO 194

<400> SEQUENCE: 194

000

<210> SEQ ID NO 195
<211> LENGTH: 21
<212> TYPE: PRT
<213> ORGANISM: Artificial Sequence
<220> FEATURE:
<223> OTHER INFORMATION: Synthetic Construct

<400> SEQUENCE: 195

Glu Val Gly Ser Tyr Pro Gln Pro Ser Ser Asp Cys Val Pro Tyr Tyr
1 5 10 15

Tyr Ala Cys Ala Tyr
20

<210> SEQ ID NO 196
<211> LENGTH: 21
<212> TYPE: PRT
<213> ORGANISM: Artificial Sequence
<220> FEATURE:
<223> OTHER INFORMATION: Synthetic Construct

<400> SEQUENCE: 196

Glu Val Gly Ser Tyr Pro Asn Pro Ala Ser Asp Cys Val Pro Tyr Tyr
1 5 10 15

Tyr Ala Cys Ala Tyr
20

<210> SEQ ID NO 197
<211> LENGTH: 41
<212> TYPE: PRT
<213> ORGANISM: Artificial Sequence
<220> FEATURE:
<223> OTHER INFORMATION: Synthetic Construct

<400> SEQUENCE: 197

Glu Val Gly Ser Tyr Ile Val His His Ser Asp Cys Asp Ala Phe Tyr
1 5 10 15

Pro Tyr Cys Asp Ser Ser Gly Arg Ser Ala Gly Gly Gly Gly Thr Pro
20 25 30

Leu Gly Leu Ala Gly Ser Gly Gly Ser
35 40

<210> SEQ ID NO 198
<211> LENGTH: 36
<212> TYPE: PRT
<213> ORGANISM: Artificial Sequence
<220> FEATURE:
<223> OTHER INFORMATION: Synthetic Construct

<400> SEQUENCE: 198

Glu Val Gly His Ser Asp Cys Asp Ala Phe Tyr Pro Tyr Cys Asp Ser
1 5 10 15

Ser Gly Arg Ser Ala Gly Gly Gly Gly Thr Pro Leu Gly Leu Ala Gly
20 25 30

Ser Gly Gly Ser
35

<210> SEQ ID NO 199
<211> LENGTH: 32
<212> TYPE: PRT
<213> ORGANISM: Artificial Sequence
<220> FEATURE:
<223> OTHER INFORMATION: Synthetic Construct

<400> SEQUENCE: 199

Glu Asp Cys Asp Ala Phe Tyr Pro Tyr Cys Asp Ser Ser Gly Arg Ser
1 5 10 15

Ala Gly Gly Gly Gly Thr Pro Leu Gly Leu Ala Gly Ser Gly Gly Ser
20 25 30

<210> SEQ ID NO 200
<211> LENGTH: 41
<212> TYPE: PRT
<213> ORGANISM: Artificial Sequence
<220> FEATURE:
<223> OTHER INFORMATION: Synthetic Construct

<400> SEQUENCE: 200

Glu Val Gly Ser Tyr Pro Asn Pro Ser Ser Asp Cys Val Pro Tyr Tyr
1 5 10 15

Tyr Ala Cys Ala Tyr Ser Gly Arg Ser Ala Gly Gly Gly Gly Thr Pro
20 25 30

Leu Gly Leu Ala Gly Ser Gly Gly Ser
35 40

<210> SEQ ID NO 201
<211> LENGTH: 36

<212> TYPE: PRT
<213> ORGANISM: Artificial Sequence
<220> FEATURE:
<223> OTHER INFORMATION: Synthetic Construct

<400> SEQUENCE: 201

Glu Val Gly Ser Ser Asp Cys Val Pro Tyr Tyr Tyr Ala Cys Ala Tyr
1               5                   10                  15

Ser Gly Arg Ser Ala Gly Gly Gly Gly Thr Pro Leu Gly Leu Ala Gly
            20                  25                  30

Ser Gly Gly Ser
        35

<210> SEQ ID NO 202
<211> LENGTH: 32
<212> TYPE: PRT
<213> ORGANISM: Artificial Sequence
<220> FEATURE:
<223> OTHER INFORMATION: Synthetic Construct

<400> SEQUENCE: 202

Glu Asp Cys Val Pro Tyr Tyr Tyr Ala Cys Ala Tyr Ser Gly Arg Ser
1               5                   10                  15

Ala Gly Gly Gly Gly Thr Pro Leu Gly Leu Ala Gly Ser Gly Gly Ser
            20                  25                  30

<210> SEQ ID NO 203
<211> LENGTH: 118
<212> TYPE: PRT
<213> ORGANISM: Artificial Sequence
<220> FEATURE:
<223> OTHER INFORMATION: Synthetic Construct

<400> SEQUENCE: 203

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Ala Gln Ile
            100                 105                 110

Tyr Val Ile Asp Pro Glu
        115

<210> SEQ ID NO 204
<211> LENGTH: 118
<212> TYPE: PRT
<213> ORGANISM: Artificial Sequence
<220> FEATURE:
<223> OTHER INFORMATION: Synthetic Construct

<400> SEQUENCE: 204

Met His Val Ala Gln Pro Ala Val Val Leu Ala Ser Ser Arg Gly Ile
1               5                   10                  15

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu
        115
```

<210> SEQ ID NO 205
<211> LENGTH: 115
<212> TYPE: PRT
<213> ORGANISM: Artificial Sequence
<220> FEATURE:
<223> OTHER INFORMATION: Synthetic Construct

<400> SEQUENCE: 205

```
Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Ile Cys
    50                  55                  60

Thr Gly Thr Ser Ser Gly Asn Gln Val Asn Leu Thr Ile Gln Gly Leu
65                  70                  75                  80

Arg Ala Met Asp Thr Gly Leu Tyr Ile Cys Lys Val Glu Leu Met Tyr
                85                  90                  95

Pro Pro Pro Tyr Tyr Leu Gly Ile Gly Asn Gly Thr Gln Ile Tyr Val
            100                 105                 110

Ile Asp Pro
        115
```

<210> SEQ ID NO 206
<211> LENGTH: 114
<212> TYPE: PRT
<213> ORGANISM: Artificial Sequence
<220> FEATURE:
<223> OTHER INFORMATION: Synthetic Construct

<400> SEQUENCE: 206

```
Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Asp Ser Ile
    50                  55                  60

Cys Thr Gly Thr Ser Ser Gly Asn Gln Val Asn Leu Thr Ile Gln Gly
65                  70                  75                  80
```

```
Leu Arg Ala Met Asp Thr Gly Leu Tyr Ile Cys Lys Val Glu Leu Met
                85                  90                  95

Tyr Pro Pro Pro Tyr Tyr Leu Gly Ile Gly Asn Gly Thr Gln Ile Tyr
            100                 105                 110

Val Ile


<210> SEQ ID NO 207
<211> LENGTH: 120
<212> TYPE: PRT
<213> ORGANISM: Homo sapiens

<400> SEQUENCE: 207

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu
        115                 120


<210> SEQ ID NO 208
<211> LENGTH: 120
<212> TYPE: PRT
<213> ORGANISM: Mus musculus

<400> SEQUENCE: 208

Glu Ala Ile Gln Val Thr Gln Pro Ser Val Val Leu Ala Ser Ser His
1               5                   10                  15

Gly Val Ala Ser Phe Pro Cys Glu Tyr Ser Pro Ser His Asn Thr Asp
            20                  25                  30

Glu Val Arg Val Thr Val Leu Arg Gln Thr Asn Asp Gln Met Thr Glu
        35                  40                  45

Val Cys Ala Thr Thr Phe Thr Glu Lys Asn Thr Val Gly Phe Leu Asp
    50                  55                  60

Tyr Pro Phe Cys Ser Gly Thr Phe Asn Glu Ser Arg Val Asn Leu Thr
65                  70                  75                  80

Ile Gln Gly Leu Arg Ala Val Asp Thr Gly Leu Tyr Leu Cys Lys Val
                85                  90                  95

Glu Leu Met Tyr Pro Pro Pro Tyr Phe Val Gly Met Gly Asn Gly Thr
            100                 105                 110

Gln Ile Tyr Val Ile Asp Pro Glu
        115                 120


<210> SEQ ID NO 209
<211> LENGTH: 31
<212> TYPE: PRT
<213> ORGANISM: Artificial Sequence
<220> FEATURE:
```

<223> OTHER INFORMATION: Synthetic Construct

<400> SEQUENCE: 209

Glu Val Gly Ser Tyr Pro Asn Pro Ser Ser Asp Cys Val Pro Tyr Tyr
1 5 10 15

Tyr Ala Cys Ala Tyr Ser Gly Arg Ser Ala Pro Leu Gly Leu Ala
20 25 30

<210> SEQ ID NO 210
<211> LENGTH: 22
<212> TYPE: PRT
<213> ORGANISM: Artificial Sequence
<220> FEATURE:
<223> OTHER INFORMATION: Synthetic Construct

<400> SEQUENCE: 210

Glu Asp Cys Val Pro Tyr Tyr Tyr Ala Cys Ala Tyr Ser Gly Arg Ser
1 5 10 15

Ala Pro Leu Gly Leu Ala
20

<210> SEQ ID NO 211
<211> LENGTH: 17
<212> TYPE: PRT
<213> ORGANISM: Artificial Sequence
<220> FEATURE:
<223> OTHER INFORMATION: Synthetic Construct

<400> SEQUENCE: 211

Glu Asp Cys Val Pro Tyr Tyr Tyr Ala Cys Ala Tyr Ser Gly Arg Ser
1 5 10 15

Ala

<210> SEQ ID NO 212
<211> LENGTH: 17
<212> TYPE: PRT
<213> ORGANISM: Artificial Sequence
<220> FEATURE:
<223> OTHER INFORMATION: Synthetic Construct

<400> SEQUENCE: 212

Glu Asp Cys Val Pro Tyr Tyr Tyr Ala Cys Ala Tyr Pro Leu Gly Leu
1 5 10 15

Ala

<210> SEQ ID NO 213
<211> LENGTH: 12
<212> TYPE: PRT
<213> ORGANISM: Artificial Sequence
<220> FEATURE:
<223> OTHER INFORMATION: Synthetic Construct

<400> SEQUENCE: 213

Glu Asp Cys Val Pro Tyr Tyr Tyr Ala Cys Ala Tyr
1 5 10

<210> SEQ ID NO 214
<211> LENGTH: 16
<212> TYPE: PRT
<213> ORGANISM: Artificial Sequence
<220> FEATURE:
<223> OTHER INFORMATION: Synthetic Construct

<400> SEQUENCE: 214

Glu Val Gly Ser Ser Asp Cys Val Pro Tyr Tyr Tyr Ala Cys Ala Tyr
1 5 10 15

<210> SEQ ID NO 215
<211> LENGTH: 12
<212> TYPE: PRT
<213> ORGANISM: Artificial Sequence
<220> FEATURE:
<223> OTHER INFORMATION: Synthetic Construct

<400> SEQUENCE: 215

Glu Asp Cys Asp Ala Phe Tyr Pro Tyr Cys Asp Ser
1 5 10

<210> SEQ ID NO 216
<211> LENGTH: 16
<212> TYPE: PRT
<213> ORGANISM: Artificial Sequence
<220> FEATURE:
<223> OTHER INFORMATION: Synthetic Construct

<400> SEQUENCE: 216

Glu Val Gly His Ser Asp Cys Asp Ala Phe Tyr Pro Tyr Cys Asp Ser
1 5 10 15

<210> SEQ ID NO 217
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Present in repeats of at least one and up to 11
<220> FEATURE:
<221> NAME/KEY: VARIANT
<222> LOCATION: 5, 6, 7, 8, 9, 10, 11, 12
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr
<220> FEATURE:
<221> NAME/KEY: VARIANT
<222> LOCATION: 3, 14, 15
<223> OTHER INFORMATION: Xaa = Asp, Ala, Tyr, Ser, Thr, Asn, Ile, Leu, Phe, Val, His, or Pro

<400> SEQUENCE: 217

Glu Val Xaa Cys Xaa Xaa Xaa Xaa Xaa Xaa Xaa Xaa Cys Xaa Xaa Ser
1 5 10 15

Gly Arg Ser Ala
20

<210> SEQ ID NO 218
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 5, 6, 7, 8, 9, 11, 12
<223> OTHER INFORMATION: Xaa = Asp, Ala, Tyr, Ser, Thr, Asn, Ile, Leu, Phe, Val, His, or Pro

<400> SEQUENCE: 218

Glu Asp Cys Xaa Xaa Xaa Xaa Xaa Xaa Cys Xaa Xaa Ser Gly Arg Ser
1 5 10 15

Ala

```
<210> SEQ ID NO 219
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 5, 6, 7, 8, 9, 11, 12
<223> OTHER INFORMATION: Xaa = Asp, Ala, Tyr, Ser, Thr, Asn, Ile, Leu,
      Phe, Val, His, or Pro

<400> SEQUENCE: 219

Glu Asp Cys Xaa Xaa Xaa Xaa Xaa Xaa Cys Xaa Xaa Pro Leu Gly Leu
1               5                   10                  15

Ala


<210> SEQ ID NO 220
<211> LENGTH: 21
<212> TYPE: PRT
<213> ORGANISM: Artificial Sequence
<220> FEATURE:
<223> OTHER INFORMATION: Synthetic Construct

<400> SEQUENCE: 220

Ser Gly Arg Ser Ala Gly Gly Gly Gly Thr Glu Asn Leu Tyr Phe Gln
1               5                   10                  15

Gly Ser Gly Gly Ser
            20


<210> SEQ ID NO 221
<211> LENGTH: 20
<212> TYPE: PRT
<213> ORGANISM: Artificial Sequence
<220> FEATURE:
<223> OTHER INFORMATION: Synthetic Construct

<400> SEQUENCE: 221

Ser Gly Arg Ser Ala Gly Gly Gly Gly Thr Pro Leu Gly Leu Ala Gly
1               5                   10                  15

Ser Gly Gly Ser
            20


<210> SEQ ID NO 222
<211> LENGTH: 10
<212> TYPE: PRT
<213> ORGANISM: Artificial Sequence
<220> FEATURE:
<223> OTHER INFORMATION: Synthetic Construct

<400> SEQUENCE: 222

Ser Gly Arg Ser Ala Pro Leu Gly Leu Ala
1               5                   10


<210> SEQ ID NO 223
<211> LENGTH: 13
<212> TYPE: PRT
<213> ORGANISM: Artificial Sequence
<220> FEATURE:
<223> OTHER INFORMATION: Synthetic Construct

<400> SEQUENCE: 223

Phe Ser Leu Ser Thr Gly Gly Val Gly Val Gly Trp Ile
1               5                   10
```

<210> SEQ ID NO 224
<211> LENGTH: 20
<212> TYPE: PRT
<213> ORGANISM: Artificial Sequence
<220> FEATURE:
<223> OTHER INFORMATION: Synthetic Construct

<400> SEQUENCE: 224

Leu Ala Leu Ile Asp Trp Ala Asp Asp Lys Tyr Tyr Ser Pro Ser Leu
1 5 10 15

Lys Ser Arg Leu
20

<210> SEQ ID NO 225
<211> LENGTH: 15
<212> TYPE: PRT
<213> ORGANISM: Artificial Sequence
<220> FEATURE:
<223> OTHER INFORMATION: Synthetic Construct

<400> SEQUENCE: 225

Ala Arg Gly Gly Ser Asp Thr Val Ile Gly Asp Trp Phe Ala Tyr
1 5 10 15

<210> SEQ ID NO 226
<211> LENGTH: 11
<212> TYPE: PRT
<213> ORGANISM: Artificial Sequence
<220> FEATURE:
<223> OTHER INFORMATION: Synthetic Construct

<400> SEQUENCE: 226

Arg Ala Ser Gln Ser Ile Gly Ser Tyr Leu Ala
1 5 10

<210> SEQ ID NO 227
<211> LENGTH: 9
<212> TYPE: PRT
<213> ORGANISM: Artificial Sequence
<220> FEATURE:
<223> OTHER INFORMATION: Synthetic Construct

<400> SEQUENCE: 227

Asp Ala Ser Asn Leu Glu Thr Gly Val
1 5

<210> SEQ ID NO 228
<211> LENGTH: 10
<212> TYPE: PRT
<213> ORGANISM: Artificial Sequence
<220> FEATURE:
<223> OTHER INFORMATION: Synthetic Construct

<400> SEQUENCE: 228

Tyr Cys Gln Gln Gly Tyr Tyr Leu Trp Thr
1 5 10

<210> SEQ ID NO 229
<211> LENGTH: 123
<212> TYPE: PRT
<213> ORGANISM: Artificial Sequence
<220> FEATURE:
<223> OTHER INFORMATION: Synthetic Construct

<400> SEQUENCE: 229

Glu Val Gln Leu Val Glu Ser Gly Gly Gly Leu Val Gln Pro Gly Gly
1 5 10 15

```
Ser Leu Arg Leu Ser Cys Ala Ala Ser Gly Phe Ser Leu Ser Thr Gly
            20                  25                  30

Gly Val Gly Val Gly Trp Ile Arg Gln Ala Pro Gly Lys Gly Leu Glu
        35                  40                  45

Trp Leu Ala Leu Ile Asp Trp Ala Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Ile Gly Asp Trp Phe Ala Tyr
            100                 105                 110

Trp Gly Gln Gly Thr Leu Val Thr Val Ser Ser
        115                 120


<210> SEQ ID NO 230
<211> LENGTH: 106
<212> TYPE: PRT
<213> ORGANISM: Artificial Sequence
<220> FEATURE:
<223> OTHER INFORMATION: Synthetic Construct

<400> SEQUENCE: 230

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Leu Trp Thr
                85                  90                  95

Phe Gly Gln Gly Thr Lys Val Glu Ile Lys
            100                 105


<210> SEQ ID NO 231
<211> LENGTH: 255
<212> TYPE: PRT
<213> ORGANISM: Artificial Sequence
<220> FEATURE:
<223> OTHER INFORMATION: Synthetic Construct

<400> SEQUENCE: 231

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
```

```
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255


<210> SEQ ID NO 232
<211> LENGTH: 13
<212> TYPE: PRT
<213> ORGANISM: Artificial Sequence
<220> FEATURE:
<223> OTHER INFORMATION: Synthetic Construct

<400> SEQUENCE: 232

Phe Ser Leu Ser Thr Gly Gly Val Gly Val Gly Trp Ile
1               5                   10


<210> SEQ ID NO 233
<211> LENGTH: 20
<212> TYPE: PRT
<213> ORGANISM: Artificial Sequence
<220> FEATURE:
<223> OTHER INFORMATION: Synthetic Construct

<400> SEQUENCE: 233

Leu Ala Leu Ile Asp Trp Ala Asp Asp Lys Tyr Tyr Ser Pro Ser Leu
1               5                   10                  15

Lys Ser Arg Leu
            20


<210> SEQ ID NO 234
<211> LENGTH: 15
<212> TYPE: PRT
<213> ORGANISM: Artificial Sequence
<220> FEATURE:
<223> OTHER INFORMATION: Synthetic Construct

<400> SEQUENCE: 234

Ala Arg Gly Gly Ser Asp Thr Val Ile Gly Asp Trp Phe Ala Tyr
1               5                   10                  15


<210> SEQ ID NO 235
<211> LENGTH: 11
<212> TYPE: PRT
<213> ORGANISM: Artificial Sequence
```

<220> FEATURE:
<223> OTHER INFORMATION: Synthetic Construct

<400> SEQUENCE: 235

Arg Ala Ser Gln Ser Ile Gly Ser Tyr Leu Ala
1 5 10

<210> SEQ ID NO 236
<211> LENGTH: 9
<212> TYPE: PRT
<213> ORGANISM: Artificial Sequence
<220> FEATURE:
<223> OTHER INFORMATION: Synthetic Construct

<400> SEQUENCE: 236

Asp Ala Ser Asn Leu Glu Thr Gly Val
1 5

<210> SEQ ID NO 237
<211> LENGTH: 10
<212> TYPE: PRT
<213> ORGANISM: Artificial Sequence
<220> FEATURE:
<223> OTHER INFORMATION: Synthetic Construct

<400> SEQUENCE: 237

Tyr Cys Gln Gln Gly Tyr Tyr Leu Trp Thr
1 5 10

<210> SEQ ID NO 238
<211> LENGTH: 123
<212> TYPE: PRT
<213> ORGANISM: Artificial Sequence
<220> FEATURE:
<223> OTHER INFORMATION: Synthetic Construct

<400> SEQUENCE: 238

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Thr Gly
20 25 30

Gly Val Gly Val Gly Trp Ile Arg Gln Ala Pro Gly Lys Gly Leu Glu
35 40 45

Trp Leu Ala Leu Ile Asp Trp Ala Asp Asp Lys Tyr Tyr Ser Pro Ser
50 55 60

Leu Lys Ser Arg Leu Thr Ile Ser Arg Asp Asn Ser Lys Asn Thr Leu
65 70 75 80

Tyr Leu Gln Leu Asn Ser Leu Arg Ala Glu Asp Thr Ala Val Tyr Tyr
85 90 95

Cys Ala Arg Gly Gly Ser Asp Thr Val Ile Gly Asp Trp Phe Ala Tyr
100 105 110

Trp Gly Gln Gly Thr Leu Val Thr Val Ser Ser
115 120

<210> SEQ ID NO 239
<211> LENGTH: 123
<212> TYPE: PRT
<213> ORGANISM: Artificial Sequence
<220> FEATURE:
<223> OTHER INFORMATION: Synthetic Construct

<400> SEQUENCE: 239

Glu Val Gln Leu Val Glu Ser Gly Gly Gly Leu Val Gln Pro Gly Gly

```
1               5                   10                  15

Ser Leu Arg Leu Ser Cys Ala Ala Ser Gly Phe Ser Leu Ser Thr Gly
            20                  25                  30

Gly Val Gly Val Gly Trp Ile Arg Gln Ala Pro Gly Lys Gly Leu Glu
        35                  40                  45

Trp Leu Ala Leu Ile Asp Trp Ala Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Ile Gly Asp Trp Phe Ala Tyr
            100                 105                 110

Trp Gly Gln Gly Thr Leu Val Thr Val Ser Ser
        115                 120
```

```
<210> SEQ ID NO 240
<211> LENGTH: 450
<212> TYPE: PRT
<213> ORGANISM: Artificial Sequence
<220> FEATURE:
<223> OTHER INFORMATION: Synthetic Construct

<400> SEQUENCE: 240

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Gly Trp Ile Arg Gln Ala Pro Gly Lys Gly Leu Glu
        35                  40                  45

Trp Leu Ala Leu Ile Asp Trp Ala Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Ile Gly Asp Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
```

```
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450


<210> SEQ ID NO 241
<211> LENGTH: 213
<212> TYPE: PRT
<213> ORGANISM: Artificial Sequence
<220> FEATURE:
<223> OTHER INFORMATION: Synthetic Construct

<400> SEQUENCE: 241

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Leu Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
```

```
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 242
<211> LENGTH: 12
<212> TYPE: PRT
<213> ORGANISM: Artificial Sequence
<220> FEATURE:
<223> OTHER INFORMATION: Synthetic Construct

<400> SEQUENCE: 242

Tyr Ser Ile Thr Ser Gly His Tyr Trp Ala Trp Ile
1               5                   10


<210> SEQ ID NO 243
<211> LENGTH: 21
<212> TYPE: PRT
<213> ORGANISM: Artificial Sequence
<220> FEATURE:
<223> OTHER INFORMATION: Synthetic Construct

<400> SEQUENCE: 243

Val Ser Ser Ile Ser Gly Tyr Gly Ser Thr Thr Tyr Tyr Ala Asp Ser
1               5                   10                  15

Val Lys Gly Arg Phe
            20


<210> SEQ ID NO 244
<211> LENGTH: 15
<212> TYPE: PRT
<213> ORGANISM: Artificial Sequence
<220> FEATURE:
<223> OTHER INFORMATION: Synthetic Construct

<400> SEQUENCE: 244

Ala Arg Gly Gly Ser Asp Ala Val Leu Gly Asp Trp Phe Ala Tyr
1               5                   10                  15


<210> SEQ ID NO 245
<211> LENGTH: 11
<212> TYPE: PRT
<213> ORGANISM: Artificial Sequence
<220> FEATURE:
<223> OTHER INFORMATION: Synthetic Construct

<400> SEQUENCE: 245

Arg Ala Ser Gln Gly Ile Gly Ser Phe Leu Ala
1               5                   10


<210> SEQ ID NO 246
<211> LENGTH: 9
<212> TYPE: PRT
<213> ORGANISM: Artificial Sequence
<220> FEATURE:
<223> OTHER INFORMATION: Synthetic Construct

<400> SEQUENCE: 246
```

Asp Ala Ser Asn Leu Glu Thr Gly Val
1 5

<210> SEQ ID NO 247
<211> LENGTH: 10
<212> TYPE: PRT
<213> ORGANISM: Artificial Sequence
<220> FEATURE:
<223> OTHER INFORMATION: Synthetic Construct

<400> SEQUENCE: 247

Tyr Cys Gln Gln Gly Tyr Tyr Leu Trp Thr
1 5 10

<210> SEQ ID NO 248
<211> LENGTH: 123
<212> TYPE: PRT
<213> ORGANISM: Artificial Sequence
<220> FEATURE:
<223> OTHER INFORMATION: Synthetic Construct

<400> SEQUENCE: 248

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Ile Thr Ser Gly
20 25 30

His Tyr Trp Ala Trp Ile Arg Gln Ala Pro Gly Lys Gly Leu Glu Trp
35 40 45

Val Ser Ser Ile Ser Gly Tyr Gly Ser Thr Thr Tyr Tyr Ala Asp Ser
50 55 60

Val Lys Gly Arg Phe Thr Ile Ser Arg Asp Asn Ser Lys Asn Thr Leu
65 70 75 80

Tyr Leu Gln Leu Asn Ser Leu Arg Ala Glu Asp Thr Ala Val Tyr Tyr
85 90 95

Cys Ala Arg Gly Gly Ser Asp Ala Val Leu Gly Asp Trp Phe Ala Tyr
100 105 110

Trp Gly Gln Gly Thr Leu Val Thr Val Ser Ser
115 120

<210> SEQ ID NO 249
<211> LENGTH: 107
<212> TYPE: PRT
<213> ORGANISM: Artificial Sequence
<220> FEATURE:
<223> OTHER INFORMATION: Synthetic Construct

<400> SEQUENCE: 249

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Gly Ser Phe
20 25 30

Leu Ala Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Tyr Tyr Leu Trp Thr
85 90 95

Phe Gly Gln Gly Thr Lys Val Glu Ile Lys Arg 100 105

<210> SEQ ID NO 250
<211> LENGTH: 450
<212> TYPE: PRT
<213> ORGANISM: Artificial Sequence
<220> FEATURE:
<223> OTHER INFORMATION: Synthetic Construct

<400> SEQUENCE: 250

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Ile Thr Ser Gly
20 25 30

His Tyr Trp Ala Trp Ile Arg Gln Ala Pro Gly Lys Gly Leu Glu Trp
35 40 45

Val Ser Ser Ile Ser Gly Tyr Gly Ser Thr Thr Tyr Tyr Ala Asp Ser
50 55 60

Val Lys Gly Arg Phe Thr Ile Ser Arg Asp Asn Ser Lys Asn Thr Leu
65 70 75 80

Tyr Leu Gln Leu Asn Ser Leu Arg Ala Glu Asp Thr Ala Val Tyr Tyr
85 90 95

Cys Ala Arg Gly Gly Ser Asp Ala Val Leu Gly Asp Trp Phe Ala Tyr
100 105 110

Trp Gly Gln Gly Thr Leu Val Thr Val Ser Ser Ala Ser Thr Lys Gly
115 120 125

Pro Ser Val Phe Pro Leu Ala Pro Cys Ser Arg Ser Thr Ser Glu Ser
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Lys Thr Tyr Thr Cys Asn Val
195 200 205

Asp His Lys Pro Ser Asn Thr Lys Val Asp Lys Arg Val Glu Ser Lys
210 215 220

Tyr Gly Pro Pro Cys Pro Pro Cys Pro Ala Pro Glu Phe Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser Gln Glu
260 265 270

Asp Pro Glu Val Gln Phe Asn Trp Tyr Val Asp Gly Val Glu Val His
275 280 285

Asn Ala Lys Thr Lys Pro Arg Glu Glu Gln Phe Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Gly Leu Pro Ser Ser Ile Glu
325 330 335

Lys Thr Ile Ser Lys Ala Lys Gly Gln Pro Arg Glu Pro Gln Val Tyr
340 345 350

Thr Leu Pro Pro Ser Gln Glu Glu Met Thr Lys Asn Gln Val Ser Leu

```
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450


<210> SEQ ID NO 251
<211> LENGTH: 213
<212> TYPE: PRT
<213> ORGANISM: Artificial Sequence
<220> FEATURE:
<223> OTHER INFORMATION: Synthetic Construct

<400> SEQUENCE: 251

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Phe
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Leu Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 252
<211> LENGTH: 13
<212> TYPE: PRT
<213> ORGANISM: Artificial Sequence
<220> FEATURE:
<223> OTHER INFORMATION: Synthetic Construct
```

<400> SEQUENCE: 252

Phe Ser Leu Ser Thr Ser Gly Val Gly Val Gly Trp Ile
1 5 10

<210> SEQ ID NO 253
<211> LENGTH: 20
<212> TYPE: PRT
<213> ORGANISM: Artificial Sequence
<220> FEATURE:
<223> OTHER INFORMATION: Synthetic Construct

<400> SEQUENCE: 253

Leu Ala Leu Ile Asp Trp Asp Asp Asp Lys Tyr Tyr Ser Pro Ser Leu
1 5 10 15

Lys Ser Arg Leu
20

<210> SEQ ID NO 254
<211> LENGTH: 15
<212> TYPE: PRT
<213> ORGANISM: Artificial Sequence
<220> FEATURE:
<223> OTHER INFORMATION: Synthetic Construct

<400> SEQUENCE: 254

Ala Arg Gly Gly Ser Asp Thr Val Leu Gly Asp Trp Phe Ala Tyr
1 5 10 15

<210> SEQ ID NO 255
<211> LENGTH: 11
<212> TYPE: PRT
<213> ORGANISM: Artificial Sequence
<220> FEATURE:
<223> OTHER INFORMATION: Synthetic Construct

<400> SEQUENCE: 255

Arg Ala Ser Gln Ser Val Ser Pro Tyr Leu Ala
1 5 10

<210> SEQ ID NO 256
<211> LENGTH: 9
<212> TYPE: PRT
<213> ORGANISM: Artificial Sequence
<220> FEATURE:
<223> OTHER INFORMATION: Synthetic Construct

<400> SEQUENCE: 256

Asp Ala Ser Ser Leu Glu Ser Gly Val
1 5

<210> SEQ ID NO 257
<211> LENGTH: 10
<212> TYPE: PRT
<213> ORGANISM: Artificial Sequence
<220> FEATURE:
<223> OTHER INFORMATION: Synthetic Construct

<400> SEQUENCE: 257

Tyr Cys Gln Gln Gly Tyr Ser Leu Trp Thr
1 5 10

<210> SEQ ID NO 258
<211> LENGTH: 123
<212> TYPE: PRT
<213> ORGANISM: Artificial Sequence
<220> FEATURE:
<223> OTHER INFORMATION: Synthetic Construct

<400> SEQUENCE: 258

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45

Trp Leu Ala Leu Ile Asp Trp Asp Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Leu Gly Asp Trp Phe Ala Tyr
            100                 105                 110

Trp Gly Gln Gly Thr Leu Val Thr Val Ser Ser
        115                 120
```

<210> SEQ ID NO 259
<211> LENGTH: 107
<212> TYPE: PRT
<213> ORGANISM: Artificial Sequence
<220> FEATURE:
<223> OTHER INFORMATION: Synthetic Construct

<400> SEQUENCE: 259

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Pro Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Leu Trp Thr
                85                  90                  95

Phe Gly Gln Gly Thr Lys Val Glu Ile Lys Arg
            100                 105
```

<210> SEQ ID NO 260
<211> LENGTH: 450
<212> TYPE: PRT
<213> ORGANISM: Artificial Sequence
<220> FEATURE:
<223> OTHER INFORMATION: Synthetic Construct

<400> SEQUENCE: 260

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45
```

-continued

```
Trp Leu Ala Leu Ile Asp Trp Asp Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Leu Gly Asp Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```

```
<210> SEQ ID NO 261
<211> LENGTH: 213
<212> TYPE: PRT
<213> ORGANISM: Artificial Sequence
<220> FEATURE:
<223> OTHER INFORMATION: Synthetic Construct

<400> SEQUENCE: 261

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Pro Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Leu Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 262
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa =  F or Y
<220> FEATURE:
<221> NAME/KEY: VARIANT
<222> LOCATION: 4
<223> OTHER INFORMATION: Xaa = S or T
<220> FEATURE:
<221> NAME/KEY: VARIANT
<222> LOCATION: 5
<223> OTHER INFORMATION: Xaa = G, N, or S
<220> FEATURE:
<221> NAME/KEY: VARIANT
<222> LOCATION: 7
<223> OTHER INFORMATION: Xaa = A, G, or W

<400> SEQUENCE: 262

Xaa Thr Phe Xaa Xaa Tyr Xaa Ile His Trp Val
1               5                   10
```

<210> SEQ ID NO 263
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = S or T
<220> FEATURE:
<221> NAME/KEY: VARIANT
<222> LOCATION: 7
<223> OTHER INFORMATION: Xaa = H or Y
<220> FEATURE:
<221> NAME/KEY: VARIANT
<222> LOCATION: 8
<223> OTHER INFORMATION: Xaa = H or Y
<220> FEATURE:
<221> NAME/KEY: VARIANT
<222> LOCATION: 10
<223> OTHER INFORMATION: Xaa = A, D, G, N, S, or T

<400> SEQUENCE: 263

```
Tyr Ser Ile Xaa Ser Gly Xaa Xaa Trp Xaa Trp Ile
1               5                   10
```

<210> SEQ ID NO 264
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = G or S
<220> FEATURE:
<221> NAME/KEY: VARIANT
<222> LOCATION: 9
<223> OTHER INFORMATION: Xaa = A or G
<220> FEATURE:
<221> NAME/KEY: VARIANT
<222> LOCATION: 11
<223> OTHER INFORMATION: Xaa = A, G, S, or T

<400> SEQUENCE: 264

```
Phe Ser Leu Ser Thr Xaa Gly Val Xaa Val Xaa Trp Ile
1               5                   10
```

<210> SEQ ID NO 265
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = A, D, or Y
<220> FEATURE:
<221> NAME/KEY: VARIANT
<222> LOCATION: 8
<223> OTHER INFORMATION: Xaa = D or G
<220> FEATURE:
<221> NAME/KEY: VARIANT
<222> LOCATION: 11
<223> OTHER INFORMATION: Xaa = R, S, or Y
<220> FEATURE:
<221> NAME/KEY: VARIANT
<222> LOCATION: 14
<223> OTHER INFORMATION: Xaa = P or T

<400> SEQUENCE: 265

Leu Ala Leu Ile Asp Trp Xaa Xaa Asp Lys Xaa Tyr Ser Xaa Ser Leu
1 5 10 15

Lys Ser Arg Leu
20

<210> SEQ ID NO 266
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = D or E
<220> FEATURE:
<221> NAME/KEY: VARIANT
<222> LOCATION: 9
<223> OTHER INFORMATION: Xaa = N or S
<220> FEATURE:
<221> NAME/KEY: VARIANT
<222> LOCATION: 13
<223> OTHER INFORMATION: Xaa = N or S

<400> SEQUENCE: 266

Ile Gly Xaa Ile Tyr His Ser Gly Xaa Thr Tyr Tyr Xaa Pro Ser Leu
1 5 10 15

Lys Ser Arg Val
20

<210> SEQ ID NO 267
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = A, G, S, V, or Y
<220> FEATURE:
<221> NAME/KEY: VARIANT
<222> LOCATION: 7
<223> OTHER INFORMATION: Xaa = A, D, S, or Y
<220> FEATURE:
<221> NAME/KEY: VARIANT
<222> LOCATION: 9
<223> OTHER INFORMATION: Xaa = D, G, or S
<220> FEATURE:
<221> NAME/KEY: VARIANT
<222> LOCATION: 10
<223> OTHER INFORMATION: Xaa = S or T

<400> SEQUENCE: 267

Val Ser Xaa Ile Ser Gly Xaa Gly Xaa Xaa Thr Tyr Tyr Ala Asp Ser
1 5 10 15

Val Lys Gly Arg Phe
20

<210> SEQ ID NO 268
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = E or G
<220> FEATURE:
<221> NAME/KEY: VARIANT
<222> LOCATION: 5
<223> OTHER INFORMATION: Xaa = E or S
<220> FEATURE:
<221> NAME/KEY: VARIANT
<222> LOCATION: 6
<223> OTHER INFORMATION: Xaa = D or T
<220> FEATURE:
<221> NAME/KEY: VARIANT
<222> LOCATION: 7
<223> OTHER INFORMATION: Xaa = A, T, or V
<220> FEATURE:
<221> NAME/KEY: VARIANT
<222> LOCATION: 9
<223> OTHER INFORMATION: Xaa = A, I, L, T, or V
<220> FEATURE:
<221> NAME/KEY: VARIANT
<222> LOCATION: 14
<223> OTHER INFORMATION: Xaa = A, D, or G

<400> SEQUENCE: 268

Ala Arg Xaa Gly Xaa Xaa Xaa Val Xaa Gly Asp Trp Phe Xaa Tyr
1 5 10 15

<210> SEQ ID NO 269
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Q or R
<220> FEATURE:
<221> NAME/KEY: VARIANT
<222> LOCATION: 5
<223> OTHER INFORMATION: Xaa = D, G, or S
<220> FEATURE:
<221> NAME/KEY: VARIANT
<222> LOCATION: 6
<223> OTHER INFORMATION: Xaa = I or V
<220> FEATURE:
<221> NAME/KEY: VARIANT
<222> LOCATION: 7
<223> OTHER INFORMATION: Xaa = G, R, S, or T
<220> FEATURE:
<221> NAME/KEY: VARIANT
<222> LOCATION: 8
<223> OTHER INFORMATION: Xaa = P, R, S, or T
<220> FEATURE:
<221> NAME/KEY: VARIANT
<222> LOCATION: 9
<223> OTHER INFORMATION: Xaa = A, D, F, S, V, or Y
<220> FEATURE:
<221> NAME/KEY: VARIANT
<222> LOCATION: 10
<223> OTHER INFORMATION: Xaa = L or V
<220> FEATURE:
<221> NAME/KEY: VARIANT
<222> LOCATION: 11
<223> OTHER INFORMATION: Xaa = A, G, or N

<400> SEQUENCE: 269

Xaa Ala Ser Gln Xaa Xaa Xaa Xaa Xaa Xaa Xaa
1 5 10

<210> SEQ ID NO 270
<211> LENGTH: 9
<212> TYPE: PRT
<213> ORGANISM: Artificial Sequence
<220> FEATURE:
<223> OTHER INFORMATION: Synthetic Construct
<220> FEATURE:

<221> NAME/KEY: VARIANT
<222> LOCATION: 1
<223> OTHER INFORMATION: Xaa = A or D
<220> FEATURE:
<221> NAME/KEY: VARIANT
<222> LOCATION: 4
<223> OTHER INFORMATION: Xaa = N, S, or T
<220> FEATURE:
<221> NAME/KEY: VARIANT
<222> LOCATION: 5
<223> OTHER INFORMATION: Xaa = L or R
<220> FEATURE:
<221> NAME/KEY: VARIANT
<222> LOCATION: 6
<223> OTHER INFORMATION: Xaa = A, E, or Q
<220> FEATURE:
<221> NAME/KEY: VARIANT
<222> LOCATION: 7
<223> OTHER INFORMATION: Xaa = S or T
<220> FEATURE:
<221> NAME/KEY: VARIANT
<222> LOCATION: 9
<223> OTHER INFORMATION: Xaa = I or V

<400> SEQUENCE: 270

Xaa Ala Ser Xaa Xaa Xaa Xaa Gly Xaa
1               5

<210> SEQ ID NO 271
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = A, G, S, or Y
<220> FEATURE:
<221> NAME/KEY: VARIANT
<222> LOCATION: 7
<223> OTHER INFORMATION: Xaa = Q, S, or Y
<220> FEATURE:
<221> NAME/KEY: VARIANT
<222> LOCATION: 8
<223> OTHER INFORMATION: Xaa = I, L, T, or Y
<220> FEATURE:
<221> NAME/KEY: VARIANT
<222> LOCATION: 9
<223> OTHER INFORMATION: Xaa = I, S, V, or W

<400> SEQUENCE: 271

Tyr Cys Gln Gln Xaa Tyr Xaa Xaa Xaa Thr
1               5                   10

<210> SEQ ID NO 272
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = E or Q
<220> FEATURE:
<221> NAME/KEY: VARIANT
<222> LOCATION: 5
<223> OTHER INFORMATION: Xaa = P, S, or Y
<220> FEATURE:
<221> NAME/KEY: VARIANT
<222> LOCATION: 6
<223> OTHER INFORMATION: Xaa = D, L, S, T, or Y
<220> FEATURE:
<221> NAME/KEY: VARIANT
<222> LOCATION: 7
<223> OTHER INFORMATION: Xaa = D, E, H, S, or T
<220> FEATURE:
<221> NAME/KEY: VARIANT
<222> LOCATION: 8
<223> OTHER INFORMATION: Xaa = D, L T, or W
<220> FEATURE:
<221> NAME/KEY: VARIANT
<222> LOCATION: 10
<223> OTHER INFORMATION: Xaa = L, P, R, or V

<400> SEQUENCE: 272

Tyr Cys Xaa Gln Xaa Xaa Xaa Xaa Pro Xaa Thr
1 5 10

<210> SEQ ID NO 273
<211> LENGTH: 163
<212> TYPE: PRT
<213> ORGANISM: Artificial Sequence
<220> FEATURE:
<223> OTHER INFORMATION: Synthetic Construct

<400> SEQUENCE: 273

Leu Gln Asp Pro Cys Ser Asn Cys Pro Ala Gly Thr Phe Cys Asp Asn
1 5 10 15

Asn Arg Asn Gln Ile Cys Ser Pro Cys Pro Pro Asn Ser Phe Ser Ser
20 25 30

Ala Gly Gly Gln Arg Thr Cys Asp Ile Cys Arg Gln Cys Lys Gly Val
35 40 45

Phe Arg Thr Arg Lys Glu Cys Ser Ser Thr Ser Asn Ala Glu Cys Asp
50 55 60

Cys Thr Pro Gly Phe His Cys Leu Gly Ala Gly Cys Ser Met Cys Glu
65 70 75 80

Gln Asp Cys Lys Gln Gly Gln Glu Leu Thr Lys Lys Gly Cys Lys Asp
85 90 95

Cys Cys Phe Gly Thr Phe Asn Asp Gln Lys Arg Gly Ile Cys Arg Pro
100 105 110

Trp Thr Asn Cys Ser Leu Asp Gly Lys Ser Val Leu Val Asn Gly Thr
115 120 125

Lys Glu Arg Asp Val Val Cys Gly Pro Ser Pro Ala Asp Leu Ser Pro
130 135 140

Gly Ala Ser Ser Val Thr Pro Pro Ala Pro Ala Arg Glu Pro Gly His
145 150 155 160

Ser Pro Gln

<210> SEQ ID NO 274
<211> LENGTH: 762
<212> TYPE: DNA
<213> ORGANISM: Artificial Sequence
<220> FEATURE:
<223> OTHER INFORMATION: Synthetic Construct

<400> SEQUENCE: 274
atggaatacg cctctgacgc ttcactggac cccgaagccc cgtggcctcc cgcgccccgc 60
gctcgcgcct gccgcgtact gccttgggcc ctggtcgcgg ggctgctgct gctgctgctg 120
ctcgctgccg cctgcgccgt cttcctcgcc tgcccctggg ccgtgtccgg ggctcgcgcc 180
tcgcccggct ccgcggccag cccgagactc cgcgagggtc ccgagctttc gcccgacgat 240
cccgccggcc tcttggacct gcggcagggc atgtttgcgc agctggtggc ccaaaatgtt 300
ctgctgatcg atgggcccct gagctggtac agtgacccag gcctggcagg cgtgtccctg 360

```
acggggggcc tgagctacaa agaggacacg aaggagctgg tggtggccaa ggctggagtc    420

tactatgtct tctttcaact agagctgcgg cgcgtggtgg ccggcgaggg ctcaggctcc    480

gtttcacttg cgctgcacct gcagccactg cgctctgctg ctggggccgc cgccctggct    540

ttgaccgtgg acctgccacc cgcctcctcc gaggctcgga actcggcctt cggtttccag    600

ggccgcttgc tgcacctgag tgccggccag cgcctgggcg tccatcttca cactgaggcc    660

agggcacgcc atgcctggca gcttacccag ggcgccacag tcttgggact cttccgggtg    720

acccccgaaa tcccagccgg actcccttca ccgaggtcgg aa                       762
```

```
<210> SEQ ID NO 275
<211> LENGTH: 254
<212> TYPE: PRT
<213> ORGANISM: Artificial Sequence
<220> FEATURE:
<223> OTHER INFORMATION: Synthetic Construct

<400> SEQUENCE: 275

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250


<210> SEQ ID NO 276
<211> LENGTH: 289
<212> TYPE: PRT
<213> ORGANISM: Artificial Sequence
<220> FEATURE:
```

<223> OTHER INFORMATION: Synthetic Construct

<400> SEQUENCE: 276

Met Arg Ile Phe Ala Val Phe Ile Phe Met Thr Tyr Trp His Leu Leu
1 5 10 15

Asn Ala Phe Thr Val Thr Val Pro Lys Asp Leu Tyr Val Val Glu Tyr
20 25 30

Gly Ser Asn Met Thr Ile Glu Cys Lys Phe Pro Val Glu Lys Gln Leu
35 40 45

Asp Leu Ala Ala Leu Ile Val Tyr Trp Glu Met Glu Asp Lys Asn Ile
50 55 60

Ile Gln Phe Val His Gly Glu Asp Leu Lys Val Gln His Ser Ser Tyr
65 70 75 80

Arg Gln Arg Ala Arg Leu Leu Lys Asp Gln Leu Ser Leu Gly Asn Ala
85 90 95

Ala Leu Gln Ile Thr Asp Val Lys Leu Gln Asp Ala Gly Val Tyr Arg
100 105 110

Cys Met Ile Ser Tyr Gly Gly Ala Asp Tyr Lys Arg Ile Thr Val Lys
115 120 125

Val Asn Ala Pro Tyr Asn Lys Ile Asn Gln Arg Ile Leu Val Val Asp
130 135 140

Pro Val Thr Ser Glu His Glu Leu Thr Cys Gln Ala Glu Gly Tyr Pro
145 150 155 160

Lys Ala Glu Val Ile Trp Thr Ser Ser Asp His Gln Val Leu Ser Gly
165 170 175

Lys Thr Thr Thr Thr Asn Ser Lys Arg Glu Glu Lys Leu Phe Asn Val
180 185 190

Thr Ser Thr Leu Arg Ile Asn Thr Thr Thr Asn Glu Ile Phe Tyr Cys
195 200 205

Thr Phe Arg Arg Leu Asp Pro Glu Glu Asn His Thr Ala Glu Leu Val
210 215 220

Ile Pro Glu Leu Pro Leu Ala His Pro Pro Asn Glu Arg Thr His Leu
225 230 235 240

Val Ile Leu Gly Ala Ile Leu Leu Cys Leu Gly Val Ala Leu Thr Phe
245 250 255

Ile Phe Arg Leu Arg Lys Gly Arg Met Met Asp Val Lys Lys Cys Gly
260 265 270

Ile Gln Asp Thr Asn Ser Lys Lys Gln Ser Asp Thr His Leu Glu Glu
275 280 285

Thr

<210> SEQ ID NO 277
<211> LENGTH: 3256
<212> TYPE: PRT
<213> ORGANISM: Artificial Sequence
<220> FEATURE:
<223> OTHER INFORMATION: Synthetic Construct

<400> SEQUENCE: 277

Met Trp Pro Thr Arg Arg Leu Val Thr Ile Lys Arg Ser Gly Val Asp
1 5 10 15

Gly Pro His Phe Pro Leu Ser Leu Ser Thr Cys Leu Phe Gly Arg Gly
20 25 30

Ile Glu Cys Asp Ile Arg Ile Gln Leu Pro Val Val Ser Lys Gln His
35 40 45

```
Cys Lys Ile Glu Ile His Glu Gln Glu Ala Ile Leu His Asn Phe Ser
    50                  55                  60

Ser Thr Asn Pro Thr Gln Val Asn Gly Ser Val Ile Asp Glu Pro Val
65                  70                  75                  80

Arg Leu Lys His Gly Asp Val Ile Thr Ile Ile Asp Arg Ser Phe Arg
                85                  90                  95

Tyr Glu Asn Glu Ser Leu Gln Asn Gly Arg Lys Ser Thr Glu Phe Pro
            100                 105                 110

Arg Lys Ile Arg Glu Gln Glu Pro Ala Arg Arg Val Ser Arg Ser Ser
        115                 120                 125

Phe Ser Ser Asp Pro Asp Glu Lys Ala Gln Asp Ser Lys Ala Tyr Ser
    130                 135                 140

Lys Ile Thr Glu Gly Lys Val Ser Gly Asn Pro Gln Val His Ile Lys
145                 150                 155                 160

Asn Val Lys Glu Asp Ser Thr Ala Asp Asp Ser Lys Asp Ser Val Ala
                165                 170                 175

Gln Gly Thr Thr Asn Val His Ser Ser Glu His Ala Gly Arg Asn Gly
            180                 185                 190

Arg Asn Ala Ala Asp Pro Ile Ser Gly Asp Phe Lys Glu Ile Ser Ser
        195                 200                 205

Val Lys Leu Val Ser Arg Tyr Gly Glu Leu Lys Ser Val Pro Thr Thr
    210                 215                 220

Gln Cys Leu Asp Asn Ser Lys Lys Asn Glu Ser Pro Phe Trp Lys Leu
225                 230                 235                 240

Tyr Glu Ser Val Lys Lys Glu Leu Asp Val Lys Ser Gln Lys Glu Asn
                245                 250                 255

Val Leu Gln Tyr Cys Arg Lys Ser Gly Leu Gln Thr Asp Tyr Ala Thr
            260                 265                 270

Glu Lys Glu Ser Ala Asp Gly Leu Gln Gly Glu Thr Gln Leu Leu Val
        275                 280                 285

Ser Arg Lys Ser Arg Pro Lys Ser Gly Gly Ser Gly His Ala Val Ala
    290                 295                 300

Glu Pro Ala Ser Pro Glu Gln Glu Leu Asp Gln Asn Lys Gly Lys Gly
305                 310                 315                 320

Arg Asp Val Glu Ser Val Gln Thr Pro Ser Lys Ala Val Gly Ala Ser
                325                 330                 335

Phe Pro Leu Tyr Glu Pro Ala Lys Met Lys Thr Pro Val Gln Tyr Ser
            340                 345                 350

Gln Gln Gln Asn Ser Pro Gln Lys His Lys Asn Lys Asp Leu Tyr Thr
        355                 360                 365

Thr Gly Arg Arg Glu Ser Val Asn Leu Gly Lys Ser Glu Gly Phe Lys
    370                 375                 380

Ala Gly Asp Lys Thr Leu Thr Pro Arg Lys Leu Ser Thr Arg Asn Arg
385                 390                 395                 400

Thr Pro Ala Lys Val Glu Asp Ala Ala Asp Ser Ala Thr Lys Pro Glu
                405                 410                 415

Asn Leu Ser Ser Lys Thr Arg Gly Ser Ile Pro Thr Asp Val Glu Val
            420                 425                 430

Leu Pro Thr Glu Thr Glu Ile His Asn Glu Pro Phe Leu Thr Leu Trp
        435                 440                 445

Leu Thr Gln Val Glu Arg Lys Ile Gln Lys Asp Ser Leu Ser Lys Pro
    450                 455                 460

Glu Lys Leu Gly Thr Thr Ala Gly Gln Met Cys Ser Gly Leu Pro Gly
```

-continued

```
465                 470                 475                 480

Leu Ser Ser Val Asp Ile Asn Asn Phe Gly Asp Ser Ile Asn Glu Ser
                485                 490                 495

Glu Gly Ile Pro Leu Lys Arg Arg Arg Val Ser Phe Gly Gly His Leu
            500                 505                 510

Arg Pro Glu Leu Phe Asp Glu Asn Leu Pro Pro Asn Thr Pro Leu Lys
        515                 520                 525

Arg Gly Glu Ala Pro Thr Lys Arg Lys Ser Leu Val Met His Thr Pro
    530                 535                 540

Pro Val Leu Lys Lys Ile Ile Lys Glu Gln Pro Gln Pro Ser Gly Lys
545                 550                 555                 560

Gln Glu Ser Gly Ser Glu Ile His Val Glu Val Lys Ala Gln Ser Leu
                565                 570                 575

Val Ile Ser Pro Pro Ala Pro Ser Pro Arg Lys Thr Pro Val Ala Ser
            580                 585                 590

Asp Gln Arg Arg Arg Ser Cys Lys Thr Ala Pro Ala Ser Ser Ser Lys
        595                 600                 605

Ser Gln Thr Glu Val Pro Lys Arg Gly Gly Arg Lys Ser Gly Asn Leu
    610                 615                 620

Pro Ser Lys Arg Val Ser Ile Ser Arg Ser Gln His Asp Ile Leu Gln
625                 630                 635                 640

Met Ile Cys Ser Lys Arg Arg Ser Gly Ala Ser Glu Ala Asn Leu Ile
                645                 650                 655

Val Ala Lys Ser Trp Ala Asp Val Val Lys Leu Gly Ala Lys Gln Thr
            660                 665                 670

Gln Thr Lys Val Ile Lys His Gly Pro Gln Arg Ser Met Asn Lys Arg
        675                 680                 685

Gln Arg Arg Pro Ala Thr Pro Lys Lys Pro Val Gly Glu Val His Ser
    690                 695                 700

Gln Phe Ser Thr Gly His Ala Asn Ser Pro Cys Thr Ile Ile Ile Gly
705                 710                 715                 720

Lys Ala His Thr Glu Lys Val His Val Pro Ala Arg Pro Tyr Arg Val
                725                 730                 735

Leu Asn Asn Phe Ile Ser Asn Gln Lys Met Asp Phe Lys Glu Asp Leu
            740                 745                 750

Ser Gly Ile Ala Glu Met Phe Lys Thr Pro Val Lys Glu Gln Pro Gln
        755                 760                 765

Leu Thr Ser Thr Cys His Ile Ala Ile Ser Asn Ser Glu Asn Leu Leu
    770                 775                 780

Gly Lys Gln Phe Gln Gly Thr Asp Ser Gly Glu Glu Pro Leu Leu Pro
785                 790                 795                 800

Thr Ser Glu Ser Phe Gly Gly Asn Val Phe Phe Ser Ala Gln Asn Ala
                805                 810                 815

Ala Lys Gln Pro Ser Asp Lys Cys Ser Ala Ser Pro Pro Leu Arg Arg
            820                 825                 830

Gln Cys Ile Arg Glu Asn Gly Asn Val Ala Lys Thr Pro Arg Asn Thr
        835                 840                 845

Tyr Lys Met Thr Ser Leu Glu Thr Lys Thr Ser Asp Thr Glu Thr Glu
    850                 855                 860

Pro Ser Lys Thr Val Ser Thr Ala Asn Arg Ser Gly Arg Ser Thr Glu
865                 870                 875                 880

Phe Arg Asn Ile Gln Lys Leu Pro Val Glu Ser Lys Ser Glu Glu Thr
                885                 890                 895
```

```
Asn Thr Glu Ile Val Glu Cys Ile Leu Lys Arg Gly Gln Lys Ala Thr
            900                 905                 910

Leu Leu Gln Gln Arg Arg Glu Gly Glu Met Lys Glu Ile Glu Arg Pro
        915                 920                 925

Phe Glu Thr Tyr Lys Glu Asn Ile Glu Leu Lys Glu Asn Asp Glu Lys
    930                 935                 940

Met Lys Ala Met Lys Arg Ser Arg Thr Trp Gly Gln Lys Cys Ala Pro
945                 950                 955                 960

Met Ser Asp Leu Thr Asp Leu Lys Ser Leu Pro Asp Thr Glu Leu Met
                965                 970                 975

Lys Asp Thr Ala Arg Gly Gln Asn Leu Leu Gln Thr Gln Asp His Ala
            980                 985                 990

Lys Ala Pro Lys Ser Glu Lys Gly Lys Ile Thr Lys Met Pro Cys Gln
        995                 1000                1005

Ser Leu Gln Pro Glu Pro Ile Asn Thr Pro Thr His Thr Lys Gln Gln
    1010                1015                1020

Leu Lys Ala Ser Leu Gly Lys Val Gly Val Lys Glu Glu Leu Leu Ala
1025                1030                1035                1040

Val Gly Lys Phe Thr Arg Thr Ser Gly Glu Thr Thr His Thr His Arg
                1045                1050                1055

Glu Pro Ala Gly Asp Gly Lys Ser Ile Arg Thr Phe Lys Glu Ser Pro
            1060                1065                1070

Lys Gln Ile Leu Asp Pro Ala Ala Arg Val Thr Gly Met Lys Lys Trp
        1075                1080                1085

Pro Arg Thr Pro Lys Glu Glu Ala Gln Ser Leu Glu Asp Leu Ala Gly
    1090                1095                1100

Phe Lys Glu Leu Phe Gln Thr Pro Gly Pro Ser Glu Glu Ser Met Thr
1105                1110                1115                1120

Asp Glu Lys Thr Thr Lys Ile Ala Cys Lys Ser Pro Pro Pro Glu Ser
                1125                1130                1135

Val Asp Thr Pro Thr Ser Thr Lys Gln Trp Pro Lys Arg Ser Leu Arg
            1140                1145                1150

Lys Ala Asp Val Glu Glu Glu Phe Leu Ala Leu Arg Lys Leu Thr Pro
        1155                1160                1165

Ser Ala Gly Lys Ala Met Leu Thr Pro Lys Pro Ala Gly Gly Asp Glu
    1170                1175                1180

Lys Asp Ile Lys Ala Phe Met Gly Thr Pro Val Gln Lys Leu Asp Leu
1185                1190                1195                1200

Ala Gly Thr Leu Pro Gly Ser Lys Arg Gln Leu Gln Thr Pro Lys Glu
                1205                1210                1215

Lys Ala Gln Ala Leu Glu Asp Leu Ala Gly Phe Lys Glu Leu Phe Gln
            1220                1225                1230

Thr Pro Gly His Thr Glu Glu Leu Val Ala Ala Gly Lys Thr Thr Lys
        1235                1240                1245

Ile Pro Cys Asp Ser Pro Gln Ser Asp Pro Val Asp Thr Pro Thr Ser
    1250                1255                1260

Thr Lys Gln Arg Pro Lys Arg Ser Ile Arg Lys Ala Asp Val Glu Gly
1265                1270                1275                1280

Glu Leu Leu Ala Cys Arg Asn Leu Met Pro Ser Ala Gly Lys Ala Met
                1285                1290                1295

His Thr Pro Lys Pro Ser Val Gly Glu Glu Lys Asp Ile Ile Ile Phe
            1300                1305                1310
```

-continued

```
Val Gly Thr Pro Val Gln Lys Leu Asp Leu Thr Glu Asn Leu Thr Gly
        1315                1320                1325

Ser Lys Arg Arg Pro Gln Thr Pro Lys Glu Glu Ala Gln Ala Leu Glu
    1330                1335                1340

Asp Leu Thr Gly Phe Lys Glu Leu Phe Gln Thr Pro Gly His Thr Glu
1345                1350                1355                1360

Glu Ala Val Ala Ala Gly Lys Thr Thr Lys Met Pro Cys Glu Ser Ser
                1365                1370                1375

Pro Pro Glu Ser Ala Asp Thr Pro Thr Ser Thr Arg Arg Gln Pro Lys
            1380                1385                1390

Thr Pro Leu Glu Lys Arg Asp Val Gln Lys Glu Leu Ser Ala Leu Lys
        1395                1400                1405

Lys Leu Thr Gln Thr Ser Gly Glu Thr Thr His Thr Asp Lys Val Pro
    1410                1415                1420

Gly Gly Glu Asp Lys Ser Ile Asn Ala Phe Arg Glu Thr Ala Lys Gln
1425                1430                1435                1440

Lys Leu Asp Pro Ala Ala Ser Val Thr Gly Ser Lys Arg His Pro Lys
                1445                1450                1455

Thr Lys Glu Lys Ala Gln Pro Leu Glu Asp Leu Ala Gly Leu Lys Glu
            1460                1465                1470

Leu Phe Gln Thr Pro Val Cys Thr Asp Lys Pro Thr Thr His Glu Lys
        1475                1480                1485

Thr Thr Lys Ile Ala Cys Arg Ser Gln Pro Asp Pro Val Asp Thr Pro
    1490                1495                1500

Thr Ser Ser Lys Pro Gln Ser Lys Arg Ser Leu Arg Lys Val Asp Val
1505                1510                1515                1520

Glu Glu Glu Phe Phe Ala Leu Arg Lys Arg Thr Pro Ser Ala Gly Lys
                1525                1530                1535

Ala Met His Thr Pro Lys Pro Ala Val Ser Gly Glu Lys Asn Ile Tyr
            1540                1545                1550

Ala Phe Met Gly Thr Pro Val Gln Lys Leu Asp Leu Thr Glu Asn Leu
        1555                1560                1565

Thr Gly Ser Lys Arg Arg Leu Gln Thr Pro Lys Glu Lys Ala Gln Ala
    1570                1575                1580

Leu Glu Asp Leu Ala Gly Phe Lys Glu Leu Phe Gln Thr Arg Gly His
1585                1590                1595                1600

Thr Glu Glu Ser Met Thr Asn Asp Lys Thr Ala Lys Val Ala Cys Lys
                1605                1610                1615

Ser Ser Gln Pro Asp Pro Asp Lys Asn Pro Ala Ser Ser Lys Arg Arg
            1620                1625                1630

Leu Lys Thr Ser Leu Gly Lys Val Gly Val Lys Glu Glu Leu Leu Ala
        1635                1640                1645

Val Gly Lys Leu Thr Gln Thr Ser Gly Glu Thr Thr His Thr His Thr
    1650                1655                1660

Glu Pro Thr Gly Asp Gly Lys Ser Met Lys Ala Phe Met Glu Ser Pro
1665                1670                1675                1680

Lys Gln Ile Leu Asp Ser Ala Ala Ser Leu Thr Gly Ser Lys Arg Gln
                1685                1690                1695

Leu Arg Thr Pro Lys Gly Lys Ser Glu Val Pro Glu Asp Leu Ala Gly
            1700                1705                1710

Phe Ile Glu Leu Phe Gln Thr Pro Ser His Thr Lys Glu Ser Met Thr
        1715                1720                1725

Asn Glu Lys Thr Thr Lys Val Ser Tyr Arg Ala Ser Gln Pro Asp Leu
```

```
    1730                1735                1740

Val Asp Thr Pro Thr Ser Ser Lys Pro Gln Pro Lys Arg Ser Leu Arg
1745                1750                1755                1760

Lys Ala Asp Thr Glu Glu Glu Phe Leu Ala Phe Arg Lys Gln Thr Pro
                1765                1770                1775

Ser Ala Gly Lys Ala Met His Thr Pro Lys Pro Ala Val Gly Glu Glu
            1780                1785                1790

Lys Asp Ile Asn Thr Phe Leu Gly Thr Pro Val Gln Lys Leu Asp Gln
        1795                1800                1805

Pro Gly Asn Leu Pro Gly Ser Asn Arg Arg Leu Gln Thr Arg Lys Glu
    1810                1815                1820

Lys Ala Gln Ala Leu Glu Glu Leu Thr Gly Phe Arg Glu Leu Phe Gln
1825                1830                1835                1840

Thr Pro Cys Thr Asp Asn Pro Thr Thr Asp Glu Lys Thr Thr Lys Lys
                1845                1850                1855

Ile Leu Cys Lys Ser Pro Gln Ser Asp Pro Ala Asp Thr Pro Thr Asn
            1860                1865                1870

Thr Lys Gln Arg Pro Lys Arg Ser Leu Lys Lys Ala Asp Val Glu Glu
        1875                1880                1885

Glu Phe Leu Ala Phe Arg Lys Leu Thr Pro Ser Ala Gly Lys Ala Met
    1890                1895                1900

His Thr Pro Lys Ala Ala Val Gly Glu Glu Lys Asp Ile Asn Thr Phe
1905                1910                1915                1920

Val Gly Thr Pro Val Glu Lys Leu Asp Leu Leu Gly Asn Leu Pro Gly
                1925                1930                1935

Ser Lys Arg Arg Pro Gln Thr Pro Lys Glu Lys Ala Lys Ala Leu Glu
            1940                1945                1950

Asp Leu Ala Gly Phe Lys Glu Leu Phe Gln Thr Pro Gly His Thr Glu
        1955                1960                1965

Glu Ser Met Thr Asp Asp Lys Ile Thr Glu Val Ser Cys Lys Ser Pro
    1970                1975                1980

Gln Pro Asp Pro Val Lys Thr Pro Thr Ser Ser Lys Gln Arg Leu Lys
1985                1990                1995                2000

Ile Ser Leu Gly Lys Val Gly Val Lys Glu Glu Val Leu Pro Val Gly
                2005                2010                2015

Lys Leu Thr Gln Thr Ser Gly Lys Thr Thr Gln Thr His Arg Glu Thr
            2020                2025                2030

Ala Gly Asp Gly Lys Ser Ile Lys Ala Phe Lys Glu Ser Ala Lys Gln
        2035                2040                2045

Met Leu Asp Pro Ala Asn Tyr Gly Thr Gly Met Glu Arg Trp Pro Arg
    2050                2055                2060

Thr Pro Lys Glu Glu Ala Gln Ser Leu Glu Asp Leu Ala Gly Phe Lys
2065                2070                2075                2080

Glu Leu Phe Gln Thr Pro Asp His Thr Glu Glu Ser Thr Thr Asp Asp
                2085                2090                2095

Lys Thr Thr Lys Ile Ala Cys Lys Ser Pro Pro Pro Glu Ser Met Asp
            2100                2105                2110

Thr Pro Thr Ser Thr Arg Arg Arg Pro Lys Thr Pro Leu Gly Lys Arg
        2115                2120                2125

Asp Ile Val Glu Glu Leu Ser Ala Leu Lys Gln Leu Thr Gln Thr Thr
    2130                2135                2140

His Thr Asp Lys Val Pro Gly Asp Glu Asp Lys Gly Ile Asn Val Phe
2145                2150                2155                2160
```

-continued

```
Arg Glu Thr Ala Lys Gln Lys Leu Asp Pro Ala Ala Ser Val Thr Gly
                2165                2170                2175

Ser Lys Arg Gln Pro Arg Thr Pro Lys Gly Lys Ala Gln Pro Leu Glu
            2180                2185                2190

Asp Leu Ala Gly Leu Lys Glu Leu Phe Gln Thr Pro Ile Cys Thr Asp
        2195                2200                2205

Lys Pro Thr Thr His Glu Lys Thr Thr Lys Ile Ala Cys Arg Ser Pro
    2210                2215                2220

Gln Pro Asp Pro Val Gly Thr Pro Thr Ile Phe Lys Pro Gln Ser Lys
2225                2230                2235                2240

Arg Ser Leu Arg Lys Ala Asp Val Glu Glu Glu Ser Leu Ala Leu Arg
                2245                2250                2255

Lys Arg Thr Pro Ser Val Gly Lys Ala Met Asp Thr Pro Lys Pro Ala
            2260                2265                2270

Gly Gly Asp Glu Lys Asp Met Lys Ala Phe Met Gly Thr Pro Val Gln
        2275                2280                2285

Lys Leu Asp Leu Pro Gly Asn Leu Pro Gly Ser Lys Arg Trp Pro Gln
    2290                2295                2300

Thr Pro Lys Glu Lys Ala Gln Ala Leu Glu Asp Leu Ala Gly Phe Lys
2305                2310                2315                2320

Glu Leu Phe Gln Thr Pro Gly Thr Asp Lys Pro Thr Thr Asp Glu Lys
                2325                2330                2335

Thr Thr Lys Ile Ala Cys Lys Ser Pro Gln Pro Asp Pro Val Asp Thr
            2340                2345                2350

Pro Ala Ser Thr Lys Gln Arg Pro Lys Arg Asn Leu Arg Lys Ala Asp
        2355                2360                2365

Val Glu Glu Glu Phe Leu Ala Leu Arg Lys Arg Thr Pro Ser Ala Gly
    2370                2375                2380

Lys Ala Met Asp Thr Pro Lys Pro Ala Val Ser Asp Glu Lys Asn Ile
2385                2390                2395                2400

Asn Thr Phe Val Glu Thr Pro Val Gln Lys Leu Asp Leu Leu Gly Asn
                2405                2410                2415

Leu Pro Gly Ser Lys Arg Gln Pro Gln Thr Pro Lys Glu Lys Ala Glu
            2420                2425                2430

Ala Leu Glu Asp Leu Val Gly Phe Lys Glu Leu Phe Gln Thr Pro Gly
        2435                2440                2445

His Thr Glu Glu Ser Met Thr Asp Asp Lys Ile Thr Glu Val Ser Cys
    2450                2455                2460

Lys Ser Pro Gln Pro Glu Ser Phe Lys Thr Ser Arg Ser Ser Lys Gln
2465                2470                2475                2480

Arg Leu Lys Ile Pro Leu Val Lys Val Asp Met Lys Glu Glu Pro Leu
                2485                2490                2495

Ala Val Ser Lys Leu Thr Arg Thr Ser Gly Glu Thr Thr Gln Thr His
            2500                2505                2510

Thr Glu Pro Thr Gly Asp Ser Lys Ser Ile Lys Ala Phe Lys Glu Ser
        2515                2520                2525

Pro Lys Gln Ile Leu Asp Pro Ala Ala Ser Val Thr Gly Ser Arg Arg
    2530                2535                2540

Gln Leu Arg Thr Arg Lys Glu Lys Ala Arg Ala Leu Glu Asp Leu Val
2545                2550                2555                2560

Asp Phe Lys Glu Leu Phe Ser Ala Pro Gly His Thr Glu Glu Ser Met
                2565                2570                2575
```

-continued

```
Thr Ile Asp Lys Asn Thr Lys Ile Pro Cys Lys Ser Pro Pro Pro Glu
            2580                2585                2590

Leu Thr Asp Thr Ala Thr Ser Thr Lys Arg Cys Pro Lys Thr Arg Pro
        2595                2600                2605

Arg Lys Glu Val Lys Glu Glu Leu Ser Ala Val Glu Arg Leu Thr Gln
    2610                2615                2620

Thr Ser Gly Gln Ser Thr His Thr His Lys Glu Pro Ala Ser Gly Asp
2625                2630                2635                2640

Glu Gly Ile Lys Val Leu Lys Gln Arg Ala Lys Lys Lys Pro Asn Pro
                2645                2650                2655

Val Glu Glu Glu Pro Ser Arg Arg Arg Pro Arg Ala Pro Lys Glu Lys
            2660                2665                2670

Ala Gln Pro Leu Glu Asp Leu Ala Gly Phe Thr Glu Leu Ser Glu Thr
        2675                2680                2685

Ser Gly His Thr Gln Glu Ser Leu Thr Ala Gly Lys Ala Thr Lys Ile
    2690                2695                2700

Pro Cys Glu Ser Pro Pro Leu Glu Val Val Asp Thr Thr Ala Ser Thr
2705                2710                2715                2720

Lys Arg His Leu Arg Thr Arg Val Gln Lys Val Gln Val Lys Glu Glu
                2725                2730                2735

Pro Ser Ala Val Lys Phe Thr Gln Thr Ser Gly Glu Thr Thr Asp Ala
            2740                2745                2750

Asp Lys Glu Pro Ala Gly Glu Asp Lys Gly Ile Lys Ala Leu Lys Glu
        2755                2760                2765

Ser Ala Lys Gln Thr Pro Ala Pro Ala Ala Ser Val Thr Gly Ser Arg
    2770                2775                2780

Arg Arg Pro Arg Ala Pro Arg Glu Ser Ala Gln Ala Ile Glu Asp Leu
2785                2790                2795                2800

Ala Gly Phe Lys Asp Pro Ala Ala Gly His Thr Glu Glu Ser Met Thr
                2805                2810                2815

Asp Asp Lys Thr Thr Lys Ile Pro Cys Lys Ser Ser Pro Glu Leu Glu
            2820                2825                2830

Asp Thr Ala Thr Ser Ser Lys Arg Arg Pro Arg Thr Arg Ala Gln Lys
        2835                2840                2845

Val Glu Val Lys Glu Glu Leu Leu Ala Val Gly Lys Leu Thr Gln Thr
    2850                2855                2860

Ser Gly Glu Thr Thr His Thr Asp Lys Glu Pro Val Gly Glu Gly Lys
2865                2870                2875                2880

Gly Thr Lys Ala Phe Lys Gln Pro Ala Lys Arg Lys Leu Asp Ala Glu
                2885                2890                2895

Asp Val Ile Gly Ser Arg Arg Gln Pro Arg Ala Pro Lys Glu Lys Ala
            2900                2905                2910

Gln Pro Leu Glu Asp Leu Ala Ser Phe Gln Glu Leu Ser Gln Thr Pro
        2915                2920                2925

Gly His Thr Glu Glu Leu Ala Asn Gly Ala Ala Asp Ser Phe Thr Ser
    2930                2935                2940

Ala Pro Lys Gln Thr Pro Asp Ser Gly Lys Pro Leu Lys Ile Ser Arg
2945                2950                2955                2960

Arg Val Leu Arg Ala Pro Lys Val Glu Pro Val Gly Asp Val Val Ser
                2965                2970                2975

Thr Arg Asp Pro Val Lys Ser Gln Ser Lys Ser Asn Thr Ser Leu Pro
            2980                2985                2990

Pro Leu Pro Phe Lys Arg Gly Gly Gly Lys Asp Gly Ser Val Thr Gly
```

```
        2995                3000                3005

Thr Lys Arg Leu Arg Cys Met Pro Ala Pro Glu Glu Ile Val Glu Glu
    3010                3015                3020

Leu Pro Ala Ser Lys Lys Gln Arg Val Ala Pro Arg Ala Arg Gly Lys
3025                3030                3035                3040

Ser Ser Glu Pro Val Val Ile Met Lys Arg Ser Leu Arg Thr Ser Ala
                3045                3050                3055

Lys Arg Ile Glu Pro Ala Glu Glu Leu Asn Ser Asn Asp Met Lys Thr
            3060                3065                3070

Asn Lys Glu Glu His Lys Leu Gln Asp Ser Val Pro Glu Asn Lys Gly
        3075                3080                3085

Ile Ser Leu Arg Ser Arg Arg Gln Asn Lys Thr Glu Ala Glu Gln Gln
    3090                3095                3100

Ile Thr Glu Val Phe Val Leu Ala Glu Arg Ile Glu Ile Asn Arg Asn
3105                3110                3115                3120

Glu Lys Lys Pro Met Lys Thr Ser Pro Glu Met Asp Ile Gln Asn Pro
                3125                3130                3135

Asp Asp Gly Ala Arg Lys Pro Ile Pro Arg Asp Lys Val Thr Glu Asn
            3140                3145                3150

Lys Arg Cys Leu Arg Ser Ala Arg Gln Asn Glu Ser Ser Gln Pro Lys
        3155                3160                3165

Val Ala Glu Glu Ser Gly Gly Gln Lys Ser Ala Lys Val Leu Met Gln
    3170                3175                3180

Asn Gln Lys Gly Lys Gly Glu Ala Gly Asn Ser Asp Ser Met Cys Leu
3185                3190                3195                3200

Arg Ser Arg Lys Thr Lys Ser Gln Pro Ala Ala Ser Thr Leu Glu Ser
                3205                3210                3215

Lys Ser Val Gln Arg Val Thr Arg Ser Val Lys Arg Cys Ala Glu Asn
            3220                3225                3230

Pro Lys Lys Ala Glu Asp Asn Val Cys Val Lys Lys Ile Arg Thr Arg
        3235                3240                3245

Ser His Arg Asp Ser Glu Asp Ile
    3250                3255
```

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286
<211> LENGTH: 10
<212> TYPE: PRT
<213> ORGANISM: Artificial Sequence
<220> FEATURE:
<223> OTHER INFORMATION: Synthetic Construct

<400> SEQUENCE: 286

Gly Phe Thr Phe Ser Asp Ser Trp Ile His
1               5                   10

<210> SEQ ID NO 287
<211> LENGTH: 17
<212> TYPE: PRT
<213> ORGANISM: Artificial Sequence
<220> FEATURE:
<223> OTHER INFORMATION: Synthetic Construct

<400> SEQUENCE: 287

Trp Ile Ser Pro Tyr Gly Gly Ser Thr Tyr Tyr Ala Asp Ser Val Lys
1               5                   10                  15

Gly

<210> SEQ ID NO 288
<211> LENGTH: 9
<212> TYPE: PRT
<213> ORGANISM: Artificial Sequence
<220> FEATURE:
<223> OTHER INFORMATION: Synthetic Construct

<400> SEQUENCE: 288

Arg His Trp Pro Gly Gly Phe Asp Tyr
1               5

<210> SEQ ID NO 289
<211> LENGTH: 11
<212> TYPE: PRT
<213> ORGANISM: Artificial Sequence
<220> FEATURE:
<223> OTHER INFORMATION: Synthetic Construct

<400> SEQUENCE: 289

Arg Ala Ser Gln Asp Val Ser Thr Ala Val Ala 1 5 10

<210> SEQ ID NO 290
<211> LENGTH: 7
<212> TYPE: PRT
<213> ORGANISM: Artificial Sequence
<220> FEATURE:
<223> OTHER INFORMATION: Synthetic Construct

<400> SEQUENCE: 290

Ser Ala Ser Phe Leu Tyr Ser
1 5

<210> SEQ ID NO 291
<211> LENGTH: 9
<212> TYPE: PRT
<213> ORGANISM: Artificial Sequence
<220> FEATURE:
<223> OTHER INFORMATION: Synthetic Construct

<400> SEQUENCE: 291

Gln Gln Tyr Leu Tyr His Pro Ala Thr
1 5

<210> SEQ ID NO 292
<211> LENGTH: 118
<212> TYPE: PRT
<213> ORGANISM: Artificial Sequence
<220> FEATURE:
<223> OTHER INFORMATION: Synthetic Construct

<400> SEQUENCE: 292

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Ser
20 25 30

Trp Ile His Trp Val Arg Gln Ala Pro Gly Lys Gly Leu Glu Trp Val
35 40 45

Ala Trp Ile Ser Pro Tyr Gly Gly Ser Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Arg His Trp Pro Gly Gly Phe Asp Tyr Trp Gly Gln Gly Thr
100 105 110

Leu Val Thr Val Ser Ser
115

<210> SEQ ID NO 293
<211> LENGTH: 110
<212> TYPE: PRT
<213> ORGANISM: Artificial Sequence
<220> FEATURE:
<223> OTHER INFORMATION: Synthetic Construct

<400> SEQUENCE: 293

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile

```
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val
            100                 105                 110


<210> SEQ ID NO 294
<211> LENGTH: 5
<212> TYPE: PRT
<213> ORGANISM: Artificial Sequence
<220> FEATURE:
<223> OTHER INFORMATION: Synthetic Construct

<400> SEQUENCE: 294

Thr Tyr Tyr Ile Ser
1               5


<210> SEQ ID NO 295
<211> LENGTH: 16
<212> TYPE: PRT
<213> ORGANISM: Artificial Sequence
<220> FEATURE:
<223> OTHER INFORMATION: Synthetic Construct

<400> SEQUENCE: 295

Tyr Ile Asn Met Gly Ser Gly Gly Thr Asn Tyr Asn Glu Lys Phe Lys
1               5                   10                  15


<210> SEQ ID NO 296
<211> LENGTH: 6
<212> TYPE: PRT
<213> ORGANISM: Artificial Sequence
<220> FEATURE:
<223> OTHER INFORMATION: Synthetic Construct

<400> SEQUENCE: 296

Ile Gly Tyr Phe Asp Tyr
1               5


<210> SEQ ID NO 297
<211> LENGTH: 16
<212> TYPE: PRT
<213> ORGANISM: Artificial Sequence
<220> FEATURE:
<223> OTHER INFORMATION: Synthetic Construct

<400> SEQUENCE: 297

Arg Ser Ser Gln Ser Leu Leu Asp Ser Asp Gly Gly Thr Tyr Leu Tyr
1               5                   10                  15


<210> SEQ ID NO 298
<211> LENGTH: 7
<212> TYPE: PRT
<213> ORGANISM: Artificial Sequence
<220> FEATURE:
<223> OTHER INFORMATION: Synthetic Construct

<400> SEQUENCE: 298

Leu Val Ser Thr Leu Gly Ser
1               5
```

<210> SEQ ID NO 299
<211> LENGTH: 9
<212> TYPE: PRT
<213> ORGANISM: Artificial Sequence
<220> FEATURE:
<223> OTHER INFORMATION: Synthetic Construct

<400> SEQUENCE: 299

Met Gln Leu Thr His Trp Pro Tyr Thr
1               5

<210> SEQ ID NO 300
<211> LENGTH: 115
<212> TYPE: PRT
<213> ORGANISM: Artificial Sequence
<220> FEATURE:
<223> OTHER INFORMATION: Synthetic Construct

<400> SEQUENCE: 300

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Thr Tyr
            20                  25                  30

Tyr Ile Ser Trp Val Arg Gln Ala Pro Gly Gln Gly Leu Glu Tyr Leu
        35                  40                  45

Gly Tyr Ile Asn Met Gly Ser Gly Gly Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Ile Gly Tyr Phe Asp Tyr Trp Gly Gln Gly Thr Met Val Thr
            100                 105                 110

Val Ser Ser
        115

<210> SEQ ID NO 301
<211> LENGTH: 112
<212> TYPE: PRT
<213> ORGANISM: Artificial Sequence
<220> FEATURE:
<223> OTHER INFORMATION: Synthetic Construct

<400> SEQUENCE: 301

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Gly Thr Tyr Leu Tyr Trp Phe Gln Gln Arg Pro Gly Gln Ser
        35                  40                  45

Pro Arg Arg Leu Ile Tyr Leu Val Ser Thr Leu Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Leu
                85                  90                  95

Thr His Trp Pro Tyr Thr Phe Gly Gln Gly Thr Lys Leu Glu Ile Lys
            100                 105                 110

<210> SEQ ID NO 302
<211> LENGTH: 28
<212> TYPE: PRT
<213> ORGANISM: Artificial Sequence
<220> FEATURE:
<223> OTHER INFORMATION: Synthetic Construct

<400> SEQUENCE: 302

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro
            20                  25
```

<210> SEQ ID NO 303
<211> LENGTH: 23
<212> TYPE: PRT
<213> ORGANISM: Artificial Sequence
<220> FEATURE:
<223> OTHER INFORMATION: Synthetic Construct

<400> SEQUENCE: 303

```
Met Glu Tyr Ala Ser Asp Ala Ser Leu Asp Pro Glu Ala Pro Trp Pro
1               5                   10                  15

Pro Ala Pro Arg Ala Arg Ala
            20
```

<210> SEQ ID NO 304
<211> LENGTH: 13
<212> TYPE: PRT
<213> ORGANISM: Artificial Sequence
<220> FEATURE:
<223> OTHER INFORMATION: Synthetic Construct

<400> SEQUENCE: 304

```
Phe Ser Leu Ser Thr Ser Gly Val Gly Val Ser Trp Ile
1               5                   10
```

<210> SEQ ID NO 305
<211> LENGTH: 20
<212> TYPE: PRT
<213> ORGANISM: Artificial Sequence
<220> FEATURE:
<223> OTHER INFORMATION: Synthetic Construct

<400> SEQUENCE: 305

```
Leu Ala Leu Ile Asp Trp Ala Gly Asp Lys Tyr Tyr Ser Pro Ser Leu
1               5                   10                  15

Lys Ser Arg Leu
            20
```

<210> SEQ ID NO 306
<211> LENGTH: 12
<212> TYPE: PRT
<213> ORGANISM: Artificial Sequence
<220> FEATURE:
<223> OTHER INFORMATION: Synthetic Construct

<400> SEQUENCE: 306

```
Ala Arg Tyr Gly Tyr Ser Ser Tyr Ala Leu Asp Tyr
1               5                   10
```

<210> SEQ ID NO 307
<211> LENGTH: 12
<212> TYPE: PRT
<213> ORGANISM: Artificial Sequence
<220> FEATURE:

<223> OTHER INFORMATION: Synthetic Construct

<400> SEQUENCE: 307

```
Arg Ala Ser Gln Ser Val Arg Gly Ser Tyr Leu Ala
1               5                   10
```

<210> SEQ ID NO 308
<211> LENGTH: 9
<212> TYPE: PRT
<213> ORGANISM: Artificial Sequence
<220> FEATURE:
<223> OTHER INFORMATION: Synthetic Construct

<400> SEQUENCE: 308

```
Ala Ala Ser Thr Leu Gln Ser Gly Val
1               5
```

<210> SEQ ID NO 309
<211> LENGTH: 10
<212> TYPE: PRT
<213> ORGANISM: Artificial Sequence
<220> FEATURE:
<223> OTHER INFORMATION: Synthetic Construct

<400> SEQUENCE: 309

```
Tyr Cys Gln Gln Tyr Ser Ser Leu Trp Thr
1               5                   10
```

<210> SEQ ID NO 310
<211> LENGTH: 120
<212> TYPE: PRT
<213> ORGANISM: Artificial Sequence
<220> FEATURE:
<223> OTHER INFORMATION: Synthetic Construct

<400> SEQUENCE: 310

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Ser Trp Ile Arg Gln Ala Pro Gly Lys Gly Leu Glu
        35                  40                  45

Trp Leu Ala Leu Ile Asp Trp Ala Gly Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Tyr Gly Tyr Ser Ser Tyr Ala Leu Asp Tyr Trp Gly Gln
            100                 105                 110

Gly Thr Leu Val Thr Val Ser Ser
        115                 120
```

<210> SEQ ID NO 311
<211> LENGTH: 108
<212> TYPE: PRT
<213> ORGANISM: Artificial Sequence
<220> FEATURE:
<223> OTHER INFORMATION: Synthetic Construct

<400> SEQUENCE: 311

```
Asp Ile Gln Leu Thr Gln Ser Pro Ser Ser Leu Ser Ala Ser Val Gly
1               5                   10                  15
```

Asp Arg Val Thr Ile Thr Cys Arg Ala Ser Gln Ser Val Arg Gly Ser
20 25 30

Tyr Leu Ala Trp Tyr Gln Gln Lys Pro Gly Lys Ala Pro Lys Leu Leu
35 40 45

Ile Tyr Ala Ala Ser Thr Leu Gln Ser Gly Val Pro Ser Arg Phe Ser
50 55 60

Gly Ser Gly Ser Gly Thr Asp Phe Thr Leu Thr Ile Ser Ser Leu Gln
65 70 75 80

Pro Glu Asp Phe Ala Thr Tyr Tyr Cys Gln Gln Tyr Ser Ser Leu Trp
85 90 95

Thr Phe Gly Gln Gly Thr Lys Val Glu Ile Lys Arg
100 105

<210> SEQ ID NO 312
<211> LENGTH: 5
<212> TYPE: PRT
<213> ORGANISM: Artificial Sequence
<220> FEATURE:
<223> OTHER INFORMATION: Synthetic Construct

<400> SEQUENCE: 312

Asp Tyr Glu Met His
1 5

<210> SEQ ID NO 313
<211> LENGTH: 17
<212> TYPE: PRT
<213> ORGANISM: Artificial Sequence
<220> FEATURE:
<223> OTHER INFORMATION: Synthetic Construct

<400> SEQUENCE: 313

Val Ile Glu Ser Glu Thr Gly Gly Thr Ala Tyr Asn Gln Lys Phe Lys
1 5 10 15

Gly

<210> SEQ ID NO 314
<211> LENGTH: 16
<212> TYPE: PRT
<213> ORGANISM: Artificial Sequence
<220> FEATURE:
<223> OTHER INFORMATION: Synthetic Construct

<400> SEQUENCE: 314

Glu Gly Ile Thr Thr Val Ala Thr Thr Tyr Tyr Trp Tyr Phe Asp Val
1 5 10 15

<210> SEQ ID NO 315
<211> LENGTH: 16
<212> TYPE: PRT
<213> ORGANISM: Artificial Sequence
<220> FEATURE:
<223> OTHER INFORMATION: Synthetic Construct

<400> SEQUENCE: 315

Arg Ser Ser Gln Ser Ile Val His Ser Asn Gly Asn Thr Tyr Leu Glu
1 5 10 15

<210> SEQ ID NO 316
<211> LENGTH: 7
<212> TYPE: PRT
<213> ORGANISM: Artificial Sequence
<220> FEATURE:

<223> OTHER INFORMATION: Synthetic Construct

<400> SEQUENCE: 316

Lys Val Ser Asn Arg Phe Ser
1               5

<210> SEQ ID NO 317
<211> LENGTH: 9
<212> TYPE: PRT
<213> ORGANISM: Artificial Sequence
<220> FEATURE:
<223> OTHER INFORMATION: Synthetic Construct

<400> SEQUENCE: 317

Phe Gln Gly Ser His Val Pro Leu Thr
1               5

<210> SEQ ID NO 318
<211> LENGTH: 125
<212> TYPE: PRT
<213> ORGANISM: Artificial Sequence
<220> FEATURE:
<223> OTHER INFORMATION: Synthetic Construct

<400> SEQUENCE: 318

Gln Gly Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Ile His Gly Leu Glu Trp Ile
        35                  40                  45

Gly Val Ile Glu Ser Glu Thr Gly Gly Thr Ala Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Thr Thr Val Ala Thr Thr Tyr Tyr Trp Tyr Phe
            100                 105                 110

Asp Val Trp Gly Gln Gly Thr Thr Val Thr Val Ser Ser
        115                 120                 125

<210> SEQ ID NO 319
<211> LENGTH: 112
<212> TYPE: PRT
<213> ORGANISM: Artificial Sequence
<220> FEATURE:
<223> OTHER INFORMATION: Synthetic Construct

<400> SEQUENCE: 319

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
85 90 95

Ser His Val Pro Leu Thr Phe Gly Gln Gly Thr Lys Leu Glu Ile Lys
100 105 110

<210> SEQ ID NO 320
<211> LENGTH: 445
<212> TYPE: PRT
<213> ORGANISM: Artificial Sequence
<220> FEATURE:
<223> OTHER INFORMATION: Synthetic Construct

<400> SEQUENCE: 320

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Ile Ser Ser Gly
20 25 30

Tyr His Trp Ser Trp Ile Arg Gln Ala Pro Gly Lys Gly Leu Glu Trp
35 40 45

Leu Ala Arg Ile Asp Trp Asp Asp Asp Lys Tyr Tyr Ser Thr Ser Leu
50 55 60

Lys Ser Arg Leu Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg Ser Tyr Val Tyr Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Leu Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly
435 440 445

<210> SEQ ID NO 321
<211> LENGTH: 446
<212> TYPE: PRT
<213> ORGANISM: Artificial Sequence
<220> FEATURE:
<223> OTHER INFORMATION: Synthetic Construct

<400> SEQUENCE: 321

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Ile Ser Ser Gly
20 25 30

Tyr His Trp Ser Trp Ile Arg Gln Ala Pro Gly Lys Gly Leu Glu Trp
35 40 45

Leu Ala Arg Ile Asp Trp Asp Asp Asp Lys Tyr Tyr Ser Thr Ser Leu
50 55 60

Lys Ser Arg Leu Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Arg Ser Tyr Val Tyr Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

```
Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 322
<211> LENGTH: 256
<212> TYPE: PRT
<213> ORGANISM: Artificial Sequence
<220> FEATURE:
<223> OTHER INFORMATION: Synthetic Construct

<400> SEQUENCE: 322

Glu Val Gly Ser Tyr Pro Asn Pro Ser Ser Asp Cys Val Pro Tyr Tyr
1               5                   10                  15

Tyr Ala Cys Ala Tyr Ser Gly Arg Ser Ala Gly Gly Gly Gly Thr Pro
            20                  25                  30

Leu Gly Leu Ala Gly Ser Gly Gly Ser Asp Ile Gln Leu Thr Gln Ser
        35                  40                  45

Pro Ser Ser Leu Ser Ala Ser Val Gly Asp Arg Val Thr Ile Thr Cys
    50                  55                  60

Arg Ala Ser Gln Ser Val Arg Gly Arg Phe Leu Ala Trp Tyr Gln Gln
65                  70                  75                  80

Lys Pro Gly Lys Ala Pro Lys Leu Leu Ile Tyr Asp Ala Ser Asn Arg
                85                  90                  95

Ala Thr Gly Ile Pro Ser Arg Phe Ser Gly Ser Gly Ser Gly Thr Asp
            100                 105                 110

Phe Thr Leu Thr Ile Ser Ser Leu Gln Pro Glu Asp Phe Ala Thr Tyr
        115                 120                 125

Tyr Cys Gln Gln Ser Ser Ser Trp Pro Pro Thr Phe Gly Gln Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175
```

```
Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255


<210> SEQ ID NO 323
<211> LENGTH: 445
<212> TYPE: PRT
<213> ORGANISM: Artificial Sequence
<220> FEATURE:
<223> OTHER INFORMATION: Synthetic Construct

<400> SEQUENCE: 323

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Ser Trp Ile Arg Gln Ala Pro Gly Lys Gly Leu Glu Trp
        35                  40                  45

Leu Ala Arg Ile Asp Trp Asp Asp Asp Lys Tyr Tyr Ser Thr Ser Leu
    50                  55                  60

Lys Ser Arg Leu Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Tyr Val Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285
```

```
Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 324
<211> LENGTH: 446
<212> TYPE: PRT
<213> ORGANISM: Artificial Sequence
<220> FEATURE:
<223> OTHER INFORMATION: Synthetic Construct

<400> SEQUENCE: 324

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Ser Trp Ile Arg Gln Ala Pro Gly Lys Gly Leu Glu Trp
        35                  40                  45

Leu Ala Arg Ile Asp Trp Asp Asp Asp Lys Tyr Tyr Ser Thr Ser Leu
    50                  55                  60

Lys Ser Arg Leu Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Tyr Val Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

-continued

```
Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 325
<211> LENGTH: 256
<212> TYPE: PRT
<213> ORGANISM: Artificial Sequence
<220> FEATURE:
<223> OTHER INFORMATION: Synthetic Construct

<400> SEQUENCE: 325

Glu Val Gly Ser Tyr Asn Phe Val Ala Asp Ser Cys Pro Asp His Pro
1               5                   10                  15

Tyr Pro Cys Ser Ala Ser Gly Arg Ser Ala Gly Gly Gly Gly Ser Pro
            20                  25                  30

Leu Gly Leu Ala Gly Ser Gly Gly Ser Asp Ile Gln Leu Thr Gln Ser
        35                  40                  45

Pro Ser Ser Leu Ser Ala Ser Val Gly Asp Arg Val Thr Ile Thr Cys
    50                  55                  60

Arg Ala Ser Gln Ser Val Arg Gly Arg Phe Leu Ala Trp Tyr Gln Gln
65                  70                  75                  80

Lys Pro Gly Lys Ala Pro Lys Leu Leu Ile Tyr Asp Ala Ser Asn Arg
                85                  90                  95

Ala Thr Gly Ile Pro Ser Arg Phe Ser Gly Ser Gly Ser Gly Thr Asp
            100                 105                 110

Phe Thr Leu Thr Ile Ser Ser Leu Gln Pro Glu Asp Phe Ala Thr Tyr
        115                 120                 125
```

Tyr Cys Gln Gln Ser Ser Ser Trp Pro Pro Thr Phe Gly Gln Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255

<210> SEQ ID NO 326
<211> LENGTH: 445
<212> TYPE: PRT
<213> ORGANISM: Artificial Sequence
<220> FEATURE:
<223> OTHER INFORMATION: Synthetic Construct

<400> SEQUENCE: 326

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Ser Trp Ile Arg Gln Ala Pro Gly Lys Gly Leu Glu Trp
        35                  40                  45

Leu Ala Arg Ile Asp Trp Asp Asp Asp Lys Tyr Tyr Ser Thr Ser Leu
    50                  55                  60

Lys Ser Arg Leu Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Tyr Val Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

-continued

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 327
<211> LENGTH: 446
<212> TYPE: PRT
<213> ORGANISM: Artificial Sequence
<220> FEATURE:
<223> OTHER INFORMATION: Synthetic Construct

<400> SEQUENCE: 327

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Ser Trp Ile Arg Gln Ala Pro Gly Lys Gly Leu Glu Trp
        35                  40                  45

Leu Ala Arg Ile Asp Trp Asp Asp Asp Lys Tyr Tyr Ser Thr Ser Leu
    50                  55                  60

Lys Ser Arg Leu Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Tyr Val Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 328
<211> LENGTH: 256
<212> TYPE: PRT
<213> ORGANISM: Artificial Sequence
<220> FEATURE:
<223> OTHER INFORMATION: Synthetic Construct

<400> SEQUENCE: 328

Glu Val Gly Ser Tyr Ile Val His His Ser Asp Cys Asp Ala Phe Tyr
1               5                   10                  15

Pro Tyr Cys Asp Ser Ser Gly Arg Ser Ala Gly Gly Gly Gly Ser Pro
            20                  25                  30

Leu Gly Leu Ala Gly Ser Gly Gly Ser Asp Ile Gln Leu Thr Gln Ser
        35                  40                  45

Pro Ser Ser Leu Ser Ala Ser Val Gly Asp Arg Val Thr Ile Thr Cys
    50                  55                  60

Arg Ala Ser Gln Ser Val Arg Gly Arg Phe Leu Ala Trp Tyr Gln Gln
65                  70                  75                  80
```

-continued

```
Lys Pro Gly Lys Ala Pro Lys Leu Leu Ile Tyr Asp Ala Ser Asn Arg
                85                  90                  95

Ala Thr Gly Ile Pro Ser Arg Phe Ser Gly Ser Gly Ser Gly Thr Asp
            100                 105                 110

Phe Thr Leu Thr Ile Ser Ser Leu Gln Pro Glu Asp Phe Ala Thr Tyr
        115                 120                 125

Tyr Cys Gln Gln Ser Ser Ser Trp Pro Pro Thr Phe Gly Gln Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255
```

COMBINATION THERAPIES FOR TREATING CANCER

CROSS REFERENCE TO RELATED APPLICATIONS

This application is a U.S. national stage application under 35 U.S.C. § 371 of International Application No. PCT/CN2022/086143, filed Apr. 11, 2022, which claims the priority of U.S. Provisional Application Nos. 63/173,479, filed Apr. 11, 2021, and 63/300,567, filed Jan. 18, 2022, the entire contents of each priority application is incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 695402001500SEQLIST.TXT, date recorded: Sep. 28, 2023, size: 216,575 bytes).

FIELD OF THE INVENTION

The present application is in the field of cancer therapeutics, and relates to combination therapies comprising antibodies that bind to human Cytotoxic T-lymphocyte Protein 4 (CTLA4).

BACKGROUND

Cytotoxic T-lymphocyte Protein 4 (CTLA4) is a member of the immunoglobulin (Ig) superfamily of proteins that acts to downregulate T-cell activation and maintain immunogenic homeostasis. It has been shown that in vivo antibody-mediated blockade of CTLA4 enhanced anti-cancer immune responses in a syngeneic murine prostate cancer model (Kwon et al. (1997) Proc Natl Acad Sci USA, 94 (15): 8099-103). In addition, blockade of CTLA4 function was shown to enhance anti-tumor T cell responses at various stages of tumor growth in tumor-bearing mice (Yang et al. (1997) Cancer Res 57 (18): 4036-41; Hurwitz et al. (1998) Proc Natl Acad Sci USA 95 (17): 10067-7). However, the development of antibody-based therapeutics suitable for human use remains difficult, as translation from pre-clinical animal models to human safety is often poor. Accordingly, a need exists for anti-CTLA4 antibodies that are cross-reactive among different species, such as humans and experimental animals (e.g., mouse, monkey, rat, etc.), to concurrently enable animal model studies and provide suitable human therapeutic candidates. In addition, a need exists for the development of safer anti-CTLA4 antibodies that are only active in certain contexts, such as in the protease-rich tumor microenvironment.

BRIEF SUMMARY

The present disclosure provides methods of treating cancer with anti-CTLA4 antibodies and activatable anti-CTLA4 antibodies. The present application further provides methods for treating cancer with an anti-CTLA4 antibody and a second therapeutic agent. The present application further provides methods for treating cancer with an activatable anti-CTLA4 antibody and a second therapeutic agent.

In one aspect, provided herein is a method of treating a cancer in a subject, comprising administering to the subject: (a) an effective amount of an activatable antibody, wherein the activatable antibody comprises: a polypeptide comprising, from N-terminus to C-terminus, a masking moiety (MM), a cleavable moiety (CM), and a target binding moiety (TBM), wherein the MM comprises an amino acid sequence selected from the group consisting of $X_m$CPDHPYPCXX (SEQ ID NO:181), $X_m$CDAFYPYCXX (SEQ ID NO:182), $X_m$CDSHYPYCXX (SEQ ID NO:183), and $X_m$CVPYYY-ACXX (SEQ ID NO:184), and where m is from 2-10, and where each X is independently an amino acid selected from the group consisting of A, C, D, E, F, G, H, I, K, L, M, N, P, Q, R, S, T, V, W, and Y; wherein the MM inhibits the binding of the activatable antibody to human CTLA4 when the CM is not cleaved; wherein the CM comprises at least a first cleavage site; wherein: a) the TBM comprises an antibody light chain variable region (VL), and the activatable antibody further comprises a second polypeptide comprising an antibody heavy chain variable region (VH); b) the TBM comprises an antibody heavy chain variable region (VH), and the activatable antibody further comprises a second polypeptide comprising an antibody light chain variable region (VL); c) the TBM comprises from the N-terminus to the C-terminus, an antibody light chain variable region (VL) and an antibody heavy chain variable region (VH); or d) the TBM comprises from the N-terminus to the C-terminus, an antibody heavy chain variable region (VH) and an antibody light chain variable region (VL); wherein the activatable antibody binds to human CTLA4 via the VH and VL when the CM is cleaved. In some embodiments, the subject is human. In some embodiments, the subject is a non-human animal or non-human mammal.

In some embodiments, the activatable anti-CTLA4 antibody can be administered as a monotherapy to a patient in need thereof. In other embodiments, the activatable anti-CTLA4 antibody can be administered in combination with one or more additional agents, as set forth herein. In some embodiments, the cancer is ovarian cancer, pancreatic cancer, cholangiocarcinoma, lung cancer, breast cancer, melanoma, hepatocellular carcinoma, glioblastoma, renal cell carcinoma, head and neck squamous cell carcinoma, or colorectal cancer. In some embodiments, the lung cancer is non-small cell lung cancer (NSCLC). In some embodiments, the colorectal cancer is microsatellite instability high (MSI-H) or mismatch repair deficient (dMMR+) colorectal cancer. In some embodiments, the melanoma is uveal (UV) melanoma.

In some embodiments, the MM of the activatable anti-CTLA4 antibody further comprises, at its N-terminus, an additional amino acid sequence. In some embodiments, the additional amino acid sequence comprises the amino acid sequence of SEQ ID NO: 148.

In some embodiments, the first cleavage site of the activatable anti-CTLA4 antibody is a protease cleavage site for a protease selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE.

In some embodiments, the CM further comprises a first linker ($L_1$)C-terminal to the first cleavage site. In some embodiments, the $L_1$ comprises an amino acid sequence selected from the group consisting of SEQ ID NOS: 156-163.

In some embodiments, the CM further comprises a second cleavage site. In some embodiments, the second cleavage site is C-terminal to the $L_1$. In some embodiments, the second cleavage site is a protease cleavage site for a protease selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments, the first and second cleavage sites are different.

In some embodiments, the CM further comprises a second linker ($L_2$)C-terminal to the second cleavage site. In some embodiments, the $L_2$ comprises an amino acid sequence selected from the group consisting of SEQ ID NOS: 156-163. In some embodiments, the CM further comprises a third linker ($L_3$)N-terminal to the first cleavage site.

In some embodiments, the CM comprises at least a first protease cleavage site and is cleaved with one or more proteases selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE.

In some embodiments, the activatable anti-CTLA4 antibody comprises an amino acid sequence selected from the group consisting of SEQ ID NOS: 165-179.

In some embodiments, the activatable anti-CTLA4 antibody has a MM amino acid sequence selected from the group consisting of SEQ ID NOS: 189-196. In other embodiments, the activatable anti-CTLA4 antibody comprises a MM amino acid sequence selected from the group consisting of SEQ ID NOS: 213-216. In other embodiments, the activatable anti-CTLA4 antibody comprises a MM amino acid sequence selected from the group consisting of SEQ ID NOS: 141-147. In particular embodiments, the activatable anti-CTLA4 antibody comprises a MM amino acid sequence of SEQ ID NO: 200.

In some embodiments, the activatable anti-CTLA4 antibody has a combined MM/CM amino acid sequence selected from the group consisting of SEQ ID NOS: 197-209. In particular embodiments, the activatable anti-CTLA4 antibody has a combined MM/CM amino acid sequence of SEQ ID NO: 192.

In some embodiments, upon cleavage of the MM, the activatable anti-CTLA4 antibody specifically binds to an epitope comprising amino acid residues Y105 and L106 of human CTLA4 but does not comprise residue 1108, wherein the numbering of the amino acid residues is according to SEQ ID NO: 207.

In some embodiments, upon cleavage of the MM, a) the cleaved anti-CTLA4 antibody binds to human CTLA4, cynomolgus monkey CTLA4, mouse CTLA4, rat CTLA4, and dog CTLA4 with a dissociation constant ($K_D$) of about 350 nM or less; b) binding of the anti-CTLA4 antibody induces antibody-dependent cell cytotoxicity (ADCC) against a CTLA4-expressing human cell or a human Treg cell, wherein the ADCC activity of the anti-CTL4 antibody is higher than the ADCC activity of ipilimumab; and/or c) the anti-CTLA4 antibody has an IC50 higher than the IC50 of ipilimumab for blocking binding of CD80 and/or CD86 to human CTLA4 in an assay wherein either when CD80 and/or CD86 are plate bound or when human CTLA4 is present on cell surface.

In some embodiments, the activatable anti-CTLA4 antibody comprises a heavy chain variable region and a light chain variable region, a) wherein the heavy chain variable region comprises an HVR-H1, an HVR-H2, and an HVR-H3, wherein the HVR-H1 comprises an amino acid sequence according to a formula selected from the group consisting of:

Formula (I): X1TFSX2YX3IHWV (SEQ ID NO: 1), wherein X1 is F or Y, X2 is D or G, and $X_3$ is A, G, or W;

Formula (II): YSIX1SGX2X3WX4WI (SEQ ID NO: 2), wherein X1 is S or T, X2 is Hor Y, X3 is H or Y, and X4 is A, D, or S; and Formula (III): FSLSTGGVAVX1WI (SEQ ID NO: 3), wherein X1 is G or S;

wherein the HVR-H2 comprises an amino acid sequence according to a formula selected from the group consisting of:

Formula (IV): IGX1IX2HSGSTYYSX3SLKSRV (SEQ ID NO: 4), wherein X1 is D or E, X2 is S or Y, and $X_3$ is P or Q;

Formula (V): IGX1ISPSX2GX3TX4YAQKFQGRV (SEQ ID NO: 5), wherein X1 is I or W, X2 is G or S, X3 is G or S, and X4 is K or N; and Formula (VI): VSX1ISGX2GX3X4TYYADSVKGRF (SEQ ID NO: 6), wherein X1 is A, G, or S, X2 is S or Y, X3 is G or S, and X4 is S or T; and wherein the HVR-H3 comprises an amino acid sequence according to a formula selected from the group consisting of:

Formula (VII): ARX1X2X3X4FDX5 (SEQ ID NO: 7), wherein X1 is G, R, or S, X2 is A, I, or Y, X3 is D, V, or Y, X4 is A, E, or Y, and X5 is I or Y;

Formula (VIII): ARX1GX2GYFDX3 (SEQ ID NO: 8), wherein X1 is D or L, X2 is F or Y, and $X_3$ is V or Y;

Formula (IX): ARX1X2X3X4AX5X6FDY (SEQ ID NO: 9), wherein X1 is L or R, X2 is I or P, X3 is A or Y, X4 is S or T, X5 is T or Y, and X6 is A or Y;

Formula (X): ARDX1X2X3GSSGYYX4GFDX5 (SEQ ID NO: 10), wherein X1 is I or V, X2 is A or H, X3 is P or S, X4 is D or Y, and X5 is For V; and b) wherein the light chain variable region comprises an HVR-L1, an HVR-L2, and an HVR-L3, wherein the HVR-L1 comprises an amino acid sequence according to a formula selected form the group consisting of:

Formula (XI): RASQX1X2X3SX4LX5 (SEQ ID NO: 11), wherein X1 is G or S, X2 is I or V, X3 is G or S, X4 is S or Y, and X5 is A or N;

Formula (XII): RASQX1VX2X3RX4LA (SEQ ID NO: 12), wherein X1 is S or T, X2 is F, R, or S, X3 is G or S, and X4 is F or Y; and Formula (XIII): RASX1SVDFX2GX3SFLX4 (SEQ ID NO: 13), wherein X1 is E or Q, X2 is D, F, H, or Y, X3 is F, I, or K, and X4 is A, D, or H;

wherein the HVR-L2 comprises an amino acid sequence according to Formula (XIV): X1ASX2X3X4X5GX6 (SEQ ID NO: 14), wherein X1 is A or D, X2 is N, S, or T, X3 is L or R, X4 is A, E, or Q, X5 is S or T, and X6 is I or V; and wherein the HVR-L3 comprises an amino acid sequence according to a formula selected from the group consisting of:

Formula (XV): YCX1X2X3X4X5X6PX7T (SEQ ID NO: 15), wherein X1 is E, Q, or V, X2 is H or Q, X3 is A, G, H, R, or S, X4 is D, L, S, or Y, X5 is E, G, P, Q, or S, X6 is L, T, V, or W, and X7 is F, L, P, W, or Y;

Formula (XVI): YCQQX1X2X3WPPWT (SEQ ID NO: 16), wherein X1 is S or Y, X2 is D or Y, and $X_3$ is Q or Y; and Formula (XVII): YCQX1YX2SSPPX3YT (SEQ ID NO: 17), wherein X1 is H or Q, X2 is T or V, and $X_3$ is E or V.

In some embodiments, the activatable anti-CTLA4 antibody comprises: a) an HVR-H1 comprising the amino acid sequence of SEQ ID NO: 18, an HVR-H2 comprising the amino acid sequence of SEQ ID NO: 30, an HVR-H3 comprising the amino acid sequence of SEQ ID NO: 40, an HVR-L1 comprising the amino acid sequence of SEQ ID NO: 53, an HVR-L2 comprising the amino acid sequence of SEQ ID NO: 66, and an HVR-L3 comprising the amino acid sequence of SEQ ID NO: 70; b) an HVR-H1 comprising the amino acid sequence of SEQ ID NO: 19, an HVR-H2 comprising the amino acid sequence of SEQ ID NO: 31, an HVR-H3 comprising the amino acid sequence of SEQ ID NO: 41, an HVR-L1 comprising the amino acid sequence of SEQ ID NO: 54, an HVR-L2 comprising the amino acid sequence of SEQ ID NO: 67, and an HVR-L3 comprising the amino acid sequence of SEQ ID NO: 71; c) an HVR-H1 comprising the amino acid sequence of SEQ ID NO: 20, an HVR-H2 comprising the amino acid sequence of SEQ ID NO: 32, an HVR-H3 comprising the amino acid sequence of SEQ ID NO: 42, an HVR-L1 comprising the amino acid sequence of SEQ ID NO: 55, an HVR-L2 comprising the amino acid sequence of SEQ ID NO: 66, and an HVR-L3 comprising the amino acid sequence of SEQ ID NO: 72; d) an HVR-H1 comprising the amino acid sequence of SEQ ID NO: 21 an HVR-H2 comprising the amino acid sequence of SEQ ID NO: 33, an HVR-H3 comprising the amino acid sequence of SEQ ID NO: 43, an HVR-L1 comprising the amino acid sequence of SEQ ID NO: 56, an HVR-L2 comprising the amino acid sequence of SEQ ID NO: 68, and an HVR-L3 comprising the amino acid sequence of SEQ ID NO: 73; e) an HVR-H1 comprising the amino acid sequence of SEQ ID NO: 22, an HVR-H2 comprising the amino acid sequence of SEQ ID NO: 34, an HVR-H3 comprising the amino acid sequence of SEQ ID NO: 44, an HVR-L1 comprising the amino acid sequence of SEQ ID NO: 57, an HVR-L2 comprising the amino acid sequence of SEQ ID NO: 66, and an HVR-L3 comprising the amino acid sequence of SEQ ID NO: 74; f) an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75; g) an HVR-H1 comprising the amino acid sequence of SEQ ID NO: 24, an HVR-H2 comprising the amino acid sequence of SEQ ID NO: 32, an HVR-H3 comprising the amino acid sequence of SEQ ID NO: 46, an HVR-L1 comprising the amino acid sequence of SEQ ID NO: 59, an HVR-L2 comprising the amino acid sequence of SEQ ID NO: 66, and an HVR-L3 comprising the amino acid sequence of SEQ ID NO: 76; h) an HVR-H1 comprising the amino acid sequence of SEQ ID NO: 25, an HVR-H2 comprising the amino acid sequence of SEQ ID NO: 36, an HVR-H3 comprising the amino acid sequence of SEQ ID NO: 47, an HVR-L1 comprising the amino acid sequence of SEQ ID NO: 60, an HVR-L2 comprising the amino acid sequence of SEQ ID NO: 69, and an HVR-L3 comprising the amino acid sequence of SEQ ID NO: 77; i) an HVR-H1 comprising the amino acid sequence of SEQ ID NO: 26, an HVR-H2 comprising the amino acid sequence of SEQ ID NO: 37, an HVR-H3 comprising the amino acid sequence of SEQ ID NO: 48, an HVR-L1 comprising the amino acid sequence of SEQ ID NO: 61, an HVR-L2 comprising the amino acid sequence of SEQ ID NO: 66, and an HVR-L3 comprising the amino acid sequence of SEQ ID NO: 78; j) an HVR-H1 comprising the amino acid sequence of SEQ ID NO: 27, an HVR-H2 comprising the amino acid sequence of SEQ ID NO: 32, an HVR-H3 comprising the amino acid sequence of SEQ ID NO: 49, an HVR-L1 comprising the amino acid sequence of SEQ ID NO: 62, an HVR-L2 comprising the amino acid sequence of SEQ ID NO: 67, and an HVR-L3 comprising the amino acid sequence of SEQ ID NO: 79; k) an HVR-H1 comprising the amino acid sequence of SEQ ID NO: 28, an HVR-H2 comprising the amino acid sequence of SEQ ID NO: 37, an HVR-H3 comprising the amino acid sequence of SEQ ID NO: 50, an HVR-L1 comprising the amino acid sequence of SEQ ID NO: 63, an HVR-L2 comprising the amino acid sequence of SEQ ID NO: 67, and an HVR-L3 comprising the amino acid sequence of SEQ ID NO: 80; 1) an HVR-H1 comprising the amino acid sequence of SEQ ID NO: 18, an HVR-H2 comprising the amino acid sequence of SEQ ID NO: 38, an HVR-H3 comprising the amino acid sequence of SEQ ID NO: 51, an HVR-L1 comprising the amino acid sequence of SEQ ID NO: 64, an HVR-L2 comprising the amino acid sequence of SEQ ID NO: 67, and an HVR-L3 comprising the amino acid sequence of SEQ ID NO: 81; or m) an HVR-H1 comprising the amino acid sequence of SEQ ID NO: 29, an HVR-H2 comprising the amino acid sequence of SEQ ID NO: 39, an HVR-H3 comprising the amino acid sequence of SEQ ID NO: 52, an HVR-L1 comprising the amino acid sequence of SEQ ID NO: 65, an HVR-L2 comprising the amino acid sequence of SEQ ID NO: 68, and an HVR-L3 comprising the amino acid sequence of SEQ ID NO: 77.

In some embodiments, the activatable anti-CTLA4 antibody, upon cleavage, comprises: a) a heavy chain variable region comprising the amino acid sequence of SEQ ID NO: 82, and a light chain variable region comprising the amino acid sequence of SEQ ID NO: 95; b) a heavy chain variable region comprising the amino acid sequence of SEQ ID NO: 83, and a light chain variable region comprising the amino acid sequence of SEQ ID NO: 96; c) a heavy chain variable region comprising the amino acid sequence of SEQ ID NO: 84, and a light chain variable region comprising the amino acid sequence of SEQ ID NO: 97; d) a heavy chain variable region comprising the amino acid sequence of SEQ ID NO: 85, and a light chain variable region comprising the amino acid sequence of SEQ ID NO: 98; e) a heavy chain variable region comprising the amino acid sequence of SEQ ID NO: 86, and a light chain variable region comprising the amino acid sequence of SEQ ID NO: 99; f) a heavy chain variable region comprising the amino acid sequence of SEQ ID NO: 87, and a light chain variable region comprising the amino acid sequence of SEQ ID NO: 100; g) a heavy chain variable region comprising the amino acid sequence of SEQ ID NO: 88, and a light chain variable region comprising the amino acid sequence of SEQ ID NO: 101; h) a heavy chain variable region comprising the amino acid sequence of SEQ ID NO: 89, and a light chain variable region comprising the amino acid sequence of SEQ ID NO: 102; i) a heavy chain variable region comprising the amino acid sequence of SEQ ID NO: 90, and a light chain variable region comprising the amino acid sequence of SEQ ID NO: 103; j) a heavy chain variable region comprising the amino acid sequence of SEQ ID NO: 91, and a light chain variable region comprising the amino acid sequence of SEQ ID NO: 104; k) a heavy chain variable region comprising the amino acid sequence of SEQ ID NO: 92, and a light chain variable region comprising the amino acid sequence of SEQ ID NO: 105; 1) a heavy chain variable region comprising the amino acid sequence of SEQ ID NO: 93, and a light chain variable region comprising the amino acid sequence of SEQ ID NO: 106; or m) a heavy chain variable region comprising the amino acid sequence of SEQ ID NO: 94, and a light chain variable region comprising the amino acid sequence of SEQ ID NO: 107.

In some embodiments, the activatable anti-CTLA4 antibody, upon cleavage, comprises: (a) a heavy chain variable region comprising an HVR-H1 comprising the amino acid sequence of SEQ ID NO: 23, an HVR-H2 comprising the amino acid sequence of SEQ ID NO: 35, and an HVR-H3 comprising the amino acid sequence of SEQ ID NO: 45, and/or a light chain variable region comprising an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75; or (b) a heavy chain variable region comprising the amino acid sequence of SEQ ID NO: 87 or an amino acid sequence having at least 90% sequence identity to the amino acid sequence of SEQ ID NO: 87, and/or a light chain variable region comprising the amino acid sequence of SEQ ID NO: 100 or an amino acid sequence having at least 90% sequence identity to the amino acid sequence of SEQ ID NO: 100.

In some embodiments, the activatable anti-CTLA4 antibody comprises a heavy chain comprising the amino acid sequence of SEQ ID NO:320 and a light chain comprising the amino acid sequence of SEQ ID NO:322. In some embodiments, the activatable antibody comprises a heavy chain comprising the amino acid sequence of SEQ ID NO:321 and a light chain comprising the amino acid sequence of SEQ ID NO:322. In some embodiments, the activatable antibody comprises a heavy chain comprising the amino acid sequence of SEQ ID NO:320 or 321 and a light chain comprising the amino acid sequence of SEQ ID NO:322. In some embodiments, the activatable antibody comprises a heavy chain comprising the amino acid sequence of SEQ ID NO:323 and a light chain comprising the amino acid sequence of SEQ ID NO: 325. In some embodiments, the activatable antibody comprises a heavy chain comprising the amino acid sequence of SEQ ID NO:324 and a light chain comprising the amino acid sequence of SEQ ID NO:325. In some embodiments, the activatable antibody comprises a heavy chain comprising the amino acid sequence of SEQ ID NO:323 or 324 and a light chain comprising the amino acid sequence of SEQ ID NO:325. In some embodiments, the activatable antibody comprises a heavy chain comprising the amino acid sequence of SEQ ID NO:326 and a light chain comprising the amino acid sequence of SEQ ID NO:328. In some embodiments, the activatable antibody comprises a heavy chain comprising the amino acid sequence of SEQ ID NO: 327 and a light chain comprising the amino acid sequence of SEQ ID NO:328. In some embodiments, the activatable antibody comprises a heavy chain comprising the amino acid sequence of SEQ ID NO:326 or 327 and a light chain comprising the amino acid sequence of SEQ ID NO:328.

In some embodiments, the activatable anti-CTLA4 antibody is administered to the subject at a dose of between about 0.1 mg/kg and about 20 mg/kg, e.g., about 0.1 mg/kg, about 0.3 mg/kg, about 1 mg/kg, about 3 mg/kg, about 6 mg/kg, about 10 mg/kg, about 15 mg/kg, or about 20 mg/kg. In some such embodiments, the activatable anti-CTLA4 antibody is administered once every three weeks.

In another aspect, provided herein is a method of treating melanoma in a subject, comprising administering to the subject an effective amount of an activatable anti-CTLA4 antibody. In some embodiments, the activatable anti-CTLA4 antibody is administered as a monotherapy. In some embodiments, the activatable anti-CTLA4 antibody is administered to the subject at a dose of between about 0.1 mg/kg and about 10 mg/kg. In some embodiments, the activatable antibody is administered to the subject at a dose of about 0.1 mg/kg, about 0.3 mg/kg, about 1 mg/kg, about 3 mg/kg, or about 10 mg/kg. In some embodiments, the activatable antibody is administered to the subject at a dose of between about 0.1 mg/kg and about 20 mg/kg. In some embodiments, the activatable antibody is administered to the subject at a dose of about 0.1 mg/kg, about 0.3 mg/kg, about 1 mg/kg, about 3 mg/kg, about 6 mg/kg, about 10 mg/kg, or about 20 mg/kg. In some embodiments, the activatable antibody is administered once every three weeks. In some of the foregoing embodiments, the activatable antibody comprises a heavy chain comprising the amino acid sequence of SEQ ID NO:320 or 321 and an light chain comprising the amino acid sequence of SEQ ID NO:322. In other of the foregoing embodiments, the activatable antibody comprises a heavy chain comprising the amino acid sequence of SEQ ID NO:323 or 324 and an light chain comprising the amino acid sequence of SEQ ID NO:325. In other of the foregoing embodiments, the activatable antibody comprises a heavy chain comprising the amino acid sequence of SEQ ID NO:326 or 327 and an light chain comprising the amino acid sequence of SEQ ID NO:328. In some embodiments, the subject is human. In some embodiments, the subject is a non-human animal or non-human mammal.

In some embodiments, the anti-CTLA4 antibodies and activatable anti-CTLA4 antibodies of the disclosure are administered to a subject in combination with a PD-1 inhibitor (e.g., an anti-PD-1 antibody). In some such embodiments, the anti-PD1 antibody is 2E5. In other such embodiments, the anti-PD1 antibody is toripalimab. In other such embodiments, the anti-PD-1 antibody is pembrolizumab. In some embodiments, the subject is human. In some embodiments, the subject is a non-human animal or non-human mammal. In some embodiments, the combination of the activatable anti-CTLA4 antibody and PD-1 inhibitor (e.g. anti-PD-1 antibody) show a synergistic effect when administered in combination. In some of the foregoing embodiments, the anti-CTLA4 antibody comprises a heavy chain variable region comprising the amino acid sequence of SEQ ID NO: 87 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 87, and/or a light chain variable region comprising the amino acid sequence of SEQ ID NO: 100 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 100. In some of the foregoing embodiments, the anti-CTLA4 antibody is an activatable anti-CTLA4 antibody that upon cleavage, comprises a heavy chain variable region comprising the amino acid sequence of SEQ ID NO: 87 or an amino acid sequence having at least 90% (e.g., at least 92%, at least 93%, at least 94%, at least 95%, at least 96%, at least 97%, at least 98% or at least 99%)

sequence identity to the amino acid sequence of SEQ ID NO: 87, and/or a light chain variable region comprising the amino acid sequence of SEQ ID NO: 100 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 100.

In some embodiments, the anti-CTLA4 antibodies and activatable CTLA4 antibodies of the disclosure are administered to a subject in combination with an anti-CD137 antibody, wherein the anti-CD137 antibody specifically binds to an extracellular domain of human CD137, wherein the antibody binds to one or more amino acid residues selected from the group consisting of amino acid residues 51, 53, 62-73, 83, 89, 92, 95-104 and 112-116 of SEQ ID NO: 231. In some embodiments, the subject is human. In some embodiments, the subject is a non-human animal or non-human mammal. In some embodiments, the combination of the activatable anti-CTLA4 antibody and the anti-CD137 antibody show a synergistic effect when administered in combination. In some embodiments, the anti-CD137 antibody binds to amino acid residues 51, 63-67, 69-73, 83, 89, 92, 98-104 and 112-114 of SEQ ID NO: 231. In some embodiments, the anti-CD137 antibody comprises a heavy chain variable region (VH) and a light chain variable region (VL), wherein the VH comprises a HVR-H1 comprising the amino acid sequence of SEQ ID NO: 232, a HVR-H2 comprising the amino acid sequence of SEQ ID NO: 233, and a HVR-H3 comprising the amino acid sequence of SEQ ID NO: 234; and wherein the VL comprises a HVR-L1 comprising the amino acid sequence of SEQ ID NO: 235, a HVR-L2 comprising the amino acid sequence of SEQ ID NO: 236, and a HVR-L3 comprising the amino acid sequence of SEQ ID NO: 237. In some embodiments, the anti-CD137 antibody comprises a VH comprising the amino acid sequence of SEQ ID NO: 238, and/or a VL comprising the amino acid sequence of SEQ ID NO: 239. In some embodiments, the anti-CD137 antibody comprises a heavy chain and a light chain, and wherein the heavy chain comprises the amino acid sequence of SEQ ID NO: 240, and/or the light chain comprises the amino acid sequence of SEQ ID NO: 241. In some embodiments, the anti-CD137 antibody comprises a VH and a VL, wherein the VH comprises a HVR-H1 comprising the amino acid sequence of SEQ ID NO: 242, a HVR-H2 comprising the amino acid sequence of SEQ ID NO: 243, and a HVR-H3 comprising the amino acid sequence of SEQ ID NO: 244; and wherein the VL comprises a HVR-L1 comprising the amino acid sequence of SEQ ID NO: 245, a HVR-L2 comprising the amino acid sequence of SEQ ID NO: 246, and a HVR-L3 comprising the amino acid sequence of SEQ ID NO: 247. In some embodiments, the anti-CD137 antibody comprises a VH comprising the amino acid sequence of SEQ ID NO: 248, and/or a VL comprising the amino acid sequence of SEQ ID NO: 249. In some embodiments, the anti-CD137 antibody comprises a heavy chain and a light chain, wherein the heavy chain comprises the amino acid sequence of SEQ ID NO: 250, and/or the light chain comprises the amino acid sequence of SEQ ID NO: 251. In some embodiments, the anti-CD137 antibody comprises a VH and a VL, wherein the VH comprises a HVR-H1 comprising the amino acid sequence of SEQ ID NO: 252, a HVR-H2 comprising the amino acid sequence of SEQ ID NO: 253, and a HVR-H3 comprising the amino acid sequence of SEQ ID NO: 254; and wherein the VL comprises a HVR-L1 comprising the amino acid sequence of SEQ ID NO: 255, a HVR-L2 comprising the amino acid sequence of SEQ ID NO: 256, and a HVR-L3 comprising the amino acid sequence of SEQ ID NO: 257. In some embodiments, the anti-CD137 antibody comprises a VH comprising the amino acid sequence of SEQ ID NO: 258, and/or a VL comprising the amino acid sequence of SEQ ID NO: 259. In some embodiments, the anti-CD137 antibody comprises a heavy chain and a light chain, wherein the heavy chain comprises the amino acid sequence of SEQ ID NO: 260, and/or the light chain comprises the amino acid sequence of SEQ ID NO: 261. In some embodiments, the anti-CD137 antibody comprises a human IgG4 Fc region, optionally wherein the human IgG4 Fc region comprises an S241P mutation, wherein numbering is according to Kabat. In some of the foregoing embodiments, the anti-CTLA4 antibody comprises a heavy chain variable region comprising the amino acid sequence of SEQ ID NO: 87 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 87, and/or a light chain variable region comprising the amino acid sequence of SEQ ID NO: 100 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 100. In some of the foregoing embodiments, the anti-CTLA4 antibody is an activatable anti-CTLA4 antibody that upon cleavage, comprises a heavy chain variable region comprising the amino acid sequence of SEQ ID NO: 87 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 87, and/or a light chain variable region comprising the amino acid sequence of SEQ ID NO: 100 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 100.

In another aspect, provided herein is a method of treating a cancer in a subject, comprising administering to the subject: (a) an effective amount of an anti-CTLA4 antibody (e.g., activatable anti-CTLA4 antibody), wherein the antibody specifically binds to an epitope comprising amino acid residues Y105 and L106 of human CTLA4 but does not comprise residue I108, wherein the numbering of the amino acid residues is according to SEQ ID NO: 207, and (b) an effective amount of a VEGF inhibitor. In some embodiments, the VEGF inhibitor is fruquintinib. In some embodiments, the cancer is colon cancer. In some embodiments, the VEGF inhibitor is anlotinib. In some embodiments, the cancer is a kidney cancer, optionally, a renal adenocarcinoma. In some of the foregoing embodiments, the anti-CTLA4 antibody comprises a heavy chain variable region comprising the amino acid sequence of SEQ ID NO: 87 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 87, and/or a light chain variable region comprising the amino acid sequence of SEQ ID NO: 100 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 100. In some of the foregoing embodiments, the anti-CTLA4 antibody is an activatable anti-CTLA4 antibody that upon cleavage, comprises a heavy chain variable region comprising the amino acid sequence of SEQ ID NO:

87 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 87, and/or a light chain variable region comprising the amino acid sequence of SEQ ID NO: 100 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 100.

In an aspect, provided herein is a method of treating a cancer in a subject, comprising administering to the subject: (a) an effective amount of an anti-CTLA4 antibody (e.g., activatable anti-CTLA4 antibody), wherein the antibody specifically binds to an epitope comprising amino acid residues Y105 and L106 of human CTLA4 but does not comprise residue I108, wherein the numbering of the amino acid residues is according to SEQ ID NO: 207, and (b) an effective amount of a chemotherapeutic agent. In some embodiments, the chemotherapeutic agent is docetaxel. In some embodiments, the cancer is breast cancer. In some embodiments, the chemotherapeutic agent is icaritin. In some embodiments, the cancer is melanoma.

In another aspect, provided herein is a method of treating a cancer in a subject, comprising administering to the subject: (a) an effective amount of an anti-CTLA4 antibody (e.g., activatable anti-CTLA4 antibody), wherein the antibody specifically binds to an epitope comprising amino acid residues Y105 and L106 of human CTLA4 but does not comprise residue I108, wherein the numbering of the amino acid residues is according to SEQ ID NO: 207, and (b) an effective amount of a PARP inhibitor. In some embodiments, the PARP inhibitor is olaparib. In some embodiments, the cancer is breast cancer.

In some embodiments according to any one of the methods described above, the cancer is resistant or refractory to a prior therapy, wherein the prior therapy is an inhibitor of CTLA4, PD-1, or a PD-1 ligand. In some embodiments, the subject is resistant to or has relapsed from a prior therapy, wherein the prior therapy is an inhibitor of CTLA4, PD-1, or a PD-1 ligand. In some embodiments, the prior therapy is an inhibitor of CTLA4, such as an anti-CTLA4 antibody, for example ipilimumab. In some embodiments, the prior therapy is an inhibitor of PD-1, such as an anti-PD-1 antibody, for example, pembrolizumab or toripalimab. In some embodiments, the prior therapy is an inhibitor of a PD-1 ligand (e.g., PD-L1), for example an anti-PD-L1 antibody. In some embodiments, the prior therapy includes both an inhibitor of CTLA4 and am inhibitor of PD-1. In some embodiments, the prior therapy includes both an inhibitor of CTLA4 and an inhibitor of PD-L1. In some of the foregoing embodiments, the activatable anti-CTLA4 antibody, upon cleavage of the MM, comprises a heavy chain variable region comprising the amino acid sequence of SEQ ID NO: 87 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 87, and/or a light chain variable region comprising the amino acid sequence of SEQ ID NO: 100 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 100. In some of the foregoing embodiments, the activatable anti-CTLA4 antibody comprises a human IgG1 Fc region, such as a wild type IgG1 Fc region or a variant that has enhanced ADCC activity. In some of the foregoing embodiments, the activatable anti-CTLA4 antibody comprises a human IgG1 Fc region, such as a wild type IgG1 Fc region or a variant that has enhanced ADCC activity. In some of the foregoing embodiments, the activatable antibody comprises a heavy chain comprising the amino acid sequence of SEQ ID NO:320 or 321, or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 320 or 321, and a light chain comprising the amino acid sequence of SEQ ID NO:322, or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 322.

It is to be understood that one, some, or all of the properties of the various embodiments described above and herein may be combined to form other embodiments of the present application. These and other aspects of the present application will become apparent to one of skill in the art. These and other embodiments of the present application are further described by the detailed description that follows.

BRIEF DESCRIPTION OF THE DRAWINGS

FIG. 31 shows treatment-related safety profile for anti-CTLA4 SAFEbody. As of Nov. 30, 2021, 16 patients have been treated at 5 dose escalation cohorts (0.1, 0.3, 1, 3, and 10 mg/kg). Anti-CTLA4 SAFEbody has been well tolerated, with only 1 ≥Grade 3 AE (Grade 3 fatigue), and 10 remaining Grade 1 AEs.

FIGS. 32A & 32B show two case studies: an ovarian cancer patient who had 5 lines of prior therapies that showed continuous tumor shrinkage for each tumor assessment after every two cycles of anti-CTLA4 SAFEbody treatment (FIG. 32A), and a uveal (UV) melanoma patient who had failed ipilimumab plus nivolumab in prior therapies that showed T cell activation and a −24% tumor shrinkage after anti-CTLA4 SAFEbody treatment (FIG. 32B).

FIG. 36A), changes relative to base level (Cycle 1 Day 1 pre-dose; FIG. 36B), changes relative to base level at different doses C1D1 vs. C1D8 (FIG. 36C), and changes relative to base level at different doses C1D1 vs. C1D15 (FIG. 36D).

DETAILED DESCRIPTION

I. Definitions

Figure 1:
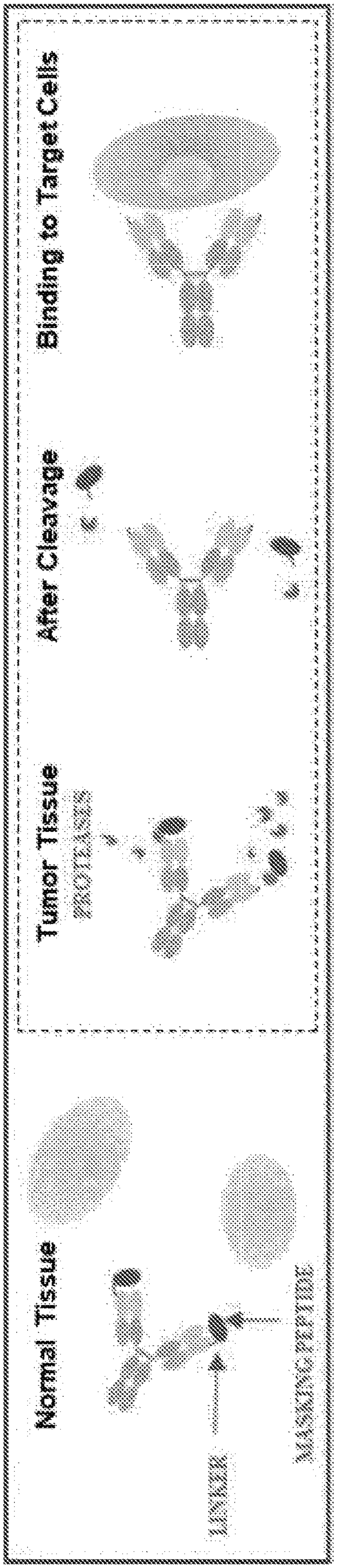
FIG. 1 shows a schematic diagram of a SAFEbody masked by a covalently linked N-terminal peptide, followed by protease cleavage sites. In normal tissues, a SAFEbody remains masked and unable to bind to its targets. However, in the tumor microenvironment, the mask is cleaved by proteases overexpressed in various tumor tissues, resulting in activation of the SAFEbody and enabling binding to its targets as depicted below for the activatable anti-CTLA4 antibody TY22404. See SEQ ID Nos: 320 and 322 for the full heavy and light chains (including mask/linker), respectively of TY22404.
Figure 2:
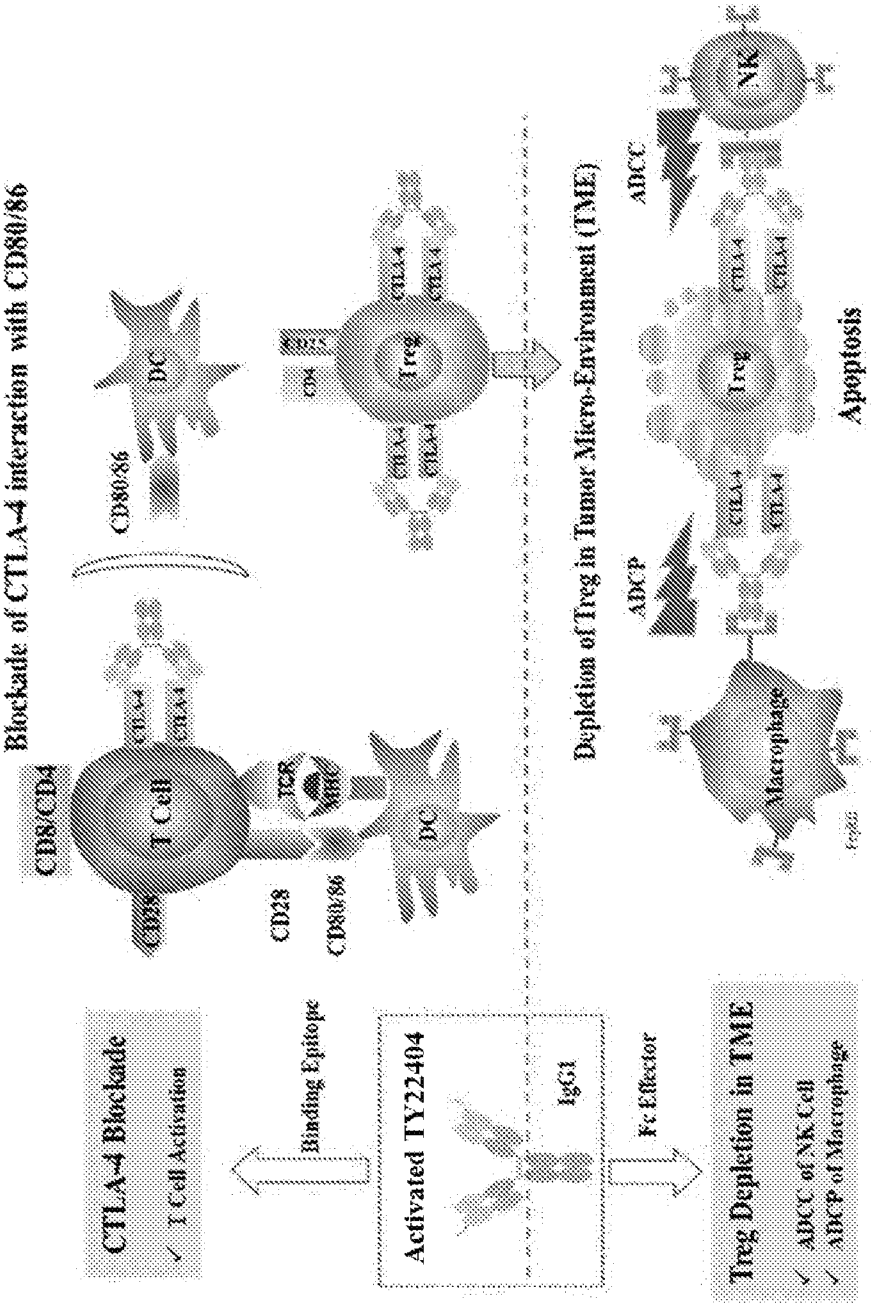
FIG. 2 shows a schematic diagram showing the mechanisms of action of TY22404 blocks CTLA4/B7 ligand interactions and potentiates T cell activation (see, e.g., Rowshanravan et al. CTLA4: a moving target in immunotherapy. Blood 2018, 131:58).

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Generally, nomenclatures used in connection with, and techniques of, antibody engineering, immunotherapy, cell and tissue culture, molecular biology, immunology, microbiology, genetics and protein and nucleic acid chemistry described herein are those well-known and commonly used in the art.

The term "antibody" is used herein in the broadest sense and specifically covers monoclonal antibodies (including full length monoclonal antibodies), polyclonal antibodies, multispecific antibodies (e.g., bispecific antibodies, trispecific antibodies), and antibody fragments (e.g., Fab, Fab', Fab'-SH, $F(ab')_2$, Fv and/or a single-chain variable fragment or scFv) so long as they exhibit the desired biological activity.

In some embodiments, the term "antibody" refers to an antigen-binding protein (i.e., immunoglobulin) having a basic four-polypeptide chain structure consisting of two identical heavy (H) chains and two identical light (L) chains. Each L chain is linked to an H chain by one covalent disulfide bond, while the two H chains are linked to each other by one or more disulfide bonds depending on the H chain isotype. Each heavy chain has, at the N-terminus, a variable region (abbreviated herein as $V_H$) followed by a constant region. The heavy chain constant region is comprised of three domains, $C_{H1}$, $C_{H2}$ and $C_{H3}$. Each light chain has, at the N-terminus, a variable region (abbreviated herein as $V_L$) followed by a constant region at its other end. The light chain constant region is comprised of one domain, $C_L$. The $V_L$ is aligned with the $V_H$ and the $C_L$ is aligned with the first constant domain of the heavy chain ($C_{H1}$). The pairing of a $V_H$ and $V_L$ together forms a single antigen-binding site. An IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain.

The $V_H$ and $V_L$ regions can be further subdivided into regions of hypervariability, termed hyper-variable regions (HVR) based on structural and sequence analysis. HVRs are interspersed with regions that are more conserved, termed framework regions (FW) (see e.g., Chen et al. (1999) J. Mol. Biol. (1999) 293, 865-881). Each $V_H$ and $V_L$ is composed of three HVRs and four FWs, arranged from amino-terminus to carboxy-terminus in the following order: FW-1_HVR-1_FW-2_HVR-2_FW-3_HVR-3_FW4. Throughout the present application, the three HVRs of the heavy chain are referred to as HVR-H1, HVR-H2, and HVR-H3. Similarly, the three HVRs of the light chain are referred to as HVR-L1, HVR-L2, and HVR-L3.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.,* 273: 927-948 (1997); MacCallum et al., J. Mol. Biol. 262:732-745 (1996); Abhinandan and Martin, *Mol. Immunol.,* 45:3832-3839 (2008); Lefranc M.P. et al., *Dev. Comp. Immunol.,* 27:55-77 (2003); and Honegger and Plückthun, *J. Mol. Biol.,* 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues, which encompass the CDRs as defined by each of the above-cited references, are set forth below in Table I as a comparison. CDR prediction algorithms and interfaces are known in the art, including, for example, Abhinandan and Martin, *Mol. Immunol.,* 45:3832-3839 (2008); Ehrenmann F. et al., *Nucleic Acids Res.,* 38: D301-D307 (2010); and Adolf-Bryfogle J. et al., *Nucleic Acids Res.,* 43: D432-D438 (2015). The contents of the references cited in this paragraph are incorporated herein by reference in their entireties for use in the present invention and for possible inclusion in one or more claims herein.

TABLE I

CDR DEFINITIONS

| | Kabat[1] | Chothia[2] | MacCallum[3] | IMGT[4] | AHo[5] |
|---|---|---|---|---|---|
| VH CDR1 | 31-35 | 26-32 | 30-35 | 27-38 | 25-40 |
| VH CDR2 | 50-65 | 53-55 | 47-58 | 56-65 | 58-77 |
| VH CDR3 | 95-102 | 96-101 | 93-101 | 105-117 | 109-137 |
| VL CDR1 | 24-34 | 26-32 | 30-36 | 27-38 | 25-40 |
| VL CDR2 | 50-56 | 50-52 | 46-55 | 56-65 | 58-77 |
| VL CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Within light and heavy chains, the variable and constant regions are joined by a "J" region of about 12 or more amino acids, with the heavy chain also including a "D" region of about 10 or more amino acids (see e.g., Fundamental Immunology Ch. 7 (Paul, W., ed., $2^{nd}$ ed. Raven Press, N.Y). (1989)).

The L chain from any vertebrate species can be assigned to one of two clearly distinct types, called kappa and lambda, based on the amino acid sequences of their constant domains. Depending on the amino acid sequence of the constant domain of their heavy chains (CH), antibodies can be assigned to different classes or isotypes. There are five classes of antibodies: IgA, IgD, IgE, IgG, and IgM, having heavy chains designated α (alpha), δ (delta), ε (epsilon), γ (gamma), and μ (mu), respectively. The IgG class of antibody can be further classified into four subclasses IgG1, IgG2, IgG3, and IgG4 by the gamma heavy chains, Y1-Y4, respectively.

The term "antibody derivative" or "derivative" of an antibody refers to a molecule that is capable of binding to the same antigen (e.g., CTLA4) that the antibody binds to and comprises an amino acid sequence of the antibody linked to an additional molecular entity. The amino acid sequence of the antibody that is contained in the antibody derivative may be a full-length heavy chain, a full-length light chain, any portion or portions of a full-length heavy chain, any portion or portions of the full-length light chain of the antibody, any other fragment(s) of an antibody, or the complete antibody. The additional molecular entity may be a chemical or biological molecule. Examples of additional molecular entities include chemical groups, amino acids, peptides, proteins (such as enzymes, antibodies), and chemical compounds. The additional molecular entity may have any utility, such as for use as a detection agent, label, marker, pharmaceutical or therapeutic agent. The amino acid sequence of an antibody may be attached or linked to the additional molecular entity by chemical coupling, genetic fusion, noncovalent association, or otherwise. The term "antibody derivative" also encompasses chimeric antibodies, humanized antibodies, and molecules that are derived from modifications of the amino acid sequences of a CTLA4 antibody, such as conservation amino acid substitutions, additions, and insertions.

The term "antigen-binding fragment" or "antigen binding portion" of an antibody refers to one or more portions of an antibody that retain the ability to bind to the antigen that the antibody bonds to (e.g., CTLA4). Examples of "antigen-binding fragments" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., Nature 341:544-546 (1989)), which consists of a $V_H$ domain; and (vi) an isolated complementarity determining region (CDR).

The term "CTLA4" is used in the present application, and includes the human CTLA4 (e.g., UniProt accession number P16410), as well as variants, isoforms, and species homologs thereof (e.g., mouse CTLA4 (UniProt accession number P09793), rat CTLA4 (UniProt accession number Q9Z1A7), dog CTLA4 (UniProt accession number Q9XSI1), cynomolgus monkey CTLA4 (UniProt accession number G7PL88), etc.). Accordingly, an anti-CTLA4 antibody (e.g., an activatable antibody) as defined and disclosed herein, may also bind CTLA4 from species other than human. In other cases, an anti-CTLA4 antibody may be completely specific for the human CTLA4 and may not exhibit species or other types of cross-reactivity.

The term "CTLA4 antibody" refers to an antibody, as defined herein, capable of binding to human CTLA4 (e.g., an activatable anti-CTLA4 antibody).

The term "chimeric antibody" refers to an antibody that comprises amino acid sequences derived from different animal species, such as those having a variable region derived from a human antibody and a murine immunoglobulin constant region.

The term "compete for binding" refers to the interaction of two antibodies in their binding to a binding target. A first antibody competes for binding with a second antibody if binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not, be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "cross-compete" with each other for binding of their respective epitope(s).

The term "epitope" refers to a part of an antigen to which an antibody (or antigen-binding fragment thereof) binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope can include various numbers of amino acids in a unique spatial conformation. Methods of determining spatial conformation of epitopes include, for example, x-ray crystallography, 2-dimensional nuclear magnetic resonance, deuterium and hydrogen exchange in combination with mass spectrometry, or site-directed mutagenesis, or all methods used in combination with computational modeling of antigen and its complex structure with its binding antibody and its variants (see e.g., Epitope Mapping Protocols in Methods in Molecular Biology, Vol. 66, G. E. Morris, Ed. (1996)). Once a desired epitope of an antigen is determined, antibodies to that epitope can be generated, e.g., using the techniques described herein. The generation and characterization of antibodies may also elucidate information about desirable epitopes. From this information, it is then possible to competitively screen antibodies for binding to the same epitope. An approach to achieve this is to conduct cross-competition studies to find antibodies that competitively bind with one another, i.e., the antibodies compete for binding to the antigen. A high throughput process for "binning" antibodies based upon their cross-competition is described in PCT Publication No. WO 03/48731.

The term "glycosylation sites" refers to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. The specific site of attachment is typically signaled by a sequence of amino acids, referred to herein as a "glycosylation site sequence". The glycosylation site sequence for N-linked glycosylation is: -Asn-X-Ser-or -Asn-X-Thr-, where X may be any of the conventional amino acids, other than proline. The terms "N-linked" and "O-linked" refer to the chemical group that serves as the attachment site between the sugar molecule and the amino acid residue. N-linked sugars are attached through an amino group; O-linked sugars are attached through a hydroxyl group. The term "glycan occupancy" refers to the existence of a carbohydrate moiety linked to a glycosylation site (i.e., the glycan site is occupied). Where there are at least two potential glycosylation sites on a polypeptide, either none (0-glycan site occupancy), one (1-glycan site occupancy) or both (2-glycan site occupancy) sites can be occupied by a carbohydrate moiety.

The term "host cell" refers to a cellular system, which can be engineered to generate proteins, protein fragments, or peptides of interest. Host cells include, without limitation, cultured cells, e.g., mammalian cultured cells derived from rodents (rats, mice, guinea pigs, or hamsters) such as CHO, BHK, NSO, SP2/0, YB2/0; human cells (e.g., HEK293F cells, HEK293T cells; or human tissues or hybridoma cells, yeast cells, insect cells (e.g., S2 cells), bacterial cells (e.g., *E. coli* cells) and cells comprised within a transgenic animal or cultured tissue. The term encompasses not only the particular subject cell but also the progeny of such a cell. Because certain modifications may occur in succeeding generations due to either mutation or environmental influences, such progeny may not be identical to the parent cell, but are still included within the scope of the term "host cell."

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "humanized antibody" refers to a chimeric antibody that contains amino acid residues derived from human antibody sequences. A humanized antibody may contain some or all of the CDRs or HVRs from a non-human animal or synthetic antibody while the framework and constant regions of the antibody contain amino acid residues derived from human antibody sequences.

The term "illustrative antibody" refers to any one of the antibodies described in the disclosure and designated as those listed in Tables A and B, and any antibodies comprising the 6 HVRs and/or the VH and VLs of the antibodies listed in Tables A and B. These antibodies may be in any class (e.g., IgA, IgD, IgE, IgG, and IgM). Thus, each antibody identified above encompasses antibodies in all five classes that have the same amino acid sequences for the $V_L$ and $V_H$ regions. Further, the antibodies in the IgG class may be in any subclass (e.g., IgG1 IgG2, IgG3, and IgG4). Thus, each antibody identified above in the IgG subclass encompasses antibodies in all four subclasses that have the same amino acid sequences for the $V_L$ and $V_H$ regions. The amino acid sequences of the heavy chain constant regions of human antibodies in the five classes, as well as in the four IgG subclasses, are known in the art.

"Antibody-dependent cell-mediated cytotoxicity" or "ADCC" refers to a form of cytotoxicity in which secreted immunoglobulin bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. PNAS (USA) 95:652-656 (1998). An exemplary assay for assessing ADCC activity is provided in the examples herein.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass), which are bound to their cognate antigen. To assess complement activation, a CDC assay, e.g., as described in Gazzano-Santoro et al., J. Immunol. Methods 202:163 (1996), may be performed. Polypeptide variants with altered Fc region amino acid sequences (polypeptides with a variant Fc region) and increased or decreased Clq binding capability are described, e.g., in U.S. Pat. No. 6,194,551 B1 and WO 1999/51642. See also, e.g., Idusogie et al. J. Immunol. 164:4178-4184 (2000).

An "isolated" antibody (e.g., an activatable antibody) is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see e.g., Flatman et al., J. Chromatogr. B 848:79-87 (2007).

The term "$K_a$" refers to the association rate constant of a particular antibody-antigen interaction, where the term "$k_d$" refers to the dissociation rate constant of a particular antibody-antigen interaction.

The term "$K_D$" refers to the equilibrium dissociation constant of a particular antibody-antigen interaction. It is obtained from the ratio of $k_d$ to $k_a$ (i.e., $k_d/k_a$) and is expressed as a molar concentration (M). $K_D$ is used as a measure for the affinity of an antibody's binding to its binding partner. The smaller the $K_D$, the more tightly bound the antibody is, or the higher the affinity between antibody and the antigen. For example, an antibody with a nanomolar (nM) dissociation constant binds more tightly to a particular antigen than an antibody with a micromolar (μM) dissociation constant. $K_D$ values for antibodies can be determined using methods well established in the art. One method for determining the $K_D$ of an antibody is by using surface plasmon resonance, typically using a biosensor system such as a BIACORE® system. For example, an assay procedure using the BIACORE™ system (BIAcore assay) is described in at least Example 3 of the present application.

The term "mammal" refers to any animal species of the Mammalia class. Examples of mammals include: humans; laboratory animals such as rats, mice, hamsters, rabbits, non-human primates, and guinea pigs; domestic animals such as cats, dogs, cattle, sheep, goats, horses, and pigs; and captive wild animals such as lions, tigers, elephants, and the like.

As used herein, "sequence identity" between two polypeptide sequences indicates the percentage of amino acids that are identical between the sequences. The amino acid sequence identity of polypeptides can be determined conventionally using known computer programs such as Bestfit, FASTA, or BLAST (see e.g., Pearson, *Methods Enzymol.* 183:63-98 (1990); Pearson, *Methods Mol. Biol.* 132:185-219 (2000); Altschul et al., *J. Mol. Biol.* 215:403-410 (1990); Altschul et al., *Nucelic Acids Res.* 25:3389-3402 (1997)). When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, fragments, or variants thereof disclosed herein.

As used herein, the term "binds", "binds to", "specifically binds" "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "treat", "treating", or "treatment", with reference to a certain disease condition in a mammal, refers causing a desirable or beneficial effect in the mammal having the disease condition. The desirable or beneficial effect may include reduced frequency or severity of one or more symptoms of the disease (i.e., tumor growth and/or metastasis, or other effect mediated by the numbers and/or activity of immune cells, and the like), or arrest or inhibition of further development of the disease, condition, or disorder. In the context of treating cancer in a mammal, the desirable or beneficial effect may include inhibition of further growth or spread of cancer cells, death of cancer cells, inhibition of reoccurrence of cancer, reduction of pain associated with the cancer, or improved survival of the mammal. The effect can be either subjective or objective. For example, if the mammal is human, the human may note improved vigor or vitality or decreased pain as subjective symptoms of improvement or response to therapy. Alternatively, the clinician may notice a decrease in tumor size or tumor burden based on physical exam, laboratory parameters, tumor markers or radiographic findings. Some laboratory signs that the clinician may observe for response to treatment include normalization of tests, such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement, such as sonograms, nuclear magnetic resonance testing and positron emissions testing.

The term "prevent" or "preventing," with reference to a certain disease condition in a mammal, refers to preventing or delaying the onset of the disease, or preventing the manifestation of clinical or subclinical symptoms thereof.

The term "isolated nucleic acid" refers to a nucleic acid molecule of genomic, cDNA, or synthetic origin, or a combination thereof, which is separated from other nucleic acid molecules present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid of interest.

The term "vector" refers to a nucleic acid molecule capable of transporting a foreign nucleic acid molecule. The foreign nucleic acid molecule is linked to the vector nucleic acid molecule by a recombinant technique, such as ligation or recombination. This allows the foreign nucleic acid molecule to be multiplied, selected, further manipulated or expressed in a host cell or organism. A vector can be a plasmid, phage, transposon, cosmid, chromosome, virus, or virion. One type of vectors can be integrated into the genome of a host cell upon introduction into the host cell, and thereby are replicated along with the host genome (e.g., non-episomal mammalian vectors). Another type of vector is capable of autonomous replication in a host cell into which it is introduced (e.g., bacterial vectors having a bacterial origin of replication and episomal mammalian vectors). Another specific type of vector capable of directing the expression of expressible foreign nucleic acids to which they are operatively linked is commonly referred to as "expression vectors." Expression vectors generally have control sequences that drive expression of the expressible foreign nucleic acids. Simpler vectors, known as "transcription vectors," are only capable of being transcribed but not translated: they can be replicated in a target cell but not expressed. The term "vector" encompasses all types of vectors regardless of their function. Vectors capable of directing the expression of expressible nucleic acids to which they are operatively linked are commonly referred to "expression vectors." Other examples of "vectors" may include display vectors (e.g., vectors that direct expression and display of an encoded polypeptide on the surface of a virus or cell (such as a bacterial cell, yeast cell, insect cell, and/or mammalian cell).

As used herein, a "subject", "patient", or "individual" may refer to a human or a non-human animal. A "non-human animal" may refer to any animal not classified as a human, such as domestic, farm, or zoo animals, sports, pet animals (such as dogs, horses, cats, cows, etc.), as well as animals used in research. Research animals may refer without limitation to nematodes, arthropods, vertebrates, mammals, frogs, rodents (e.g., mice or rats), fish (e.g., zebrafish or pufferfish), birds (e.g., chickens), dogs, cats, and non-human primates (e.g., rhesus monkeys, cynomolgus monkeys, chimpanzees, etc.). In some embodiments, the subject, patient, or individual is a human.

An "effective amount" refers to at least an amount effective, at dosages and for periods of time necessary, to achieve one or more desired or indicated effects, including a therapeutic or prophylactic result. An effective amount can be provided in one or more administrations. For purposes of the present application, an effective amount of antibody, drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition (e.g., an effective amount as administered as a monotherapy or combination therapy). Thus, an "effective amount" may be considered in the context of administering one or more therapeutic agents, and a single agent may be considered to be given in an effective amount if, in conjunction with one or more other agents, a desirable result may be or is achieved.

The terms "recurrence," "relapse" or "relapsed" refers to the return of a cancer or disease after clinical assessment of the disappearance of disease. A diagnosis of distant metastasis or local recurrence can be considered a relapse.

The term "refractory" or "resistant" refers to a cancer or disease that has not responded to treatment.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" (ORR) refers to the sum of complete response (CR) rate and partial response (PR) rate.

As used herein, "overall survival" refers to the percentage of individuals in a group who are likely to be alive after a particular duration of time.

As used herein, the term "biomarker" or "marker" refers generally to a molecule (e.g., pre-mRNA, mRNA, protein, etc.) or cell population (e.g., effector memory T cell or $T_{em}$ cell, or regulatory T cell or Treg cell), the level of which in or on a subject's tissue (e.g., tumor), or in case of a molecule, secreted by the subject's tissue or cell, can be detected by known methods (or methods disclosed herein) and is predictive or can be used to predict (or aid prediction) for a subject's sensitivity to, and in some embodiments, to predict (or aid prediction) a subject's responsiveness to, treatment regimens (e.g., treatments with an anti-CTLA4 antibody).

As used herein, the term "sample", refers to a composition that is obtained or derived from a subject of interest that contains a cellular and/or other molecular entity that is to be characterized and/or identified, for example based on physical, biochemical, chemical and/or physiological characteristics.

As used herein, the term "tissue or cell sample" refers to a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells. Optionally, the tissue or cell sample is obtained from a disease tissue or organ. The tissue sample may contain compounds, which are not naturally intermixed with the tissue in nature such as preservatives, anticoagulants, buffers, fixatives, nutrients, antibiotics, or the like. As used herein, a "reference value" or "reference level" may be an absolute value; a relative value; a value that has an upper and/or lower limit; a range of values; an average value; a median value; a mean value; or a value as compared to a particular level or baseline level.

As used herein, a "baseline level" or "baseline value" refers to a level or a value of a subject before the subject begins a treatment, such as an anti-CTLA4 antibody treatment.

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of biomarker analysis or protocol, one may use the results of the biomarker level analysis or protocol to determine whether a specific therapeutic regimen should be performed. With respect to the embodiment of biomarker level analysis or protocol, one may use the results of the biomarker level analysis or protocol to determine whether a specific therapeutic regimen should be performed.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer.

A patient who "does not have an effective response" to treatment refers to a patient who does not have any one of extending survival (including overall survival and progression free survival); resulting in an objective response (including a complete response or a partial response); or improving signs or symptoms of cancer.

The methods and techniques of the present application are generally performed according to methods well known in the art and as described in various general and more specific references that are cited and discussed throughout the present specification unless otherwise indicated. Such references include, e.g., Sambrook and Russell, *Molecular Cloning, A Laboratory Approach*, Cold Spring Harbor Press, Cold Spring Harbor, N.Y. (2001), Ausubel et al., *Current Protocols in Molecular Biology*, John Wiley & Sons, NY (2002), and Harlow and Lane *Antibodies: A Laboratory Manual*, Cold Spring Harbor Laboratory Press, Cold Spring Harbor, N.Y. (1990). Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)).

As used herein, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the present application described herein include "comprising," "consisting," and "consisting essentially of" aspects and embodiments.

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

The term "and/or" as used herein a phrase such as "A and/or B" is intended to include both A and B; A or B; A (alone); and B (alone). Likewise, the term "and/or" as used herein a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Methods of Treatment

The present application provides methods for treating cancers in a subject using an anti-CTLA4 antibody that specifically binds to human CTLA4. Any one of the anti-CTLA4 antibodies (including full-length antibodies and antigen-binding fragments thereof, and activatable antibodies) in Section III "Anti-CTLA4 Antibodies" may be used in the methods described herein. The anti-CTLA4 antibody (e.g., activatable antibody) may be administered alone as monotherapy, or administered in combination with one or more additional therapeutic agents or therapies.

The methods described herein are useful for treating a variety of cancers. In some embodiments, the cancer is a solid cancer. In some embodiments, the cancer is a liquid cancer. A variety of cancers where CTLA4 is implicated, whether malignant or benign and whether primary or secondary, may be treated or prevented with a method provided by the disclosure. Exemplary cancers include, but are not limited to, liver cancer, a cancer of the digestive system (e.g., colon cancer, colorectal cancer), lung cancer, bone cancer, heart cancer, brain cancer, kidney cancer, bladder cancer, a hematological cancer (e.g., leukemia), skin cancer, breast cancer, thyroid cancer, pancreatic cancer, a head and/or neck cancer, an eye-related cancer, a male reproductive system cancer (e.g., prostate cancer, testicular cancer), or a female reproductive system cancer (e.g., uterine cancer, cervical cancer). In some embodiments, the cancer is kidney cancer, such as renal cell carcinoma, or urothelial carcinoma. In some embodiments, the cancer is ovarian cancer, pancreatic cancer, cholangiocarcinoma, lung cancer (e.g., NSCLC), breast cancer, melanoma, hepatocellular carcinoma, glioblastoma, renal cell carcinoma, head and neck squamous cell carcinoma, or colorectal cancer (e.g., MSI-H or dMMR+ colorectal cancer). In some embodiments, the cancer is melanoma, NSCLC, hepatocellular carcinoma, renal cell carcinoma, head and neck squamous cell carcinoma, or colorectal cancer (e.g., MSI-H or dMMR+ colorectal cancer).

In some embodiments, the anti-CTLA4 (e.g., activatable antibody) is administered to a cancer patient as a monotherapy. In some embodiments, the cancer is melanoma. In other embodiments, the cancer is ovarian cancer, pancreatic cancer, cholangiocarcinoma, lung cancer, breast cancer, hepatocellular carcinoma, glioblastoma, renal cell carcinoma, head and neck squamous cell carcinoma, colorectal cancer. In some embodiments, the lung cancer is non-small cell lung cancer (NSCLC).

In some embodiments, the anti-CTLA4 antibody (e.g., activatable antibody) is administered to a cancer patient in combination with one or more additional therapeutic agents for separate, sequential or simultaneous administration. The term "additional therapeutic agent" refers to any therapeutic agent other than an anti-CTLA4 antibody provided by the disclosure. In some embodiments, there is provided a combination therapy for treating cancer in a subject, which comprises administering to the subject a therapeutically effective amount of an anti-CTLA4 antibody (e.g., activatable antibody) described herein in combination with one or more additional therapeutic agents. In some embodiments, the anti-CTLA4 antibody (e.g., activatable antibody) is administered in combination with one or more additional therapeutic agents comprising chemotherapeutic agents, immunotherapeutic agents, and/or hormone therapeutic agents. In some embodiments, the one or more additional therapeutic agents are selected from the group consisting of selected from the group consisting of viral gene therapy, immune checkpoint inhibitors, targeted therapies, radiation therapies, and chemotherapies.

In some embodiments, the anti-CTLA4 antibody (e.g., activatable antibody) is administered in combination with an anti-PD-1 antibody. In some embodiments, the anti-CTLA4 antibody (e.g., activatable antibody) is administered in combination with an anti-PD-L1 antibody. In some embodiments, the anti-CTLA4 antibody (e.g., activatable antibody) is administered in combination with an anti-CD137 antibody. In some embodiments, the anti-CTLA4 antibody (e.g., activatable antibody) is administered in combination with a VEGF inhibitor. In some embodiments, the anti-CTLA4 antibody (e.g., activatable antibody) is administered in combination with a chemotherapeutic agent. In some embodiments, the anti-CTLA4 antibody (e.g., activatable antibody) is administered in combination with a PARP inhibitor.

In some embodiments, provided herein is a method of treating a cancer in a subject, comprising administering to the subject: (a) an effective amount of an activatable anti-CTLA4 antibody, and (b) an effective amount of an anti-PD-1 antibody; wherein the activatable antibody comprises: a polypeptide comprising, from N-terminus to C-terminus, a masking moiety (MM), a cleavable moiety (CM), and a target binding moiety (TBM), wherein the MM comprises an amino acid sequence selected from the group consisting of XmCPDHPYPCXX (SEQ ID NO: 181), $X_m$CDAFYPYCXX (SEQ ID NO:182), $X_m$CDSHYPYCXX (SEQ ID NO:183), and $X_m$CVPYYYACXX (SEQ ID NO:184), and where m is from 2-10, and where each X is independently an amino acid selected from the group consisting of A, C, D, E, F, G, H, I, K, L, M, N, P, Q, R, S, T, V, W, and Y; wherein the MM inhibits the binding of the activatable anti-CTLA4 antibody to human CTLA4 when the CM is not cleaved; wherein the CM comprises at least a first cleavage site; wherein: a) the TBM comprises an antibody light chain variable region (VL), and the activatable antibody further comprises a second polypeptide comprising an antibody heavy chain variable region (VH); b) the TBM comprises an antibody heavy chain variable region (VH), and the activatable antibody further comprises a second polypeptide comprising an antibody light chain variable region (VL); c) the TBM comprises from the N-terminus to the C-terminus, an antibody light chain variable region (VL) and an antibody heavy chain variable region (VH); or d) the TBM comprises from the N-terminus to the C-terminus, an antibody heavy chain variable region (VH) and an antibody light chain variable region (VL); wherein the activatable antibody binds to human CTLA4 via the VH and VL when the CM is cleaved. In some embodiments, the anti-PD1 antibody is 2E5. In some embodiments, the anti-PD-1 antibody comprises a heavy chain variable region (VH) and a light chain variable region (VL), wherein the VH comprises a HVR-H1 comprising the amino acid sequence of SEQ ID NO: 294, a HVR-H2 comprising the amino acid sequence of SEQ ID NO: 295, and a HVR-H3 comprising the amino acid sequence of SEQ ID NO: 296; and wherein the VL comprises a HVR-L1 comprising the amino acid sequence of SEQ ID NO: 297, a HVR-L2 comprising the amino acid sequence of SEQ ID NO: 298, and a HVR-L3 comprising the amino acid sequence of SEQ ID NO: 299. In some embodiments, the anti-PD-1 antibody comprises a VH comprising the amino acid sequence of SEQ ID NO: 300. In some embodiments, the anti-PD-1 antibody comprises a VL comprising the amino acid sequence of SEQ ID NO: 301. In some of the foregoing embodiments, the cancer is lung cancer. In some embodiments, the lung cancer is non-small cell lung cancer (NSCLC). In other of the foregoing embodiments, the cancer is ovarian cancer, pancreatic cancer, cholangiocarcinoma, breast cancer, hepatocellular carcinoma, glioblastoma, renal cell carcinoma, head and neck squamous cell carcinoma, or colorectal cancer.

In some embodiments, provided herein is a method of treating a cancer in a subject, comprising administering to the subject: (a) an effective amount of an activatable anti-CTLA4 antibody, and (b) an effective amount of an anti-CD137 antibody; wherein the activatable anti-CTLA4 antibody comprises: a polypeptide comprising, from N-terminus to C-terminus, a masking moiety (MM), a cleavable moiety (CM), and a target binding moiety (TBM), wherein the MM comprises an amino acid sequence selected from the group consisting of XmCPDHPYPCXX (SEQ ID NO:181), $X_m$CDAFYPYCXX (SEQ ID NO:182), $X_m$CDSHYPYCXX (SEQ ID NO:183), and $X_m$CVPYYYACXX (SEQ ID NO:184), and where m is from 2-10, and where each X is independently an amino acid selected from the group consisting of A, C, D, E, F, G, H, I, K, L, M, N, P, Q, R, S, T, V, W, and Y; wherein the MM inhibits the binding of the activatable anti-CTLA4 antibody to human CTLA4 when the CM is not cleaved; wherein the CM comprises at least a first cleavage site; wherein: a) the TBM comprises an antibody light chain variable region (VL), and the activatable antibody further comprises a second polypeptide comprising an antibody heavy chain variable region (VH); b) the TBM comprises an antibody heavy chain variable region (VH), and the activatable antibody further comprises a second polypeptide comprising an antibody light chain variable region (VL); c) the TBM comprises from the N-terminus to the C-terminus, an antibody light chain variable region (VL) and an antibody heavy chain variable region (VH); or d) the TBM comprises from the N-terminus to the C-terminus, an antibody heavy chain variable region (VH) and an antibody light chain variable region (VL); wherein the activatable antibody binds to human CTLA4 via the VH and VL when the CM is cleaved; and wherein the anti-CD137 antibody specifically binds to an extracellular domain of human CD137, wherein the antibody binds to one or more amino acid residues selected from the group consisting of amino acid residues 51, 53, 62-73, 83, 89, 92, 95-104 and 112-116 of SEQ ID NO: 231. In some embodiments, the cancer is breast cancer. In other of the foregoing embodiments, the cancer is lung cancer, non-small cell lung cancer (NSCLC), ovarian cancer, pancreatic cancer, cholangiocarcinoma, hepatocellular carcinoma, glioblastoma, renal cell carcinoma, head and neck squamous cell carcinoma, or colorectal cancer.

In some embodiments, provided herein is a method of treating a cancer in a subject, comprising administering to the subject: (a) an effective amount of an anti-CTLA4 antibody, wherein the antibody specifically binds to an epitope comprising amino acid residues Y105 and L106 of human CTLA4 but does not comprise residue 1108, wherein the numbering of the amino acid residues is according to SEQ ID NO: 207, and (b) an effective amount of a VEGF inhibitor. In some embodiments, the VEGF inhibitor is fruquintinib. In some embodiments, the cancer is colon cancer. In some embodiments, the VEGF inhibitor is anlotinib. In some embodiments, the cancer is a kidney cancer. In some embodiments, the cancer is a renal adenocarcinoma. In some embodiments, provided herein is a method of treating a cancer in a subject, comprising administering to the subject: (a) an effective amount of an anti-CTLA4 antibody, wherein the antibody specifically binds to an epitope comprising amino acid residues Y105 and L106 of human CTLA4 but does not comprise residue 1108, wherein the numbering of the amino acid residues is according to SEQ ID NO: 207, and (b) an effective amount of a chemotherapeutic agent. In some embodiments, the chemotherapeutic agent is docetaxel. In some embodiments, the cancer is breast cancer. In some embodiments, provided herein is a method of treating a cancer in a subject, comprising administering to the subject: (a) an effective amount of an anti-CTLA4 antibody, wherein the antibody specifically binds to an epitope comprising amino acid residues Y105 and L106 of human CTLA4 but does not comprise residue 1108, wherein the numbering of the amino acid residues is according to SEQ ID NO: 207, and (b) an effective amount of a PARP inhibitor. In some embodiments, the PARP inhibitor is olaparib. In some of the foregoing embodiments, the cancer is breast cancer. In other of the foregoing embodiments, the cancer is lung cancer, non-small cell lung cancer (NSCLC), ovarian cancer, pancreatic cancer, cholangiocarcinoma, hepatocellular carcinoma, glioblastoma, renal cell carcinoma, head and neck squamous cell carcinoma, or colorectal cancer.

Cancer treatments can be evaluated by, e.g., tumor regression, tumor weight or size shrinkage, time to progression, duration of survival, progression free survival, overall response rate, duration of response, quality of life, protein expression and/or activity. Approaches to determining efficacy of therapy can be employed, including for example, measurement of response through radiological imaging.

The anti-CTLA4 antibodies (e.g., activatable antibodies), one or more additional therapeutic agents, and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The antibodies and compositions of the disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific antibody being used, the rate of absorption desired, specific formulation or dosage form used, type or severity of the disorder being treated, the specific site of action, and conditions of the patient, and can be readily selected by a person skilled in the art. In some embodiments, the anti-CTLA4 antibody is administered intravenously.

In some embodiments, the anti-CTLA4 antibody (e.g., activatable antibody) is administered at a dose of no more than any one of 20 mg/kg, 15 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.8 mg/kg, 0.6 mg/kg, 0.5 mg/kg, 0.4 mg/kg, 0.3 mg/kg, 0.2 mg/kg, 0.1 mg/kg, 0.08 mg/kg, 0.05 mg/kg, 0.04 mg/kg, 0.03 mg/kg, 0.01 mg/kg, 0.003 mg/kg, or 0.001 mg/kg. In some embodiments, the dose of the anti-CTLA4 antibody is within any one of the following ranges, wherein the ranges have an upper limit of any one of: 20 mg/kg, 19 mg/kg, 18 mg/kg, 17 mg/kg, 16 mg/kg, 15 mg/kg, 14 mg/kg, 13 mg/kg, 12 mg/kg, 11 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.8 mg/kg, 0.6 mg/kg, 0.5 mg/kg, 0.4 mg/kg, 0.3 mg/kg, 0.2 mg/kg, 0.1 mg/kg, 0.08 mg/kg, 0.05 mg/kg, 0.04 mg/kg, 0.03 mg/kg, or 0.003 mg/kg, and an independently selected lower limit of any one of 19 mg/kg, 18 mg/kg, 17 mg/kg, 16 mg/kg, 15 mg/kg, 14 mg/kg, 13 mg/kg, 12 mg/kg, 11 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.8 mg/kg, 0.6 mg/kg, 0.5 mg/kg, 0.4 mg/kg, 0.3 mg/kg, 0.2 mg/kg, 0.1 mg/kg, 0.08 mg/kg, 0.05 mg/kg, 0.04 mg/kg, 0.03 mg/kg, 0.01 mg/kg, 0.003 mg/kg or 0.001 mg/kg, and wherein the lower limit is less than the upper limit. In some embodiments, the anti-CTLA4 antibody is administered at a dose of any one of about 0.03 mg/kg to about 20 mg/kg, about 0.1 mg/kg to about 20 mg/kg, about 0.3 mg/kg to about 20 mg/kg, about 1 mg/kg to about 20 mg/kg, about 3 mg/kg to about 20 mg/kg, about 5 mg/kg to about 20 mg/kg, about 0.03 mg/kg to about 10 mg/kg, about 0.1 mg/kg to about 10 mg/kg, about 0.3 mg/kg to about 10 mg/kg, about 1 mg/kg to about 10 mg/kg, about 3 mg/kg to about 10 mg/kg, about 5 mg/kg to about 10 mg/kg, about 0.03 mg/kg to about 0.1 mg/kg, about 0.1 mg/kg to about 0.3 mg/kg, about 0.3 mg/kg to about 1 mg/kg, about 1 mg/kg to about 3 mg/kg, about 3 mg/kg to about 5 mg/kg, about 0.1 mg/kg to about 3 mg/kg, or about 1 mg/kg to about 5 mg/kg. The doses described herein may refer to a suitable dose for a human, or an equivalent dose for the specific species of the subject. In some embodiments, the anti-CTLA4 antibody is administered at a dose equivalent to about 0.03 mg/kg to about 20 mg/kg, such as about 0.03 mg/kg, about 0.1 mg/kg, about 0.3 mg/kg, about 1.0 mg/kg, about 3.0 mg/kg, about 6.0 mg/kg, about 10 mg/kg, or about 20 mg/kg for a human subject. In some embodiments, the anti-CTLA4 antibody (e.g., activatable antibody) is administered at a dose of between about 0.1 mg/kg and about 20 mg/kg, e.g., about 0.1 mg/kg, about 0.3 mg/kg, about 1 mg/kg, about 3 mg/kg, about 6 mg/kg, about 10 mg/kg, about 15 mg/kg, or about 20 mg/kg. In some embodiments, the anti-CTLA4 antibody (e.g., activatable antibody) is administered at a dose of between 0.1 mg/kg and 20 mg/kg, e.g., 0.1 mg/kg, 0.3 mg/kg, 1 mg/kg, 3 mg/kg, 6 mg/kg, 10 mg/kg, 15 mg/kg, or 20 mg/kg.

The effective amount of the anti-CTLA4 antibody (e.g., activatable antibody) and/or one or more additional therapeutic agents may be administered in a single dose or in multiple doses. For methods that comprises administration of the anti-CTLA4 antibody in multiple doses, exemplary dosing frequencies include, but are not limited to, weekly, weekly without break, weekly for two out of three weeks, weekly for three out of four weeks, once every three weeks, once every two weeks, monthly, every six months, yearly, etc. In some embodiments, the anti-CTLA4 antibody is administered about weekly, once every 2 weeks, once every 3 weeks, once every 6 weeks, or once every 12 weeks. In some embodiments, the intervals between each administration are less than about any of 3 years, 2 years, 12 months, 11 months, 10 months, 9 months, 8 months, 7 months, 6 months, 5 months, 4 months, 3 months, 2 months, 1 month, 4 weeks, 3 weeks, 2 weeks, or 1 week. In some embodiments, the intervals between each administration are more than about any of 1 week, 2 weeks, 3 weeks, 4 weeks, 1 month, 2 months, 3 months, 4 months, 5 months, 6 months, 7 months, 8 months, 9 months, 10 months, 11 months, 12 months, 2 years, or 3 years. In some embodiments, there is no break in the dosing schedule.

In some embodiments, the anti-CTLA4 antibody (e.g., activatable antibody) and/or one or more additional therapeutic agents is administered at a low frequency, for example, any one of no more frequent than once per week, once every other week, once per three weeks, once per month, once per 2 months, once per 3 months, once per 4 months, once per 5 months, once per 6 months, once per 7 months, once per 8 months, once per 9 months, once per 10 months, once per 11 months, once per year, or less. In some embodiments, the anti-CTLA4 antibody and/or one or more additional therapeutic agents is administered in a single dose. In some embodiments, the anti-CTLA4 antibody and/or one or more additional therapeutic agents is administered about once every three weeks.

In some embodiments, the anti-CTLA4 antibody (e.g., activatable antibody) and/or one or more additional therapeutic agents is administered for 2 or more cycles, such as about any one of 2, 3, 4, 5, 6, 7, 8, 9, 10, 11, 12, or more cycles. In some embodiments, the anti-CTLA4 antibody is administered for at least 4 cycles.

In some embodiments, the treatment comprises an initial phase and a subsequent maintenance phase. In some embodiments, the anti-CTLA4 antibody (e.g., activatable antibody) and/or one or more additional therapeutic agents is administered less frequently in the maintenance phase than in the initial phase. In some embodiments, the anti-CTLA4 antibody and/or one or more additional therapeutic agents is administered at the same frequently in the maintenance phase as in the initial phase. In some embodiments, the treatment comprises an initial phase wherein the anti-CTLA4 antibody and/or one or more additional therapeutic agents is administered about once every three weeks for at least 4 cycles, and a maintenance phase wherein the anti-CTLA4 antibody and/or one or more additional therapeutic agents is administered about once every 4 weeks to once every 12 weeks, such as once every 4 weeks, once every 6 weeks, once every 8 weeks, once every 10 weeks, or once every 12 weeks. In some embodiments, the dosing frequency in the maintenance phase is adjusted depending on one or more biomarkers, such as $T_{reg}$ cells, CD8+ $T_{em}$ cells, CD4+ $T_{em}$ cells, a ratio of CD8+ $T_{em}$ cells to $T_{reg}$ cells, a ratio of CD4+ $T_{em}$ cells to $T_{reg}$ cells, CD25+ T cells, and/or NK cells. For example, if the subject shows an increase in the ratio of CD8+ $T_{em}$ cells to $T_{reg}$ cells after receiving the anti-CTLA4 antibody, the subject may be further administered an anti-CTLA4 antibody at about every 4 weeks.

The administration of the anti-CTLA4 antibody (e.g., activatable antibody) and/or one or more additional therapeutic agents can be extended over an extended period of time, such as from about a week to about a month, from about a month to about a year, from about a year to about several years. In some embodiments, the anti-CTLA4 antibody and/or one or more additional therapeutic agents is administered over a period of at least any of about 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 1 year, 2 years, 3 years, 4 years, or more.

In some embodiments where the activatable anti-CTLA4 antibody, upon cleavage of the MM, comprises a heavy chain variable region comprising the amino acid sequence of SEQ ID NO: 87 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 87, and/or a light chain variable region comprising the amino acid sequence of SEQ ID NO: 100 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 100, the activatable anti-CTLA4 antibody is administered at a dose of between about 3 mg/kg to about 20 mg/kg once every three weeks, about 3 mg/kg to about 15 mg/kg once every three weeks, about 6 mg/kg to about 15 mg/kg once every three weeks, or from about 6 mg/kg to about 10 mg/kg once every three weeks. In some such embodiments, the activatable anti-CTLA4 antibody is administered at a dose of about 3 mg/kg once every three weeks. In other such embodiments, the activatable anti-CTLA4 antibody is administered at a dose of about 6 mg/kg once every three weeks. In other such embodiments, the activatable anti-CTLA4 antibody is administered at a dose of about 10 mg/kg once every three weeks. In some of the foregoing embodiments, the activatable antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some of the foregoing embodiments, the activatable anti-CTLA4 antibody comprises a human IgG1 Fc region, such as a wild type IgG1 Fc region or a variant that has enhanced ADCC activity. In some of the foregoing embodiments, the activatable anti-CTLA4 antibody comprises an MM amino acid sequence selected from the group consisting of SEQ ID NOS: 189-196. In some of the foregoing embodiments, the activatable anti-CTLA4 antibody comprises a MM amino acid sequence selected from the group consisting of SEQ ID NOS: 213-216 .... In some of the foregoing embodiments, the activatable anti-CTLA4 antibody comprises a MM amino acid sequence selected from the group consisting of SEQ ID NOS: 141-147. In some of the foregoing embodiments, the activatable anti-CTLA4 antibody comprises a MM amino acid sequence of SEQ ID NO: 200. In some of the foregoing embodiments, the activatable anti-CTLA4 antibody comprises a heavy chain comprising the amino acid sequence of SEQ ID NO:320 or 321, or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 320 or 321, and a light chain comprising the amino acid sequence of SEQ ID NO:322, or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 322. In some of the foregoing embodiments, the activatable anti CTLA4 antibody is administered to a patient with melanoma, non-small cell lung cancer, renal cell carcinoma, or hepatocellular carcinoma. In other of the foregoing embodiments, the activatable anti CTLA4 antibody is administered to a patient with a MSI-H or dMMR cancer. In other of the foregoing embodiments, the activatable anti CTLA4 antibody is administered to a patient with a cancer that has metastasized. In some of the foregoing embodiments, the activatable anti-CTLA4 antibody is administered to a patient that is resistant or refractory to prior cancer therapy, including other anti-CTLA4 antibodies, anti-PD-1 antibodies, anti PD-L1 antibodies, or combinations thereof.

In some embodiments where the activatable anti-CTLA4 antibody, upon cleavage of the MM, comprises a heavy chain variable region comprising the amino acid sequence of SEQ ID NO: 87 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 87, and/or a light chain variable region comprising the amino acid sequence of SEQ ID NO: 100 or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 100, the activatable anti-CTLA4 antibody is administered at a first higher dose (e.g., between about 10 mg/kg and about 20 mg) for at least one treatment cycle (as defined herein) followed by a lower dose (e.g., between about 3 mg/kg to about 10 mg/kg) in subsequent cycles. In some such embodiments, the activatable anti-CTLA4 antibody is administered at a dose of about 10 mg/kg for at least one treatment cycle (e.g., one to three treatment cycles) and at a dose of about 6 mg/kg in subsequent treatment cycles. In other such embodiments, the activatable anti-CTLA4 antibody is administered at a dose of about 10 mg/kg for at least one treatment cycle (e.g., one to three treatment cycles) and at a dose of about 3 mg/kg in subsequent treatment cycles. In other such embodiments, the activatable anti-CTLA4 antibody is administered at a dose of about 15 mg/kg for at least one treatment cycle (e.g., one to three treatment cycles) and at a dose of about 10 mg/kg in subsequent treatment cycles. In other such embodiments, the activatable anti-CTLA4 antibody is administered at a dose of about 20 mg/kg for at least one treatment cycle (e.g., one to three treatment cycles) and at a dose of about 10 mg/kg in subsequent treatment cycles. In some of the foregoing embodiments, the activatable antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some of the foregoing embodiments, the activatable anti-CTLA4 antibody comprises a heavy chain comprising the amino acid sequence of SEQ ID NO:320 or 321, or an amino acid sequence having at least 90% (e.g., at least 92%, at least 93%, at least 94%, at least 95%, at least 96%, at least 97%, at least 98% or at least 99%) sequence identity to the amino acid sequence of SEQ ID NO: 320 or 321, and a light chain comprising the amino acid sequence of SEQ ID NO:322, or an amino acid sequence having at least 90% (e.g., at least 92%, at least 93%, at least 94%, at least 95%, at least 96%, at least 97%, at least 98% or at least 99%)

sequence identity to the amino acid sequence of SEQ ID NO: 322. In some of the foregoing embodiments, the activatable anti CTLA4 antibody is administered to a patient with melanoma, non-small cell lung cancer, renal cell carcinoma, or hepatocellular carcinoma. In other of the foregoing embodiments, the activatable anti CTLA4 antibody is administered to a patient with a MSI-H or dMMR cancer. In other of the foregoing embodiments, the activatable anti CTLA4 antibody is administered to a patient with a cancer that has metastasized. In some of the foregoing embodiments, the activatable anti-CTLA4 antibody is administered to a patient that is resistant or refractory to prior cancer therapy, including other anti-CTLA4 antibodies, anti-PD-1 antibodies, anti PD-L1 antibodies, or combinations thereof.

In any of the embodiments of the preceding two paragraphs, the anti-CTLA4 antibody can be administered as a monotherapy or in combination with one or more anticancer agents, as disclosed herein. For instance, the anti-CTLA4 antibody can be administered in combination with an anti-PD-1 antibody or an anti-CD137 antibody. In some embodiments, the combination of the anti-CTLA4 antibody and the anti-PD-1 antibody or anti-CD137 antibody displays a synergistic effect.

In some embodiments, treatment with an anti-CTLA4 antibody and/or one or more additional therapeutic agents depletes Treg cells in tumors. In some embodiments, treatment with an anti-CTLA4 antibody and/or one or more additional therapeutic agents does not deplete Treg cells in peripheral tissues.

In some embodiments, the subject has been previously treated with a prior therapy. In some embodiments, the subject has previously received any one of 1, 2, 3, 4, or more prior therapies. In some embodiments, the subject has exhausted all other available therapies. In some embodiments, the subject is unresponsive or resistant to a prior therapy. In some embodiments, the subject has disease reoccurrence subsequent to a prior therapy. In some embodiments, the subject is refractory to a prior therapy. In some embodiments, the subject has failed a prior therapy within about 1 year, 6 months, 3 months or less. In some embodiments, the subject has not previously received a prior therapy.

In some embodiments, the subject has been previously treated with a standard therapy for the cancer. In some embodiments, the subject is unresponsive or resistant to a standard therapy. In some embodiments, the subject has disease reoccurrence subsequent to a standard therapy. In some embodiments, the subject is refractory to a standard therapy. In some embodiments, the subject has failed a standard therapy within about 1 year, 6 months, 3 months or less. In some embodiments, the subject has not previously received a standard therapy. In some embodiments, the subject has refused or is ineligible for a standard therapy.

In some embodiments, the prior therapy (e.g., standard therapy) is selected from the group consisting of viral gene therapy, immunotherapy, targeted therapy, radiation therapy, and chemotherapy. In some embodiments, the prior therapy is an immune checkpoint inhibitor. In some embodiments, the prior therapy is an inhibitor of CTLA4, PD-1, or a PD-1 ligand (e.g., PD-L1 or PD-L2). In some embodiments, the prior therapy is an inhibitor of CTLA4, such as an anti-CTLA4 antibody that is different from the anti-CTLA4 antibodies described herein. In some embodiments, the prior therapy is ipilimumab. In some embodiments, the prior therapy is ipilimumab and/or nivolumab.

In some embodiments, the prior therapy is an inhibitor of PD-1 or a PD-1 ligand, including a PD-1 binding antagonist, a PDL1 binding antagonist and a PDL2 binding antagonist. Alternative names for "PD-1" include CD279 and SLEB2. Alternative names for "PDL1" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the inhibitor of PD-1 is a molecule that inhibits the binding of PD-1 to its ligand binding partners. In some embodiments, the inhibitor of a PD-1 ligand is an inhibitor of PD-L1 and/or PD-L2. In some embodiments, the inhibitor of PD-L1 is a molecule that inhibits the binding of PDL1 to its binding partners. In some embodiments, a PD-L2 binding partner is PD-1 and/or B7-1. In some embodiments, the inhibitor of a PD-1 ligand is a molecule that inhibits the binding of PD-L2 to its binding partners. In some embodiments, a PD-L2 binding partner is PD-1. The inhibitor may be an antibody, an antigen binding fragment thereof, an immunoadhesin, a fusion protein, or oligopeptide.

In some embodiments, the inhibitor of PD-1 is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the inhibitor of PD-1 is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the inhibitor of PD-1 is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342. In some embodiments, the anti-PD-1 antibody is nivolumab (CAS Registry Number: 946414-94-4). In some embodiments, the anti-PD-1 antibody is pembrolizumab (CAS Registry Number: 1374853-91-4).

In some embodiments, the inhibitor of PD-L1 is anti-PD-L1 antibody. In some embodiments, the inhibitor of PD-L1 is selected from the group consisting of YW243.55.S70, MPDL3280A, MDX-1105, and MEDI4736. MDX-1105, also known as BMS-936559, is an anti-PD-L1 antibody described in WO2007/005874. Antibody YW243.55.S70 is an anti-PD-L1 described in WO 2010/077634 A1. MEDI4736 is an anti-PD-L1 antibody described in WO2011/066389 and US2013/034559. Examples of anti-PD-L1 antibodies useful for the methods of this application, and methods for making thereof are described in PCT patent application WO 2010/077634 A1 and U.S. Pat. No. 8,217,149, which are incorporated herein by reference.

Prior therapies (e.g., standard therapies) also encompass surgery to remove a tumor and radiation therapy. Exemplary radiation therapies include, but are not limited to, ionizing (electromagnetic) radiotherapy (e.g., X-rays or gamma rays) and particle beam radiation therapy (e.g., high linear energy radiation). The source of radiation can be external or internal to the subject.

The methods described herein are useful for various aspects of cancer treatment. In some embodiments, there is provided a method of inhibiting cell proliferation (such as tumor growth) in an individual, comprising administering to the individual an effective amount of any one of the anti- CTLA4 antibodies described herein. In some embodiments, at least about 10% (including for example at least about any of 20%, 30%, 40%, 60%, 70%, 80%, 90%, 95% or more) cell proliferation is inhibited.

In some embodiments, there is provided a method of inhibiting tumor metastasis in an individual, comprising administering to the individual an effective amount of any one of the anti-CTLA4 antibodies described herein. In some embodiments, at least about 10% (including for example at least about any of 20%, 30%, 40%, 60%, 70%, 80%, 90%, 95% or more) metastasis is inhibited.

In some embodiments, there is provided a method of reducing (such as eradicating) pre-existing tumor metastasis (such as metastasis to the lymph node) in an individual, comprising administering to the individual an effective amount of any one of the anti-CTLA4 antibodies described herein. In some embodiments, at least about 10% (including for example at least about any of 20%, 30%, 40%, 60%, 70%, 80%, 90%, 95% or more) metastasis is reduced.

In some embodiments, there is provided a method of reducing incidence or burden of preexisting tumor metastasis (such as metastasis to the lymph node) in an individual, comprising administering to the individual an effective amount of any one of the anti-CTLA4 antibodies described herein.

In some embodiments, there is provided a method of reducing tumor size in an individual, comprising administering to the individual an effective amount of any one of the anti-CTLA4 antibodies described herein. In some embodiments, the method reduces tumor size by at least about 10% (including for example at least about any of 20%, 30%, 40%, 60%, 70%, 80%, 90%, 95% or more).

In some embodiments, there is provided a method of prolonging time to disease progression of cancer in an individual, comprising administering to the individual an effective amount of any one of the anti-CTLA4 antibodies described herein. In some embodiments, the method prolongs the time to disease progression by at least any of 1, 2, 3, 4, 5, 6, 7, 8, 9, 10, 11, 12, 16, 20, 24, 28, 32, 36, or more weeks.

In some embodiments, there is provided a method of prolonging survival (e.g., overall survival or progression-free survival) of an individual having cancer, comprising administering to the individual an effective amount of any one of the anti-CTLA4 antibodies described herein. In some embodiments, the method prolongs the survival of the individual by at least any of 1, 2, 3, 4, 5, 6, 7, 8, 9, 10, 11, 12, 18, or 24 months.

In some embodiments, there is provided a method of alleviating one or more symptoms in an individual having cancer, comprising administering to the individual an effective amount of any one of the anti-CTLA4 antibodies described herein. In some embodiments, the anti-CTLA4 antibody is administered in combination with one or more additional therapeutic agents.

In some embodiments, there is provided a method of improving the quality of life in an individual having cancer, comprising administering to the individual an effective amount of any one of the anti-CTLA4 antibodies described herein.

Combination Therapies

Provided herein are methods of treating a cancer in a subject, comprising administering to the subject an anti-CTLA4 antibody in combination with one or more additional therapeutic agents.

In some embodiments, the anti-CTLA4 antibody is administered in combination with an immunotherapeutic agent. The term “immunotherapeutic agents” refers to a chemical or biological substance that can enhance an immune response of a mammal. Examples of immunotherapeutic agents include: bacillus Calmette-Guerin (BCG); cytokines such as interferons; vaccines such as MyVax personalized immunotherapy, Onyvax-P, Oncophage, GRNVAC1, Favld, Provenge, GVAX, Lovaxin C, BiovaxID, GMXX, and NeuVax; and antibodies such as alemtuzumab (CAMPATH®), bevacizumab (AVASTIN®), cetuximab (ERBITUX®), gemtuzunab ozogamicin (MYLOTARG®), ibritumomab tiuxetan (ZEVALIN®) panitumumab (VECTIBIX®), rituximab (RITUXAN®, MABTHERA®), trastuzumab (HERCEPTIN®), tositumomab (BEXXAR®), ipilimumab (YERVOY®), tremelimumab, CAT-3888, agonist antibodies to OX40 receptor (such as those disclosed in WO2009/079335), agonist antibodies to CD40 receptor (such as those disclosed in WO2003/040170, and TLR-9 agonists (such as those disclosed in WO2003/015711, WO2004/016805, and WO2009/022215).

In some embodiments, the anti-CTLA4 antibody is administered in combination with a hormone therapeutic agent. The term “hormone therapeutic agent” refers to a chemical or biological substance that inhibits or eliminates the production of a hormone, or inhibits or counteracts the effect of a hormone on the growth and/or survival of cancerous cells. Examples of such agents suitable for the methods herein include those that are disclosed in US20070117809. Examples of particular hormone therapeutic agents include tamoxifen (NOLVADEX®), toremifene (FARESTON®), fulvestrant (FASLODEX®), anastrozole (ARIMIDEX®), exemestane (AROMASIN®), letrozole (FEMARA®), megestrol acetate (MEGACE®), goserelin (ZOLADEX®), and leuprolide (LUPRON®). The anti-CTLA4 antibodies of this disclosure may also be used in combination with non-drug hormone therapies such as (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

In some embodiments, the additional therapeutic agent is one or more of pomalyst, revlimid, lenalidomide, pomalidomide, thalidomide, a DNA-alkylating platinum-containing derivative, cisplatin, 5-fluorouracil, cyclophosphamide, an anti-CD137 antibody, an anti-PD-1 antibody, an anti-PD-L1 antibody, an anti-CD20 antibody, an anti-CD40 antibody, an anti-DR5 antibody, an anti-CD1d antibody, an anti-TIM3 antibody, an anti-SLAMF7 antibody, an anti-KIR receptor antibody, an anti-OX40 antibody, an anti-HER2 antibody, an anti-ErbB-2 antibody, an anti-EGFR antibody, cetuximab, rituximab, trastuzumab, pembrolizumab, radiotherapy, single dose radiation, fractionated radiation, focal radiation, whole organ radiation, IL-12, IFNa, GM-CSF, a chimeric antigen receptor, adoptively transferred T cells, an anti-cancer vaccine, and an oncolytic virus. In some embodiments, the additional therapeutic agent is an anti-PD-1 antibody. In some embodiments, the additional therapeutic agent is an anti-PD-1 antibody.

The combination therapy for treating cancer also encompasses the combination of an anti-CTLA4 antibody with surgery to remove a tumor. The anti-CTLA4 antibody may be administered to the mammal before, during, or after the surgery.

The combination therapy for treating cancer also encompasses combination of an anti-CTLA4 antibody with radiation therapy, such as ionizing (electromagnetic) radiotherapy (e.g., X-rays or gamma rays) and particle beam radiation therapy (e.g., high linear energy radiation). The source of radiation can be external or internal to the mammal. The anti-CTLA4 antibody may be administered to the mammal before, during, or after the radiation therapy.

Also provided are compositions of any one of the anti-CTLA4 antibodies described herein for use in the methods described in this section, and use of the anti-CTLA4 antibodies in the manufacture of a medicament for treating cancer (such as a solid cancer, e.g., urothelial carcinoma).

Immune Checkpoint Inhibitors

In some embodiments, an anti-CTLA4 antibody (e.g., activatable antibody) is administered in combination with an immune checkpoint inhibitor, e.g., an anti-PD-1 antibody or an anti-PD-L1 antibody. Immune checkpoint inhibitors are compounds that inhibit the activity of control mechanisms of the immune system. Immune system checkpoints, or immune checkpoints, are inhibitory pathways in the immune system that generally act to maintain self-tolerance or modulate the duration and amplitude of physiological immune responses to minimize collateral tissue damage. Checkpoint inhibitors can inhibit an immune system checkpoint by stimulating the activity of a stimulatory checkpoint molecule, or inhibiting the activity of an inhibitory checkpoint molecule in the pathway. Immune system checkpoint molecules include, but are not limited to, cytotoxic T-lymphocyte antigen 4 (CTLA4), programmed cell death 1 protein (PD-1), programmed cell death 1 ligand 1 (PD-L1), programmed cell death 1 ligand 2 (PD-L2), lymphocyte activation gene 3 (LAG3), B7-1, B7-H3, B7-H4, T cell membrane protein 3 (TIM3), B-and T-lymphocyte attenuator (BTLA), V-domain immunoglobulin (Ig)-containing suppressor of T-cell activation (VISTA), Killer-cell immunoglobulin-like receptor (KIR), and A2A adenosine receptor (A2aR). As such, checkpoint inhibitors include antagonists of CTLA4, PD-1, PD-L1, PD-L2, LAG3, B7-1, B7-H3, B7-H4, BTLA, VISTA, KIR, A2aR, or TIM3. For example, antibodies that bind to CTLA4, PD-1, PD-L1, PD-L2, LAG3, B7-1, B7-H3, B7-H4, BTLA, VISTA, KIR, A2aR, or TIM3 and antagonize their function are checkpoint inhibitors. Moreover, any molecule (e.g., peptide, nucleic acid, small molecule, etc.) that inhibits the inhibitory function of an immune system checkpoint is a checkpoint inhibitor.

In some embodiments, the immune checkpoint inhibitor is an antibody that specifically binds to an immune checkpoint molecule. In some embodiments, the immune checkpoint inhibitor is selected from the group consisting of an anti-PD-1 antibody, an anti-PD-L1 antibody, and an anti-CTLA4 antibody.

In some embodiments, the immune checkpoint inhibitor is an anti-PD-1 antibody. Exemplary anti-PD-1 antibodies include, but are not limited to, 2E5 (Cstone Pharmaceuticals), tislelizumab (BGB-A317), BGB-108, STI-A1110, AM0001, BI 754091, sintilimab (IBI308), cetrelimab (JNJ-63723283), toripalimab (JS-001), camrelizumab (SHR-1210, INCSHR-1210, HR-301210), MEDI-0680 (AMP-514), MGA-012 (INCMGA 0012), nivolumab (BMS-936558, MDX1106, ONO-4538), spartalizumab (PDR001), pembrolizumab (MK-3475, SCH 900475), PF-06801591, cemiplimab (REGN-2810, REGEN2810), dostarlimab (TSR-042, ANB011), pidilizumab (CT-011), FITC-YT-16 (PD-1 binding peptide), APL-501 or CBT-501 or genolimzumab (GB-226), AB-122, AK105, AMG 404, BCD-100, F520, HLX10, HX008, JTX-4014, LZM009, Sym021, PSB205, AMP-224 (fusion protein targeting PD-1), CX-188 (PD-1 probody), AGEN-2034, GLS-010, budigalimab (ABBV-181), AK-103, BAT-1306, CS-1003, AM-0001, TILT-123, BH-2922, BH-2941, BH-2950, ENUM-244C8, ENUM-388D4, HAB-21, HEISCOI 11-003, IKT-202, MCLA-134, MT-17000, PEGMP-7, PRS-332, RXI-762, STI-1110, VXM-10, XmAb-23104, AK-112, HLX-20, SSI-361, AT-16201, SNA-01, AB122, PD1-PIK, PF-06936308, RG-7769, CAB PD-1 Abs, AK-123, MEDI-3387, MEDI-5771, 4H1128Z-E27, REMD-288, SG-001, BY-24.3, CB-201, IBI-319, ONCR-177, Max-1, CS-4100, JBI-426, CCC-0701, CCX-4503, biosimilars thereof, and derivatives thereof. In some embodiments, the antibodies that compete with any of these art-recognized antibodies for binding to PD-1 also can be used. In some embodiments, the immune checkpoint inhibitor is 2E5. 2E5 and related anti-PD-1 antibodies have been described, for example, in CN107840887A, which is incorporated herein by reference in its entirety. In some embodiments, the immune checkpoint inhibitor is toripalimab. Toripalimab and related anti-PD-1 antibodies have been described, for example, in U.S. Pat. No. 10,066,013B2, which is incorporated herein by reference in its entirety.

In some embodiments, the anti-PD-1 antibody comprises a heavy chain variable region (VH) and a light chain variable region (VL), wherein the VH comprises a HVR-H1 comprising the amino acid sequence of SEQ ID NO: 294, a HVR-H2 comprising the amino acid sequence of SEQ ID NO: 295, and a HVR-H3 comprising the amino acid sequence of SEQ ID NO: 296; and wherein the VL comprises a HVR-L1 comprising the amino acid sequence of SEQ ID NO: 297, a HVR-L2 comprising the amino acid sequence of SEQ ID NO: 298, and a HVR-L3 comprising the amino acid sequence of SEQ ID NO: 299. In some embodiments, the anti-PD-1 antibody comprises a VH comprising the amino acid sequence of SEQ ID NO: 300. In some embodiments, the anti-PD-1 antibody comprises a VL comprising the amino acid sequence of SEQ ID NO: 301.

In some embodiments, the immune checkpoint inhibitor is an anti-PD-L1 antibody. Exemplary anti-PD-L1 antibodies include, but are not limited to, atezolizumab, avelumab, durvalumab (imfinzi), BGB-A333, SHR-1316 (HTI-1088), CK-301, BMS-936559, envafolimab (KN035, ASC22), CS1001, MDX-1105 (BMS-936559), LY3300054, STI-A1014, FAZ053, CX-072, INCB086550, GNS-1480, CA-170, CK-301, M-7824, HTI-1088 (HTI-131, SHR-1316), MSB-2311, AK-106, AVA-004, BBI-801, CA-327, CBA-0710, CBT-502, FPT-155, IKT-201, IKT-703, 10-103, JS-003, KD-033, KY-1003, MCLA-145, MT-5050, SNA-02, BCD-135, APL-502 (CBT-402 or TQB2450), IMC-001, KD-045, INBRX-105, KN-046, IMC-2102, IMC-2101, KD-005, IMM-2502, 89Zr-CX-072, 89Zr-DFO-6E11, KY-1055, MEDI-1109, MT-5594, SL-279252, DSP-106, Gensci-047, REMD-290, N-809, PRS-344, FS-222, GEN-1046, BH-29xx, FS-118, biosimilars thereof, and derivatives thereof. In some embodiments, the antibodies that compete with any of these art-recognized antibodies for binding to PD-L1 also can be used. In some embodiments, the immune checkpoint inhibitor is atezolizumab.

Anti-CD137 Antibodies

In some embodiments, an anti-CTLA4 antibody (e.g., activatable antibody) is administered in combination with an anti-CD137 antibody. In some embodiments, the anti-CD137 antibody is any one of the anti-CD137 antibodies (including full-length antibodies and antigen-binding fragments thereof) described herein (see Section IV. Anti-CD137 antibodies).

CD137 (also referred to as CD137 receptor, 4-1BB, TNFRSF9, etc.) is a transmembrane protein of the Tumor Necrosis Factor Receptor Superfamily (TNFRS). Current understanding of CD137 indicates that its expression is generally activation dependent and is present in a broad subset of immune cells including activated NK and NKT cells, regulatory T cells, dendritic cells (DC), stimulated mast cells, differentiating myeloid cells, monocytes, neutrophils, and eosinophils (Wang, 2009, *Immunological Reviews* 229:192-215). CD137 expression has also been demonstrated on tumor vasculature (Broll, 2001, Amer. J. Clin. Pathol. 115 (4): 543-549; Seaman, 2007, Cancer Cell 11:539-554) and at sites of inflamed or atherosclerotic endothelium (Drenkard, 2007 FASEB J. 21:456-463; Olofsson, 2008, Circulation 117:1292-1301). The ligand that stimulates CD137, i.e., CD137 Ligand (CD137L), is expressed on activated antigen-presenting cells (APCs), myeloid progenitor cells, and hematopoietic stem cells.

VEGF Inhibitors

In some embodiments, an anti-CTLA4 antibody (e.g., activatable antibody) is administered in combination with a VEGF inhibitor. Vascular endothelial growth factor (VEGF) inhibitors are a type of angiogenesis inhibitor. Vascular endothelial growth factor (VEGF)-mediated angiogenesis is thought to play a critical role in tumor growth and metastasis. In some embodiments, anti-CTLA4 antibody is administered in combination with a VEGF inhibitor. In some embodiments, the VEGF inhibitor is selected from the group consisting of fruquintinib, anlotinib, Sunitinib, Sorafenib, Pazopanib, Brivanib alaninate, Cediranib, Vandetanib, Linifinib, Linifinib, Aflibercept, and an anti-VEGF bispecific antibody.

Chemotherapeutic Agents

In some embodiments, anti-CTLA4 antibody is administered in combination with a chemotherapeutic agent. The term "chemotherapeutic agent" refers to a chemical or biological substance that can cause death of cancer cells, or interfere with growth, division, repair, and/or function of cancer cells. Examples of chemotherapeutic agents include those that are disclosed in WO 2006/129163, and US20060153808, the disclosures of which are incorporated herein by reference. Examples of particular chemotherapeutic agents include: (1)alkylating agents, such as chlorambucil (LEUKERAN®), mcyclophosphamide (CYTOXAN®), ifosfamide (IFEX®), mechlorethamine hydrochloride (MUSTARGEN®), thiotepa (THIOPLEX®), streptozotocin (ZANOSAR®), carmustine (BICNU®, GLIADEL WAFER®), lomustine (CEENU®), and dacarbazine (DTIC-DOME®); (2)alkaloids or plant *vinca* alkaloids, including cytotoxic antibiotics, such as doxorubicin (ADRIAMYCIN®), epirubicin (ELLENCE®, PHARMORUBICIN®), daunorubicin (CERUBIDINE®, DAUNOXOME®), nemorubicin, idarubicin (IDAMYCIN PFS®, ZAVEDOS®), mitoxantrone (DHAD®, NOVANTRONE®). dactinomycin (actinomycin D, COSMEGEN®), plicamycin (MITHRACIN®), mitomycin (MUTAMYCIN®), and bleomycin (BLENOXANE®), vinorelbine tartrate (NAVELBINE®), vinblastine (VELBAN®), vincristine (ONCOVIN®), and vindesine (ELDISINE®); (3) antimetabolites, such as capecitabine (XELODA®), cytarabine (CYTOSAR-U®), fludarabine (FLUDARA®), gemcitabine (GEMZAR®), hydroxyurea (HYDRA®), methotrexate (FOLEX®, MEXATE, TREXALL®), nelarabine (ARRANON®), trimetrexate (NEUTREXIN®), and pemetrexed (ALIMTA®); (4) Pyrimidine antagonists, such as 5-fluorouracil (5-FU); capecitabine (XELODA®), raltitrexed (TOMUDEX®), tegafur-uracil (UFTORAL®), and gemcitabine (GEMZAR®); (5) taxanes, such as docetaxel (TAXOTERE®), paclitaxel (TAXOL®); (6) platinum drugs, such as cisplatin (PLATINOL®) and carboplatin (PARAPLATIN®), and oxaliplatin (ELOXATIN®); (7) topoisomerase inhibitors, such as irinotecan (CAMPTOSAR®), topotecan (HYCAMTIN®), etoposide (ETOPOPHOS®, VEPESSID®, TOPOSAR®), and teniposide (VUMON®); (8) epipodophyllotoxins (podophyllotoxin derivatives), such as etoposide (ETOPOPHOS®, VEPESSID®, TOPOSAR®); (9) folic acid derivatives, such as leucovorin (WELLCOVORIN®); (10) nitrosoureas, such as carmustine (BICNU®), lomustine (CEENU®); (11) inhibitors of receptor tyrosine kinase, including epidermal growth factor receptor (EGFR), vascular endothelial growth factor (VEGF), insulin receptor, insulin-like growth factor receptor (IGFR), hepatocyte growth factor receptor (HGFR), and platelet-derived growth factor receptor (PDGFR), such as gefitinib (IRESSA®), erlotinib (TARCEVA®), bortezomib (VELCADE®), imatinib mesylate (GLEEVEC®), genefitinib, lapatinib, sorafenib, thalidomide, sunitinib (SUTENT®), axitinib, rituximab (RITUXAN, MABTHERA®), trastuzumab (HERCEPTIN®), cetuximab (ERBITUX®), bevacizumab (AVASTIN®), and ranibizumab (LUCENTIS®), lym-1 (ONCOLYM®), antibodies to insulin-like growth factor-1 receptor (IGF-1R) that are disclosed in WO2002/053596); (12) angiogenesis inhibitors, such as bevacizumab (AVASTIN®), suramin (GERMANIN®), angiostatin, SU5416, thalidomide, and matrix metalloproteinase inhibitors (such as batimastat and marimastat), and those that are disclosed in WO2002055106; and (13) proteasome inhibitors, such as bortezomib (VELCADE®).

In some embodiments, an anti-CTLA4 antibody is administered in combination with icaritin (3,5,7-trihydroxy-2-(4-methoxyphenyl)-8-(3-methylbut-2-enyl) chromen-4-one; PubChem CID No. 5318980). Icaritin is a compound extracted from a traditional Chinese herb, genus Epimedium, that demonstrated an antitumor effect in various neoplasms including hematological malignancies such as leukemia, lymphoma, and multiple myeloma. Icaritin may also be referred to as "SNG 162". The structure of icaritin is set forth below.

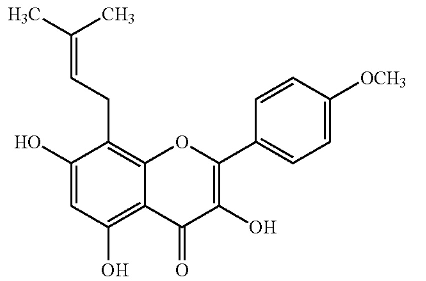 [SMILES: COc1ccc(-c2oc3c(CC=C(C)C)c(O)cc(O)c3c(=O)c2O)cc1]

Icaritin (3,5,7-trihydroxy-2-(4-methoxyphenyl)-8-(3-methylbut-2-enyl) chromen-4-one) PARP inhibitors In some embodiments, an anti-CTLA4 antibody is administered in combination with a PARP inhibitor. PARP inhibitors are a group of pharmacological inhibitors of the enzyme poly ADP ribose polymerase (PARP). In some embodiments, anti-CTLA4 antibody is administered in combination with a PARP inhibitor. In some embodiments, the PARP inhibitor is olaparib.

III. Anti-CTLA4 Antibodies

The method described herein comprise administration of an anti-CTLA4 antibody that specifically binds to human CTLA4, including CTLA4 antibodies, antigen-binding fragments of the CTLA4 antibodies, and derivatives of the CTLA4 antibodies. Exemplary anti-CTLA4 antibodies have been described, for example, in International Publication No. WO2019149281A1, which is incorporated herein by reference in its entirety.

In some embodiments, the anti-CTLA4 antibody is any one of the antibodies described herein, including antibodies described with reference to specific amino acid sequences of HVRs, variable regions (VL, VH), and light and heavy chains (e.g., IgG1, IgG2, IgG4). In some embodiments, the antibodies are human antibodies. In some embodiments, the antibodies are humanized antibodies and/or chimeric antibodies. In some embodiments, the anti-CTLA4 antibody binds to human CTLA4, and have at least one (e.g., at least one, at least two, at least three, at least four, at least five, at least six, at least seven, at least eight, or all nine) of the following functional properties: (a) bind to human, cynomolgus monkey, mouse, rat, and/or dog CTLA4 with a $K_D$ of 500 nM or less; (b) have antagonist activity on human CTLA4; (c) do not bind to human PD-1, PD-L1, PD-L2, LAG3, TIM3, B7-H3, CD95, CD120a, OX40, CD40, BTLA, VISTA, ICOS, and/or B7-H4 at concentration up to 100 nM; (d) are cross-reactive with monkey, mouse, rat, and/or dog CTLA4; (e) induces ADCC effects (e.g., on Tregs); (f) activates human PBMCs (e.g., stimulates secretion of IL-2 and/or IFNy); (g) are capable of inhibiting tumor cell growth; (h) have therapeutic effect on a cancer; and (i) block binding of human CTLA4 to human CD80 and/or human CD86. In some embodiments, the anti-CTLA4 antibodies described herein have lower activity in blocking binding of CD80 and/or CD86 to human CTLA4 as compared to ipilimumab in an assay wherein either when human CD80 and/or CD86 are immobilized (or plate bound) or when human CTLA4 protein is present on cell surface. In some embodiments, the anti-CTLA4 antibodies described herein deplete Treg cells selectively in tumor microenvironment as compared to Treg depletions in PBMC or spleen. In some embodiments, the anti-CTLA4 antibodies described herein have higher Treg depletion activity in tumor microenvironment as compared to ipilimumab. Also provided herein are one or more anti-CTLA4 antibodies or antigen-binding fragments that cross-compete for binding to human CTLA4 with one or more of the antibodies or antigen-binding fragments described herein.

In some embodiments, the antibodies or antigen-binding fragments bind to human, cynomolgus monkey, mouse, rat, and/or dog CTLA4 with a $K_D$ of about 500 nM or less (e.g., about 500 nM or less, about 450 nM or less, about 400 nM or less, about 350 nM or less, about 300 nM or less, about 250 nM or less, about 200 nM or less, about 150 nM or less, about 100 nM or less, about 90 nM or less, about 80 nM or less, about 70 nM or less, about 60 nM or less, about 50 nM or less, about 40 nM or less, about 30 nM or less, about 25 nM or less, about 20 nM or less, about 10 nM or less, about 1 nM or less, about 0.1 nM or less, etc.) In some embodiments, the antibodies or antigen-binding fragments bind to human, cynomolgus monkey, mouse, rat, and/or dog CTLA4 with a $K_D$ of about 350 nM or less. In some embodiments, the antibodies or antigen-binding fragments bind to human CTLA4 with a $K_D$ of about 100 nM or less. In some embodiments, the antibodies or antigen-binding fragments bind to human CTLA4 with a $K_D$ of about 50 nM or less. In some embodiments, the antibodies or antigen-binding fragments bind to human CTLA4 with a $K_D$ of about 10 nM or less. Methods of measuring the $K_D$ of an antibody or antigen-binding fragment may be carried out using any method known in the art, including for example, by surface plasmon resonance, an ELISA, isothermal titration calorimetry, a filter binding assay, an EMSA, etc. In some embodiments, the $K_D$ is measured by surface plasmon resonance or an ELISA (see e.g., Example 3 below).

In some embodiments, the antibodies or antigen-binding fragments described herein have antagonist activity on human CTLA4. In some embodiments, the antibodies or antigen-binding fragments repress one or more activities of human CTLA4 when a cell (e.g., a human cell) expressing human CTLA4 is contacted by the antibody or antigen binding fragment (e.g., CTLA4 blockade as measured by an increase in a reporter gene signal using a CLA4 blockage reporter gene assay).

In some embodiments, the antibodies or antigen-binding fragments are cross-reactive with monkey (e.g., cynomolgus monkey), mouse, rat, and/or dog CTLA4. In some embodiments, the antibodies or antigen-binding fragments are cross-reactive with monkey CTLA4. In some embodiments, the antibodies or antigen-binding fragments are cross-reactive with mouse CTLA4. In some embodiments, the antibodies or antigen-binding fragments are cross-reactive with rat CTLA4. In some embodiments, the antibodies or antigen-binding fragments are cross-reactive with dog CTLA4. In some embodiments, the antibodies or antigen binding fragments are cross reactive with monkey and mouse CTLA4; monkey and rat CTLA4; monkey and dog CTLA4; mouse and rat CTLA4; mouse and dog CTLA4; rat and dog CTLA4; monkey, mouse, and rat CTLA4; monkey, mouse, and dog CTLA4; monkey, rat, and dog CTLA4; mouse, rat, and dog CTLA4; or monkey, mouse, rat, and dog CTLA4. In some embodiments, the antibodies or antigen binding fragments are cross-reactive if the antibodies or antigen-binding fragments binds to a non-human CTLA4 molecule with a $K_D$ less than about 500 nM (e.g., less than about 1nM, less than about 10 nM, less than about 25 nM, less than about 50 nM, less than about 75 nM, less than about 100 nM, less than about 150 nM, less than about 200 nM, less than about 250 nM, less than about 300 nM, less than about 350 nM, etc.). Methods of measuring antibody cross-reactivity are known in the art, including, without limitation, surface plasmon resonance, an ELISA, isothermal titration calorimetry, a filter binding assay, an EMSA, etc. In some embodiments, the cross-reactivity is measured by ELISA.

In some embodiments, the antibodies induce ADCC effects against a CTLA4 expressing cell (e.g., against CTLA4-expressing human cells such as Tregs) after the antibody binds to the cell-expressed CTLA4. Methods of measuring ADCC effects (e.g., in vitro methods) are known in the art. In some embodiments, the antibodies induce ADCC effects by more than about 10% (e.g., induce ADCC by more than about 10%, more than about 15%, more than about 20%, more than about 25%, more than about 30%, more than about 35%, more than about 40%, etc.) relative to a control (e.g., an isotype control or ipilimumab).

In some embodiments, the antibodies or antigen-binding fragments are capable of inhibiting tumor cell growth and/or proliferation. In some embodiments, the tumor cell growth and/or proliferation is inhibited by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) when contacted with the antibodies or antigen-binding fragments relative to corresponding tumor cells not contacted with the antibodies or antigen-binding fragments (or relative to corresponding tumor cells contacted with an isotype control antibody). In some embodiments, the antibodies or antigen-binding fragments are capable of reducing tumor volume in a subject when the subject is administered the antibodies or antigen-binding fragments. In some embodiments, the antibodies or antigen-binding fragments are capable of reducing tumor volume in a subject by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) relative to the initial tumor volume in the subject (e.g., prior to administration of the antibodies or antigen-binding fragments; as compared to a corresponding tumor in a subject administered an isotype control antibody). Methods of monitoring tumor cell growth/proliferation, tumor volume, and/or tumor inhibition are known in the art.

In some embodiments, the antibodies or antigen-binding fragments have therapeutic effect on a cancer. In some embodiments, the antibodies or antigen-binding fragments reduce one or more signs or symptoms of a cancer. In some embodiments, a subject suffering from a cancer goes into partial or complete remission when administered the antibodies or antigen-binding fragments.

In another aspect, the disclosure provides isolated antibodies that compete or cross-compete for binding to human CTLA4 with any of the illustrative antibodies of the disclosure, such as TY21585, TY21586, TY21587, TY21588, TY21589, TY21580, TY21591, TY21686, TY21687, TY21689, TY21680, TY21691, and/or TY21692. In a particular embodiment, the present application provides isolated antibodies that compete or cross-compete for binding to the same epitope on the human CTLA4 with any of the illustrative antibodies of the disclosure. The ability of an antibody to compete or cross-compete for binding with another antibody can be determined using standard binding assays known in the art, such as BIAcore analysis, ELISA assays, or flow cytometry. For example, one can allow an illustrative antibody of the disclosure to bind to human CTLA4 under saturating conditions and then measure the ability of the test antibody to bind to the CTLA4. If the test antibody is able to bind to the CTLA4 at the same time as the illustrative antibody, then the test antibody binds to a different epitope as the illustrative antibody. However, if the test antibody is not able to bind to the CTLA4 at the same time, then the test antibody binds to the same epitope, an overlapping epitope, or an epitope that is in close proximity to the epitope bound by the illustrative antibody. This experiment can be performed using various methods, such as ELISA, RIA, FACS or surface plasmon resonance.

In some embodiments, the antibodies or antigen-binding fragments block the binding between CTLA4 and one or more of its binding partners (e.g., human CTLA4 and human CD80, human CTLA4 and human CD86). In some embodiments, the antibodies or antigen-binding fragments block the binding between CTLA4 and its ligand in vitro. In some embodiments, the antibody or antigen-binding fragment has a half maximal inhibitory concentration (IC50) of about 500 nM or less (e.g., about 500 nM or less, about 400 nM or less, about 300 nM or less, about 200 nM or less, about 100 nM or less, about 50 nM or less, about 25 nM or less, about 10 nM or less, about 1 nM or less, etc.) for blocking binding of CTLA4 to CD80 and/or CD86. In some embodiments, the antibody or antigen-binding fragment has a half maximal inhibitory concentration (IC50) of about 100 nM or less for blocking binding of CTLA4 to CD80 and/or CD86. In some embodiments, the antibody or antigen-binding fragment completely blocks binding of human CTLA4 to CD80 and/or CD86 when provided at a concentration of about 100 nM or greater (e.g., about 100 nM or greater, about 500 nM or greater, about 1 μM or greater, about 10 μM or greater, etc.). As used herein, the term "complete blocking" or "completely blocks" refers to the antibody or antigen-binding fragment's ability to reduce binding between a first protein and a second protein by at least about 80% (e.g., at least about 80%, at least about 85%, at least about 90%, at least about 95%, at least about 99%, etc.). Methods of measuring the ability of an antibody or antigen-binding fragment to block binding of a first protein (e.g., human CTLA4) and a second protein (e.g., human CD80 or human CD86) are known in the art, including, without limitation, via BIAcore analysis, ELISA assays, and flow cytometry. In some embodiments, the anti-CTLA4 antibodies described herein have lower activity in blocking ligand binding than ipilimumab.

In some embodiments, the anti-CTLA4 antibody binds human CTLA4 with a $K_D$ of 1000 nM or less (e.g., 50 nM or less, 10 nM or less) as measured by surface plasmon resonance. In some embodiments, the antibody is cross-reactive with at least one non-human species selected from cynomolgus monkey, mouse, rat, and dog.

In some embodiments, the anti-CTLA4 antibody specifically binds to an epitope similar to a ligand binding site of human CTLA4. In some embodiments, the antibody specifically binds to an epitope similar to CD80 binding site of human CTLA4. In some embodiments, the antibody specifically binds to an epitope similar to CD86 binding site of human CTLA4. In some embodiments, the antibody specifically binds to an epitope comprising one or more amino acid residues in a ligand binding site (e.g., CD80 and/or CD86 binding site) of human CTLA4. In some embodiments, the antibody specifically binds to an epitope on human CTLA4 that is different from the epitope of ipilimumab. In some embodiments, the epitope does not comprise amino acid residues in the CC' loop motif of human CTLA4. In some embodiments, the epitope does not comprise amino acid residue L106 or 1108 of human CTLA4. In some embodiments, the antibody specifically binds to an epitope comprising amino acid residues Y105 and L106, but not 1108 of human CTLA4, wherein the numbering of the amino acid residues is according to

```
                                           (SEQ ID NO: 207)
KAMHVAQPAVVLASSRGIASFVCEYASPGKATEVRVTVLRQADSQVTEV
CAATYMMGNELTFLDDSICTGTSSGNQVNLTIQGLRAMDTGLYICKVEL
MYPPPYYLGIGNGTQIYVIDPE.
```

In some embodiments, the anti-CTLA4 antibody comprising a heavy chain variable region and a light chain variable region, a) where the heavy chain variable region comprises an HVR-H1, an HVR-H2, and an HVR-H3, where the HVR-H1 comprises an amino acid sequence according to a formula selected from: Formula (I): X1TFSX2YX3IHWV (SEQ ID NO: 1), where X1 is For Y, X2 is D or G, and $X_3$ is A, G, or W; Formula (II): YSIX1SGX2X3WX4WI (SEQ ID NO: 2), where X1 is S or T, X2 is H or Y, X3 is H or Y, and X4 is A, D, or S; and Formula (III): FSLSTGGVAVX1WI (SEQ ID NO: 3), where X1 is G or S; the HVR-H2 comprises an amino acid sequence according to a formula selected from: Formula (IV): IGX1IX2HSGSTYYSX3SLKSRV (SEQ ID NO: 4), where X1 is D or E, X2 is S or Y, and X3 is P or Q; Formula (V): IGX1ISPSX2GX3TX4YAQKFQGRV (SEQ ID NO: 5), where X1 is I or W, X2 is G or S, X3 is G or S, and X4 is K or N; and Formula (VI):

VSX1ISGX2GX3X4TYYADSVKGRF (SEQ ID NO: 6), where X1 is A, G, or S, X2 is S or Y, X3 is G or S, and X4 is S or T; and the HVR-H3 comprises an amino acid sequence according to a formula selected from: Formula (VII): ARX1X2X3X4FDX5 (SEQ ID NO: 7), where X1 is G, R, or S, X2 is A, I, or Y, X3 is D, V, or Y, X4 is A, E, or Y, and X5 is I or Y; Formula (VIII): ARX1GX2GYFDX3 (SEQ ID NO: 8), where X1 is D or L, X2 is For Y, and X3 is V or Y; Formula (IX): ARX1X2X3X4AX5X6FDY (SEQ ID NO: 9), where X1 is L or R, X2 is I or P, X3 is A or Y, X4 is S or T, X5 is T or Y, and X6 is A or Y; and Formula (X): ARDX1X2X3GSSGYYX4GFDX5 (SEQ ID NO: 10), where X1 is I or V, X2 is A or H, X3 is P or S, X4 is D or Y, and X5 is F or V; and/or b) where the light chain variable region comprises an HVR-L1, an HVR-L2, and an HVR-L3, where the HVR-L1 comprises an amino acid sequence according to a formula selected from: Formula (XI): RASQX1X2X3SX4LX5 (SEQ ID NO: 11), where X1 is G or S, X2 is I or V, X3 is G or S, X4 is S or Y, and X5 is A or N; Formula (XII): RASQX1VX2X3RX4LA (SEQ ID NO: 12), where X1 is S or T, X2 is F, R, or S, X3 is G or S, and X4 is F or Y; and Formula (XIII): RASX1SVDFX2GX3SFLX4 (SEQ ID NO: 13), where X1 is E or Q, X2 is D, F, H, or Y, X3 is F, I, or K, and X4 is A, D, or H; the HVR-L2 comprises an amino acid sequence according to Formula (XIV): X1ASX2X3X4X5GX6 (SEQ ID NO: 14), where X1 is A or D, X2 is N, S, or T, X3 is L or R, X4 is A, E, or Q, X5 is S or T, and X6 is I or V; and the HVR-L3 comprises an amino acid sequence according to a formula selected from: Formula (XV): YCX1X2X3X4X5X6PX7T (SEQ ID NO: 15), where X1 is E, Q, or V, X2 is H or Q, X3 is A, G, H, R, or S, X4 is D, L, S, or Y, X5 is E, G, P, Q, or S, X6 is L, T, V, or W, and X7 is F, L, P, W, or Y; Formula (XVI): YCQQX1X2X3WPPWT (SEQ ID NO: 16), where X1 is S or Y, X2 is D or Y, and $X_3$ is Q or Y; and Formula (XVII): YCQX1YX2SSPPX3YT (SEQ ID NO: 17), where X1 is H or Q, X2 is T or V, and $X_3$ is E or V.

In some embodiments, the antibody comprises: a) an HVR-H1 comprising an amino acid sequence selected from SEQ ID NOS: 18-29; an HVR-H2 comprising an amino acid sequence selected from SEQ ID NOS: 30-39; and an HVR-H3 comprising an amino acid sequence selected from SEQ ID NOS: 40-52; and/or b) an HVR-L1 comprising an amino acid sequence selected from SEQ ID NOS: 53-65; an HVR-L2 comprising an amino acid sequence selected from SEQ ID NOS: 66-69; and an HVR-L3 comprising an amino acid sequence selected from SEQ ID NOS: 70-81. In some embodiments, the antibody comprises one, two, three, four, five, or all six of the HVRs shown for any of the exemplary antibodies described in Table A below.

TABLE A anti-CTLA4 HVR sequences

| Ab name: | HVR-H1 | HVR-H2 | HVR-H3 | HVR-L1 | HVR-L2 | HVR-L3 |
|---|---|---|---|---|---|---|
| TY21 585 | FTFSDYAI HWV (SEQ ID NO: 18) | IGIISPSSGSTNYA QKFQGRV (SEQ ID NO: 30) | ARDIHSGSSGY YYGFDV (SEQ ID NO: 40) | RASESVDFF GISFLA (SEQ ID NO: 53) | DASNR ATGI (SEQ ID NO: 66) | YCQHYTSS PPVYT (SEQ ID NO: 70) |
| TY21 586 | YSITSGYY WAWI (SEQ ID NO: 19) | VSSISGSGSTTYYA DSVKGRF (SEQ ID NO: 31) | ARDGFGYFDY (SEQ ID NO: 41) | SASSSVSYV Y (SEQ ID NO: 54) | DASSLE SGV (SEQ ID NO: 67) | YCVQGLQ TPWT (SEQ ID NO: 71) |
| TY21 587 | FTFSDYGI HWV (SEQ ID NO: 20) | IGEIYHSGSTYYSP SLKSRV (SEQ ID NO: 32) | ARDVAPGSSG YYDGFDF (SEQ ID NO: 42) | RASQGIGSSL A (SEQ ID NO: 55) | DASNR ATGI (SEQ ID NO: 66) | YCQQYDQ WPPWT (SEQ ID NO: 72) |
| TY21 588 | YSISSGYH WDWI (SEQ ID NO: 21) | VSGISGYGGSTYY ADSVKGRF (SEQ ID NO: 33) | ARHSYYGSGN FDY (SEQ ID NO: 43) | RASESVDFF GKSFLH (SEQ ID NO: 56) | DASNL ETGV (SEQ ID NO: 68) | YCQQSYS WPPT (SEQ ID NO: 73) |
| TY21 589 | FTFSDYWI HWV (SEQ ID NO: 22) | IGWISPSGGGTKY AQKFQGRV (SEQ ID NO: 34) | ARGAYEFDY (SEQ ID NO: 44) | RASQSVSSR FLA (SEQ ID NO: 57) | DASNR ATGI (SEQ ID NO: 66) | YCQQSYPT PLT (SEQ ID NO: 74) |
| TY21 580 | YSISSGYH WSWI (SEQ ID NO: 23) | LARIDWDDDKYY STSLKSRL (SEQ ID NO: 35) | ARSYVYFDY (SEQ ID NO: 45) | RASQSVRGR FLA (SEQ ID NO: 58) | DASNR ATGI (SEQ ID NO: 66) | YCQQSSSW PPT (SEQ ID NO: 75) |
| TY21 591 | FSLSTGGV AVSWI (SEQ ID NO: 24) | IGEIYHSGSTYYSP SLKSRV (SEQ ID NO: 32) | ARRIATATYFD Y (SEQ ID NO: 46) | RASQTVFSR YLA (SEQ ID NO: 59) | DASNR ATGI (SEQ ID NO: 66) | YCQQSYY WPPWT (SEQ ID NO: 76) |
| TY21 686 | FSLSTGGV AVGWI (SEQ ID NO: 25) | VSAISGYGSTTYY ADSVKGRF (SEQ ID NO: 36) | ARLPYSAYAF DY (SEQ ID NO: 47) | RASQGVSSY LA (SEQ ID NO: 60) | AASTL QSGV (SEQ ID NO: 69) | YCQHHYG TPLT (SEQ ID NO: 77) |

TABLE A-continued anti-CTLA4 HVR sequences

| Ab name: | HVR-H1 | HVR-H2 | HVR-H3 | HVR-L1 | HVR-L2 | HVR-L3 |
|---|---|---|---|---|---|---|
| TY21 687 | FTFSGYAI HWV (SEQ ID NO: 26) | IGIISPSGGGTKYA QKFQGRV (SEQ ID NO: 37) | ARHPFAY (SEQ ID NO: 48) | RASQSVDFY GISFLD (SEQ ID NO: 61) | DASNR ATGI (SEQ ID NO: 66) | YCQQYVSS PPEYT (SEQ ID NO: 78) |
| TY21 689 | YTFSGYGI HWV (SEQ ID NO: 27) | IGEIYHSGSTYYSP SLKSRV (SEQ ID NO: 32) | ARRIDAFDI (SEQ ID NO: 49) | RASQSVDFD GFSFLH (SEQ ID NO: 62) | DASSLE SGV (SEQ ID NO: 67) | YCQQRDS WPYT (SEQ ID NO: 79) |
| TY21 680 | YTFSGYAI HWV (SEQ ID NO: 28) | IGIISPSGGGTKYA QKFQGRV (SEQ ID NO: 37) | ARLYDVAY (SEQ ID NO: 50) | RASQSVDFH GKSFLH (SEQ ID NO: 63) | DASSLE SGV (SEQ ID NO: 67) | YCEQSLEV PFT (SEQ ID NO: 80) |
| TY21 691 | FTFSDYAI HWV (SEQ ID NO: 18) | IGIISPSGGSTKYA QKFQGRV (SEQ ID NO: 38) | ARLGYGYFDV (SEQ ID NO: 51) | RASQSVDFY GISFLH (SEQ ID NO: 64) | DASSLE SGV (SEQ ID NO: 67) | YCVQALQ LPLT (SEQ ID NO: 81) |
| TY21 692 | YSITSGHY WSWI (SEQ ID NO: 29) | IGDISHSGSTYYSQ SLKSRV (SEQ ID NO: 39) | ARGSRTGYFD Y (SEQ ID NO: 52) | RASQSISSYL N (SEQ ID NO: 65) | DASNL ETGV (SEQ ID NO: 68) | YCQHHYG TPLT (SEQ ID NO: 77) |

In some embodiments, the antibody comprises an HVR-H1 comprising the amino acid sequence of SEQ ID NO: 18, an HVR-H2 comprising the amino acid sequence of SEQ ID NO: 30, an HVR-H3 comprising the amino acid sequence of SEQ ID NO: 40, an HVR-L1 comprising the amino acid sequence of SEQ ID NO: 53, an HVR-L2 comprising the amino acid sequence of SEQ ID NO: 66, and an HVR-L3 comprising the amino acid sequence of SEQ ID NO: 70. In some embodiments, the antibody comprises an HVR-H1 comprising the amino acid sequence of SEQ ID NO: 19, an HVR-H2 comprising the amino acid sequence of SEQ ID NO: 31, an HVR-H3 comprising the amino acid sequence of SEQ ID NO: 41, an HVR-L1 comprising the amino acid sequence of SEQ ID NO: 54, an HVR-L2 comprising the amino acid sequence of SEQ ID NO: 67, and an HVR-L3 comprising the amino acid sequence of SEQ ID NO: 71. In some embodiments, the antibody comprises an HVR-H1 comprising the amino acid sequence of SEQ ID NO: 20, an HVR-H2 comprising the amino acid sequence of SEQ ID NO: 32, an HVR-H3 comprising the amino acid sequence of SEQ ID NO: 42, an HVR-L1 comprising the amino acid sequence of SEQ ID NO: 55, an HVR-L2 comprising the amino acid sequence of SEQ ID NO: 66, and an HVR-L3 comprising the amino acid sequence of SEQ ID NO: 72. In some embodiments, the antibody comprises an HVR-H1 comprising the amino acid sequence of SEQ ID NO: 21 an HVR-H2 comprising the amino acid sequence of SEQ ID NO: 33, an HVR-H3 comprising the amino acid sequence of SEQ ID NO: 43, an HVR-L1 comprising the amino acid sequence of SEQ ID NO: 56, an HVR-L2 comprising the amino acid sequence of SEQ ID NO: 68, and an HVR-L3 comprising the amino acid sequence of SEQ ID NO: 73. In some embodiments, the antibody comprises an HVR-H1 comprising the amino acid sequence of SEQ ID NO: 22, an HVR-H2 comprising the amino acid sequence of SEQ ID NO: 34, an HVR-H3 comprising the amino acid sequence of SEQ ID NO: 44, an HVR-L1 comprising the amino acid sequence of SEQ ID NO: 57, an HVR-L2 comprising the amino acid sequence of SEQ ID NO: 66, and an HVR-L3 comprising the amino acid sequence of SEQ ID NO: 74. In some embodiments, the antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some embodiments, the antibody comprises an HVR-H1 comprising the amino acid sequence of SEQ ID NO: 24, an HVR-H2 comprising the amino acid sequence of SEQ ID NO: 32, an HVR-H3 comprising the amino acid sequence of SEQ ID NO: 46, an HVR-L1 comprising the amino acid sequence of SEQ ID NO: 59, an HVR-L2 comprising the amino acid sequence of SEQ ID NO: 66, and an HVR-L3 comprising the amino acid sequence of SEQ ID NO: 76. In some embodiments, the antibody comprises an HVR-H1 comprising the amino acid sequence of SEQ ID NO: 25, an HVR-H2 comprising the amino acid sequence of SEQ ID NO: 36, an HVR-H3 comprising the amino acid sequence of SEQ ID NO: 47, an HVR-L1 comprising the amino acid sequence of SEQ ID NO: 60, an HVR-L2 comprising the amino acid sequence of SEQ ID NO: 69, and an HVR-L3 comprising the amino acid sequence of SEQ ID NO: 77. In some embodiments, the antibody comprises an HVR-H1 comprising the amino acid sequence of SEQ ID NO: 26, an HVR-H2 comprising the amino acid sequence of SEQ ID NO: 37, an HVR-H3 comprising the amino acid sequence of SEQ ID NO: 48, an HVR-L1 comprising the amino acid sequence of SEQ ID NO: 61, an HVR-L2 comprising the amino acid sequence of SEQ ID NO: 66, and an HVR-L3 comprising the amino acid sequence of SEQ ID NO: 78. In some embodiments, the antibody comprises an HVR-H1 comprising the amino acid sequence of SEQ ID NO: 27, an HVR-H2 comprising the amino acid sequence of SEQ ID NO: 32, an HVR-H3 comprising the amino acid sequence of SEQ ID NO: 49, an HVR-L1 comprising the amino acid sequence of SEQ ID NO: 62, an HVR-L2 comprising the amino acid sequence of SEQ ID NO: 67, and an HVR-L3 comprising the amino acid sequence of SEQ ID NO: 79. In some embodiments, the antibody comprises an HVR-H1 comprising the amino acid sequence of SEQ ID NO: 28, an HVR-H2 comprising the amino acid sequence of SEQ ID NO: 37, an HVR-H3 comprising the amino acid sequence of SEQ ID NO: 50, an HVR-L1 comprising the amino acid sequence of SEQ ID NO: 63, an HVR-L2 comprising the amino acid sequence of SEQ ID NO: 67, and an HVR-L3 comprising the amino acid sequence of SEQ ID NO: 80. In some embodiments, the antibody comprises an HVR-H1 comprising the amino acid sequence of SEQ ID NO: 18, an HVR-H2 comprising the amino acid sequence of SEQ ID NO: 38, an HVR-H3 comprising the amino acid sequence of SEQ ID NO: 51, an HVR-L1 comprising the amino acid sequence of SEQ ID NO: 64, an HVR-L2 comprising the amino acid sequence of SEQ ID NO: 67, and an HVR-L3 comprising the amino acid sequence of SEQ ID NO: 81. In some embodiments, the antibody comprises an HVR-H1 comprising the amino acid sequence of SEQ ID NO: 29, an HVR-H2 comprising the amino acid sequence of SEQ ID NO: 39, an HVR-H3 comprising the amino acid sequence of SEQ ID NO: 52, an HVR-L1 comprising the amino acid sequence of SEQ ID NO: 65, an HVR-L2 comprising the amino acid sequence of SEQ ID NO: 68, and an HVR-L3 comprising the amino acid sequence of SEQ ID NO: 77.

In some embodiments, the antibody comprises: a) a heavy chain variable region comprising an amino acid sequence selected from SEQ ID NOS: 82-94; and/or b) a light chain variable region comprising an amino acid sequence selected from SEQ ID NOS: 95-107. In some embodiments, the antibody comprises a heavy chain variable region comprising an amino acid sequence having at least 90% (e.g., at least 90%, 91%, 92%, 93%, 94%, 95%, 96%, 97%, 98%, or 99%) sequence identity to a sequence selected from SEQ ID NOS: 82-94, and/or a light chain variable region comprising an amino acid sequence having at least 90% (e.g., at least 90%, 91%, 92%, 93%, 94%, 95%, 96%, 97%, 98%, or 99%) sequence identity to a sequence selected from SEQ ID NOS: 95-107. In some embodiments, the antibody comprises a heavy chain variable region and a light chain variable region of any of the exemplary antibodies described in Table B below. In some embodiments, the antibody comprises one, two, or all three HVRs of the heavy chain variable region, and/or one, two, or all three HVRs of the light chain variable region shown for any of the exemplary antibodies described in Table B below.

TABLE B anti-CTLA4 variable region amino acid sequences

| Ab name: | VH: | VL: |
|---|---|---|
| TY21585 | EVQLVESGGGLVQPGGSLRLSCAASGFTFSDY<br>AIHWVRQAPGKGLEWIGIISPSSGSTNYAQKF<br>QGRVTISRDNSKNTLYLQLNSLRAEDTAVYYC<br>ARDIHSGSSGYYYGFDVWGQGTLVTVSS<br>(SEQ ID NO: 82) | DIQLTQSPSSLSASVGDRVTITCRASESVDFF<br>GISFLAWYQQKPGKAPKLLIYDASNRATGI<br>PSRFSGSGSGTDFTLTISSLQPEDFATYYCQ<br>HYTSSPPVYTFGQGTKVEIKR<br>(SEQ ID NO: 95) |
| TY21586 | EVQLVESGGGLVQPGGSLRLSCAASGYSITSG<br>YYWAWIRQAPGKGLEWVSSISGSGSTTYYAD<br>SVKGRFTISRDNSKNTLYLQLNSLRAEDTAVY<br>YCARDGFGYFDYWGQGTLVTVSS<br>(SEQ ID NO: 83) | DIQLTQSPSSLSASVGDRVTITCSASSSVSYV<br>YWYQQKPGKAPKLLIYDASSLESGVPSRFS<br>GSGSGTDFTLTISSLQPEDFATYYCVQGLQT<br>PWTFGQGTKVEIKR<br>(SEQ ID NO: 96) |
| TY21587 | EVQLVESGGGLVQPGGSLRLSCAASGFTFSDY<br>GIHWVRQAPGKGLEWIGEIYHSGSTYYSPSLK<br>SRVTISRDNSKNTLYLQLNSLRAEDTAVYYCA<br>RDVAPGSSGYYDGFDFWGQGTLVTVSS<br>(SEQ ID NO: 84) | DIQLTQSPSSLSASVGDRVTITCRASQGIGSS<br>LAWYQQKPGKAPKLLIYDASNRATGIPSRF<br>SGSGSGTDFTLTISSLQPEDFATYYCQQYDQ<br>WPPWTFGQGTKVEIKR<br>(SEQ ID NO: 97) |
| TY21588 | EVQLVESGGGLVQPGGSLRLSCAASGYSISSG<br>YHWDWIRQAPGKGLEWVSGISGYGGSTYYA<br>DSVKGRFTISRDNSKNTLYLQLNSLRAEDTAV<br>YYCARHSYYGSGNFDYWGQGTLVTVSS<br>(SEQ ID NO: 85) | DIQLTQSPSSLSASVGDRVTITCRASESVDFF<br>GKSFLHWYQQKPGKAPKLLIYDASNLETG<br>VPSRFSGSGSGTDFTLTISSLQPEDFATYYC<br>QQSYSWPPTFGQGTKVEIKR<br>(SEQ ID NO: 98) |
| TY21589 | EVQLVESGGGLVQPGGSLRLSCAASGFTFSDY<br>WIHWVRQAPGKGLEWIGWISPSGGGTKYAQK<br>FQGRVTISRDNSKNTLYLQLNSLRAEDTAVYY<br>CARGAYEFDYWGQGTLVTVSS<br>(SEQ ID NO: 86) | DIQLTQSPSSLSASVGDRVTITCRASQSVSS<br>RFLAWYQQKPGKAPKLLIYDASNRATGIPS<br>RFSGSGSGTDFTLTISSLQPEDFATYYCQQS<br>YPTPLTFGQGTKVEIKR<br>(SEQ ID NO: 99) |
| TY21580 | EVQLVESGGGLVQPGGSLRLSCAASGYSISSG<br>YHWSWIRQAPGKGLEWLARIDWDDDKYYST<br>SLKSRLTISRDNSKNTLYLQLNSLRAEDTAVYY<br>CARSYVYFDYWGQGTLVTVSS<br>(SEQ ID NO: 87) | DIQLTQSPSSLSASVGDRVTITCRASQSVRG<br>RFLAWYQQKPGKAPKLLIYDASNRATGIPS<br>RFSGSGSGTDFTLTISSLQPEDFATYYCQQS<br>SSWPPTFGQGTKVEIKR<br>(SEQ ID NO: 100) |
| TY21591 | EVQLVESGGGLVQPGGSLRLSCAASGFSLSTG<br>GVAVSWIRQAPGKGLEWIGEIYHSGSTYYSPS<br>LKSRVTISRDNSKNTLYLQLNSLRAEDTAVYY<br>CARRIATATYFDYWGQGTLVTVSS<br>(SEQ ID NO: 88) | DIQLTQSPSSLSASVGDRVTITCRASQTVFS<br>RYLAWYQQKPGKAPKLLIYDASNRATGIPS<br>RFSGSGSGTDFTLTISSLQPEDFATYYCQQS<br>YYWPPWTFGQGTKVEIKR<br>(SEQ ID NO: 101) |

TABLE B-continued

| anti-CTLA4 variable region amino acid sequences | | |
|---|---|---|
| Ab name: | VH: | VL: |
| TY21686 | EVQLVESGGGLVQPGGSLRLSCAASGFSLSTG GVAVGWIRQAPGKGLEWVSAISGYGSTTYYA DSVKGRFTISRDNSKNTLYLQLNSLRAEDTAV YYCARLPYSAYAFDYWGQGTLVTVSS (SEQ ID NO: 89) | DIQLTQSPSSLSASVGDRVTITCRASQGVSS YLAWYQQKPGKAPKLLIYAASTLQSGVPSR FSGSGSGTDFTLTISSLQPEDFATYYCQHHY GTPLTFGQGTKVEIKR (SEQ ID NO: 102) |
| TY21687 | EVQLVESGGGLVQPGGSLRLSCAASGFTFSGY AIHWVRQAPGKGLEWIGIISPSGGGTKYAQKF QGRVTISRDNSKNTLYLQLNSLRAEDTAVYYC ARHPFAYWGQGTLVTVSS (SEQ ID NO: 90) | DIQLTQSPSSLSASVGDRVTITCRASQSVDF YGISFLDWYQQKPGKAPKLLIYDASNRATG IPSRFSGSGSGTDFTLTISSLQPEDFATYYCQ QYVSSPPEYTFGQGTKVEIKR (SEQ ID NO: 103) |
| TY21689 | EVQLVESGGGLVQPGGSLRLSCAASGYTFSGY GIHWVRQAPGKGLEWIGEIYHSGSTYYSPSLK SRVTISRDNSKNTLYLQLNSLRAEDTAVYYCA RRIDAFDIWGQGTLVTVSS (SEQ ID NO: 91) | DIQLTQSPSSLSASVGDRVTITCRASQSVDF DGFSFLHWYQQKPGKAPKLLIYDASSLESG VPSRFSGSGSGTDFTLTISSLQPEDFATYYC QQRDSWPYTFGQGTKVEIKR (SEQ ID NO: 104) |
| TY21680 | EVQLVESGGGLVQPGGSLRLSCAASGYTFSGY AIHWVRQAPGKGLEWIGIISPSGGGTKYAQKF QGRVTISRDNSKNTLYLQLNSLRAEDTAVYYC ARLYDVAYWGQGTLVTVSS (SEQ ID NO: 92) | DIQLTQSPSSLSASVGDRVTITCRASQSVDF HGKSFLHWYQQKPGKAPKLLIYDASSLES GVPSRFSGSGSGTDFTLTISSLQPEDFATYY CEQSLEVPFTFGQGTKVEIKR (SEQ ID NO: 105) |
| TY21691 | EVQLVESGGGLVQPGGSLRLSCAASGFTFSDY AIHWVRQAPGKGLEWIGIISPSGGSTKYAQKF QGRVTISRDNSKNTLYLQLNSLRAEDTAVYYC ARLGYGYFDVWGQGTLVTVSS (SEQ ID NO: 93) | DIQLTQSPSSLSASVGDRVTITCRASQSVDF YGISFLHWYQQKPGKAPKLLIYDASSLESG VPSRFSGSGSGTDFTLTISSLQPEDFATYYC VQALQLPLTFGQGTKVEIKR (SEQ ID NO: 106) |
| TY21692 | EVQLVESGGGLVQPGGSLRLSCAASGYSITSG HYWSWIRQAPGKGLEWIGDISHSGSTYYSQSL KSRVTISRDNSKNTLYLQLNSLRAEDTAVYYC ARGSRTGYFDYWGQGTLVTVSS (SEQ ID NO: 94) | DIQLTQSPSSLSASVGDRVTITCRASQSISSY LNWYQQKPGKAPKLLIYDASNLETGVPSR FSGSGSGTDFTLTISSLQPEDFATYYCQHHY GTPLTFGQGTKVEIKR (SEQ ID NO: 107) |

In some embodiments, the antibody comprises a heavy chain variable region comprising the amino acid sequence of SEQ ID NO: 82, and a light chain variable region comprising the amino acid sequence of SEQ ID NO: 95. In some embodiments, the antibody comprises a heavy chain variable region comprising the amino acid sequence of SEQ ID NO: 83, and a light chain variable region comprising the amino acid sequence of SEQ ID NO: 96. In some embodiments, the antibody comprises a heavy chain variable region comprising the amino acid sequence of SEQ ID NO: 84, and a light chain variable region comprising the amino acid sequence of SEQ ID NO: 97. In some embodiments, the antibody comprises a heavy chain variable region comprising the amino acid sequence of SEQ ID NO: 85, and a light chain variable region comprising the amino acid sequence of SEQ ID NO: 98. In some embodiments, the antibody comprises a heavy chain variable region comprising the amino acid sequence of SEQ ID NO: 86, and a light chain variable region comprising the amino acid sequence of SEQ ID NO: 99. In some embodiments, the antibody comprises a heavy chain variable region comprising the amino acid sequence of SEQ ID NO: 87, and a light chain variable region comprising the amino acid sequence of SEQ ID NO: 100. In some embodiments, the antibody comprises a heavy chain variable region comprising the amino acid sequence of SEQ ID NO: 88, and a light chain variable region comprising the amino acid sequence of SEQ ID NO: 101. In some embodiments, the antibody comprises a heavy chain variable region comprising the amino acid sequence of SEQ ID NO: 89, and a light chain variable region comprising the amino acid sequence of SEQ ID NO: 102. In some embodiments, the antibody comprises a heavy chain variable region comprising the amino acid sequence of SEQ ID NO: 90, and a light chain variable region comprising the amino acid sequence of SEQ ID NO: 103. In some embodiments, the antibody comprises a heavy chain variable region comprising the amino acid sequence of SEQ ID NO: 91, and a light chain variable region comprising the amino acid sequence of SEQ ID NO: 104. In some embodiments, the antibody comprises a heavy chain variable region comprising the amino acid sequence of SEQ ID NO: 92, and a light chain variable region comprising the amino acid sequence of SEQ ID NO: 105. In some embodiments, the antibody comprises a heavy chain variable region comprising the amino acid sequence of SEQ ID NO: 93, and a light chain variable region comprising the amino acid sequence of SEQ ID NO: 106. In some embodiments, the antibody comprises a heavy chain variable region comprising the amino acid sequence of SEQ ID NO: 94, and a light chain variable region comprising the amino acid sequence of SEQ ID NO: 107. In some embodiments, the antibody comprises a heavy chain comprising the amino acid sequence of SEQ ID NO: 320, and a light chain comprising the amino acid sequence of SEQ ID NO: 322. In some embodiments, the antibody comprises a heavy chain comprising the amino acid sequence of SEQ ID NO: 321, and a light chain comprising the amino acid sequence of SEQ ID NO: 322. In some embodiments, the antibody refers to a mix of antibody species, wherein each antibody species has a light chain comprising the amino acid sequence of SEQ ID NO: 322 and a heavy chain comprising either the amino acid sequence of SEQ ID NO: 320 or 321. In some embodiments, the antibody comprises a heavy chain comprising the amino acid sequence of SEQ ID NO: 323, and a light chain comprising the amino acid sequence of SEQ ID NO: 325. In some embodiments, the antibody comprises a heavy chain comprising the amino acid sequence of SEQ ID NO: 324, and a light chain comprising the amino acid sequence of SEQ ID NO: 325. In some embodiments, the antibody refers to a mix of antibody species, wherein each antibody species has a light chain comprising the amino acid sequence of SEQ ID NO: 325 and a heavy chain comprising either the amino acid sequence of SEQ ID NO: 323 or 324. In some embodiments, the antibody comprises a heavy chain comprising the amino acid sequence of SEQ ID NO: 326, and a light chain comprising the amino acid sequence of SEQ ID NO: 328. In some embodiments, the antibody comprises a heavy chain comprising the amino acid sequence of SEQ ID NO: 327, and a light chain comprising the amino acid sequence of SEQ ID NO: 328. In some embodiments, the antibody refers to a mix of antibody species, wherein each antibody species has a light chain comprising the amino acid sequence of SEQ ID NO: 328 and a heavy chain comprising either the amino acid sequence of SEQ ID NO: 326 or 321.

In some embodiments, an antibody of the present application cross-competes for binding to human CTLA4 with an antibody comprising: a) an HVR-H1 comprising an amino acid sequence selected from SEQ ID NOS: 18-29; an HVR-H2 comprising an amino acid sequence selected from SEQ ID NOS: 30-39; and an HVR-H3 comprising an amino acid sequence selected from SEQ ID NOS: 40-52; and/or b) an HVR-L1 comprising an amino acid sequence selected from SEQ ID NOS: 53-65; an HVR-L2 comprising an amino acid sequence selected from SEQ ID NOS: 66-69; and an HVR-L3 comprising an amino acid sequence selected from SEQ ID NOS: 70-81. In some embodiments, an antibody of the present application cross-competes for binding to human CTLA4 with an antibody comprising one, two, three, four, five, or all six of the HVRs shown for any of the exemplary antibodies described in Table A. In some embodiments, an antibody of the present application cross-competes for binding to human CTLA4 with an antibody comprising: a) a heavy chain variable region comprising an amino acid sequence selected from SEQ ID NOS: 82-94; and/or b) a light chain variable region comprising an amino acid sequence selected from SEQ ID NOS: 95-107. In some embodiments, an antibody of the present application cross-competes for binding to human CTLA4 with an antibody comprising a VH and/or VL shown for any of the exemplary antibodies described in Table B.

The CTLA4 antibodies described herein may be in any class, such as IgG, IgM, IgE, IgA, or IgD. In some embodiments, the CTLA4 antibodies are in the IgG class, such as IgG1, IgG2, IgG3, or IgG4 subclass. A CTLA4 antibody can be converted from one class or subclass to another class or subclass using methods known in the art. An exemplary method for producing an antibody in a desired class or subclass comprises the steps of isolating a nucleic acid encoding a heavy chain of a CTLA4 antibody and a nucleic acid encoding a light chain of a CTLA4 antibody, isolating the sequence encoding the VH region, ligating the VH sequence to a sequence encoding a heavy chain constant region of the desired class or subclass, expressing the light chain gene and the heavy chain construct in a cell, and collecting the CTLA4 antibody. Antibodies of the present application may be monoclonal antibodies or polyclonal antibodies. Antibodies of the present application may be monospecific antibodies or multispecific (e.g., bispecific, trispecific, etc.) antibodies. In some embodiments, the CTLA4 antibodies described herein may include one or more Fc mutations (e.g., that modulate (increase or decrease) ADCC or CDC activities). Any suitable Fc mutations known in the art may be used in the CTLA4 antibodies of the present application.

In some embodiments, the anti-CTLA4 antibody is an antigen-binding fragment of an anti-CTLA4 antibody, the antigen-binding fragments of a CTLA4 antibody include: (i) a Fab fragment, which is a monovalent fragment consisting of the $V_L$, $V_H$, $C_L$ and $C_H$ domains; (ii) a $F(ab')_2$ fragment, which is a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody; (v) a dAb fragment (Ward et al., (1989) Nature 341:544-546), which consists of a $V_H$ domain; (vi) an isolated CDR, and (vii) single chain antibody (scFv), which is a polypeptide comprising a $V_L$ region of an antibody linked to a VHregion of an antibody (see e.g., Bird et al. (1988) Science 242:423-426; Huston et al. (1988) Proc. Natl. Acad. Sci. USA 85:5879-5883).

In some embodiments, the anti-CTLA4 antibody is a derivative of any one of the anti-CTLA4 antibodies described herein. In some embodiments, the antibody derivative is derived from modifications of the amino acid sequences of an illustrative antibody (e.g., a "parent antibody") of the present application while conserving the overall molecular structure of the parent antibody amino acid sequence. Amino acid sequences of any regions of the parent antibody chains may be modified, such as framework regions, HVR regions, or constant regions. Types of modifications include substitutions, insertions, deletions, or combinations thereof, of one or more amino acids of the parent antibody.

In some embodiments, the antibody derivative comprises a $V_L$ or $V_H$ region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 82-107 In some embodiments, the antibody derivative comprises an HVR-H1 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 18-29. In some embodiments, the antibody derivative comprises an HVR-H2 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 30-39. In some embodiments, the antibody derivative comprises an HVR-H3 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 40-52. In some embodiments, the antibody derivative comprises an HVR-L1 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 53-65. In some embodiments, the antibody derivative comprises an HVR- L2 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 66-69. In some embodiments, the antibody derivative comprises an HVR-L3 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 70-81.

In some particular embodiments, the derivative comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to an amino acid sequence as set forth in any of SEQ ID NOS: 18-107.

Amino acid substitutions encompass both conservative substitutions and non-conservative substitutions. The term "conservative amino acid substitution" means a replacement of one amino acid with another amino acid where the two amino acids have similarity in certain physico-chemical properties such as polarity, charge, solubility, hydrophobicity, hydrophilicity, and/or the amphipathic nature of the residues involved. For example, substitutions typically may be made within each of the following groups: (a) nonpolar (hydrophobic) amino acids, such as alanine, leucine, isoleucine, valine, proline, phenylalanine, tryptophan, and methionine; (b) polar neutral amino acids, such as glycine, serine, threonine, cysteine, tyrosine, asparagine, and glutamine; (c) positively charged (basic) amino acids, such as arginine, lysine, and histidine; and (d) negatively charged (acidic) amino acids, such as aspartic acid and glutamic acid.

The modifications may be made in any positions of the amino acid sequences of the antibody, including the HVRs, framework regions, or constant regions. In one embodiment, the present application provides an antibody derivative that contains the $V_H$ and $V_L$ HVR sequences of an illustrative antibody of this disclosure, yet contains framework sequences different from those of the illustrative antibody. Such framework sequences can be obtained from public DNA databases or published references that include germline antibody gene sequences. For example, germline DNA sequences for human heavy and light chain variable region genes can be found in the Genbank database or in the "VBase" human germline sequence database (Kaba et al., Sequences of Proteins of Immunological Interest, Fifth Edition, U.S. Department of Health and Human Services, NIH Publication No. 91-3242 (1991); Tomlinson et al., *J. Mol. Biol.* 227:776-798 (1992); and Cox et al., *Eur. J. Immunol.* 24:827-836 (1994)). Framework sequences that may be used in constructing an antibody derivative include those that are structurally similar to the framework sequences used by illustrative antibodies of the disclosure For example, the HVR-H1, HVR-H2, and HVR-H3 sequences, and the HVR-L1, HVR-L2, and HVR-L3 sequences of an illustrative antibody can be grafted onto framework regions that have the identical sequence as that found in the germline immunoglobulin gene from which the framework sequence derive, or the HVR sequences can be grafted onto framework regions that contain one or more mutations as compared to the germline sequences.

In some embodiments, the antibody derivative is a chimeric antibody, which comprises an amino acid sequence of an illustrative antibody of the disclosure. In one example, one or more HVRs from one or more illustrative antibodies are combined with HVRs from an antibody from a non-human animal, such as mouse or rat. In another example, all of the HVRs of the chimeric antibody are derived from one or more illustrative antibodies. In some particular embodiments, the chimeric antibody comprises one, two, or three HVRs from the heavy chain variable region and/or one, two, or three HVRs from the light chain variable region of an illustrative antibody. Chimeric antibodies can be generated using conventional methods known in the art.

Another type of modification is to mutate amino acid residues within the HVR regions of the $V_H$ and/or $V_L$ chain. Site-directed mutagenesis or PCR-mediated mutagenesis can be performed to introduce the mutation(s) and the effect on antibody binding, or other functional property of interest, can be evaluated in in vitro or in vivo assays known in the art. Typically, conservative substitutions are introduced. The mutations may be amino acid additions and/or deletions. Moreover, typically no more than one, two, three, four or five residues within an HVR region are altered. In some embodiments, the antibody derivative comprises 1, 2, 3, or 4 amino acid substitutions in the heavy chain HVRs and/or in the light chain HVRs. In another embodiment, the amino acid substitution is to change one or more cysteines in an antibody to another residue, such as, without limitation, alanine or serine. The cysteine may be a canonical or non-canonical cysteine. In one embodiment, the antibody derivative has 1, 2, 3, or 4 conservative amino acid substitutions in the heavy chain HVR regions relative to the amino acid sequences of an illustrative antibody.

Modifications may also be made to the framework residues within the $V_H$ and/or $V_L$ regions. Typically, such framework variants are made to decrease the immunogenicity of the antibody. One approach is to "back mutate" one or more framework residues to the corresponding germline sequence. An antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back mutated" to the germline sequence by, for example, site-directed mutagenesis or PCR-mediated mutagenesis.

In addition, modifications may also be made within the Fc region of an illustrative antibody, typically to alter one or more functional properties of the antibody, such as serum half-life, complement fixation, Fc receptor binding, and/or antigen-dependent cellular cytotoxicity. In one example, the hinge region of CHI is modified such that the number of cysteine residues in the hinge region is altered, e.g., increased or decreased. This approach is described further in U.S. Pat. No. 5,677,425. The number of cysteine residues in the hinge region of CHI is altered to, for example, facilitate assembly of the light and heavy chains or to increase or decrease the stability of the antibody. In another case, the Fc hinge region of an antibody is mutated to decrease the biological half-life of the antibody.

Furthermore, an antibody of the present application may be modified to alter its potential glycosylation site or pattern in accordance with routine experimentation known in the art. In another aspect, the present application provides a derivative of a CTLA4 antibody that contains at least one mutation in a variable region of a light chain or heavy chain that changes the pattern of glycosylation in the variable region. Such an antibody derivative may have an increased affinity and/or a modified specificity for binding an antigen. The mutations may add a novel glycosylation site in the V region, change the location of one or more V region glycosylation site(s), or remove a pre-existing V region glycosylation site. In one embodiment, the present application provides a derivative of a CTLA4 antibody having a potential N-linked glycosylation site at asparagine in the heavy chain variable region, wherein the potential N-linked glycosylation site in one heavy chain variable region is removed. In another embodiment, the present application provides a derivative of a CTLA4 antibody having a potential N-linked glycosylation site at asparagine in the heavy chain variable region, wherein the potential N-linked glycosylation site in both heavy chain variable regions is removed. Method of altering the glycosylation pattern of an antibody is known in the art, such as those described in U.S. Pat. No. 6,933,368, the disclosure of which incorporated herein by reference.

Activatable Binding Polypeptides Targeting CTLA4

The present disclosure also relates, in part, to precision/context-dependent activatable binding polypeptides (i.e., activatable antibodies) that bind to human CTLA4, including activatable antibodies comprising any of the anti-CTLA4 antibodies described herein (e.g., anti-CTLA4 antibodies, anti-CTLA4 antibody binding fragments, and/or anti-CTLA4 antibody derivatives), antigen binding fragments of the activatable anti-CTLA4 antibodies, and/or derivatives of the activatable anti-CTLA4 antibodies. In some embodiments, the activatable anti-CTLA4 antibodies described herein may have improved safety profiles. For example, the anti-CTLA4 antibodies described herein may have better safety margin as assessed by spleen weight change. The change in spleen size with the increase in drug dose administered is used as a benchmark to assess the safety margin of the drug candidate used. The activatable anti-CTLA4 antibodies described herein have a better safety margin relative to the parental antibody (the antibody without the masking moiety). In some embodiments, an activatable antibody is referred to as a "SAFEbody". In some embodiments, the activatable antibody is TY22404. In some embodiments, the activatable antibody is a bispecific antibody (e.g., an anti-CTLA4 and PD1 antibody, an anti-CTLA4 and PD-L1 antibody, or an anti-CTLA4 and CD137 antibody).

In some embodiments, an activatable antibody of the present disclosure comprises: (a) a masking moiety (MM); (b) a cleavable moiety (CM); and (c) a target binding moiety (TBM). In some embodiments, the MM is any of the masking moieties described herein. In some embodiments, the CM is any of the cleavable moieties described herein. In some embodiments, the TBM is any of the target binding moieties described herein (e.g., a target binding moiety (TBM) comprising an antibody light chain variable region and/or an antibody heavy chain variable region, such as a VH and/or VL of any of the anti-CTLA4 antibodies described herein). In some embodiments, the MM interferes with and/or inhibits the binding of the activatable antibody to its target (e.g., human CTLA4 or human CD137) when the CM is not cleaved. In some embodiments, the activatable antibody is capable of binding to its target (e.g., human CTLA4 or human CD137) when the CM is cleaved.

In some embodiments, the activatable antibody comprises: (a) a polypeptide comprising, from N-terminus to C-terminus, a masking moiety (MM), a cleavable moiety (CM), and a target binding moiety (TBM), where the MM is any of the masking moieties described herein, the CM is any of the cleavable moieties described herein, and where the TBM comprises an antibody light chain variable region (VL); and (b) an antibody heavy chain variable region (VH).

In some embodiments, the activatable antibody comprises: (a) a polypeptide comprising, from N-terminus to C-terminus, a masking moiety (MM), a cleavable moiety (CM), and a target binding moiety (TBM), where the MM is any of the masking moieties described herein, the CM is any of the cleavable moieties described herein, and where the TBM comprises an antibody heavy chain variable region (VH); and (b) an antibody light chain variable region (VL).

In some embodiments, the activatable antibody comprises: a polypeptide comprising, from N-terminus to C-terminus, a masking moiety (MM), a cleavable moiety (CM), and a target binding moiety (TBM), where the MM is any of the masking moieties described herein, the CM is any of the cleavable moieties described herein, and where the TBM comprises an antibody heavy chain variable region (VH) and an antibody light chain variable region (VL).

The term "activatable binding polypeptide", "ABP", or "activatable antibody" includes a polypeptide that comprises a target binding moiety (TBM), a cleavable moiety (CM), and a masking moiety (MM). In some embodiments, the TBM comprises an amino acid sequence that binds to a target. In some embodiments, the TBM comprises an antigen binding domain (ABD) of an antibody or antibody fragment thereof (e.g., any of the antibodies or antigen binding fragments described herein). In some embodiments, the antigen binding domain comprises a heavy chain variable region comprising one, two, or three of the heavy chain variable region HVRs described herein, and a light chain variable region comprising one, two, or three of the light chain variable region HVRs described herein (e.g., one, two, or three of the heavy chain variable region HVR sequences, and/or one, two, or three of the light chain variable region HVR sequences as shown in Table A, including all six HVRs of any of the exemplary antibodies as shown in Table A). In some embodiments, the antigen binding domain comprises a heavy chain variable region comprising any of the heavy chain variable region sequences described herein, and a light chain variable region comprising any of the light chain variable region sequences described herein (e.g., a heavy chain variable region sequence and/or a light chain variable region sequence as shown in Table B). In some embodiments, the TBM (e.g., comprising an ABD) comprises an antibody light chain variable region (VL) and an antibody heavy chain variable region (VH), wherein the VH and VL forms a binding domain that binds to the target in the absence of the MM. In some embodiments, the VH and VL are covalently linked, e.g., in an scFv. In some embodiments, the VH and VL are not covalently linked. In some embodiments, the VH and VL form a Fab fragment. In some embodiments, the VH is linked to an antibody heavy chain constant region, and the VL is linked to an antibody light chain constant region.

In some embodiments, the activatable antibody comprises a polypeptide comprising the structure, from N-terminus to C-terminus, of: masking moiety (MM)-cleavable moiety (CM)-VL, and the activatable antibody further comprises a second polypeptide comprising a VH (e.g., a Fab fragment). In some embodiments, the activatable antibody comprises a polypeptide comprising the structure, from N-terminus to C-terminus, of: masking moiety (MM)-cleavable moiety (CM)-VL-VH (e.g., an scFv). In some embodiments, the activatable antibody comprises a polypeptide comprising the structure, from N-terminus to C-terminus, of: masking moiety (MM)-cleavable moiety (CM)-VH, and the activatable antibody further comprises a second polypeptide comprising a VL (e.g., a Fab fragment). In some embodiments, the activatable antibody comprises a polypeptide comprising the structure, from N-terminus to C-terminus, of: masking moiety (MM)-cleavable moiety (CM)-VH-VL (e.g., an scFv).

The CM generally includes an amino acid sequence that is cleavable, for example, serves as the substrate for an enzyme and/or a cysteine-cysteine pair capable of forming a reducible disulfide bond. As such, when the terms "cleavage," "cleavable," "cleaved" and the like are used in connection with a CM, the terms encompass enzymatic cleavage, e.g., by a protease, as well as disruption of a disulfide bond between a cysteine-cysteine pair via reduction of the disulfide bond that can result from exposure to a reducing agent.

The MM refers to an amino acid sequence that, when the CM of the activatable antibody is intact (e.g., uncleaved by a corresponding enzyme, and/or containing an unreduced cysteine-cysteine disulfide bond), the MM interferes with or inhibits binding of the TBM to its target. In some embodiments, the MM interferes with or inhibits binding of the TBM to its target so efficiently that binding of the TBM to its target is extremely low and/or below the limit of detection (e.g., binding cannot be detected in an ELISA or flow cytometry assay). The amino acid sequence of the CM may overlap with or be included within the MM. It should be noted that for sake of convenience "ABP" or "activatable antibody" are used herein to refer to an ABP or activatable antibody in both their uncleaved (or "native") state, as well as in their cleaved state. It will be apparent to the ordinarily skilled artisan that in some embodiments a cleaved ABP may lack an MM due to cleavage of the CM, e.g., by a protease, resulting in release of at least the MM (e.g., where the MM is not joined to the ABP by a covalent bond (e.g., a disulfide bond between cysteine residues)). Exemplary ABPs are described in more detail below.

In some embodiments, the masking moiety (MM) interferes with, obstructs, reduces the ability of, prevents, inhibits, or competes with the target binding moiety for binding to its target (e.g., an "inactive activatable antibody). In some embodiments, the masking moiety (MM) interferes with, obstructs, reduces, prevents, inhibits, or competes with the target binding moiety for binding to its target only when the polypeptide has not been activated (e.g., activated by a change in pH (increased or decreased), activated by a temperature shift (increased or decreased), activated after being contacted with a second molecule (such as a small molecule or a protein ligand), etc.). In some embodiments, activation induces cleavage of the polypeptide within the cleavage moiety. In some embodiments, activation induces conformation changes in the polypeptide (e.g., displacement of the masking moiety (MM)), leading to the masking moiety no longer preventing the activatable antibody from binding to its target. In some embodiments, the masking moiety (MM) interferes with, obstructs, reduces the ability of, prevents, inhibits, or competes with the target binding moiety for binding to its target only when the cleavable moiety (CM) has not been cleaved by one or more proteases that cleave within the cleavable moiety (CM). In some embodiments, the masking moiety (MM) has a masking efficiency of at least about 2.0 (e.g., at least about 2.0, at least about 3.0, at least about 4.0, at least about 5.0, at least about 6.0, at least about 7.0, at least about 8.0, at least about 9.0, at least about 10, at least about 25, at least about 50, at least about 75, at least about 100, at least about 150, at least about 200, at least about 300, at least about 400, at least about 500, etc.) prior to activation. In some embodiments, masking efficiency is measured as the difference in affinity of an activatable antibody comprising the masking moiety (MM) for binding its target (before activation) relative to the affinity of a polypeptide lacking the masking moiety for binding its target (e.g., the difference in affinity for a target antigen (such as CTLA4) of an activatable antibody comprising a masking moiety (MM) (before activation) relative to a parental antibody lacking the masking moiety (MM), or the difference in affinity for a target antigen (such as CTLA4) of an activatable antibody comprising a masking moiety (MM) (before activation) relative to the affinity for the target antigen of the activatable antibody after activation). In some embodiments, the masking efficiency is measured by dividing the EC50 for binding of an activatable antibody comprising a masking moiety (MM) (before activation) by the EC50 of the parental antibody (e.g., by measuring EC50 by ELISA; see e.g., the methods of Example 8). In some embodiments, masking efficiency is measured as the difference in affinity of an activatable antibody comprising the masking moiety (MM) for binding its target before activation relative to the affinity of the activatable antibody comprising the masking moiety (MM) for binding its target after activation (e.g., the difference in affinity for a target antigen (such as CTLA4) of an activatable antibody before activation relative to the activatable antibody after activation). In some embodiments, the masking moiety (MM) binds to the target binding moiety (TBM), and prevents the activatable antibody from binding to its target (e.g., an "inactive" activatable antibody). In some embodiments, the masking moiety (MM) has a dissociation constant for binding to the target binding moiety (TBM) that is greater than the dissociation constant of the target binding moiety (TBM) for its target.

In some embodiments, the masking moiety (MM) does not interfere with, obstruct, reduce the ability of, prevent, inhibit, or compete with the target binding moiety (TBM) for binding to its target after the activatable antibody has been activated (e.g., activated by treatment with one or more proteases that cleave within the cleavable moiety (CM), activated by a change in pH (increased or decreased), activated by a temperature shift (increased or decreased), activated after being contacted with a second molecule (such as an enzyme or a protein ligand), etc.). In some embodiments, the masking moiety (MM) does not interfere with, obstruct, reduce the ability of, prevent, inhibit, or compete with the target binding moiety (TBM) for binding its target after the cleavable moiety (CM) has been cleaved by one or more proteases that cleave within the cleavable moiety (CM). In some embodiments, the masking moiety (MM) has a masking efficiency of at most about 1.75 (e.g., at most about 1.75, at most about 1.5, at most about 1.4, at most about 1.3, at most about 1.2, at most about 1.1, at most about 1.0, at most about 0.9, at most about 0.8, at most about 0.7, at most about 0.6, or at most about 0.5, etc.) after activation (e.g., the relative affinity of the activatable antibody after activation as compared to the affinity of a parental antibody).

In some embodiments, an activatable antibody of the present disclosure: contains a masking moiety (MM) comprising a pair of cysteine residues at fixed positions to ensure that the activatable antibodies have constrained conformations, and/or harbor few or no chemically labile residues (such as methionine or tryptophan). Advantageously, the inclusion of a pair of cysteine residues at fixed positions ensured that the activatable antibodies had constrained conformations, tending to exhibit increased binding affinity and/or specificity. Furthermore, activatable antibodies of the present disclosure included masking moieties with few to no unfavorable residues for manufacturing processes, such as methionine or tryptophan.

In some embodiments, activatable antibodies of the present disclosure are context-dependent (e.g., are activated (are only capable of binding their targets) in certain contexts (such as in the protease-rich tumor microenvironment)). In some embodiments, the activatable antibodies of the present disclosure provide improved safety over more traditional, non-activatable antibodies (e.g., show reduced toxicity, do not induce significant alterations to the weights of many organs, do not alter liver histopathology, hematology, and/or blood biochemistry, etc.). In some embodiments, activatable antibodies of the present disclosure have improved pharmacokinetic properties as compared to more traditional, non-activatable antibodies (e.g., have longer in vivo half-lives).

Anti-CTLA4 Activatable Antibody Activities

In some embodiments, the present disclosure relates to activatable antibodies that bind to human CTLA4 when in active form (e.g., the activatable antibodies are active after cleavage in the cleavable moiety (e.g., with one or more proteases), but inactive prior to cleavage in the cleavable moiety (e.g., with one or more proteases)). In some embodiments, the activatable antibodies when in active form have at least one (e.g., at least one, at least two, at least three, at least four, at least five, at least six, at least seven, at least eight, or all nine) of the following functional properties: (a) bind to human, cynomolgus monkey, mouse, rat, and/or dog CTLA4 with a $K_D$ of 500 nM or less, e.g., about 10 nM or less; (b) have antagonist activity on human CTLA4; (c) do not bind to human PD-1, PD-L1, PD-L2, LAG3, TIM3, B7-H3, CD95, CD120a, OX40, CD40, BTLA, VISTA, ICOS, and/or B7-H4 at concentration up to 100 nM; (d) are cross-reactive with monkey, mouse, rat, and/or dog CTLA4; (e) induces ADCC effects (e.g., on Tregs); (f) activates human PBMCs (e.g., stimulates secretion of IL-2 and/or IFNY); (g) are capable of inhibiting tumor cell growth; (h) have therapeutic effect on a cancer; and (i) inhibit binding of human CTLA4 to human CD80 and/or human CD86. Also provided herein are one or more activatable antibodies that compete or cross-compete for binding to human CTLA4 with one or more of the CTLA4-targeting activatable antibodies and/or anti-CTLA4 antibodies described herein.

In some embodiments, the activatable antibodies bind to human, cynomolgus monkey, mouse, rat, and/or dog CTLA4 with a $K_D$ of about 500 nM or more when in inactive form. In some embodiments, the activatable antibodies bind to human, cynomolgus monkey, mouse, rat, and/or dog CTLA4 with a $K_D$ of about 500 nM or less when in active form (e.g., about 500 nM or less, about 450 nM or less, about 400 nM or less, about 350 nM or less, about 300 nM or less, about 250 nM or less, about 200 nM or less, about 150 nM or less, about 100 nM or less, about 90 nM or less, about 80 nM or less, about 70 nM or less, about 60 nM or less, about 50 nM or less, about 40 nM or less, about 30 nM or less, about 25 nM or less, about 20 nM or less, about 10 nM or less, about 1 nM or less, about 0.1 nM or less, etc.) In some embodiments, the activatable antibodies bind to human, cynomolgus monkey, mouse, rat, and/or dog CTLA4 with a $K_D$ of about 350 nM or less when in active form. In some embodiments, the activatable antibodies bind to human CTLA4 with a $K_D$ of about 100 nM or less when in active form. In some embodiments, the activatable antibodies bind to human CTLA4 with a $K_D$ of about 50 nM or less when in active form. In some embodiments, the activatable antibodies bind to human CTLA4 with a $K_D$ of about 10 nM or less when in active form. Methods of measuring the $K_D$ of an activatable antibody may be carried out using any method known in the art, including for example, by surface plasmon resonance, an ELISA, isothermal titration calorimetry, a filter binding assay, an EMSA, etc. In some embodiments, the $K_D$ is measured by an ELISA (see e.g., the Examples below).

In some embodiments, the activatable antibodies do not have antagonist activity on human CTLA4 when in inactive form. In some embodiments, the activatable antibodies have antagonist activity on human CTLA4 when in active form (e.g., induces ADCC effects (such as against Tregs), activates PBMCs (such as by activating, inducing, and/or stimulating IL-2 and/or IFNγ secretion), bocks binding of human CTLA4 to human CD80 and/or human CD86, etc.). In some embodiments, the activatable antibodies repress one or more activities of human CTLA4 when in active form (e.g., repress one or more activities of human CTLA4 when a cell (such as a human cell) expressing human CTLA4 is contacted by an activatable antibody).

In some embodiments, when in inactive form, the activatable antibodies are not cross-reactive with monkey (e.g., cynomolgus monkey), mouse, rat, and/or dog CTLA4. In some embodiments, when in active form, the activatable antibodies are cross-reactive with monkey (e.g., cynomolgus monkey), mouse, rat, and/or dog CTLA4. In some embodiments, when in active form, the activatable antibodies are cross-reactive with monkey CTLA4. In some embodiments, when in active form, the activatable antibodies are cross-reactive with mouse CTLA4. In some embodiments, when in active form, the activatable antibodies are cross-reactive with rat CTLA4. In some embodiments, when in active form, the activatable antibodies are cross-reactive with dog CTLA4. In some embodiments, when in active form, the activatable antibodies are cross reactive with monkey and mouse CTLA4; monkey and rat CTLA4; monkey and dog CTLA4; mouse and rat CTLA4; mouse and dog CTLA4; rat and dog CTLA4; monkey, mouse, and rat CTLA4; monkey, mouse, and dog CTLA4; monkey, rat, and dog CTLA4; mouse, rat, and dog CTLA4; or monkey, mouse, rat, and dog CTLA4. In some embodiments, when in active form, the activatable binding polypeptides are cross-reactive at about 350 nM (e.g., at about 1 nM, at about 10 nM, at about 25 nM, at about 50 nM, at about 75 nM, at about 100 nM, at about 150 nM, at about 200 nM, at about 250 nM, at about 300 nM, at about 350 nM). Methods of measuring cross-reactivity are known in the art, including, without limitation, surface plasmon resonance, an ELISA, isothermal titration calorimetry, a filter binding assay, an EMSA, etc.

In some embodiments, the activatable antibodies do not induce ADCC effects (e.g., against CTLA4-expressing human cells such as Tregs) when in inactive form. In some embodiments, the activatable antibodies have reduced ADCC effects (e.g., against CTLA4-expressing human cells such as Tregs) when in inactive form as compared to a control binding polypeptide (e.g., a parental antibody). In some embodiments, the activatable antibodies induce ADCC effects (e.g., against CTLA4-expressing such as Tregs) when in active form. Methods of measuring ADCC effects (e.g., in vitro methods) are known in the art, including, without limitation, via the methods described in the Examples below. In some embodiments, when in inactive form, the activatable antibodies induce ADCC effects by less than about 10% (e.g., induce ADCC by less than about 10%, less than about 5%, less than about 1%, etc.) relative to a control (e.g., a parental antibody). In some embodiments, when in active form, the activatable antibodies induce ADCC effects by more than about 10% (e.g., induce ADCC by more than about 10%, more than about 15%, more than about 20%, more than about 25%, more than about 30%, more than about 35%, more than about 40%, etc.) relative to a control (e.g., an isotype control).

In some embodiments, the activatable antibodies are capable of inhibiting tumor cell growth and/or proliferation. In some embodiments, the tumor cell growth and/or proliferation is inhibited by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) when contacted with the activatable antibodies relative to corresponding tumor cells not contacted with the activatable antibodies (or relative to corresponding tumor cells contacted with an isotype control antibody). In some embodiments, the activatable antibodies are capable of reducing tumor volume in a subject when the subject is administered the activatable antibodies. In some embodiments, the activatable antibodies are capable of reducing tumor volume in a subject by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) relative to the initial tumor volume in the subject (e.g., prior to administration of the activatable antibodies; as compared to a corresponding tumor in a subject administered an isotype control antibody). Methods of monitoring tumor cell growth/proliferation, tumor volume, and/or tumor inhibition are known in the art, including, for example, via the methods described in the Examples below.

In some embodiments, the activatable antibodies have therapeutic effect on a cancer. In some embodiments, the activatable antibodies reduce one or more signs or symptoms of a cancer. In some embodiments, a subject suffering from a cancer goes into partial or complete remission when administered the activatable antibodies.

In some embodiments, the present disclosure provides isolated activatable antibodies that, when in active form, compete or cross-compete for binding to human CTLA4 with an antibody comprising: a) an HVR-H1 comprising the amino acid sequence of SEQ ID NO: 23; an HVR-H2 comprising the amino acid sequence of SEQ ID NO: 35; and an HVR-H3 comprising the amino acid sequence of SEQ ID NO: 45; and/or b) an HVR-L1 comprising the amino acid sequence of SEQ ID NO: 58; an HVR-L2 comprising the amino acid sequence of SEQ ID NO: 66; and an HVR-L3 comprising the amino acid sequence of SEQ ID NO: 75. In some embodiments, the present disclosure provides isolated activatable antibodies that, when in active form, compete or cross-compete for binding to human CTLA4 with an antibody comprising: a) a heavy chain variable region comprising the amino acid sequence of SEQ ID NO: 87; and/or b) a light chain variable region comprising the amino acid sequence of SEQ ID NO: 100. The ability of an activatable antibody to compete or cross-compete for binding with an antibody can be determined using standard binding assays known in the art, such as BIAcore analysis, ELISA assays, or flow cytometry. For example, one can allow an antibody (e.g., as described above) to bind to human CTLA4 under saturating conditions and then measure the ability of the test activatable antibody (when in active form) to bind to the CTLA4. If the test activatable antibody is able to bind to the CTLA4 at the same time as the antibody, then the test activatable antibody binds to a different epitope then the antibody. However, if the test activatable antibody is not able to bind to the CTLA4 at the same time, then the test activatable antibody binds to the same epitope, an overlapping epitope, or an epitope that is in close proximity to the epitope bound by the antibody. This experiment can be performed using various methods, such as ELISA, RIA, FACS or surface plasmon resonance.

In some embodiments, the activatable antibodies (when in inactive form) do not inhibit the binding between CTLA4 and one or more of its binding partners (e.g., human CTLA4 and human CD80, human CTLA4 and human CD86). In some embodiments, the activatable antibodies (when in active form) inhibit the binding between CTLA4 and one or more of its binding partners (e.g., human CTLA4 and human CD80, human CTLA4 and human CD86). In some embodiments, the activatable antibodies inhibit the binding between CTLA4 and its ligand in vitro. In some embodiments, the activatable antibodies have a half maximal inhibitory concentration (IC50) of about 500 nM or less (e.g., about 500 nM or less, about 400 nM or less, about 300 nM or less, about 200 nM or less, about 100 nM or less, about 50 nM or less, about 25 nM or less, about 10 nM or less, about 1 nM or less, etc.) for inhibiting binding of CTLA4 to CD80 and/or CD86. In some embodiments, the activatable antibodies have a half maximal inhibitory concentration (IC50) of about 100 nM or less for inhibiting binding of CTLA4 to CD80 and/or CD86. In some embodiments, the activatable antibodies completely inhibit binding of human CTLA4 to CD80 and/or CD86 when provided at a concentration of about 100 nM or greater (e.g., about 100 nM or greater, about 500 nM or greater, about luM or greater, about 10 μM or greater, etc.). As used herein, the term “complete inhibiting” or “completely inhibits” refers to the activatable antibody’s ability to reduce binding between a first protein and a second protein by at least about 80% (e.g., at least about 80%, at least about 85%, at least about 90%, at least about 95%, at least about 99%, etc.). Methods of measuring the ability of an a polypeptide to inhibit binding of a first protein (e.g., human CTLA4) and a second protein (e.g., human CD80 or human CD86) are known in the art, including, without limitation, via BIAcore analysis, ELISA assays, and flow cytometry.

Masking Moieties (MMs)

In some embodiments, the present disclosure relates to activatable antibodies comprising a masking moiety (MM). In some embodiments, the masking moiety (MM) comprises an amino acid sequence according to Formula (XVIII): $X_mCX_nC_o$ (SEQ ID NO: 134), where m is from 2-10, n is from 3-10, and o is from 1-10, where each X is independently an amino acid selected from the group consisting of A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P. In some embodiments, X is not W, M, and/or C. In some embodiments, each X in $X_m$ of formula (XVIII) is independently an amino acid selected from the group consisting of D, A, Y, S, T, N, I, L, F, V, H, and P and/or each X in Xn of formula (XVIII) is independently an amino acid selected from the group consisting of D, A, Y, S, T, N, I, L, F, V, H, and P. In some embodiments, the MM comprises a polypeptide encoded by a polynucleotide sequence according to Formula (XX): $(NNK)_mTGY(NNK)_nTGY(NHC)_o$ (SEQ ID NO: 136), wherein each N is independently A, G, T, or C, wherein each K is independently T or G, wherein each Y is independently T or C, and wherein each His independently A, T, or C.

In some embodiments, the masking moiety (MM) comprises an amino acid sequence according to Formula (XIX): $Z_mCZ_nCZ_o$ (SEQ ID NO: 135), where m is from 2-10, n is from 3-10, and o is from 1-10, and each Z is independently an amino acid selected from the group consisting of D, A, Y, S, T, N, I, L, F, V, H, and P.

In some embodiments, m is from 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10. In some embodiments, m is from 6-8. In some embodiments, m is 3, 4, 5, 6, 7, 8, 9, or 10. In some embodiments, m is 6.

In some embodiments, n is from 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10. In some embodiments, n is from 6-8. In some embodiments, n is 3, 4, 5, 6, 7, 8, 9, or 10. In some embodiments, n is 6. In some embodiments, n is 8.

In some embodiments, o is from 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10. In some embodiments, o is from 1-2. In some embodiments, o is 1, 2, 3, 4, 5, 6, 7, 8, 9, or 10. In some embodiments, o is 2.

In some embodiments, the masking moiety (MM) comprises an amino acid sequence according to Formula (XXI): $Z_6CX_6CZ_2$ (SEQ ID NO: 137), where each X is independently an amino acid selected from the group consisting of A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P.

In some embodiments, the masking moiety (MM) comprises an amino acid sequence according to Formula (XXII): $Z_6CX_8CZ_2$ (SEQ ID NO: 138), where each X is independently an amino acid selected from the group consisting of A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P.

In some embodiments, the first peptide (FP) comprises an amino acid sequence according to Formula (XXIII): $(Z_6)C(Z_6)C(Z_2)$ (SEQ ID NO: 139), where each Z is independently an amino acid selected from the group consisting of D, A, Y, S, T, N, I, L, F, V, H, and P.

In some embodiments, the masking moiety (MM) comprises an amino acid sequence according to Formula (XXIV): $(Z_6)C(Z_8)C(Z_2)$ (SEQ ID NO: 140), where each Z is independently an amino acid selected from the group consisting of D, A, Y, S, T, N, I, L, F, V, H, and P. In some embodiments, an activatable antibody comprises a masking moiety (MM) comprising a sequence selected from the group consisting of XmCPDHPYPCXX (SEQ ID NO: 181), $X_m$CDAFYPYCXX (SEQ ID NO:182), $X_m$CDSHYPYCXX (SEQ ID NO:183), and $X_m$CVPYYYACXX (SEQ ID NO:184), where m is from 2-10, and where each X is independently an amino acid selected from the group consisting of A, C, D, E, F, G, H, I, K, L, M, N, P, Q, R, S, T, V, W, and Y. In some embodiments, an activatable antibody comprises a masking moiety (MM) comprising the sequence EVGSYNFVADSCPDHPYPCSA (SEQ ID NO: 189), EVGSYIVHHSDCDAFYPYCDS (SEQ ID NO:190), EVGSYYSAYPACDSHYPYCNS (SEQ ID NO:191), EVGSYPNPSSDCVPYYYACAY (SEQ ID NO: 192), EVGSYYSAYPACDSHYPYCQS (SEQ ID NO:193), EVGSYPQPSSDCVPYYYACAY (SEQ ID NO:195), or EVGSYPNPASDCVPYYYACAY (SEQ ID NO:196). In some embodiments, the MM comprises the sequence of

EDCVPYYYACAY, (SEQ ID NO: 213)

EVGSSDCVPYYYACAY, (SEQ ID NO: 214)

EDCDAFYPYCDS, (SEQ ID NO: 215)
or

EVGHSDCDAFYPYCDS. (SEQ ID NO: 216)

In some embodiments, the masking moiety (MM) comprises an amino acid sequence selected from NFVADSCPDHPYPCSA (SEQ ID NO: 141), IVHHSDCDAFYPYCDS (SEQ ID NO: 142), YSAYPACDSHYPYCNS (SEQ ID NO: 143), PNPSSDCVPYYYACAY (SEQ ID NO: 144), YSAYPACDSHYPYCQS (SEQ ID NO: 145), PQPSSDCVPYYYACAY (SEQ ID NO: 146), and PNPASDCVPYYYACAY (SEQ ID NO: 147).

In some embodiments, any of the masking moieties (MMs) described herein may further comprise one or more additional amino acid sequences (e.g., one or more polypeptide tags). Examples of suitable additional amino acid sequence may include, without limitation, purification tags (such as his-tags, flag-tags, maltose binding protein and glutathione-S-transferase tags), detection tags (such as tags that may be detected photometrically (e.g., red or green fluorescent protein, etc.)), tags that have a detectable enzymatic activity (e.g., alkaline phosphatase, etc.), tags containing secretory sequences, leader sequences, and/or stabilizing sequences, protease cleavage sites (e.g., furin cleavage sites, TEV cleavage sites, Thrombin cleavage sites), and the like. In some embodiments, the one or more additional amino acid sequences are at the N-terminus of the masking moiety (MM). In some embodiments, the additional amino acid sequence comprises or consists of the sequence EVGSY (SEQ ID NO: 148).

In some embodiments, the masking moiety binds to the target binding moiety (TBM) and inhibits the activatable antibody from binding to its target before activation (e.g., before treatment with one or more proteases that cleave within the cleavable moiety (CM), before undergoing a (local) change in pH (increased or decreased), before a temperature shift (increased or decreased), before being contacted with a second molecule (such as a small molecule or a protein ligand), etc.), but does not bind to the TBM and/or inhibit the activatable antibody from binding to its target after activation (e.g., after treatment with one or more proteases that cleave within the cleavable moiety (CM), after undergoing a (local) change in pH (increased or decreased), after a temperature shift (increased or decreased), after being contacted with a second molecule (such as a small molecule or a protein ligand), etc.). In some embodiments, the masking moiety (MM) inhibits binding of an activatable antibody to its target when the CM is not cleaved, but does not inhibit binding of the activatable antibody to its target when the CM is cleaved. In some embodiments, the masking moiety (MM) has a dissociation constant for binding to the TBM that is greater (e.g., at least about 1.5-fold greater, at least about 2-fold greater, at least about 2.5-fold greater, at least about 3-fold greater, at least about 3.5-fold greater, at least about 4-fold greater, at least about 4.5-fold greater, at least about 5-fold greater, at least about 10-fold greater, at least about 100-fold greater, at least about 500-fold greater, etc.) than the dissociation constant of the activatable antibody for its target (when in active form).

Cleavable Moieties (CMS)

In some embodiments, the present disclosure relates to activatable antibodies comprising a cleavable moiety (CM). In some embodiments, the cleavable moiety (CM) is cleaved and/or disrupted by treatment with one or more proteases that cleave within the cleavable moiety (CM), by a change in pH (increased or decreased), by a temperature shift (increased or decreased), and/or by contact with a second molecule (such as a small molecule or a protein ligand), etc.)

In some embodiments, the cleavable moiety (CM) comprises at least a first cleavage site ($CS_1$) (e.g., a first protease cleavage site). In some embodiments, the first cleavage site is a first protease cleavage site. Any suitable protease cleavage site recognized and/or cleaved by any protease (e.g., a protease that is known to be co-localized with a target of an activatable antibody comprising the CM) known in the art may be used, including, for example, a protease cleavage site recognized and/or cleaved by urokinase-type plasminogen activator (uPA); matrix metalloproteinases (e.g., MMP-1, MMP-2, MMP-3, MMP-7, MMP-8, MMP-9, MMP-10, MMP-11, MMP-12, MMP-13, MMP-14, MMP-15, MMP-16, MMP-17, MMP-19, MMP-20, MMP-23, MMP-24, MMP-26, and/or MMP-27); Tobacco Etch Virus (TEV) protease; plasmin; Thrombin; PSA; PSMA; ADAMS/ADAMTS (e.g., ADAM 8, ADAM 9, ADAM10, ADAM12, ADAM15, ADAM17/TACE, ADAMDEC1, ADAMTS1, ADAMTS4, and/or ADAMTS5); caspases (e.g., Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, and/or Caspase-14); aspartate proteases (e.g., RACE and/or Renin); aspartic cathepsins (e.g., Cathepsin D and/or Cathepsin E); cysteine cathepsins (e.g., Cathepsin B, Cathepsin C, Cathepsin K, Cathepsin L, Cathepsin S, Cathepsin V/L2, and/or Cathepsin X/Z/P); cysteine proteinases (e.g., Cruzipain, Legumain, and/or Otubain-2); KLKs (e.g., KLK4, KLK5, KLK6, KLK7, KLK8, KLK10, KLK11, KLK13, and/or KLK14); metallo proteainases (e.g., Meprin, Neprilysin, PSMA, and/or BMP-1); serine proteases (e.g., activated protein C, Cathepsin A, Cathepsin G, Chymase, and/or coagulation factor proteases (such as FVIIa, FIXa, FXa, FXIa, FXIIa)); elastase; granzyme B; guanidinobenzoatase; HtrA1; human neutrophil elastase; lactoferrin; marapsin; NS3/4A; PACE4; tPA; tryptase; type II transmembrane serine proteases (TTSPs) (e.g., DESC1, DPP-4, FAP, Hepsin, Matriptase-2, MT-SP1/Matriptase, TMPRSS2, TMPRSS3 and/or TMPRSS4); etc. In some embodiments, the first protease cleavage site is a cleavage site for a protease selected from uPA, MMP-1, MMP-2, MMP-3, MMP-8, MMP-9, MMP-14, TEV protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments, the first protease cleavage site is a cleavage site for a protease selected from uPA, MMP-2, MMP-9, and/or TEV protease. In some embodiments, the protease cleavage comprises an amino acid sequence selected from SGRSA (SEQ ID NO: 149), PLGLAG (SEQ ID NO: 150), and ENLYFQG (SEQ ID NO: 151).

In some embodiments, an activatable antibody comprises a masking moiety (MM) and a cleavable moiety (CM) comprising an amino acid sequence according to Formula (XXV): EVGSY($Z_6$)C($Z_6$)C($Z_2$)SGRSA (SEQ ID NO: 152), where each Z is independently an amino acid selected from D, A, Y, S, T, N, I, L, F, V, H, and P.

In some embodiments, an activatable antibody comprises a masking moiety (MM) and a cleavable moiety (CM) comprising an amino acid sequence according to Formula (XXVI): EVGSY($Z_6$)C($X_6$)C($Z_2$) SGRSA (SEQ ID NO: 153), where each X is independently an amino acid selected from A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P.

In some embodiments, an activatable antibody comprises a masking moiety (MM) and a cleavable moiety (CM) comprising an amino acid sequence according to Formula (XXVII): EVGSY($Z_6$)C($Z_8$)C($Z_2$)SGRSA (SEQ ID NO: 154), where each Z is independently an amino acid selected from D, A, Y, S, T, N, I, L, F, V, H, and P.

In some embodiments, an activatable antibody comprises a masking moiety (MM) and a cleavable moiety (CM) comprising an amino acid sequence according to Formula (XXVIII): EVGSY($Z_6$)C($X_8$)C($Z_2$)SGRSA (SEQ ID NO: 155), where each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P.

In some embodiments, the cleavable moiety (CM) further comprises a first linker ($L_1$). In some embodiments, the first linker ($L_1$) is C-terminal to the first cleavage site ($CS_1$) (e.g., a first protease cleavage site). In some embodiments, the cleavable moiety (CM) comprises a structure, from N-terminus to C-terminus, of: ($CS_1$)-$L_1$.

Any suitable linker (e.g., a flexible linker) known in the art may be used, including, for example: glycine polymers (G) n, where n is an integer of at least 1 (e.g., at least one, at least 2, at least 3, at least 4, at least 5, at least 6, at least 7, at least 8, at least 9, at least 10, etc.); glycine-serine polymers (GS) n, where n is an integer of at least 1 (e.g., at least one, at least 2, at least 3, at least 4, at least 5, at least 6, at least 7, at least 8, at least 9, at least 10, etc.) such as GGGGS (SEQ ID NO: 156), SGGS (SEQ ID NO: 157), GGSG (SEQ ID NO: 158), GGSGG (SEQ ID NO: 159), GSGSG (SEQ ID NO: 160), GSGGG (SEQ ID NO: 161), GGGSG (SEQ ID NO: 162), and/or GSSSG (SEQ ID NO: 163)); glycine-alanine polymers; alanine-serine polymers; and the like. Linker sequences may be of any length, such as from about 1 amino acid (e.g., glycine or serine) to about 20 amino acids (e.g., 20 amino acid glycine polymers or glycine-serine polymers), about 1 amino acid to about 15 amino acids, about 3 amino acids to about 12 amino acids, about 4 amino acids to about 10 amino acids, about 5 amino acids to about 9 amino acids, about 6 amino acids to about 8 amino acids, etc. In some embodiments, the linker is any of about 1, 2, 3, 4, 5, 6, 7, 8, 9, 10, 11, 12, 13, 14, 15, 16, 17, 18, 19, or 20 amino acids in length. In some embodiments, the linker comprises an amino acid sequence selected from SEQ ID NOS: 159-163. In some embodiments, the linker comprises an amino acid sequence of SEQ ID NO: 156 or 157.

In some embodiments, the cleavable moiety (CM) further comprises at least a second cleavage site (e.g., at least a second, at least a third, at least a fourth, at least a fifth, etc.). In some embodiments, the cleavable moiety (CM) further comprises a second cleavage site ($CS_2$). In some embodiments, the second cleavage site is a second protease cleavage site. The second protease cleavage site may be any suitable protease cleavage site recognized and/or cleaved by any of the proteases described above. In some embodiments, the first ($CS_1$) and second ($CS_2$) cleavage sites are protease cleavage sites recognized and/or cleaved by the same protease. In some embodiments, the first ($CS_1$) and second ($CS_2$) cleavage sites are protease cleavage sites recognized and/or cleaved by different proteases (e.g., the first protease cleavage site is recognized and/or cleaved by uPA, and the second protease cleavage site is recognized and/or cleaved by MMP-2; the first protease cleavage site is recognized and/or cleaved by uPA, and the second protease cleavage site is recognized and/or cleaved by MMP-9; the first protease cleavage site is recognized and/or cleaved by uPA, and the second protease cleavage site is recognized and/or cleaved by TEV protease; etc.). In some embodiments, the at least second cleavage site (CS2) is C-terminal to the first linker ($L_1$). In some embodiments, the cleavable moiety (CM) comprises a structure, from N-terminus to C-terminus, of: $(CS_1)$-$L_1$-$(CS_2)$.

In some embodiments, the cleavable moiety (CM) further comprises at least a second linker (e.g., at least a second, at least a third, at least a fourth, at least a fifth, etc.). In some embodiments, the cleavable moiety (CM) further comprises a second linker ($L_2$). The second linker ($L_2$) may be any suitable linker described above. In some embodiments, the second linker comprises an amino acid sequence selected from SEQ ID NO: 156-163. In some embodiments, the first ($L_1$) and second ($L_2$) linkers are the same (e.g., both linkers comprise the sequence of SEQ ID NO: 156 or 157). In some embodiments, the first ($L_1$) and second ($L_2$) linkers are different (e.g., the first linker ($L_1$) comprises the amino acid sequence of SEQ ID NO: 156, and the second linker ($L_2$) comprises the amino acid sequence of SEQ ID NO: 157, etc.). In some embodiments, the at least second linker ($L_2$) is C-terminal to the second cleavage site (CS2). In some embodiments, the cleavable moiety (CM) comprises a structure, from N-terminus to C-terminus, of: $(CS_1)$-$L_1$-$(CS_2)$-$L_2$.

Exemplary MM-CM Sequences

In some embodiments, an activatable antibody of the present disclosure comprises the structure, from N-terminus to C-terminus, of: (FP)-(PCS1)-$L_1$-$(PCS_2)$-$L_2$. In some embodiments, an activatable antibody comprises an amino acid sequence according to Formula (XXIX), EVGSY$X_1X_2X_3X_4X_5X_6$C$X_7X_8X_9X_{10}X_{11}X_{12}$C$X_{13}X_{14}$SGRSAGGGGTENLYFQGSGGS (SEQ ID NO: 164), where X1 is A, D, I, N, P, or Y, X2 is A, F, N, S, or V, X3 is A, H, L, P, S, V, or Y, X4 is A, H, S, or Y, X5 is A, D, P, S, V, or Y, X6 is A, D, L, S, or Y, X7 is D, P, or V, X8 is A, D, H, P, S, or T, X9 is A, D, F, H, P, or Y, X10 is L, P, or Y, X11 is F, P, or Y, X12 is A, P, S, or Y, X13 is A, D, N, S, T, or Y, and X14 is A, S, or Y. In some embodiments, an activatable antibody of the present disclosure comprises the amino acid sequence of: EVGSYDALHYACPPDYYACYYSGRSAGGGGTENLYFQGSGGS (SEQ ID NO: 165); EVGSYNSYHAYCPHPLYPCTASGRSAGGGGTENLYFQGSGGS (SEQ ID NO: 166); EVGSYASSAVLCVTAYFSCNSSGRSAGGGGTENLYFQGSGGS (SEQ ID NO: 167); EVGSYNFVADSCPDHPYPCSASGRSAGGGGSPLGLAGSGGS (SEQ ID NO: 168); EVGSYNFVADSCPDHPYPCSASGRSAGGGGTENLYFQGSGGS (SEQ ID NO: 169); EVGSYIVHHSDCDAFYPYCDSSGRSAGGGGSPLGLAGSGGS (SEQ ID NO: 170); EVGSYIVHHSDCDAFYPYCDSSGRSAGGGGTENLYFQGSGGS (SEQ ID NO: 171); EVGSYYSAYPACDSHYPYCNSSGRSAGGGGSPLGLAGSGGS (SEQ ID NO: 172); EVGSYYSAYPACDSHYPYCNSSGRSAGGGGTENLYFQGSGGS (SEQ ID NO: 173); EVGSYPNPSSDCVPYYYACAYSGRSAGGGGSPLGLAGSGGS (SEQ ID NO: 174); EVGSYPNPSSDCVPYYYACAYSGRSAGGGGTENLYFQGSGGS (SEQ ID NO: 175); EVGSYYSAYPACDSHYPYCQSSGRSAGGGGSPLGLAGSGGS (SEQ ID NO: 176); EVGSYYSAYPACDSHYPYCNSAGRSAGGGGSPLGLAGSGGS (SEQ ID NO: 177); EVGSYPQPSSDCVPYYYACAYSGRSAGGGGSPLGLAGSGGS (SEQ ID NO: 178); and/or EVGSYPNPASDCVPYYYACAYSGRSAGGGGSPLGLAGSGGS (SEQ ID NO: 179). In some embodiments, a polypeptide of the present disclosure comprises the structure, from N-terminus to C-terminus, of: (FP)-$(PCS_1)$-$L_1$-$(PCS_2)$-$L_2$-(TBM).

In some embodiments, an activatable antibody comprises an amino acid sequence SGRSAGGGGTENLYFQGSGGS (SEQ ID NO:220), SGRSAGGGGTPLGLAGSGGS (SEQ ID NO: 221), or SGRSAPLGLA (SEQ ID NO:222). In some embodiments, an activatable antibody comprises the sequence of EV(Zn)C($X_8$)C($Z_2$)SGRSA (SEQ ID NO:217), EDC($Z_6$)C($Z_2$)SGRSA (SEQ ID NO:218), or EDC($Z_6$)C($Z_2$)PLGLA (SEQ ID NO:219), where each X is independently an amino acid selected from the group consisting of A, C, D, E, F, G, H, I, K, L, M, N, P, Q, R, S, T, V, W, and Y, wherein n is 1-11 and wherein each Z is independently an amino acid selected from the group consisting of D, A, Y, S, T, N, I, L, F, V, H, and P.

Target Binding Moieties (TBMs)

In some embodiments, the present disclosure relates to activatable antibodies comprising a target binding moiety (TBM). In some embodiments, the target binding moiety (TBM) comprises an antibody light chain variable region and/or an antibody heavy chain variable region. In some embodiments, the target binding moiety (TBM) comprises an antibody light chain variable region. In some embodiments, the target binding moiety (TBM) comprises an antibody heavy chain variable region. In some embodiments, the target binding moiety (TBM) comprises an antibody light chain variable region and an antibody heavy chain variable region.

In some embodiments, the target binding moiety (TBM) comprises a full length antibody light chain and/or a full length antibody heavy chain. The antibody light chain may be a kappa or lambda light chain. The antibody heavy chain may be in any class, such as IgG, IgM, IgE, IgA, or IgD. In some embodiments, the antibody heavy chain is in the IgG class, such as IgG1, IgG2, IgG3, or IgG4 subclass. An antibody heavy chain described herein may be converted from one class or subclass to another class or subclass using methods known in the art.

Any one or more of the target binding moieties (TBMs) described herein may incorporate: any of the HVR sequences described herein (e.g., one, two, or three of the heavy chain variable region HVR sequences, and/or one, two, or three of the light chain variable region HVR sequences as shown in Table A above); any of the heavy chain variable region sequences and/or light chain variable region sequences described herein (e.g., a heavy chain variable region sequence and/or a light chain variable region sequence as shown in Table B above); and/or any of any of the antibodies described herein.

In some embodiments, the target binding moiety (TBM) comprises a sequence of one or more of the anti-CTLA4 antibodies described herein, including antibodies described with reference to specific amino acid sequences of HVRs, variable regions (VL, VH), and/or light and heavy chains (e.g., IgG1, IgG2, IgG4). In some embodiments, the target binding moiety (TBM) comprises an antibody light chain variable region comprising an HVR-L1 comprising the amino acid sequence RASQSVRGRFLA (SEQ ID NO: 58), an HVR-L2 comprising the amino acid sequence DASNRATGI (SEQ ID NO: 66), and/or an HVR-L3 comprising the amino acid sequence YCQQSSSWPPT (SEQ ID NO: 75). In some embodiments, the target binding moiety (TBM) comprises an antibody light chain variable region comprising the amino acid sequence of SEQ ID NO: 100 or a sequence having at least 90% (e.g., 95%, 96%, 97%, 98% or 99%) sequence identity to the sequence of SEQ ID NO:100. In some embodiments, the target binding moiety (TBM) comprises an antibody heavy chain variable region comprising an HVR-H1 comprising the amino acid sequence YSISSGYHWSWI (SEQ ID NO: 23), an HVR-H2 comprising the amino acid sequence LARIDWDDDKYYSTSLKSRL (SEQ ID NO: 35), and/or an HVR-H3 comprising the amino acid sequence ARSYVYFDY (SEQ ID NO: 45). In some embodiments, the target binding moiety (TBM) comprises an antibody heavy chain variable region comprising the amino acid sequence of SEQ ID NO: 87 or a sequence having at least 90% (e.g., 95%, 96%, 97%, 98% or 99%) sequence identity to the sequence of SEQ ID NO:87. In some embodiments, the target binding moiety (TBM) comprises: a) an antibody light chain variable region comprising an HVR-L1 comprising the amino acid sequence RASQSVRGRFLA (SEQ ID NO: 58), an HVR-L2 comprising the amino acid sequence DASNRATGI (SEQ ID NO: 66), and/or an HVR-L3 comprising the amino acid sequence YCQQSSSWPPT (SEQ ID NO: 75); and b) an antibody heavy chain variable region comprising an HVR-H1 comprising the amino acid sequence YSISSGYHWSWI (SEQ ID NO: 23), an HVR-H2 comprising the amino acid sequence LARIDWDDDKYYSTSLKSRL (SEQ ID NO: 35), and/or an HVR-H3 comprising the amino acid sequence ARSYVYFDY (SEQ ID NO: 45). In some embodiments, the target binding moiety (TBM) comprises an antibody light chain variable region comprising the amino acid sequence of SEQ ID NO: 100, and an antibody heavy chain variable region comprising the amino acid sequence of SEQ ID NO: 87.

Activatable Binding Polypeptide Properties

In some embodiments, an activatable binding polypeptide (i.e., activatable antibody) of the present disclosure comprises: (a) a masking moiety (MM), (b) a cleavable moiety, and (c) a target binding moiety. In some embodiments, the masking moiety (MM) binds to the target binding moiety (TBM) of the activatable antibody and reduces or inhibits binding of the activatable binding moiety to CTLA4 (e.g., human CTLA4), as compared to the binding of a corresponding binding polypeptide lacking the masking moiety to CTLA4 (e.g., human CTLA4) and/or as compared to the binding of a parental antibody to CTLA4 (e.g., human CTLA4).

In some embodiments, an "activatable" binding polypeptides refers to a binding polypeptide that exhibits a first level of binding to CTLA4 when in an inhibited, masked, and/or uncleaved state, and exhibits a second level of binding to CTLA4 in an uninhibited, unmasked, and/or cleaved state, where the second level of CTLA4 binding is greater than the first level of CTLA4 binding. In some embodiments, access to CTLA4 by the activatable binding polypeptide is greater after cleavage within the cleavable moiety (e.g., by one or more proteases).

In some embodiments, an activatable antibody of the present disclosure is generally considered to be an "activatable" binding polypeptide when binding affinity of the polypeptide to CTLA4 (e.g., human CTLA4) increases by at least about 2-fold (e.g., at least about 2-fold, at least about 2.5-fold, at least about 3, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 25-fold, at least about 50-fold, at least about 75-fold, at least about 100-fold, at least about 250-fold, at least about 500-fold, at least about 750-fold, or at least about 1000-fold, or more) after activation of the activatable antibody as compared to prior to activation of the activatable antibody (e.g., after activation by treatment with one or more proteases that cleave within the cleavable moiety (CM), after activation by a change in pH (increased or decreased), after activation by a temperature shift (increased or decreased), after activation by being contacted with a second molecule (such as a small molecule), etc.). In some embodiments, an activatable antibody of the present disclosure is generally considered "activatable" if the $EC_{50}$ of the activatable antibody decreases by at least about 2-fold (e.g., at least about 2-fold, at least about 2.5-fold, at least about 3, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 25-fold, at least about 50-fold, at least about 75-fold, at least about 100-fold, at least about 250-fold, at least about 500-fold, at least about 750-fold, or at least about 1000-fold, or more) after "activation" (e.g., as measured by an ELISA or FACS assay; see the examples below). In some embodiments, an activatable antibody of the present disclosure is generally considered "activatable" if the $EC_{50}$ of the polypeptide decreases by at least about 2-fold after treatment with a protease that cleaves within the cleavable moiety (CM) (e.g., as measured by an ELISA or FACS assay; see the examples below).

In some embodiments, when the masking moiety (MM) is bound to the target binding moiety (TBM) of the activatable antibody, the $K_D$ of the activatable antibody for CTLA4 is about 2 (e.g., about 2, about 2.5, about 3, about 3.5 about 4, about 4.5, about 5, about 5.5, about 6, about 6.5, about 7, about 7.5, about 8, about 8.5, about 9, about 9.5, about 10, about 25, about 50, about 75, about 100, about 250, about 500, about 750, or about 1000 or more) times greater than when the masking moiety (MM) is not bound to the target binding moiety (TBM) (e.g., after "activation" of the activatable antibody (such as after protease treatment to cleave within the cleavable moiety (CM))) and/or than the $K_D$ of the parental antibody for CTLA4. Methods of measuring affinity are known in the art, including, for example, by the methods described in the Examples below).

In some embodiments, when the masking moiety is bound to the target binding moiety of the activatable antibody, the $K_D$ of the activatable antibody for CTLA4 is reduced by at least about 25% (e.g., at least about 25%, at least about 30%, at least about 40%, at least about 50%, at least about 60%, at least about 70%, at least about 80%, at least about 90%, at least about 95%, at least about 99%) relative to when the masking moiety is not bound to the target binding moiety (e.g., after "activation" of the activatable antibody (such as after protease treatment to cleave within the cleavable moiety (CM))) and/or relative to the $K_D$ of the parental antibody for CTLA4. Methods of measuring affinity are known in the art, including, for example, by the methods described in the Examples below).

In some embodiments, the masking moiety sterically hinders binding of the activatable antibody to CTLA4 and/or allosterically hinders binding of the activatable antibody to CTLA4. In some embodiments, the masking moiety does not comprise an amino acid sequence of a natural binding partner of the activatable antibody and/or parental antibody.

In some embodiments, the dissociation constant of the masking moiety for the target binding moiety is greater than the dissociation constant for the activatable antibody for CTLA4 (when activated). In some embodiments, the dissociation constant of the masking moiety for the target binding moiety is about 2 (e.g., about 2, about 2.5, about 3, about 3.5 about 4, about 4.5, about 5, about 5.5, about 6, about 6.5, about 7, about 7.5, about 8, about 8.5, about 9, about 9.5, about 10, about 25, about 50, about 75, about 100, about 250, about 500, about 750, or about 1000 or more) times greater than the dissociation constant for the activatable antibody for CTLA4 (when activated). In some embodiments, the dissociation constant of the masking moiety for the target binding moiety is about equal to the dissociation constant for the activatable antibody for CTLA4 (when activated).

The activatable antibodies described herein may be further modified. In some embodiments, the activatable antibodies are linked to an additional molecular entity. Examples of additional molecular entities include pharmaceutical agents, peptides or proteins, detection agent or labels, and antibodies.

In some embodiments, an activatable antibody of the present disclosure is linked to a pharmaceutical agent. Examples of pharmaceutical agents include cytotoxic agents or other cancer therapeutic agents, and radioactive isotopes. Specific examples of cytotoxic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for linking a polypeptide to a pharmaceutical agent are known in the art, such as using various linker technologies. Examples of linker types include hydrazones, thioethers, esters, disulfides and peptide-containing linkers. For further discussion of linkers and methods for linking therapeutic agents to antibodies see e.g., Saito et al., *Adv. Drug Deliv. Rev.* 55:199-215 (2003); Trail, et al., *Cancer Immunol. Immunother.* 52:328-337 (2003); Payne, *Cancer Cell* 3:207-212 (2003); Allen, Nat. Rev. Cancer 2:750-763 (2002); Pastan and Kreitman, *Curr. Opin. Investig. Drugs* 3:1089-1091 (2002); Senter and Springer (2001) *Adv. Drug Deliv. Rev.* 53:247-264.

IV. Anti-CD137 Antibodies

In some embodiments, the method described herein comprise administration of an anti-CD137 antibody that specifically binds to an extracellular domain of human CD137. The anti-CD137 antibodies described herein include full-length anti-CD137 antibodies, antigen-binding fragments of the CD137 antibodies, and derivatives of the CD137 antibodies. In some embodiments, the anti-CD137 antibody is any one of the antibodies described herein, including antibodies described with reference to epitope binding and antibodies described with reference to specific amino acid sequences of CDRs, variable regions (VL, VH), and IgG (e.g., IgG4) light and heavy chains. In some embodiments, the anti-CD137 antibody has at least one (e.g., at least one, at least two, at least three, at least four, at least five, at least six, at least seven, eight, or all nine) of the following functional properties: (a) bind to human CD137 with a $K_D$ of 500 nM or less; (b) have agonist activity on human CD137; (c) do not bind to human OX40, CD40, GITR and/or CD27 receptor at concentration up to 1000 nM; (d) is cross-reactive with monkey, mouse, rat, or dog CD137; (e) do not induce ADCC effects; (f) are capable of inhibiting tumor cell growth; (g) have therapeutic effect on a cancer; (h) blocks binding between CD137 and CD137L; and (i) blocks CD137 signaling stimulated by CD137L (e.g., CD137L-stimulated NF-κB-dependent transcription) in a cell that expresses CD137. In some embodiments, the antibodies disclosed herein can also block, e.g., completely block, the binding between CD137 and its ligand CD137L. In some embodiments, the anti-CD137 antibody is an antibody (or an antigen-binding fragment thereof) that cross-competes for binding to human CD137 with one or more of the antibodies or antigen-binding fragments as described herein. Exemplary anti-CD137 antibodies that are suitable for the methods described herein have been described, for example, in US20190055314A1, WO2019036855A1, and WO2019037711A1, which are incorporated herein by reference in their entirety.

Human CD137 is a 255 amino acid protein (e.g., GenBank Accession No. NM_001561; NP_001552; SEQ ID NO: 231). The protein comprises a signal sequence (amino acid residues 1-17), followed by an extracellular domain (169 amino acids), a transmembrane region (27 amino acids), and an intracellular domain (42 amino acids) (Cheuk ATC et al. 2004 Cancer Gene Therapy 11:215-226). The receptor is expressed on the cell surface in monomer and dimer forms and likely trimerizes with CD137 ligand to signal.

In some embodiments, the anti-CD137 antibody specifically binds to one or more amino acid residues within amino acid residues 34-108 of SEQ ID NO: 231. In some embodiments, the anti-CD137 antibody specifically binds to one or more amino acid residues within amino acid residues 34-93 of SEQ ID NO: 231. In some embodiments, the anti-CD137 antibody specifically binds to one or more amino acid residues selected from the group consisting of amino acid residues 34-36, 53-55, and 92-93 of SEQ ID NO: 231. In some embodiments, the anti-CD137 antibody specifically binds to one or more of amino acid residues 34-36, one or more of amino acid residues 53-55, and one or more or amino acid residues 92-93 of SEQ ID NO: 231. In some embodiments, the anti-CD137 antibody does not bind to one or more of amino acid residues selected from the group consisting of amino acid residues 109-112, 125, 126, 135-138, 150 and 151 of SEQ ID NO: 231. In some embodiments, the anti-CD137 antibody specifically does not bind to amino acid residues 109-112, 125, 126, 135-138, 150 and 151 of SEQ ID NO: 231. Methods of measuring an antibody or antigen-binding fragment's ability to bind a target antigen may be carried out using any method known in the art, including for example, by surface plasmon resonance, an ELISA, isothermal titration calorimetry, a filter binding assay, an EMSA, etc., or based on the crystal structure of the anti-CD137 antibody with CD137.

In some embodiments, the anti-CD137 antibody specifically binds to one or more amino acid residues selected from the group consisting of amino acid residues 51, 53, 62-73, 83, 89, 92, 95-104 and 112-116 of SEQ ID NO: 231. In some embodiments, the anti-CD137 antibody specifically binds to one or more amino acid residues selected from the group consisting of amino acid residues 51, 53, 63-67, 69-73, 83, 89, 92, 98-104, and 112-116 of SEQ ID NO: 231. In some embodiments, the anti-CD137 antibody specifically binds to one or more amino acid residues selected from the group consisting of amino acid residues 51, 63-67, 69-73, 83, 89, 92, 98-104 and 112-114 of SEQ ID NO: 231.

In some embodiments, the anti-CD137 antibody specifically binds to amino acid residues 51, 53, 62-73, 83, 89, 92, 95-104 and 112-116 of SEQ ID NO: 231. In some embodiments, the anti-CD137 antibody specifically binds to amino acid residues 51, 53, 63-67, 69-73, 83, 89, 92, 98-104, and 112-116 of SEQ ID NO: 231. In some embodiments, the anti-CD137 antibody specifically binds to amino acid residues 51, 63-67, 69-73, 83, 89, 92, 98-104 and 112-114 of SEQ ID NO: 231.

In some embodiments, the anti-CD137 antibody specifically binds to human CD137 with a KD of about 500 nM or less (e.g., about 500 nM or less, about 400 nM or less, about 300 nM or less, about 200 nM or less, about 150 nM or less, about 100 nM or less, about 90 nM or less, about 80 nM or less, about 75 nM or less, about 70 nM or less, about 60 nM or less, about 50 nM or less, about 40 nM or less, about 30 nM or less, about 25 nM or less, about 20 nM or less, about 10 nM or less, about 1 nM or less, about 0.1 nM or less, etc.) In some embodiments, the anti-CD137 antibody specifically binds to human CD137 with a KD of about 100 nM or less. In some embodiments, the anti-CD137 antibody specifically binds to human CD137 with a KD of about 50 nM or less. Methods of measuring the KD of an antibody or antigen-binding fragment may be carried out using any method known in the art, including for example, by surface plasmon resonance, an ELISA, isothermal titration calorimetry, a filter binding assay, an EMSA, etc.

Anti-CD137 antibodies need to be cross-linked to become agonistic. For example, cross-linking is achieved in vivo through Fcgamma receptors, while typically polyclonal anti-Fc antibodies are used in cell-based experiments in vitro. In some embodiments, the anti-CD137 antibodies described herein have agonist activity on human CD137. In some embodiments, the anti-CD137 antibody induces one or more (e.g., one or more, two or more, three or more, etc.) activities of human CD137 when a cell (e.g., a human cell) expressing human CD137 is contacted by the anti-CD137 antibody. Various CD137 activities are known in the art and may include, without limitation, induction of NF-κB-dependent transcription, induction of T cell proliferation, prolonging T cell survival, co-stimulation of activated T cells, induction of cytokine secretion (such as IL-2), and induction of monocyte activation. In some embodiments, the one or more CD137 activities is not CD137 binding to its ligand. Methods of measuring CD137 activity (e.g., the induction of NF-κB-dependent transcription and/or T cell proliferation, etc.) are known in the art. In some embodiments, the anti-CD137 antibody increases NF-κB dependent transcription in cells (e.g., human cells) expressing human CD137. In some embodiments, NF-κB dependent transcription is increased by about 10% or more, about 20% or more, about 30% or more, about 40% or more, about 50% or more, about 60% or more, about 70% or more, about 80% or more, about 90% or more, or about 99% or more in cells (e.g., human cells) expressing CD137 contacted with the anti-CD137 antibody, relative to a corresponding cell not contacted with the anti-CD137 antibody (e.g., a corresponding cell not contacted with an antibody, or contacted with an isotype control antibody). In some embodiments, NF-κB dependent transcription is increased by about 2-fold, 3-fold, 4-folr, 5-fold, 6-fold, 7-fold, 8-fold, 9-fold, 10-fold, 100-fold, 1000-fold or more in cells (e.g., human cells) expressing CD137 contacted with the anti-CD137 antibody, relative to a corresponding cell not contacted with the anti-CD137 antibody (e.g., a corresponding cell not contacted with an antibody, or contacted with an isotype control antibody).

In some embodiments, the anti-CD137 antibody is cross-reactive with monkey (e.g., cynomolgus monkey), mouse, rat, and/or dog CD137. In some embodiments, the anti-CD137 antibody is cross-reactive with monkey CD137. In some embodiments, the anti-CD137 antibody is cross-reactive with mouse CD137. In some embodiments, the anti-CD137 antibody is cross-reactive with rat CD137. In some embodiments, the anti-CD137 antibody is cross-reactive with dog CD137. In some embodiments, the anti-CD137 antibody is cross-reactive with monkey and mouse CD137; monkey and rat CD137; monkey and dog CD137; mouse and rat CD137; mouse and dog CD137; rat and dog CD137; monkey, mouse, and rat CD137; monkey, mouse, and dog CD137; monkey, rat, and dog CD137; mouse, rat, and dog CD137; or monkey, mouse, rat, and dog CD137. In some embodiments, the anti-CD137 antibody is cross-reactive at about 100 nM (e.g., at about 1 nM, at about 10 nM, at about 25 nM, at about 50 nM, at about 75 nM, at about 100 nM). Methods of measuring antibody cross-reactivity are known in the art, including, without limitation, surface plasmon resonance, an ELISA, isothermal titration calorimetry, a filter binding assay, an EMSA, etc.

In some embodiments, the anti-CD137 antibody does not induce ADCC effects. Methods of measuring ADCC effects (e.g., in vivo methods) are known in the art. In some embodiments, the anti-CD137 antibody does not ADCC effects by more than about 10% (do not induce ADCC by more than about 10%, more than about 5%, more than about 1%, more than about 0.1%, more than about 0.01%) relative to a control.

In some embodiments, the anti-CD137 antibody is capable of inhibiting tumor cell growth/proliferation. In some embodiments, the tumor cell growth/proliferation is inhibited by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) when contacted with the anti-CD137 antibody relative to corresponding tumor cells not contacted with the anti-CD137 antibody. In some embodiments, the anti-CD137 antibody is capable of reducing tumor volume in a subject when the subject is administered the anti-CD137 antibody. In some embodiments, the anti-CD137 antibody is capable of reducing tumor volume in a subject by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) relative to the initial tumor volume in the subject (e.g., prior to administration of the anti-CD137 antibody). Methods of monitoring tumor cell growth/proliferation, tumor volume, and/or tumor inhibition are known in the art.

In some embodiments, the anti-CD137 antibody has therapeutic effect on a cancer. In some embodiments, the anti-CD137 antibody reduces one or more signs or symptoms of a cancer. In some embodiments, a subject suffering from a cancer goes into partial or complete remission when administered the anti-CD137 antibody.

In some embodiments, the anti-CD137 antibody is selected from the group consisting of AG10058, AG10059 and ADG106. In some embodiments, the anti-CD137 antibody competes or cross-competes for binding to human CD137 with any of the illustrative antibodies of the present application, such as AG10058, AG10059 and ADG106. In some embodiments, the anti-CD137 antibody is an antibody that competes or cross-competes for binding to the same epitope on human CD137 as AG10058, AG10059 or ADG106. The ability of an antibody to compete or cross-compete for binding with another antibody can be determined using standard binding assays known in the art, such as BIAcore analysis, ELISA assays, or flow cytometry. For example, one can allow an illustrative antibody of the disclosure to bind to human CD137 under saturating conditions and then measure the ability of the test antibody to bind to the CD137. If the test antibody is able to bind to the CD137 at the same time as the illustrative antibody, then the test antibody binds to a different epitope as the illustrative antibody. However, if the test antibody is not able to bind to the CD137 at the same time, then the test antibody binds to the same epitope, an overlapping epitope, or an epitope that is in close proximity to the epitope bound by the illustrative antibody. This experiment can be performed using various methods, such as ELISA, RIA, FACS or surface plasmon resonance.

In some embodiments, the anti-CD137 antibody blocks the binding between CD137 and its ligand (e.g., human CD137 and human CD137L). In some embodiments, the anti-CD137 antibody blocks the binding between CD137 and its ligand in vitro. In some embodiments, the anti-CD137 antibody has a half maximal inhibitory concentration (IC50) of about 500 nM or less (e.g., about 500 nM or less, about 400 nM or less, about 300 nM or less, about 200 nM or less, about 100 nM or less, about 50 nM or less, about 25 nM or less, about 10 nM or less, about 1 nM or less, etc.) for blocking binding of CD137 its ligand. In some embodiments, the anti-CD137 antibody has a half-maximal inhibitory concentration (IC50) of about 100 nM or less for blocking binding of CD137 its ligand. In some embodiments, the anti-CD137 antibody completely blocks binding of human CD137 to its ligand when provided at a concentration of about 100 nM or greater (e.g., about 100 nM or greater, about 500 nM or greater, about 1 μM or greater, about 10 μM or greater, etc.). As used herein, the term "complete blocking" or "completely blocks" refers to the antibody or antigen-binding fragment's ability to reduce binding between a first protein and a second protein by at least about 80% (e.g., at least about 80%, at least about 85%, at least about 90%, at least about 95%, at least about 99%, etc.). Methods of measuring the ability of an antibody or antigen-binding fragment to block binding of a first protein (e.g., a CD137) and a second protein (e.g., CD137L) are known in the art, including, without limitation, via BIAcore analysis, ELISA assays, and flow cytometry.

In some embodiments, the anti-CD137 antibody comprises a heavy chain variable region (VH) and a light chain variable region (VL), a) wherein the VH comprises an HVR-H1, an HVR-H2, and an HVR-H3, wherein the HVR-H1 comprises an amino acid sequence according to a formula selected from the group consisting of: Formula (I): X1TFX2X3YX4IHWV (SEQ ID NO: 262), wherein X1 is For Y, X2 is S or T, X3 is G, N, or S, and X4 is A, G, or W; Formula (II): YSIX1SGX2X3WX4WI (SEQ ID NO: 263), wherein X1 is S or T, X2 is H or Y, X3 is H or Y, and X4 is A, D, G, N, S, or T; and Formula (III): FSLSTX1GVX2VX3WI (SEQ ID NO: 264), wherein X1 is G or S, X2 is A or G, and $X_3$ is A, G, S, or T; wherein the HVR-H2 comprises an amino acid sequence according to a formula selected from the group consisting of: Formula (IV): LALIDWX1X2DKX3YSX4SLKSRL (SEQ ID NO: 265), wherein X1 is A, D, or Y, X2 is D or G, X3 is R, S, or Y, and X4 is P or T; Formula (V): IGX1IYHSGX2TYYX3PSLKSRV (SEQ ID NO: 266), wherein X1 is D or E, X2 is N or S, and X3 is N or S; and Formula ($V_I$): VSX1ISGX2GX3X4TYYADSVKGRF (SEQ ID NO: 267), wherein X1 is A, G, S, V, or Y, X2 is A, D, S, or Y, X3 is D, G, or S, and X4 is S or T; and wherein the HVR-H3 comprises an amino acid sequence according to Formula (VII): ARX1GX2X3X4VX5GDWFX6Y (SEQ ID NO: 268), wherein X1 is E or G, X2 is E or S, X3 is D or T, X4 is A, T, or V, X5 is A, I, L, T, or V, and X6 is A, D, or G; and/or b) wherein the $V_L$ comprises an HVR-L1, an HVR-L2, and an HVR-L3, wherein the HVR-L1 comprises an amino acid sequence according to Formula (VIII): X1ASQX2X3X4X5X6X7X8 (SEQ ID NO: 269), wherein X1 is Q or R, X2 is D, G, or S, X3 is I or V, X4 is G, R, S, or T, X5 is P, R, S, or T, X6 is A, D, F, S, V, or Y, X7 is L or V, and X8 is A, G, or N; wherein the HVR-L2 comprises an amino acid sequence according to Formula (IX): X1ASX2X3X4X5GX6 (SEQ ID NO: 270), wherein X1 is A or D, X2 is N, S, or T, X3 is L or R, X4 is A, E, or Q, X5 is S or T, and X6 is I or V; and wherein the HVR-L3 comprises an amino acid sequence according to a formula selected from the group consisting of: Formula (X): YCQQX1YX2X3X4T (SEQ ID NO: 271), wherein X1 is A, G, S, or Y, X2 is Q, S, or Y, X3 is I, L, T, or Y, and X4 is I, S, V, or W; and Formula (XI): YCX1QX2X3X4X5PX6T (SEQ ID NO: 272), wherein X1 is E or Q, X2 is P, S, or Y, X3 is D, L, S, T, or Y, X4 is D, E, H, S, or T, X5 is D, L T, or W, and X6 is L, P, R, or V.

In some embodiments, the anti-CD137 antibody comprises a VH and a VL, wherein the VH comprises a HVR-H1 comprising the amino acid sequence of SEQ ID NO: 264, a HVR-H2 comprising the amino acid sequence of SEQ ID NO: 265, and a HVR-H3 comprising the amino acid sequence of SEQ ID NO: 268; and/or wherein the VL comprises a HVR-L1 comprising the amino acid sequence of SEQ ID NO: 269, a HVR-L2 comprising the amino acid sequence of SEQ ID NO: 270, and a HVR-L3 comprising the amino acid sequence of SEQ ID NO: 271.

Sequences of exemplary anti-CD137 antibodies are shown in Table C below.

TABLE C

| Exemplary anti-CD137 antibodies. | | | | | | |
|---|---|---|---|---|---|---|
| Antibody | HVR-H1 | HVR-H2 | HVR-H3 | HVR-L1 | HVR-L2 | HVR-L3 |
| ADG106 | FSLSTGGV GVGWI (SEQ ID NO: 232) | LALIDWA DDKYYSP SLKSRL (SEQ ID NO: 233) | ARGGSDT VIGDWFA Y (SEQ ID NO: 234) | RASQSIGS YLA (SEQ ID NO: 235) | DASNLET GV (SEQ ID NO: 236) | YCQQGYYL WT (SEQ ID NO: 237) |
| AG10059 | YSITSGHY WAWI (SEQ ID NO: 242) | VSSISGYG STTYYAD SVKGRF (SEQ ID NO: 243) | ARGGSDA VLGDWFA Y (SEQ ID NO: 244) | RASQGIGS FLA (SEQ ID NO: 245) | DASNLET GV (SEQ ID NO: 246) | YCQQGYYL WT (SEQ ID NO: 247) |
| AG10058 | FSLSTSGV GVGWI (SEQ ID NO: 252) | LALIDWD DDKYYSP SLKSRL (SEQ ID NO: 253) | ARGGSDT VLGDWFA Y (SEQ ID NO: 254) | RASQSVSP YLA (SEQ ID NO: 255) | DASSLESG V (SEQ ID NO: 256) | YCQQGYSL WT (SEQ ID NO: 257) |

In some embodiments, the anti-CD137 antibody comprises a VH and a VL, wherein the VH comprises a HVR-H1 comprising the amino acid sequence of SEQ ID NO: 232, a HVR-H2 comprising the amino acid sequence of SEQ ID NO: 233, and a HVR-H3 comprising the amino acid sequence of SEQ ID NO: 234; and/or wherein the VL comprises a HVR-L1 comprising the amino acid sequence of SEQ ID NO: 235, a HVR-L2 comprising the amino acid sequence of SEQ ID NO: 236, and a HVR-L3 comprising the amino acid sequence of SEQ ID NO: 237.

In some embodiments, the anti-CD137 antibody comprises a VH comprising a heavy chain complementarity determining region (HC-CDR) 1, a HC-CDR2, and a HC-CDR3 of the amino acid sequence of SEQ ID NO: 238; and/or a VL comprising a light chain complementarity determining region (LC-CDR) 1, a LC-CDR2, and a LC-CDR3 of the amino acid sequence of SEQ ID NO: 239. In certain embodiments, the anti-CD137 antibody comprises a heavy chain variable region comprises the amino acid sequence of SEQ ID NO: 238, and/or a light chain variable region comprising the amino acid sequence of SEQ ID NO: 239. In certain embodiments, the anti-CD137 antibody comprises a heavy chain comprising the amino acid sequence of SEQ ID NO: 240, and/or a light chain comprising the amino acid sequence of SEQ ID NO: 241.

In some embodiments, the anti-CD137 antibody comprises a VH and a VL, wherein the VH comprises a HVR-H1 comprising the amino acid sequence of SEQ ID NO: 242, a HVR-H2 comprising the amino acid sequence of SEQ ID NO: 243, and a HVR-H3 comprising the amino acid sequence of SEQ ID NO: 244; and/or wherein the VL comprises a HVR-L1 comprising the amino acid sequence of SEQ ID NO: 245, a HVR-L2 comprising the amino acid sequence of SEQ ID NO: 246, and a HVR-L3 comprising the amino acid sequence of SEQ ID NO: 247.

In some embodiments, the anti-CD137 antibody comprises a VH comprising a HC-CDR1, a HC-CDR2, and a HC-CDR3 of the amino acid sequence of SEQ ID NO: 248; and/or a VL comprising a LC-CDR1, a LC-CDR2, and a LC-CDR3 of the amino acid sequence of SEQ ID NO: 249. In certain embodiments, the anti-CD137 antibody comprises a heavy chain variable region comprises the amino acid sequence of SEQ ID NO: 248, and/or a light chain variable region comprising the amino acid sequence of SEQ ID NO: 249. In certain embodiments, the anti-CD137 antibody comprises a heavy chain comprising the amino acid sequence of SEQ ID NO: 250, and/or a light chain comprising the amino acid sequence of SEQ ID NO: 251.

In some embodiments, the anti-CD137 antibody comprises a VH and a VL, wherein the VH comprises a HVR-H1 comprising the amino acid sequence of SEQ ID NO: 252, a HVR-H2 comprising the amino acid sequence of SEQ ID NO: 253, and a HVR-H3 comprising the amino acid sequence of SEQ ID NO: 254; and/or wherein the VL comprises a HVR-L1 comprising the amino acid sequence of SEQ ID NO: 255, a HVR-L2 comprising the amino acid sequence of SEQ ID NO: 256, and a HVR-L3 comprising the amino acid sequence of SEQ ID NO: 257.

In some embodiments, the anti-CD137 antibody comprises a VH comprising a HC-CDR1, a HC-CDR2, and a HC-CDR3 of the amino acid sequence of SEQ ID NO: 258; and/or a VL comprising a LC-CDR1, a LC-CDR2, and a LC-CDR3 of the amino acid sequence of SEQ ID NO: 259. In certain embodiments, the anti-CD137 antibody comprises heavy chain variable region comprises the amino acid sequence of SEQ ID NO: 258, and/or a light chain variable region comprising the amino acid sequence of SEQ ID NO: 259. In certain embodiments, the anti-CD137 antibody comprises a heavy chain comprising the amino acid sequence of SEQ ID NO: 260, and/or a light chain comprising the amino acid sequence of SEQ ID NO: 261.

The CD137 antibodies described herein can be in any class, such as IgG, IgM, IgE, IgA, or IgD. It is preferred that the CD137 antibodies are in the IgG class, such as IgG1, IgG2, IgG3, or IgG4 subclass. A CD137 antibody can be converted from one class or subclass to another class or subclass using methods known in the art. An exemplary method for producing an antibody in a desired class or subclass comprises the steps of isolating a nucleic acid encoding a heavy chain of an CD137 antibody and a nucleic acid encoding a light chain of a CD137 antibody, isolating the sequence encoding the VH region, ligating the VH sequence to a sequence encoding a heavy chain constant region of the desired class or subclass, expressing the light chain gene and the heavy chain construct in a cell, and collecting the CD137 antibody. In some embodiments, the anti-CD137 antibody comprises a human IgG4 Fc region. In some embodiments, the human IgG4 Fc region comprises an S241P mutation, wherein numbering is according to Kabat.

V. Pharmaceutical Compositions, Kits, and Articles of Manufacture

In other aspects, the present application provides a composition comprising any one of the anti-CTLA4 antibodies (e.g., activatable antibodies) described herein. In some embodiments, the composition is a pharmaceutical composition comprising the anti-CTLA4 antibody (e.g., activatable antibodies) and a pharmaceutically acceptable carrier. In some embodiments, provided herein is a composition comprising one or more additional therapeutic agents (e.g., an anti-PD-1 antibody, an anti-PD-L1 antibody, an anti-CD137 antibody, and a VEGF inhibitor, a chemotherapeutic agent, or a PARP inhibitor). The compositions can be prepared by conventional methods known in the art.

The term "pharmaceutically acceptable carrier" refers to any inactive substance that is suitable for use in a formulation for the delivery of an active agent (e.g., the anti-CTLA4 antibody). A carrier may be an anti-adherent, binder, coating, disintegrant, filler or diluent, preservative (such as antioxidant, antibacterial, or antifungal agent), sweetener, absorption delaying agent, wetting agent, emulsifying agent, buffer, and the like. Examples of suitable pharmaceutically acceptable carriers include water, ethanol, polyols (such as glycerol, propylene glycol, polyethylene glycol, and the like) dextrose, vegetable oils (such as olive oil), saline, buffer, buffered saline, and isotonic agents such as sugars, polyalcohols, sorbitol, and sodium chloride. The compositions may be in any suitable forms, such as liquid, semi-solid, and solid dosage forms. Examples of liquid dosage forms include solution (e.g., injectable and infusible solutions), microemulsion, liposome, dispersion, or suspension. Examples of solid dosage forms include tablet, pill, capsule, microcapsule, and powder. A particular form of the composition suitable for delivering an anti-CTLA4 antibody is a sterile liquid, such as a solution, suspension, or dispersion, for injection or infusion. Sterile solutions can be prepared by incorporating the antibody in the required amount in an appropriate carrier, followed by sterilization microfiltration. Generally, dispersions are prepared by incorporating the antibody into a sterile vehicle that contains a basic dispersion medium and other carriers. In the case of sterile powders for the preparation of sterile liquid, methods of preparation include vacuum drying and freeze-drying (lyophilization) to yield a powder of the active ingredient plus any additional desired ingredient from a previously sterile-filtered solution thereof. The various dosage forms of the compositions can be prepared by conventional techniques known in the art.

The relative amount of an anti-CTLA4 antibody included in the composition will vary depending upon a number of factors, such as the specific anti-CTLA4 antibody and carriers used, dosage form, and desired release and pharmacodynamic characteristics. The amount of an anti-CTLA4 antibody in a single dosage form will generally be that amount which produces a therapeutic effect, but may also be a lesser amount. Generally, this amount will range from about 0.01 percent to about 99 percent, from about 0.1 percent to about 70 percent, or from about 1 percent to about 30 percent relative to the total weight of the dosage form.

In addition to the anti-CTLA4 antibody, one or more additional therapeutic agents may be included in the composition. Examples of additional therapeutic agents are described herein in the "Methods of Treatment" section. The suitable amount of the additional therapeutic agent to be included in the composition can be readily selected by a person skilled in the art, and will vary depending on a number of factors, such as the particular agent and carriers used, dosage form, and desired release and pharmacodynamic characteristics. The amount of the additional therapeutic agent included in a single dosage form will generally be that amount of the agent, which produces a therapeutic effect, but may be a lesser amount as well.

In some embodiments, there is provided an article of manufacture comprising materials useful for the treatment of a cancer. The article of manufacture can comprise a container and a label or package insert on or associated with the container. Suitable containers include, for example, bottles, vials, syringes, etc. The containers may be formed from a variety of materials such as glass or plastic. Generally, the container holds a composition, which is effective for treating a cancer, described herein, and may have a sterile access port (for example, the container may be an intravenous solution bag or a vial having a stopper pierceable by a hypodermic injection needle). Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a cancer. The label or package insert may further comprise instructions for administering the composition to a patient.

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of a cancer described herein, optionally in combination with the articles of manufacture. Kits of the present application include one or more containers comprising any one of the compositions described herein (or unit dosage form and/or article of manufacture). In some embodiments, the kit further comprises other agents (e.g., one or more additional therapeutic agents) and/or instructions for use in accordance with any of the methods described herein. The kit may further comprise a description of selection of individuals suitable for treatment. Instructions supplied in the kits of the present application are typically written instructions on a label or package insert (e.g., a paper sheet included in the kit), but machine-readable instructions (e.g., instructions carried on a magnetic or optical storage disk) are also acceptable.

For example, in some embodiments, there is provided a kit comprising a pharmaceutical composition comprising any one of the anti-CTLA4 antibodies described herein and a pharmaceutically acceptable carrier; and instructions for administering the pharmaceutical composition to a subject having a cancer. In some embodiments, the kit further comprises a pharmaceutical composition comprising an additional therapeutic agent, such as a chemotherapeutic agent. In some embodiments, the kit further comprises a pharmaceutical composition comprising an anti-PD-1 antibody, an anti-PD-L1 antibody, an anti-CD137 antibody, and a VEGF inhibitor, a chemotherapeutic agent, or a PARP inhibitor. In some embodiments, the kit comprises one or more assays or reagents thereof for determining a level of one or more biomarkers described herein (e.g., CD8+ T cells, CD4+ T cells, CD8+ $T_{em}$ cells, CD4+ $T_{em}$ cells, $T_{reg}$ cells, a ratio of CD8+ $T_{em}$ cells to $T_{reg}$ cells, a ratio of CD4+ $T_{em}$ cells to $T_{reg}$ cells, NK cells, B cells).

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The containers may be unit doses, bulk packages (e.g., multi-dose packages) or sub-unit doses. Kits may also include multiple unit doses of the pharmaceutical compositions and instructions for use and packaged in quantities sufficient for storage and use in pharmacies, for example, hospital pharmacies and compounding pharmacies.

The foregoing written description is considered to be sufficient to enable one skilled in the art to practice the present disclosure. The following Examples are offered for illustrative purposes only, and are not intended to limit the scope of the present disclosure in any way. Indeed, various modifications of the present disclosure in addition to those shown and described herein will become apparent to those skilled in the art from the foregoing description and fall within the scope of the appended claims.

EXAMPLES

The invention can be further understood by reference to the following examples, which are provided by way of illustration and are not meant to be limiting.

Example 1. a Novel Anti-CTLA4 Checkpoint Inhibitor Prodrug to Address On-Target Off-Tumor Toxicity for Cancer Immunotherapy As the first FDA approved immune checkpoint inhibitor targeting CTLA4, ipilimumab has proven the clinical benefit of checkpoint blockade in cancer immunotherapy, especially in combination with anti-PD-1 therapy. However, ipilimumab can induce severe and sometimes fatal immune-mediated adverse reactions due to autoimmune responses in normal tissues which may involve many organ systems, thus restricting its clinical applications. Consequently, development of next generation anti-CTLA4 antibodies with enhanced antitumor efficacy and improved safety profiles are urgently needed.

TY22404 is a novel anti-CTLA4 fully human IgG1 antibody prodrug engineered using SAFEbody technology. TY22404 is designed for an antibody to be preferentially activated in the tumor microenvironment, limiting its on-target off-tumor toxicities in normal tissues. As shown in FIG. 1, a SAFEbody is masked by a covalently linked N-terminal peptide, followed by protease cleavage sites. In normal tissues, the SAFEbody masking moiety functions to block TY22404 binding to CTLA4, however, after cleavage by proteases known to be highly expressed and active in tumor tissues, the masking moiety is released enabling the activated TY22404 antibody to bind and inhibit CTLA4 function in situ.

Nonclinical pharmacological studies demonstrated that unmasked or activated TY22404 binds to a unique and conserved epitope of CTLA4 with species cross-reactivity and partially blocks the CTLA4/B7 ligand interactions. Activated TY22404 potentiated T cell activation by inducing IL-2 cytokine production in the presence of a primary stimulatory signal, depleted immunosuppressive Tregs through enhanced ADCC, and reduced immunosuppressive Treg activity specifically in the tumor microenvironment to mediate anti-tumor responses. TY22404 demonstrated efficacious anti-tumor activity in multiple syngeneic murine tumor models as a single agent, as well as in combination with other immune modulatory agents. Nonclinical toxicology studies demonstrated that TY22404 is well-tolerated in cynomolgus monkeys. These results suggested that activation of the masked TY22404 prodrug preferentially in the local tumor microenvironment may allow treatments that deliver higher efficacious dose levels to the tumor concomitant with a superior systemic safety profile compared with other traditional anti-CTLA4 antibodies. Thus, TY22404 holds great promise to achieve much better efficacy and safety profiles for immunotherapy against a broad spectrum of human cancers.

Preclinical Toxicology Results

In the nonobese diabetic (NOD) mouse model, all mice survived after six treatments of TY22404 at 50 mg/kg, No abnormal findings attributable to TY22404 were observed.

In a 4-week GLP repeat-dose toxicology study, intravenous infusion of TY22404 to cynomolgus monkeys at 5, 30, and 200 mg/kg/dose once weekly for five doses, followed by a 28-day recovery period, was well tolerated. Adverse, but reversible, microscopic findings of minimal to moderate mixed perivascular infiltrates were observed at 200 mg/kg in both sexes in multiple organs and tissues.

The no-observed-adverse-effect-level (NOAEL) was determined to be 30 mg/kg/dose in both rats and cynomolgus monkeys, and the highest non-severely toxic dose (HNSTD) was determined to be 200 mg/kg/dose.

Binding Affinity of TY22404 to Human, Monkey, Mouse and Rat CTLA4

The binding affinity of masked TY22404 vs its activated forms (activated TY22404 by condition 1 and 2) to recombinant CTLA4 proteins of human, cynomolgus monkey, mouse or rat origin, was evaluated. In brief, recombinant CTLA4 proteins (extracellular domain) of human, cynomolgus monkey, mouse or rat origin are coated onto ELISA microplates, to capture TY22404, activated TY22404 forms (activated TY22404 by condition 1 and 2), or a human IgG1 isotype control antibody at serial dilutions, followed by detection of the captured antibodies with a HRP-labeled anti-human IgG (Fab specific) secondary antibody. The half maximal effective concentration (EC50) is calculated based on the fitted binding curve.

Figure 3:
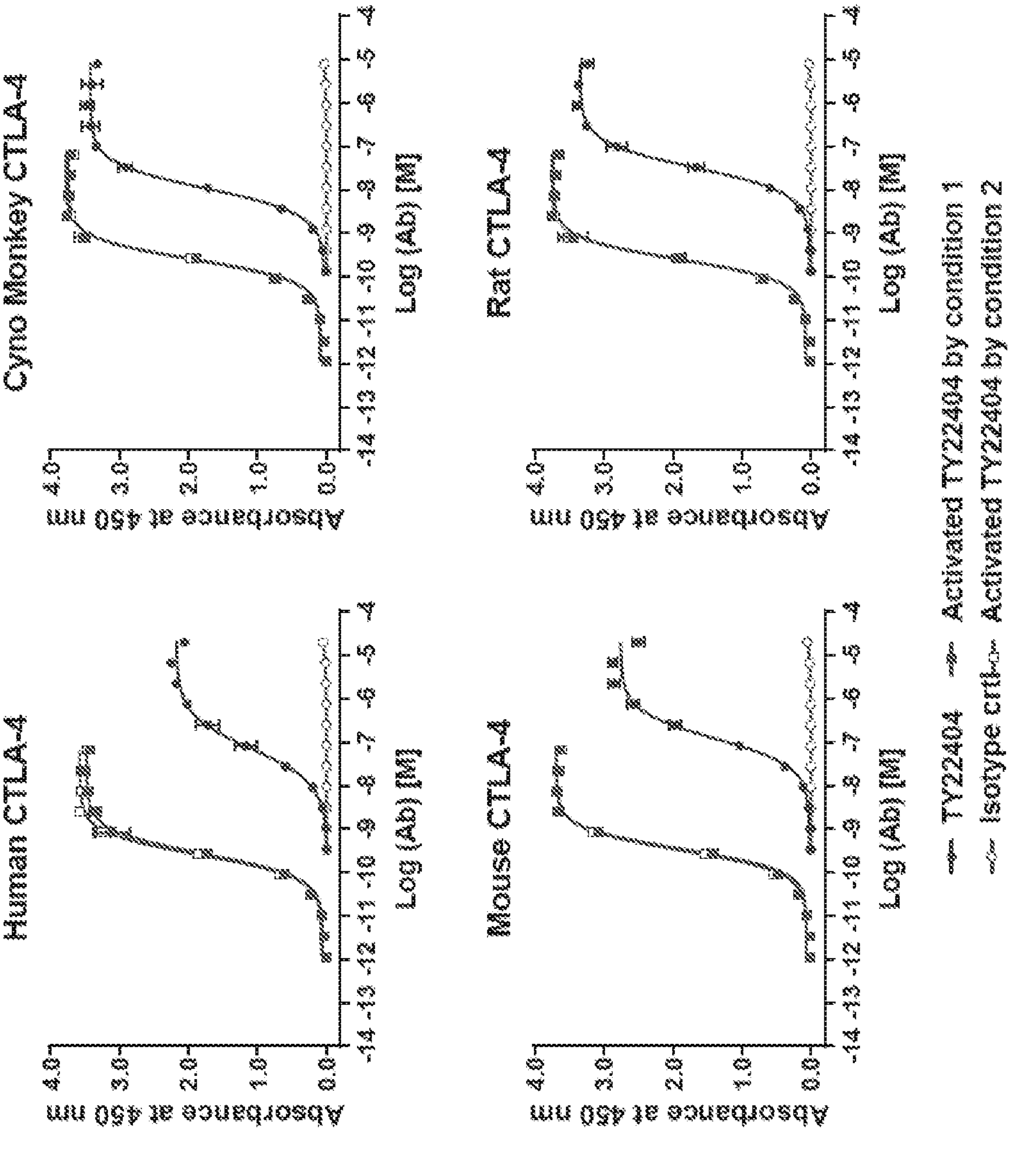
FIG. 3 shows that the target binding site of the TY22404 SAFEbody is highly masked and binds weakly to CTLA4 protein at low concentration (around nM), but can bind with target at much higher concentration (around uM or sub uM, higher than nM). However, once proteases cleave off the masking peptide, TY22404 is activated and can bind at high affinity to the cross species CTLA4 proteins of human, monkey, and rodent origins.

As shown in FIG. 3, masked TY22404 can bind to the recombinant CTLA4 proteins of human, cynomolgus monkey, mouse and rat, but with quite low affinities. While its activated forms bind to the recombinant CTLA4 proteins of all four species, with comparable high affinities (all around 0.3 nM). Compared to masked TY22404 antibody, cleaved TY22404 bind to its target CTLA4 proteins with dramatically increased affinities, with more than250-fold increased affinity for human CTLA4, about 40-fold increased affinity for monkey CTLA4, more than 300-fold increased affinity for mouse CTLA4 and more than 100-fold increased affinity for rat CTLA4, respectively.

Effects of TY22404 on CD28 Signaling Activation by In Vitro Cellular CTLA4 Blockade Bioassay The functional activity of masked TY22404 and its activated forms vs Ipilimumab to stimulate CD28 mediated downstream cell signaling by blocking CTLA4 sequestration of CD80 and CD86 ligands, was evaluated.

This study employs the Promega CTLA4 blockade bioassay system, a bioluminescent cell-based assay, to assess the CTLA4 blocking function of the anti-CTLA4 mAbs. This assay system involves two genetically engineered cell lines: CTLA4 effector cells-Jurkat T cells expressing human CTLA4 ($1.0\times10^5$/well) and a luciferase reporter driven by a IL-2 native promoter which responds to TCR/CD28 activation; and aAPC/Raji cells ($2.0\times10^5$)-Raji cells expressing cell surface protein designed to activate TCRs in an antigen-independent manner and endogenously expressing CTLA4 ligands CD80 and CD86. When the two cell types are co-cultured, CTLA4 competes with CD28 for their shared ligands, CD80 and CD86, and thus inhibits CD28 pathway activation and promoter-mediated luminescence. Finally serially diluted TY22404, its activated forms, ipilimumab or isotype antibody are added to block the interaction of CTLA4 with its ligands CD80 and CD86, which results in promoter-mediated luminescence. The bioluminescent signal can then be detected using the Bio-Glo™ Luciferase Assay System.

Figure 4:
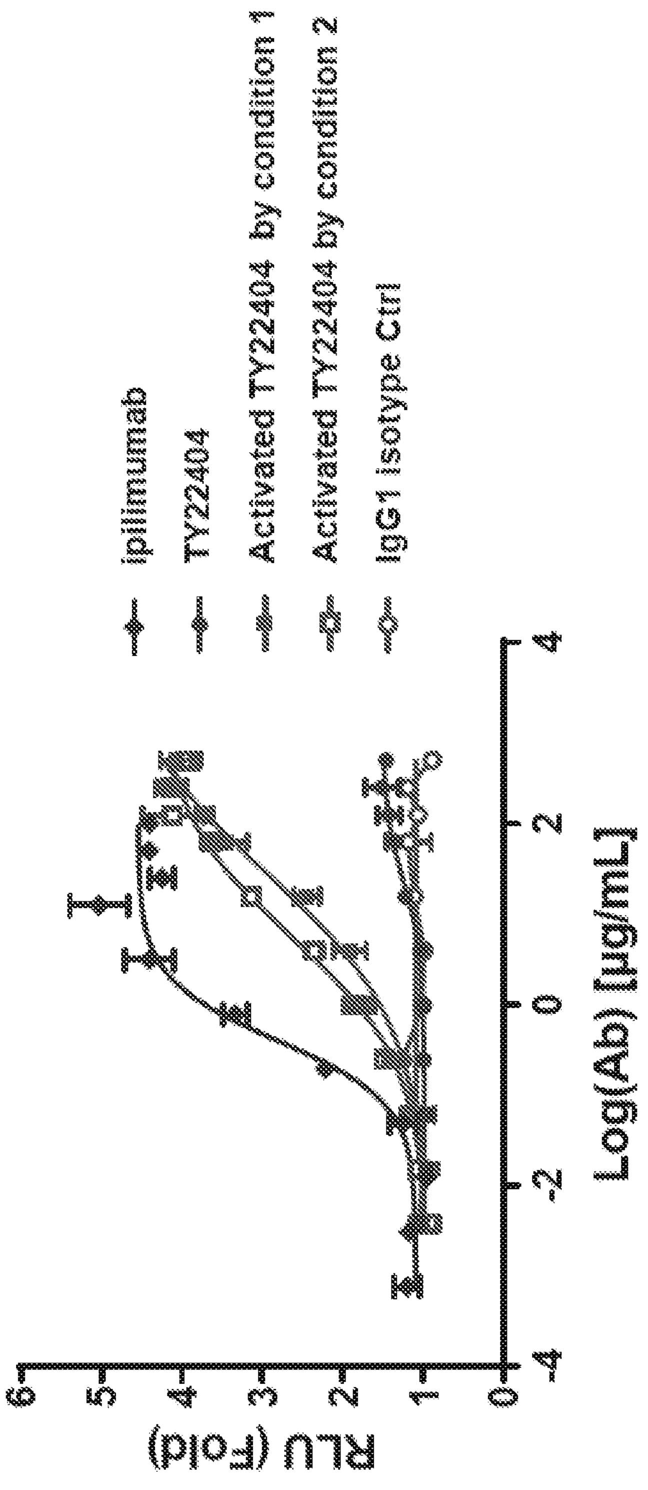
FIG. 4 shows the results of a cell-based CTLA4 blockade bioassay (Promega) employed to evaluate anti-CTLA4 mediated CD28 signaling activation. Protease-activated TY22404 was a softer CTLA4 checkpoint inhibitor than ipilimumab.

As shown in FIG. 4, masked TY22404 can't induce the downstream luminescent cell signaling. After activated by either condition 1 or 2 cleavage in vitro, both activated antibodies by condition 1 and 2 can stimulate CTLA4 blockade mediated reporter signaling in a dose dependent manner. However, the activity of TY22404 activated forms are much lower than ipilimumab.

Evaluation of ADCC Reporter Gene Activity of TY22404 on 293F Overexpressing Human CTLA4

The reporter gene activity of antibody-dependent cell-mediated cytotoxicity (ADCC) of TY22404 and its activated forms vs ipilimumab on their target cells (293F-CTLA4) was evaluated. In brief, the effector cells, Jurkat-NFAT-CD16, are engineered from the human T-lymphocyte Jurkat cell line. Jurkat cells naturally express a functional NFAT transcription factor, which is involved in the early signal events in ADCC. The target cells ($2.0\times10^4$) used here are 293F overexpressing CTLA4 target molecules. The ADCC reporter activity of the anti-CTLA4 mAbs are assessed by co-incubation of 293F-CTLA4 target cells with effector cells ($1.2\times10^5$) in the presence and absence of the anti-CTLA4 mAbs at different concentrations, followed by analysis of the luciferase. The IgG1 isotype control mAb is used as negative control for ADCC reporter activity.

Figure 5:
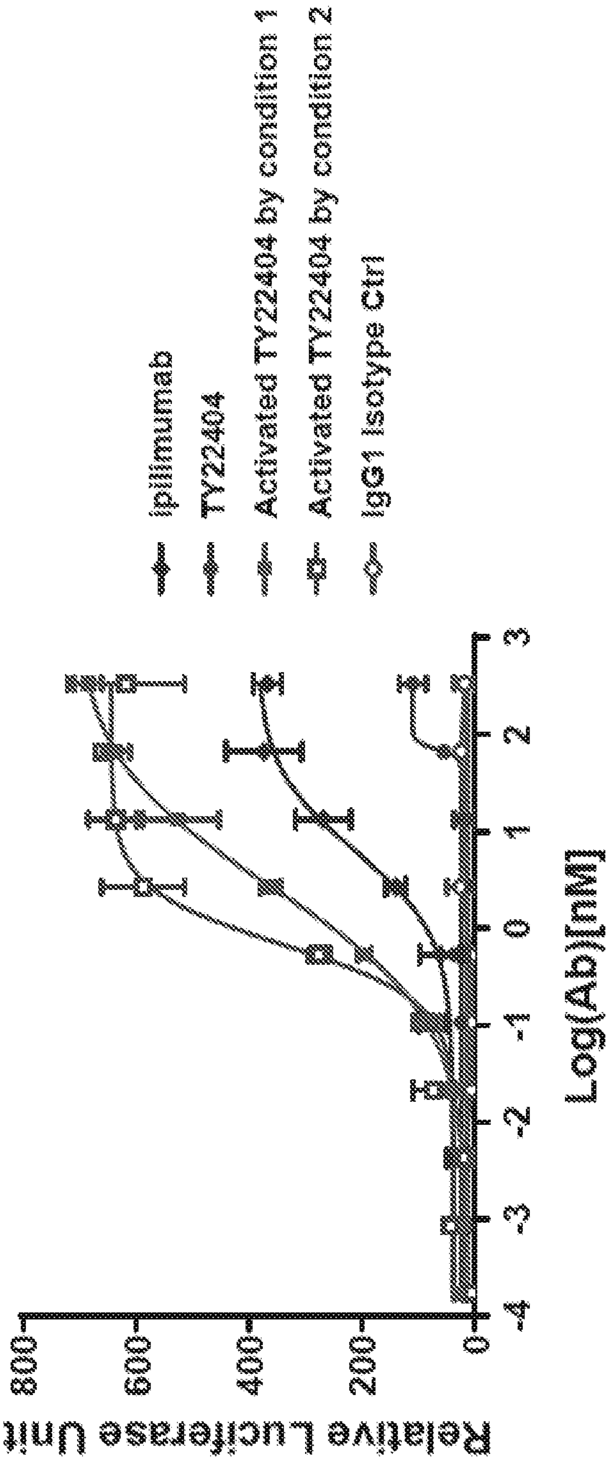
FIG. 5 shows the results of an in vitro ADCC reporter assay using CTLA4 expressing target cells and Jurkat NFAT-Luc/CD16 reporter cells was employed to evaluate TY22404 mediated ADCC signaling activation. Protease activated, but not the masking peptide-intact TY22404, exhibits ADCC signaling activity that is stronger than ipilimumab.

As shown in FIG. 5, these results suggest that TY22404 with masking peptide shows no ADCC reporter gene activity, and its activated forms (activated TY22404 by condition 1 and by condition 2) with masking peptide removed by protease cleavage, have significant dose-dependent ADCC reporter activity towards 293F cells overexpressing CTLA4 molecules. Of note, both activated TY22404 by condition 1 and by condition 2 have stronger ADCC reporter activity than Ipilimumab on 293F-CTLA4 cells, as manifested by much lower EC50s.

In Vitro Activation of Human T Cells by TY22404 in the Presence of SEA in PBMC

In vitro biological activity of the TY22404 and its activated forms (activated TY22404 by condition 1 and 2) to enhance Staphylococcal enterotoxin A (SEA) peptide stimulated human T cell activation in the context of PBMCs, was evaluated. SEA as a superantigen is known to activate a large fraction of human T cells by binding to MHCII from APC and T cell receptor (TCR) from T cells, and thus is chosen in this study to prime T cell activation. Human PBMCs (peripheral blood mononuclear cells, $2.0\times10^5$/well) are isolated from one healthy donor (D #69) and stimulated with a sub-optimal concentration of the SEA peptide (50 ng/ml) and serially diluted concentrations of TY22404, its activated forms or an isotype control antibody. Replicate cell supernatants are collected after 4 days for measurement of IL-2 with ELISA as an endpoint for enhanced T cell activation.

Figure 6:
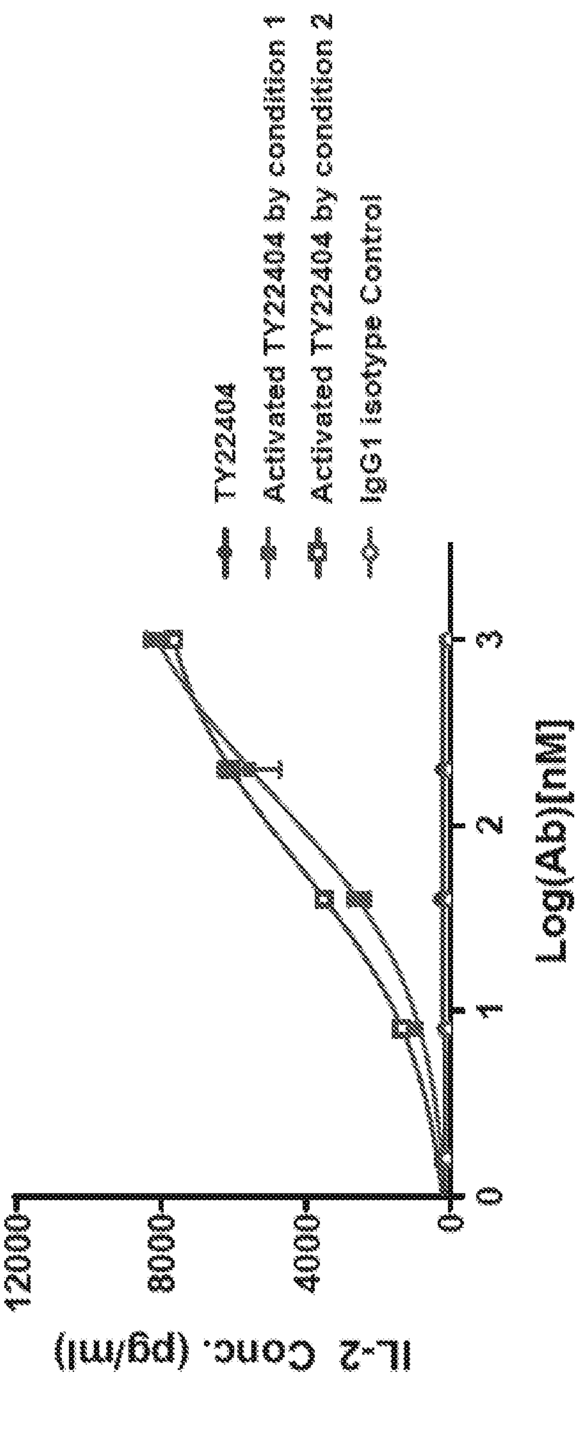
FIG. 6 shows IL-2 levels measured as a function of T cell activation. Protease activated TY22404, but not the masking peptide-intact TY22404, can enhance the SEA (*staphylococcus* enterotoxin A) induced human T cell activation.

As shown in FIG. 6, these results from this in vitro T cell activation assay suggest that TY22404's activated forms (both activated TY22404 by condition 1 and 2) can enhance SEA peptide-stimulated IL-2 cytokine release in PBMCs from one healthy donor, whereas the masked TY22404 has no such activity. In addition, activated TY22404 by condition 2 exhibits more potent activity than activated TY22404 by condition 1 in enhancing antigen-stimulated T cell activation in human PBMC context.

Anti-Tumor Efficacy of TY22404 in H22 Murine Liver Cancer Model

Figure 7:
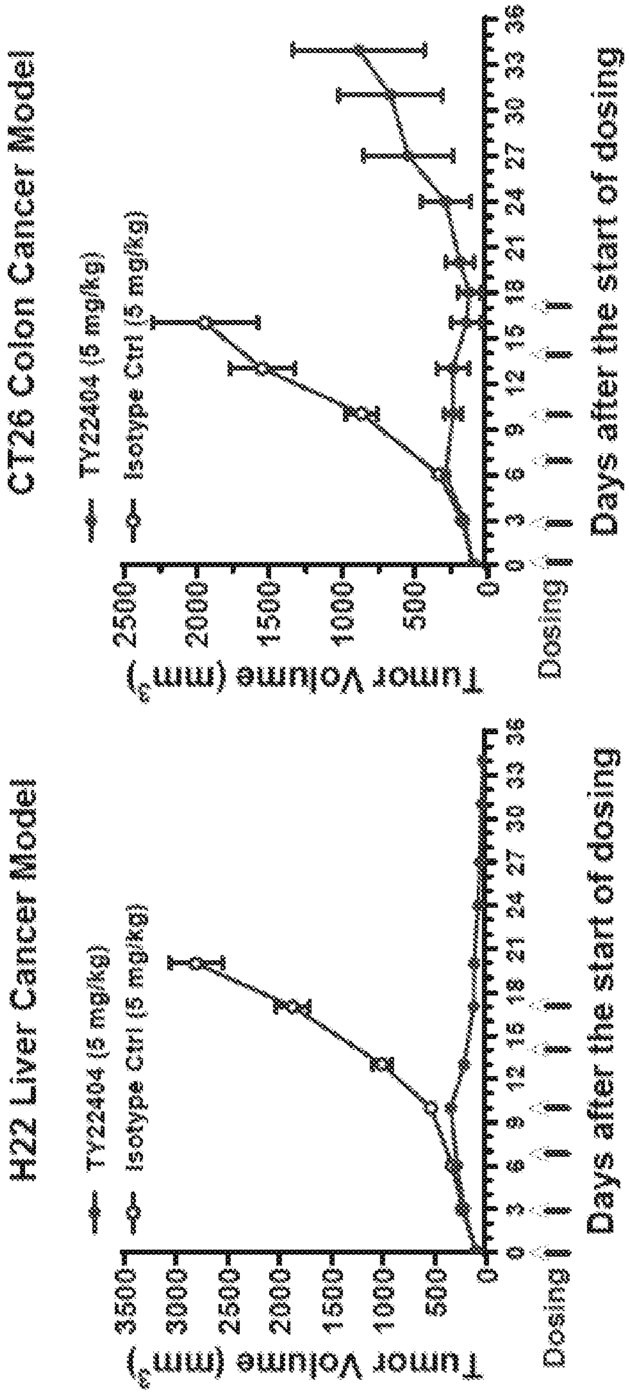
FIG. 7 shows TY22404 (5 mg/kg) tested in liver and colon cancer models, demonstrating efficacious anti-tumor activity in vivo as a single agent in syngeneic mouse tumor models.

BALB/c mice (n=8 per group, female, 6-7 weeks old) were inoculated subcutaneously with H22 (CCTCC) murine liver cancer cells. Treatment began when the average tumor volume reached about 97 mm3. The mice were administrated with Isotype Ctrl and TY22404 at 5 mg/kg by i.p. injection. The mice were administered with these antibodies twice a week for a total of six doses. Tumor growth was monitored twice a week and reported as the mean tumor volume+s.e.m over time. As shown in FIG. 7 (left panel), TY22404 showed very strong anti-tumor efficacy in H22 model as a mono therapy.

Anti-Tumor Efficacy of TY22404 in CT26 Murine Colon Cancer Model

BALB/c mice (n=8 per group, female, 7-8 weeks old) were inoculated subcutaneously with CT26 (SIBS) murine colon cancer cells. Treatment began when the average tumor volume reached about 98 mm3. The mice were administrated with Isotype Ctrl and TY22404 at 5 mg/kg by i.p. injection. The mice were administered with these antibodies twice a week for a total of six doses. Tumor growth was monitored twice a week and reported as the mean tumor volume±s.e.m over time. As shown in FIG. 7 (right panel), TY22404 showed very strong anti-tumor efficacy in CT26 model as a mono therapy.

Figure 8:
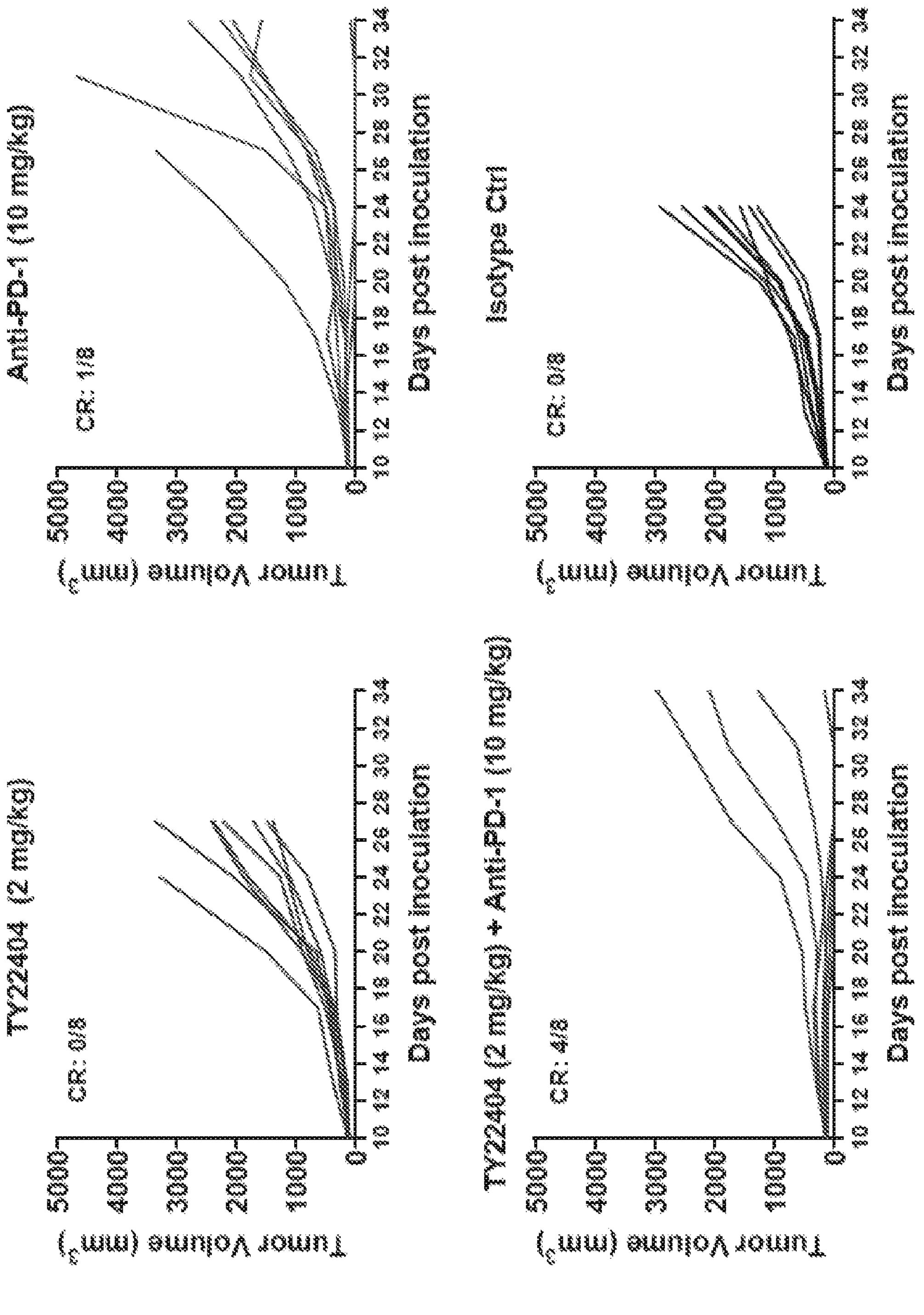
FIG. 8 shows TY22404 (2 mg/kg) demonstrating efficacious anti-tumor activity in vivo in combination with anti-PD-1 in the mouse Lewis lung cancer model.
Figure 10:
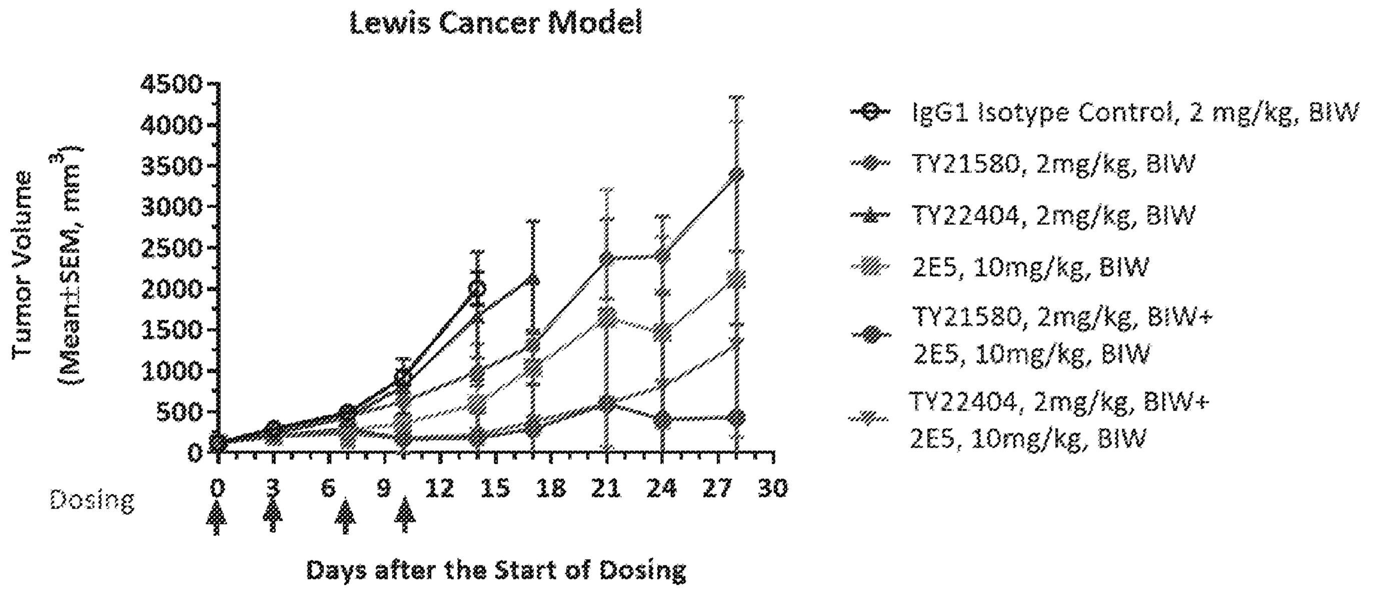
FIG. 10 shows the effect of TY22404 administered in combination with anti-PD-1 antibody in the Lewis cancer model.

FIG. 8 is the individual curve of FIG. 10. (TY22404 administered in combination with anti-PD-lantibody in the Lewis cancer model).

$T_{reg}$ Depletion of TY22404 in CT26 Murine Colon Cancer Model

BALB/c mice (n=10 per group, female, 7-8 weeks old) were inoculated subcutaneously with CT26 (SIBS) murine colon cancer cells. Treatment began at Day 9 post tumor inoculation when the average tumor volume reached about 121 mm3. The mice were administrated with Isotype Ctrl and TY22404 at 5 mg/kg by i.p. injection. The mice were administered with these antibodies at Day 9 and Day 12 and terminated at Day 14 for peripheral and tumor infiltrating lymphocytes analysis.

Figure 9:
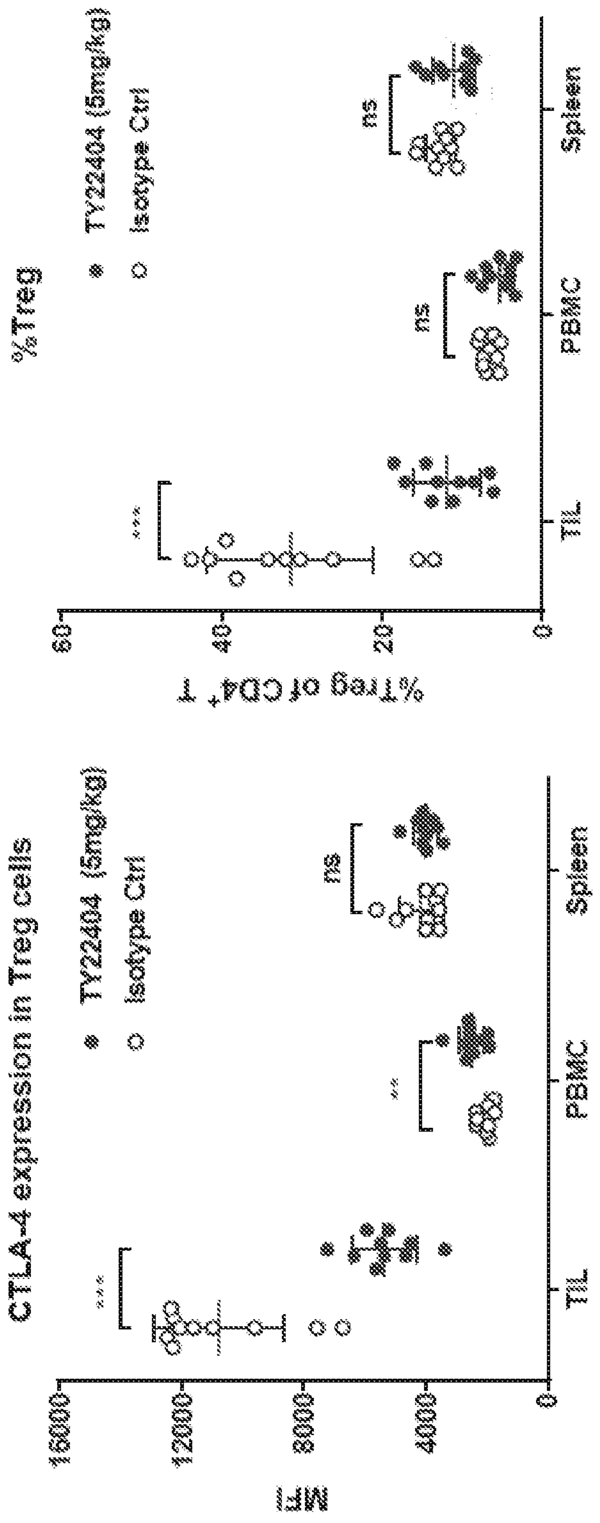
FIG. 9 shows that Treg cells in tumor tissues exhibiting higher CTLA4 expression than that in peripheral tissues and are efficiently depleted upon treatment with TY22404 (5 mg/kg) in the CT26 colon tumor model.

As shown in FIG. 9, TY22404 significantly reduced the percentage of Tregs in CD4+ T cells comparing with Isotype Ctrl in TILs. However, TY22404 did not influence the percentage of Tregs in CD4+ T cells in peripheral lymphocytes in blood and spleen. As shown in Figure Y, the CTLA4 expression levels on Treg cells in TILs was significantly decreased after treated with TY22404. However, the CTLA4 expression levels were slightly upregulated (PBMC) or not changed (spleen) on peripheral Treg cells after treated with TY22404.

SUMMARY

TY22404 is an activatable prodrug, that binds specifically to CTLA4 across multiple species upon protease cleavage to remove the masking peptide (FIG. 3).

Activated TY22404 was a softer ligand blocker than ipilimumab but has more potent ADCC activity targeting high density CTLA4 expressing cells (FIGS. 4-5).

Activated TY22404, but not the masking peptide-intact TY22404 SAFEbody, can potently enhance T cell activation (FIG. 6).

TY22404 exhibited potent antitumor activity as a single agent in different mouse tumor models (FIG. 7).

TY22404 combined synergistically with other IO agents, such as anti-PD-1 antibody, to inhibit tumor growth in vivo (FIG. 8). Combination therapy significantly slowed tumor growth and caused complete regression (CR) in four of the eight tumors.

TY22404 can efficiently deplete Treg cells in tumors, which express higher levels of CTLA4, but not Treg cells in peripheral tissues (FIG. 9).

TY22404 was well tolerated in animals, including NOD mice and cynomolgus monkeys, suggesting the potential for a high therapeutic index.

Example 2. Combination Therapies with Anti-CTLA4 Antibodies

The efficacy of anti-CTLA4 antibody combination therapies was tested in various cancer models.

FIG. 10 provides the results of TY22404 administered in combination with anti-PD-1 antibody in the Lewis cancer model. In vivo antitumor efficacy of TY22404 and anti-PD-1 combination treatment was assessed. Mice were inoculated subcutaneously with Lewis murine lung tumor cells. When the mean tumor volume reached 118 $mm^3$, the tumor bearing mice were randomized into different treatment groups of eight mice each. Intraperitoneal administration of test antibodies was initiated on a biweekly schedule for four doses. Tumor growth inhibition (TGI) relative to the isotype control group was evaluated 14 days after the start of dosing. As shown in FIG. 10, monotherapy of TY21580 and TY22404 at 2 mg/kg showed antitumor activity, with TGI of 51% and 18%, respectively. FC1225 anti-PD-1 monotherapy at 10 mg/kg showed anti-tumor effect (TGI=69%). Combination of TY21580 or TY22404 with anti-PD-1 FC1225 exhibited significantly enhanced anti-tumor effect, with TGI of 92% and 91%, respectively. The responses to combination therapies were superior to all monotherapy regimens tested and suggests that both TY21580 and TY22404 could synergize with anti-PD1 in tumor inhibition.

Figure 11:
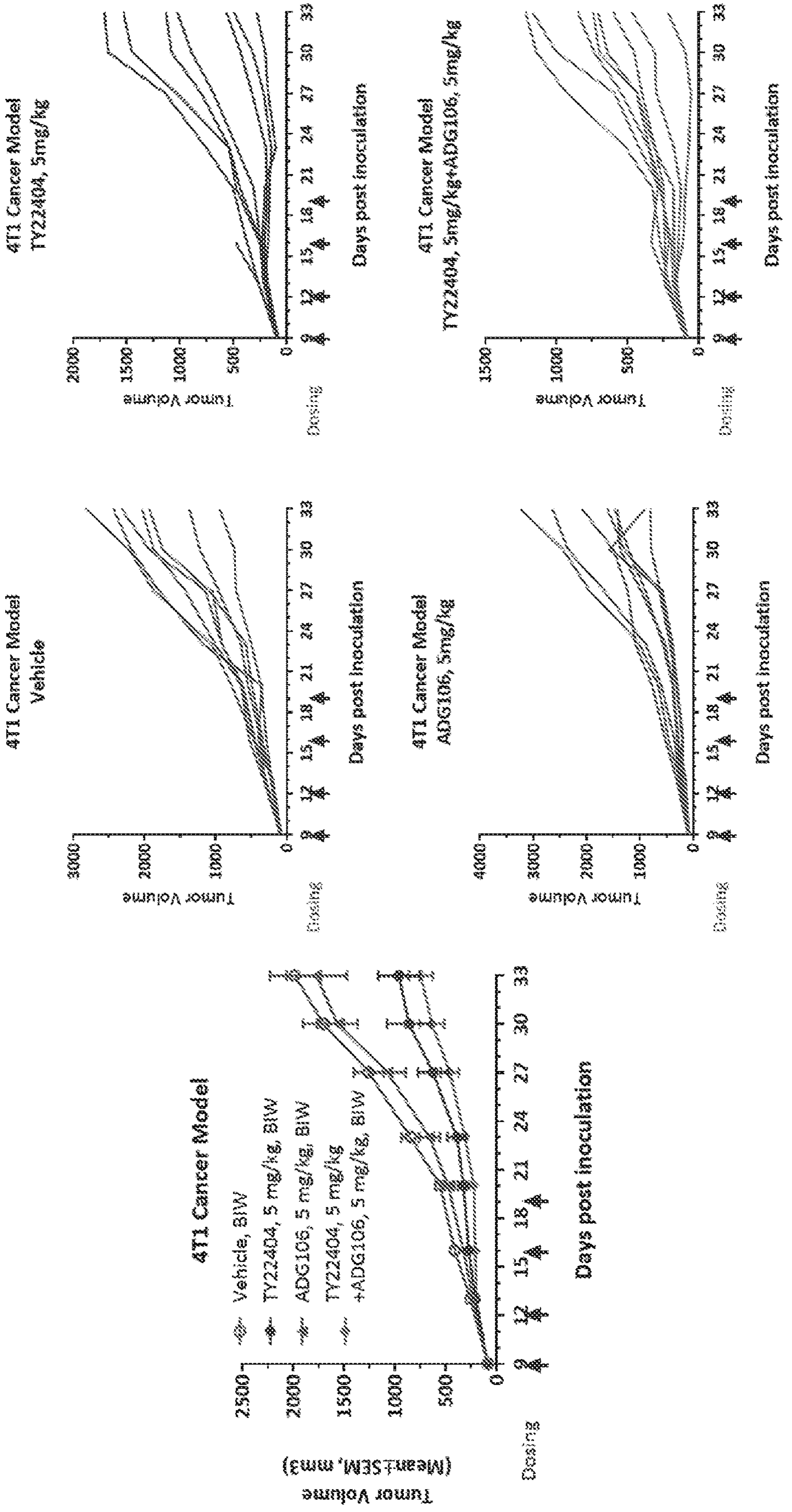
FIG. 11 shows the effect of TY22404 administered in combination with the anti-CD137 antibody ADG106 in the 4T1 cancer model.

FIG. 11 provides the results of TY22404 administered in combination with the anti-CD137 antibody ADG106 in the 4T1 cancer model to assess in vivo antitumor efficacy of TY22404 and ADG106 combination treatment. Mice were inoculated subcutaneously with 4T1 murine breast cancer cells. When the mean tumor volume reached 90 $mm^3$, the tumor bearing mice were randomized into different treatment groups of eight mice each. Intraperitoneal administration of Vehicle, 5 mg/kg TY22404 or ADG106, or combination of these two agents, was initiated on a biweekly schedule for four doses. As shown in FIG. 11, compared to the vehicle control group, TY22404 showed partial antitumor effect with Day 33 TGI of 49%, whereas ADG106 had no significant antitumor activity (TGI of 10%). Combination of TY22404 with ADG106 exhibited slightly enhanced anti-tumor effect in this model (TGI 63%).

Figure 12A:
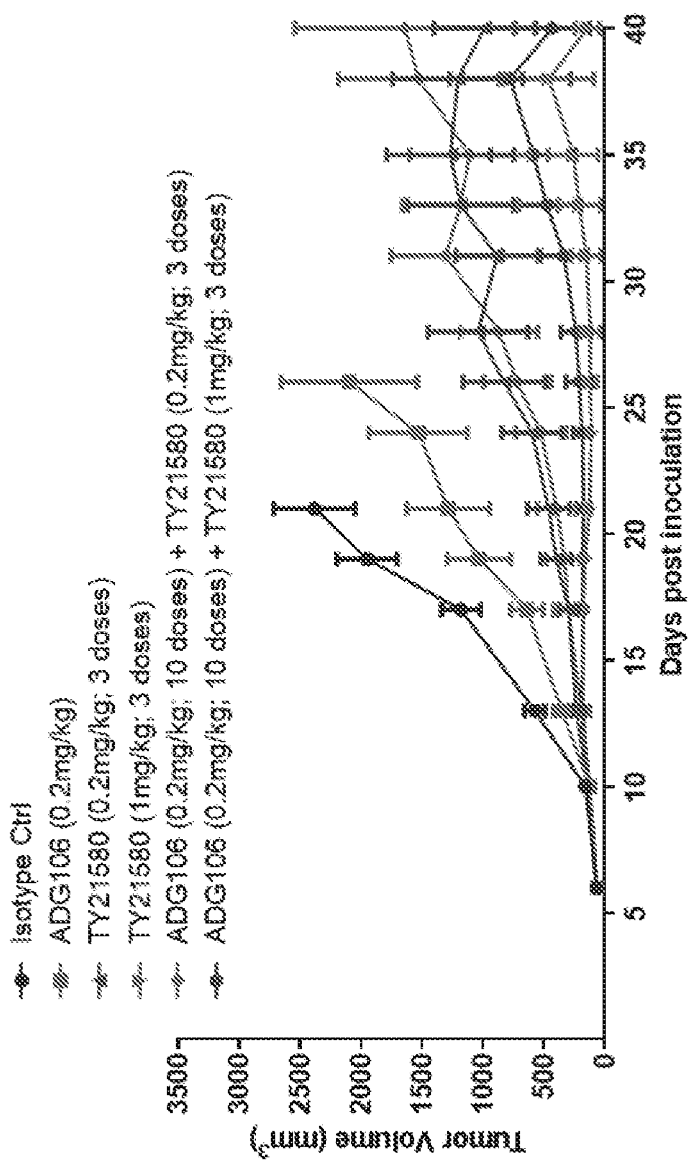
FIGS. 12A-12B show the effect of ADG106 administered in combination with TY21580 in the mouse CT26 colon cancer model.
Figure 12B:
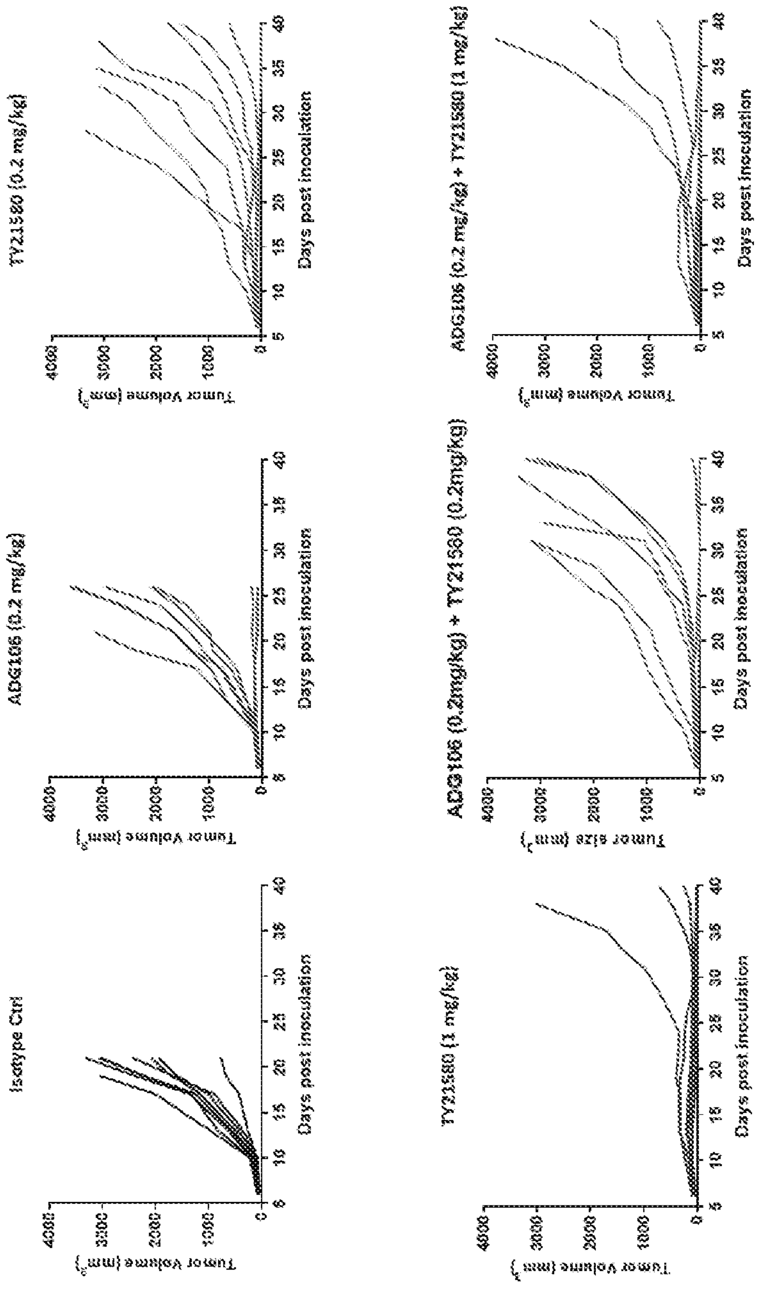

FIGS. 12A-12B provide the results of ADG106 administered in combination with TY21580 in the mouse CT26 colon cancer model to assess in vivo antitumor efficacy of ADG106 and TY21580 combination treatment. Mice were inoculated subcutaneously with CT26 murine colon tumor cells. When the mean tumor volume reached 67 mm3, the tumor bearing mice were randomized into different treatment groups of eight mice each. These groups received either 1 mg/kg isotype control, 0.2 mg/kg ADG106, 0.2 or 1 mg/kg TY21580, or a combination of ADG106 and TY21580 at the same doses by IP injection. All antibodies were dosed twice a week. As shown in FIGS. 12A-12B, compared to the isotype control group on Day 19, ADG106 treatment alone showed partial tumor growth inhibition with TGI of 47%, TY21580 alone exhibited even stronger dose-dependent inhibition of tumor growth, with TGI of 79% at the 0.2 mg/kg dose and 92% at the 1 mg/kg dose. The combination of ADG106 with either 0.2 or 1 mg/kg TY21580 showed no enhanced antitumor activity with TGIs of 83% and 91%, respectively. These results demonstrate potent single agent antitumor activity of ADG106 and TY21580, although no synergistic effect in this model.

Figure 13A:
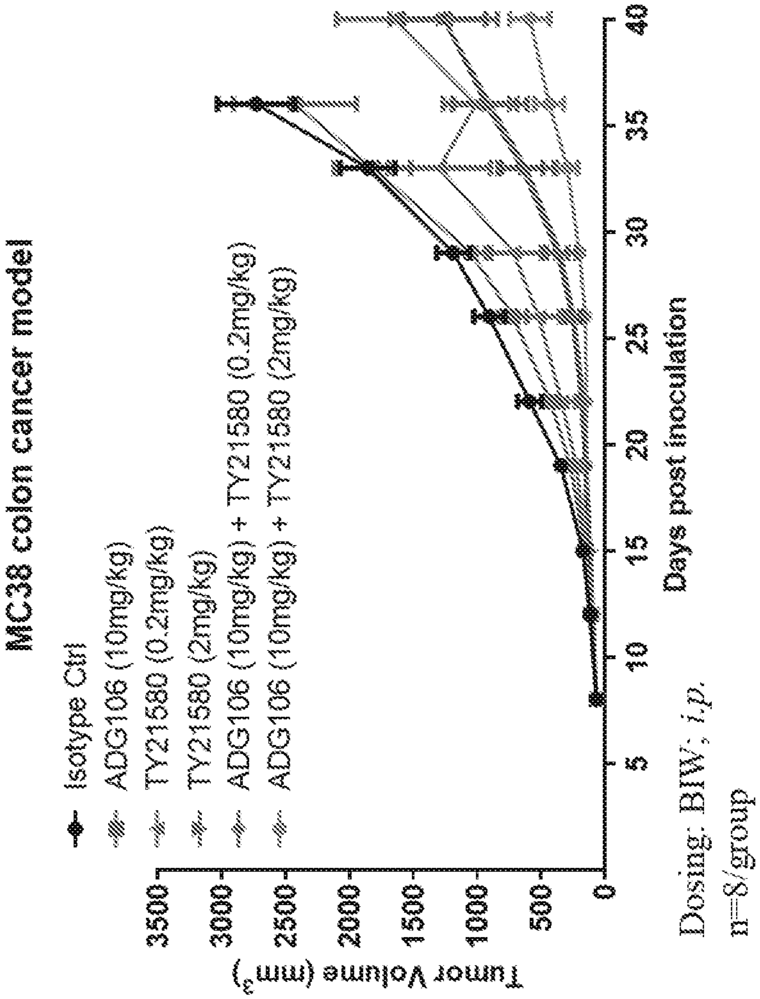
FIGS. 13A-13B show the effect of ADG106 administered in combination with TY21580 in the mouse MC38 colon cancer model.
Figure 13B:
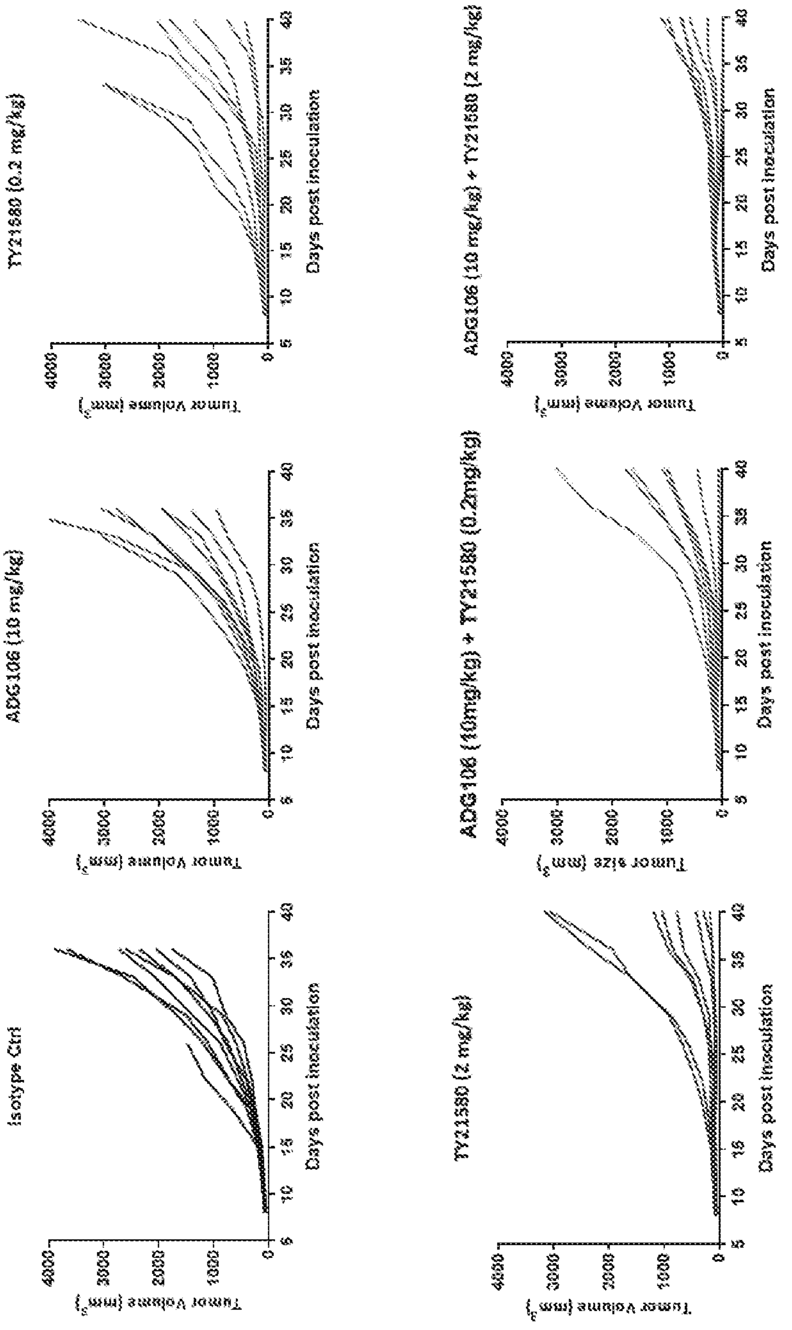

FIGS. 13A-13B provide the results of ADG106 administered in combination with TY21580 in the mouse MC38 colon cancer model to assess in vivo antitumor efficacy of TY21580 and ADG106 combination treatment. Mice were inoculated subcutaneously with MC38 murine colon tumor cells. When the mean tumor volume reached 69 mm3, the tumor bearing mice were randomized into different treatment groups of eight mice each. These groups received either 10 mg/kg isotype control, 10 mg/kg ADG106, 0.2 or 2 mg/kg TY21580, or a combination of ADG106 and TY21580 at the same doses by IP injection. All antibodies were dosed twice a week for 4 weeks. As shown in FIGS. 13A-13B, compared to the isotype control group on Day 33, ADG106 treatment alone did not inhibit tumor growth, whereas TY21580 exhibited dose-dependent inhibition of tumor growth, with Day 33 TGI of 30% at the 0.2 mg/kg dose and 67% at the 2 mg/kg dose. The combination of ADG106 with either 0.2 or 2 mg/kg TY21580 showed enhanced antitumor activity with TGIs of 65% and 84%, respectively. No adverse effects were observed on body weights with these treatments. These results demonstrate that ADG106 combined with TY21580 induced an enhanced anti-tumor response in the murine MC38 colon cancer model.

Figure 14A:
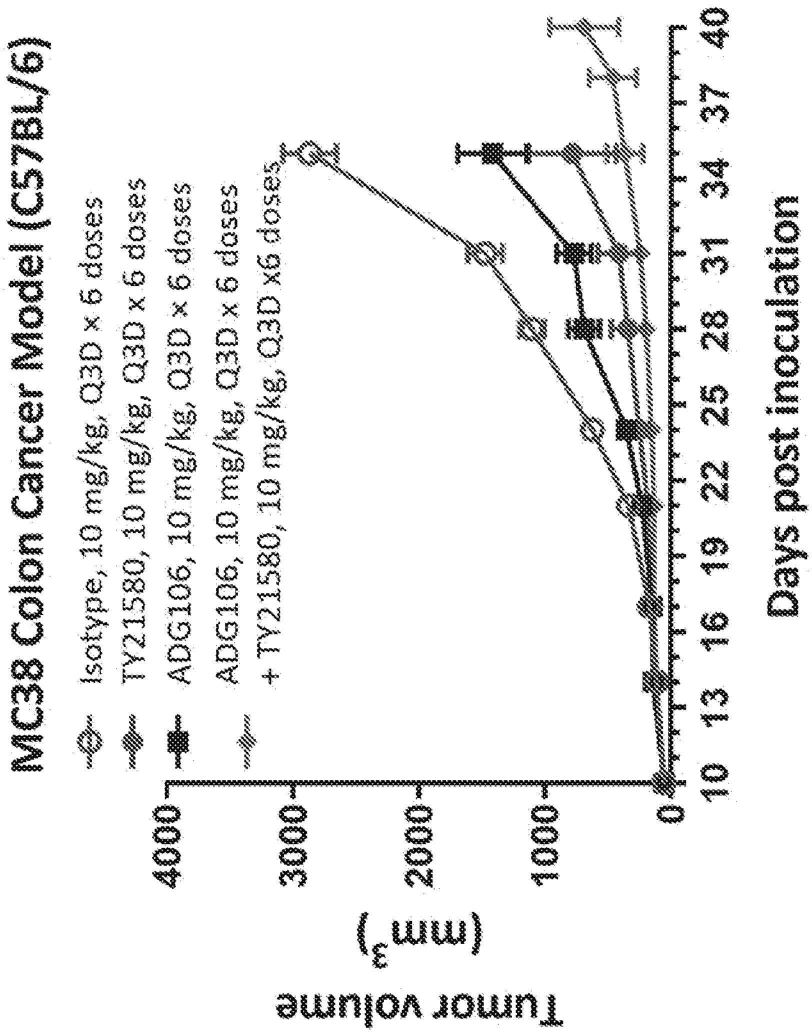
FIGS. 14A-14B show the effect of ADG106 administered in combination with TY21580 in the mouse MC38 colon cancer model.
Figure 14B:
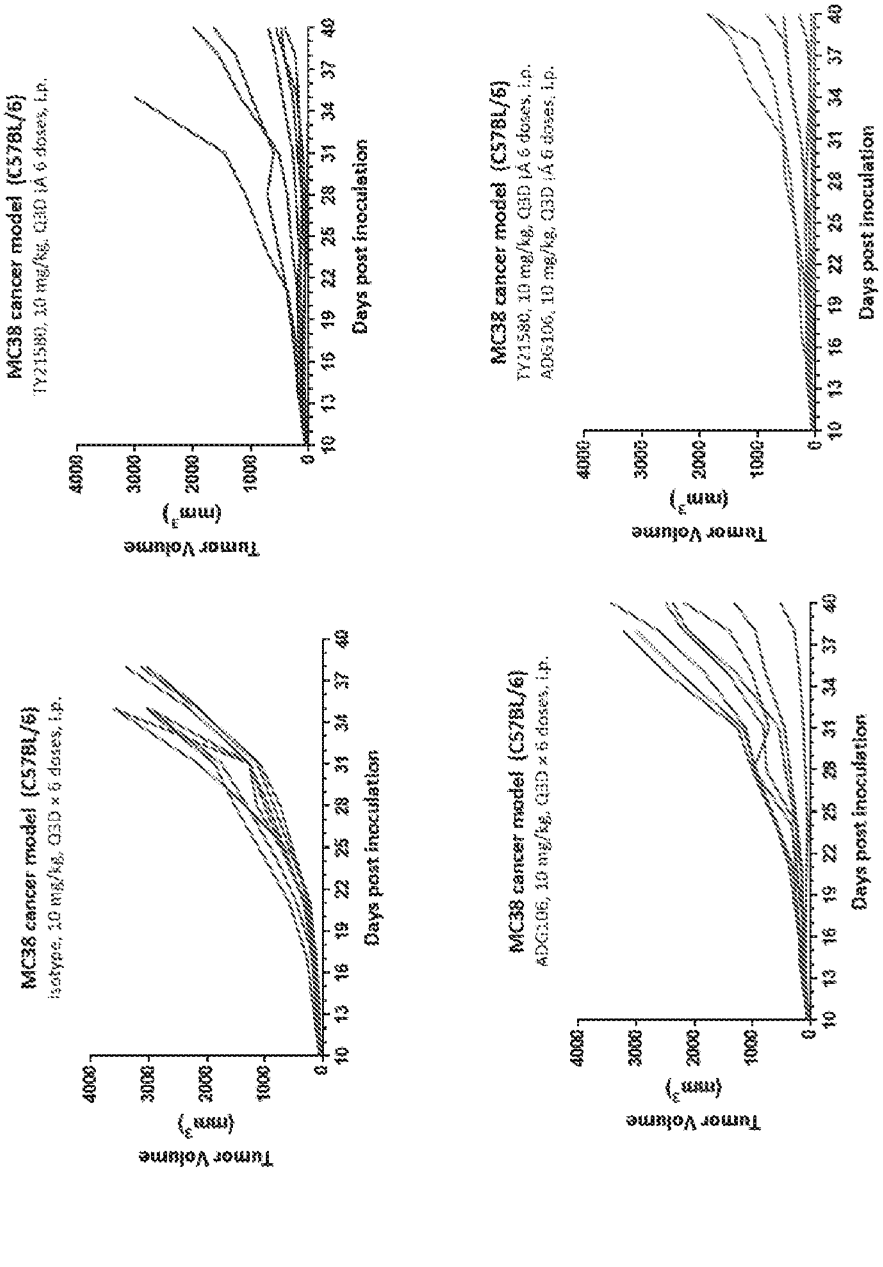

FIGS. 14A-14B provide the results of ADG106 administered in combination with TY21580 in the mouse MC38 colon cancer model. Dosing started when the average TV reached about 53 $mm^3$ (n-8). There was 1/10 complete response (CR) in the TY21580 monotherapy group, 1/10 complete response (CR) and 2/10 stable disease (SD) in the ADG106+TY21580 combination group. TY21580 and ADG106 had a synergistic effect in this study.

Figure 15:
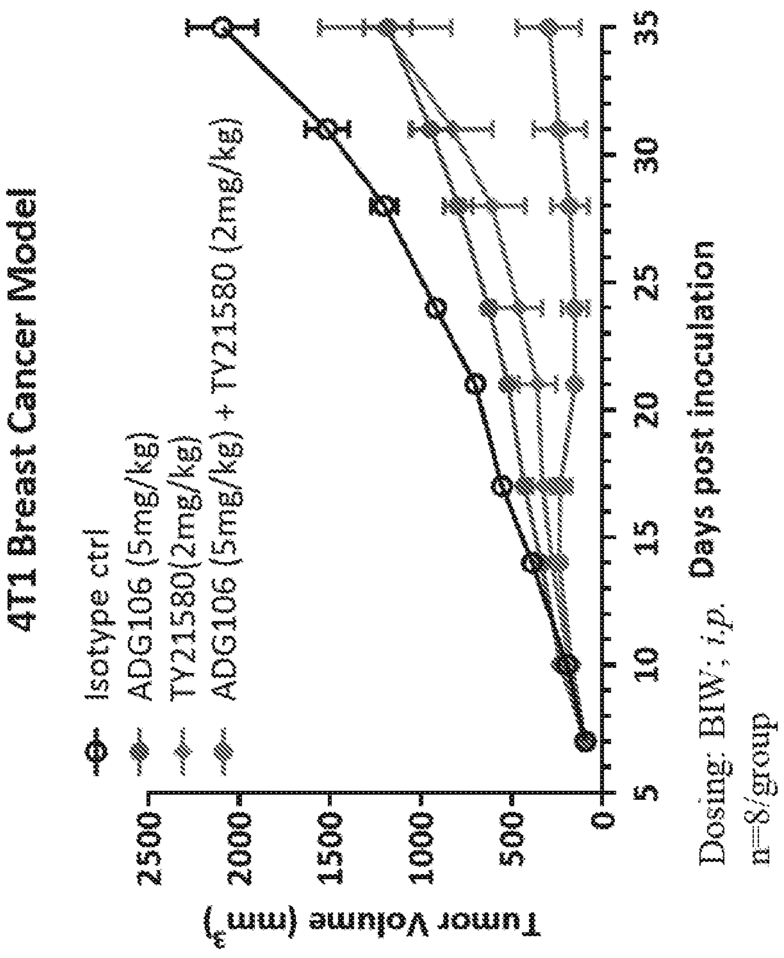
FIG. 15 shows the effect of ADG106 administered in combination with TY21580 in the mouse 4T1 breast cancer model.
Figure 16:
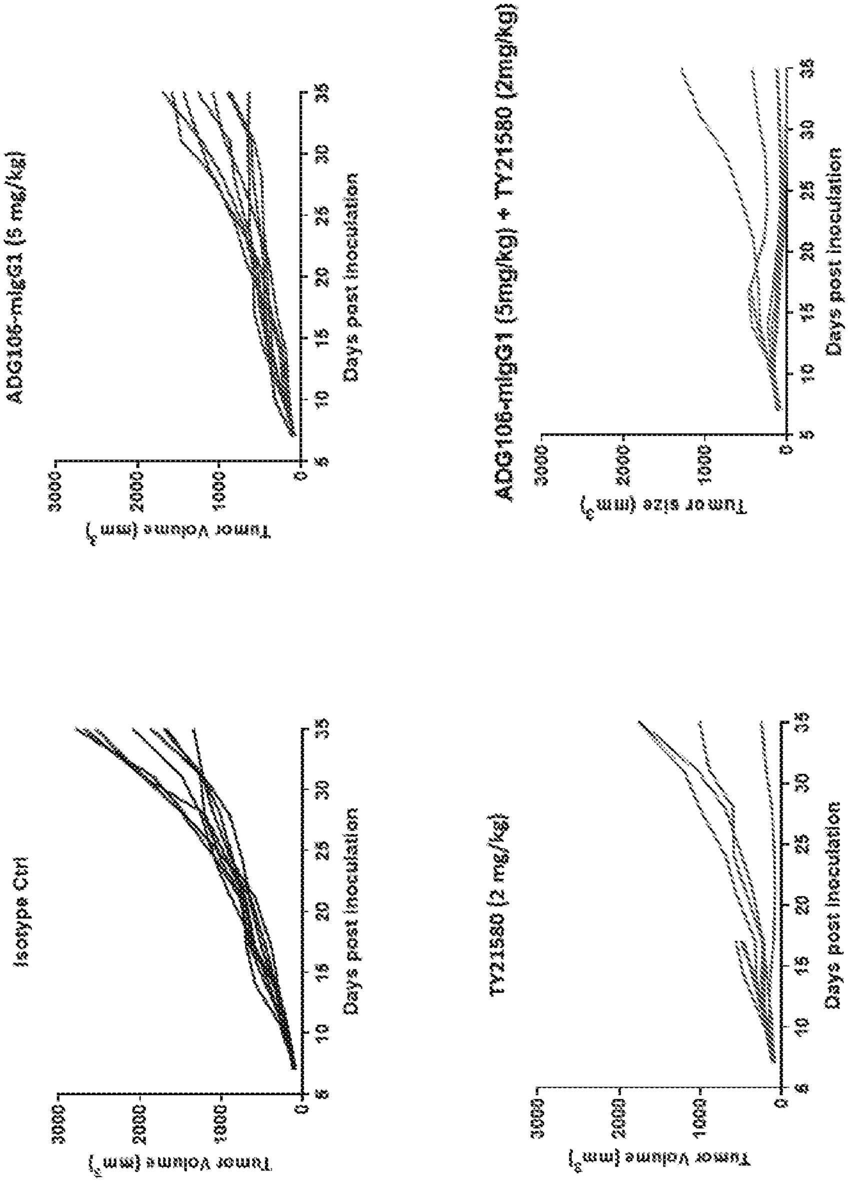
FIG. 16 shows the effect of ADG106 administered in combination with TY21580 in the mouse 4T1 breast cancer model.

FIGS. 15-16 provide the results of ADG106 administered in combination with TY21580 in the mouse 4T1 breast cancer model. BALB/c mice (n=8 per group, female, 6-8 weeks old) were transplanted subcutaneously with 3×105 4T1 breast cancer cells, a triple-negative mouse breast cancer cell line. After tumors were established (i.e., having reached a volume of 96 mm3), mice were treated with isotype control antibody, anti-CD137 antibody ADG106 (5 mg/kg), anti-CTLA-4 antibody TY21580 (2 mg/kg), or the combination of ADG106 (5 mg/kg) and TY21580 (2 mg/kg) by intraperitoneal injection twice a week for 2 weeks. Tumor growth was monitored twice weekly and is reported as mean tumor volume+SEM over time. There were 4/8 deaths in the TY21580 group and ⅛ death in the ADG106+TY21580 group. As shown in FIGS. 15-16, compared to the isotype control antibody, both TY21580 and ADG106 monotherapies showed anti-tumor activity, and the combination of TY21580 with ADG106 exhibited synergistic anti-tumor efficacy in the 4T1 breast cancer model.

Figure 17:
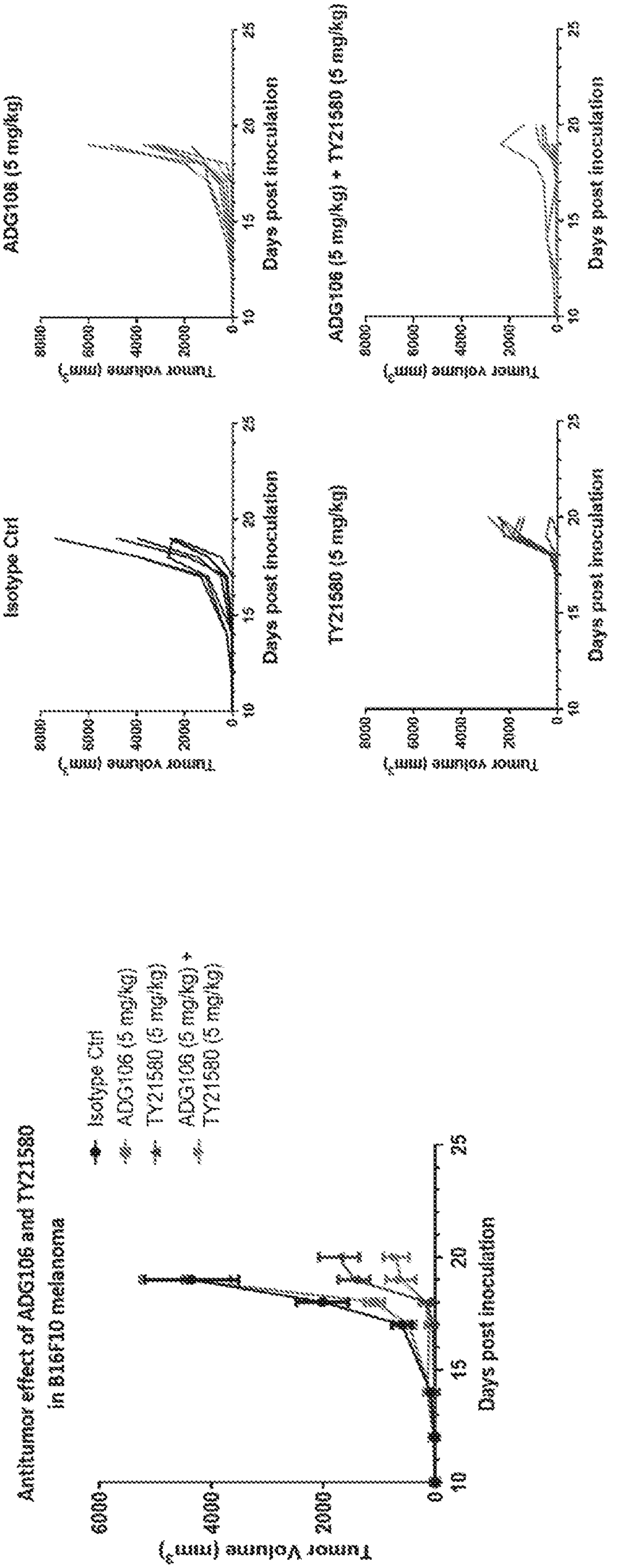
FIG. 17 shows the effect of ADG106 administered in combination with TY21580 combination in the syngeneic mouse B16F10 melanoma model.

FIG. 17 provides the results of ADG106 administered in combination with TY21580 combination in the syngeneic mouse B16F10 melanoma model to assess in vivo antitumor efficacy of TY21580 and ADG106 combination treatment. Mice were inoculated subcutaneously with B16F10 murine melanoma tumor cells. Mice were randomized into different treatment groups of eight mice each upon tumor inoculation, and received either isotype control, ADG106, or TY21580 at 5 mg/kg, or a combination of ADG106 and TY21580 at the same doses by IP injection. All antibodies were dosed twice a week. As shown in FIG. 17, compared to the isotype control group, ADG106 treatment alone did not inhibit tumor growth, whereas TY21580 exhibited single agent antitumor activity. The combination of ADG106 and TY21580 further enhanced tumor growth inhibition, suggesting ADG106 and TY21580 could synergize in antitumor effect.

Figure 18A:
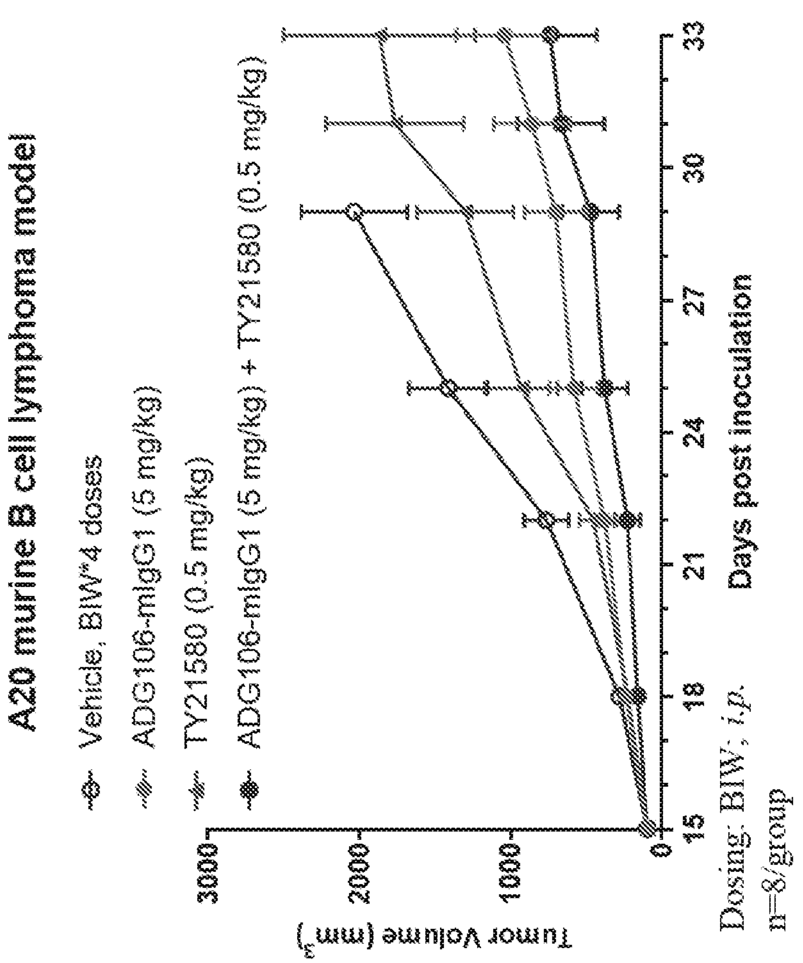
FIGS. 18A-18B show the effect of ADG106 administered in combination with TY21580 in the A20 cancer model.
Figure 18B:
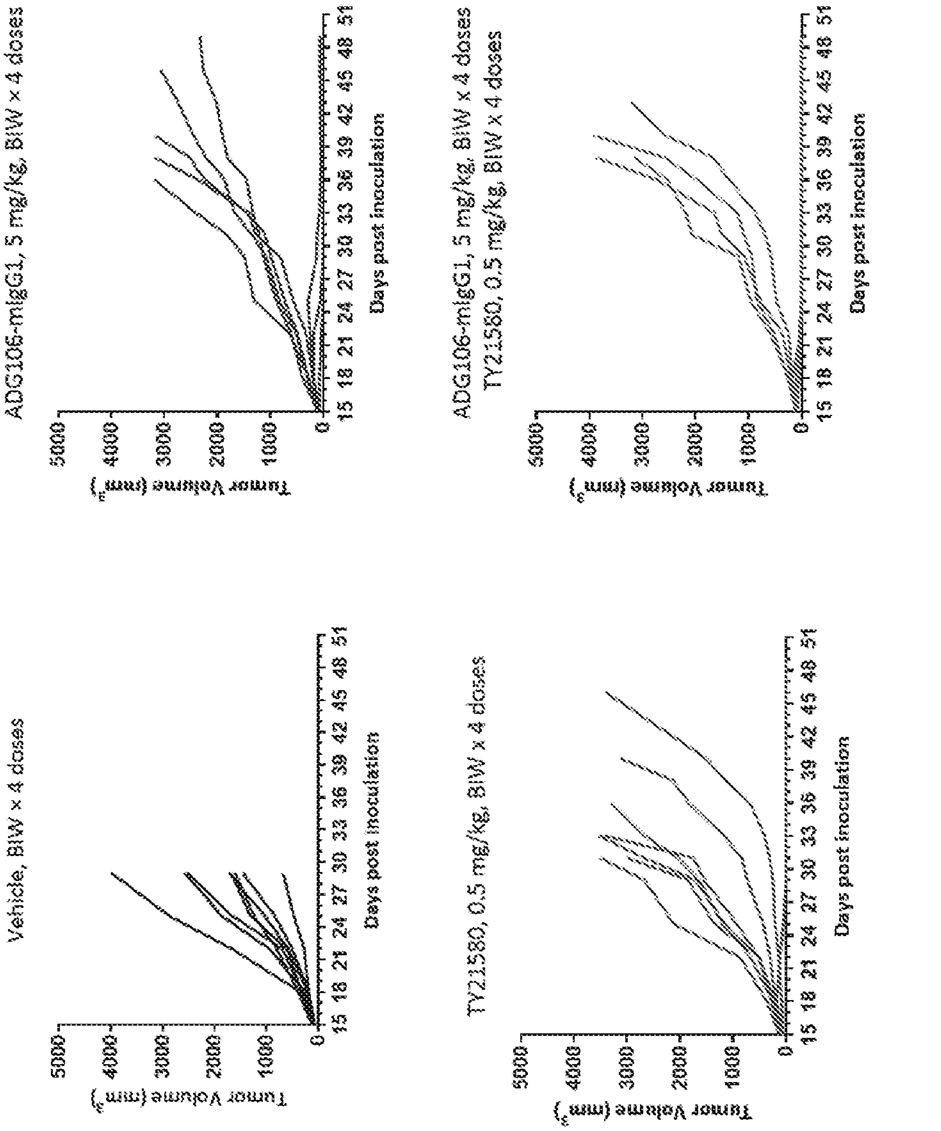

FIGS. 18A-18B provide the results of ADG106 administered in combination with TY21580 in the A20 cancer model to assess in vivo antitumor efficacy of ADG106 and TY21580 combination treatment. Mice were inoculated subcutaneously with A20 murine B lymphoma cells. When the mean tumor volume reached 101 mm3, the tumor bearing mice were randomized into different treatment groups of eight mice each. Intraperitoneal administration of 5 mg/kg ADG106 or 0.5 mg/kg TY21580, or combination of these two agents, was initiated on a biweekly schedule for 4 doses. As shown in FIGS. 18A-18B, compared to the vehicle control group, both 5 mg/kg ADG106 or 0.5 mg/kg TY21580 alone showed partial antitumor activity. Combination of ADG106 with TY21580 exhibited further enhanced anti-tumor effect with 4 complete responses, suggesting that ADG106 and TY21580 could synergize in tumor inhibition.

Figure 19A:
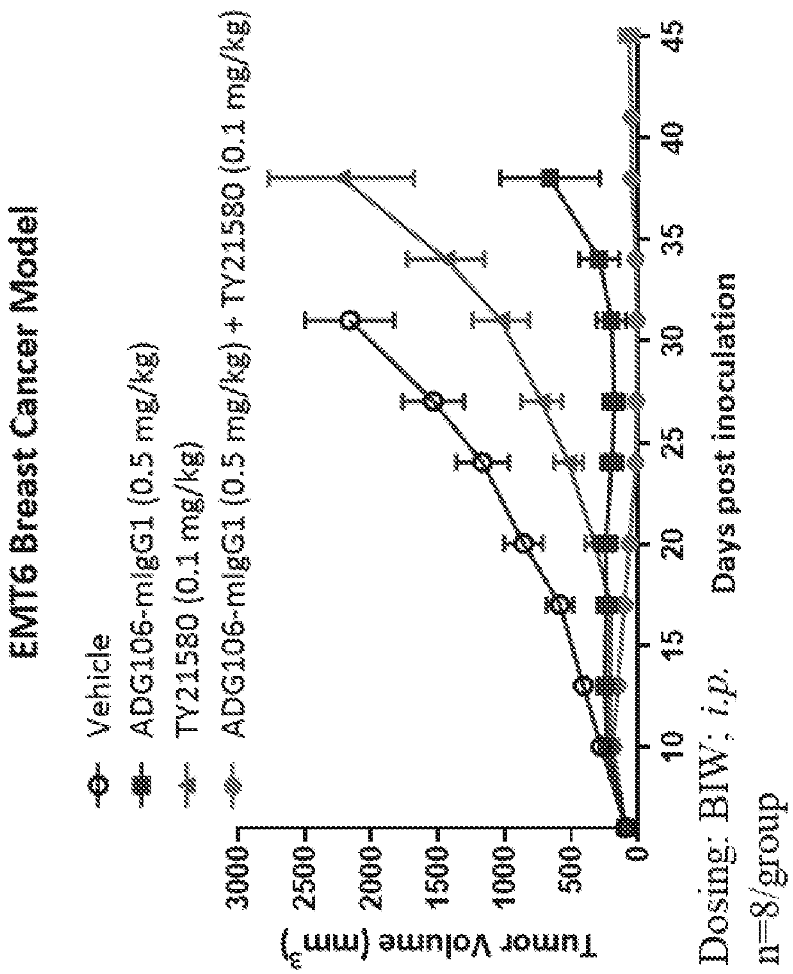
FIGS. 19A-19B show the effect of ADG106 administered in combination with TY21580 in the EMT6 cancer model.
Figure 19B:
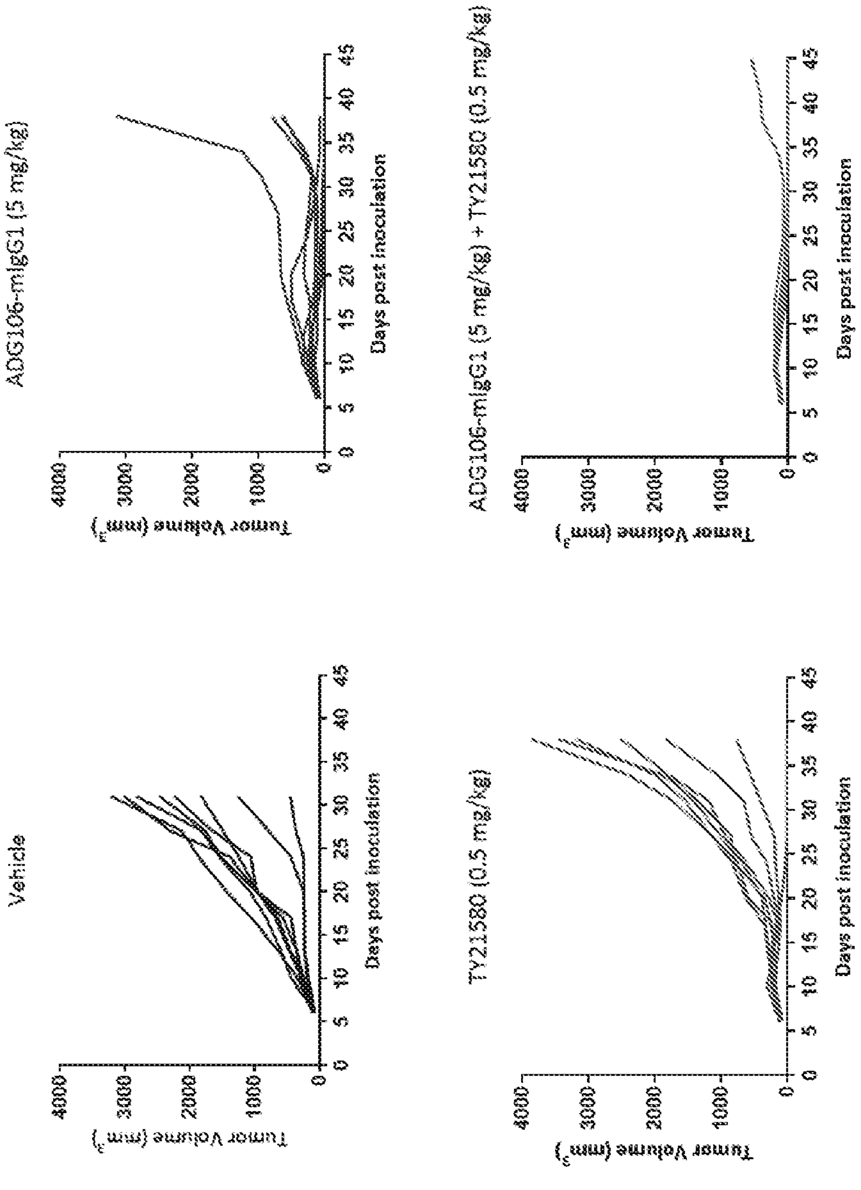

FIGS. 19A-19B provide the results of ADG106 administered in combination with TY21580 in the EMT6 cancer model to assess in vivo antitumor efficacy of ADG106 and TY21580 combination treatment. Mice were inoculated subcutaneously with EMT6 murine breast cancer cells. When the mean tumor volume reached 95 mm3, the tumor bearing mice were randomized into different treatment groups of eight mice each. Intraperitoneal administration of 0.5 mg/kg ADG106 or 0.1 mg/kg TY21580, or combination of these two agents, was initiated on a biweekly schedule. As shown in FIGS. 19A-19B, compared to the vehicle control group, both 0.5 mg/kg ADG106 or 0.1 mg/kg TY21580 alone showed significant antitumor activity. Combination of ADG106 with TY21580 exhibited further enhanced anti-tumor effect with 7 complete responses, suggesting that ADG106 and TY21580 could synergize in tumor inhibition.

Figure 20A:
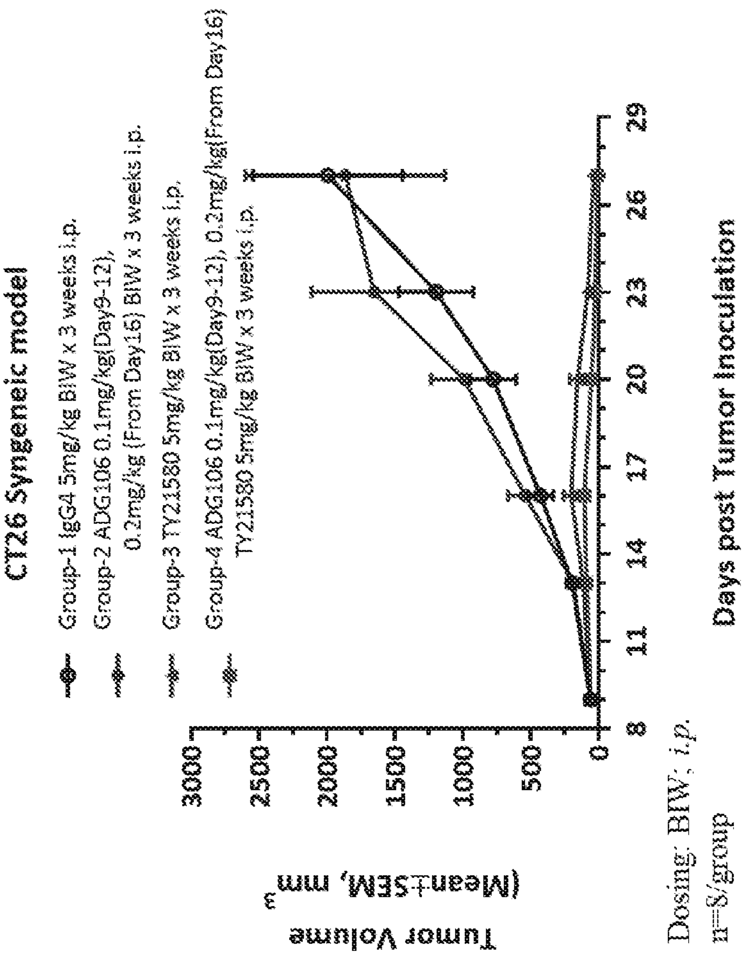
FIGS. 20A-20B show the effect of TY21580 administered in combination with ADG106 in the CT26 colon cancer model.
Figure 20B:
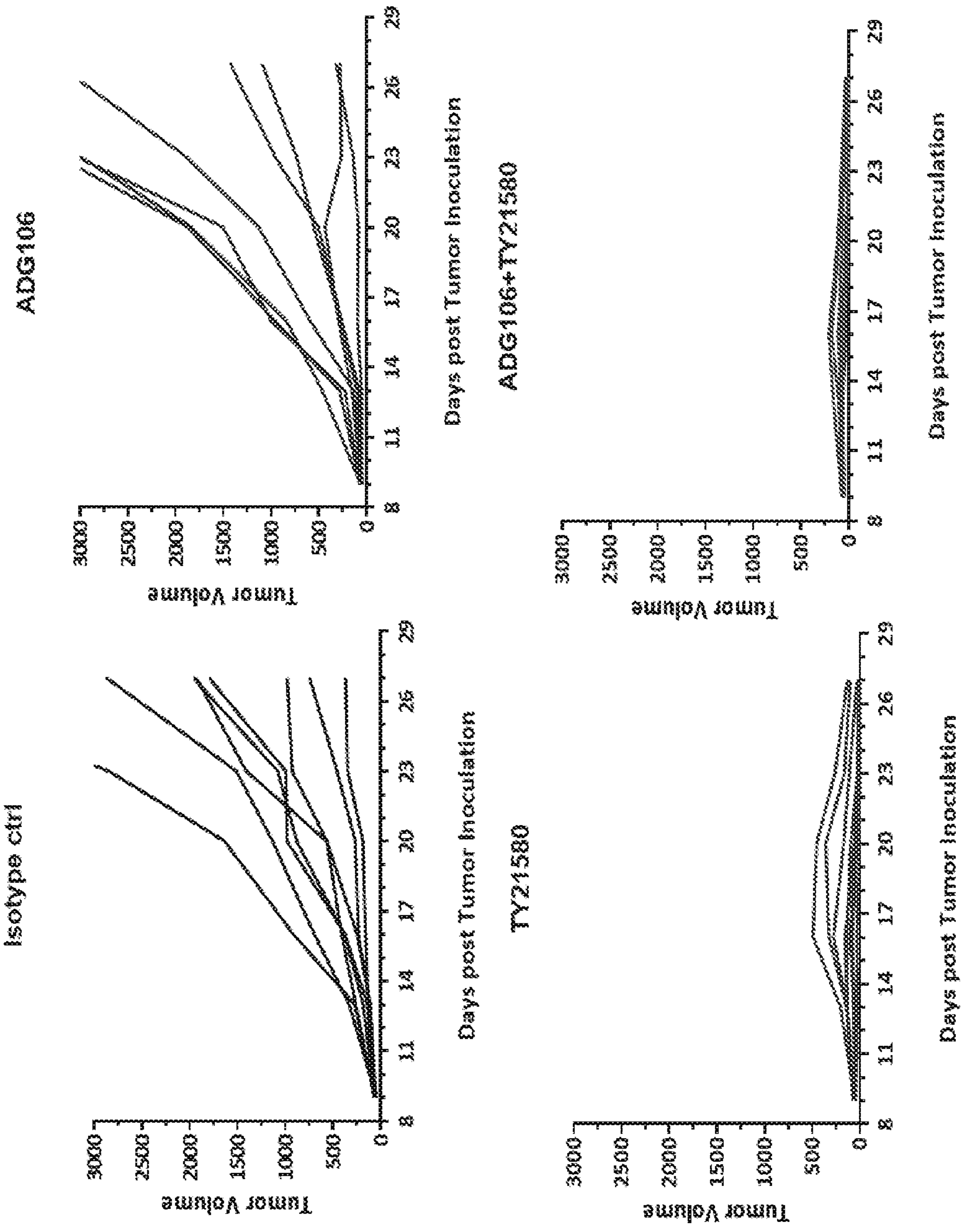

FIGS. 20A-20B provide the results of TY21580 administered in combination with ADG106 in the CT26 colon cancer model. BALB/c mice (n=8 per group, female, 7-8 weeks old) were inoculated subcutaneously with CT26 (SIBS) murine colon cancer cells. Treatment began when the average tumor volume reached about 62 mm3. The mice were administrated with Isotype Ctrl (5 mg/kg), TY21580 (5 mg/kg), ADG106 (0.1 mg/kg for 2 doses, 0.2 mg/kg for another 4 doses) and the combination of TY21580 and ADG106 by i.p. injection. The mice were administered with these antibodies twice a week for a total of six doses. Tumor growth was monitored twice a week and reported as the mean tumor volume+s.e.m over time. As shown in FIG. 20, bothTY21580 monotherapies showed anti-tumor activity, and the combination of TY21580 with ADG106 exhibited synergistic anti-tumor efficacy in CT26 model.

Figure 21A:
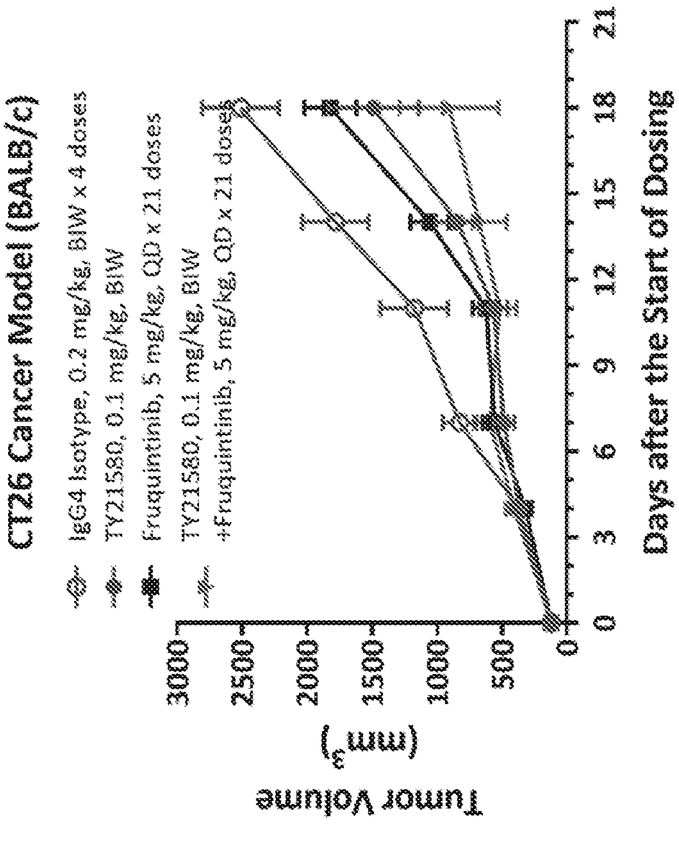
FIGS. 21A-21B show the effect of TY21580 administered in combination with Fruquintinib in the CT26 cancer model.
Figure 21B:
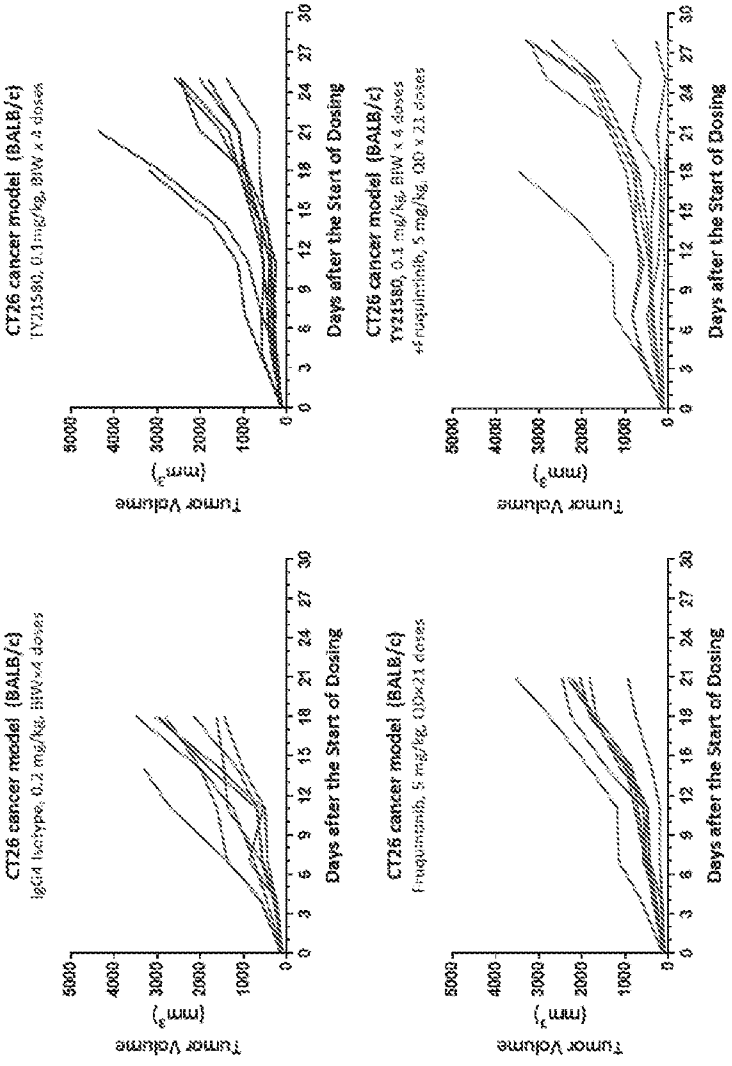

FIGS. 21A-21B provide the results of TY21580 administered in combination with Fruquintinib in the CT26 cancer model to assess in vivo antitumor efficacy of TY21580 and the VEGFR inhibitor Fruquintinib combination treatment. Dosing started when average tumor volume reached about 120 $mm^3$ (n=8 per group). The tumor bearing mice were randomized into different treatment groups of eight mice each. Intraperitoneal administration of TY21580 at 0.1 mg/kg was initiated on a biweekly schedule for four doses. Fruquintinib at 5 mg/kg was p.o. dosed daily for 3 weeks. As shown in FIGS. 21A-21B, compared to the isotype control group, both 0.1 mg/kg TY21580 or 5 mg/kg Fruquintinib alone showed partial antitumor activity. Combination of TY21580 with Fruquintinib exhibited further enhanced anti-tumor effect, suggesting that TY21580 may synergize with Fruquintinib in tumor inhibition. There was 1/8 complete response (CR) in the combo group and no complete response (CR) in TY21580 or Fruquintinib monotherapy groups.

Figure 22A:
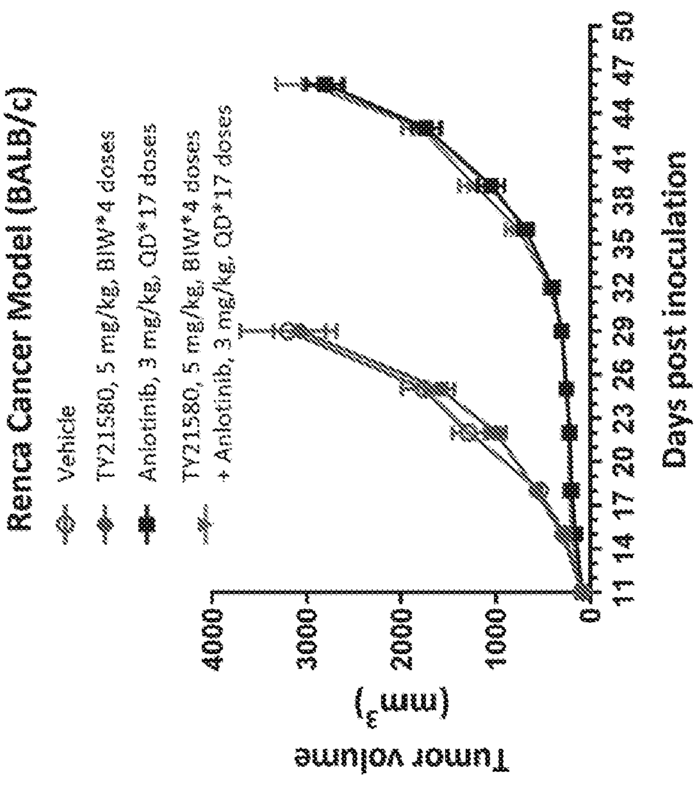
FIGS. 22A-22B show the effect of TY21580 administered in combination with Anlotinib in the Renca cancer model.
Figure 22B:
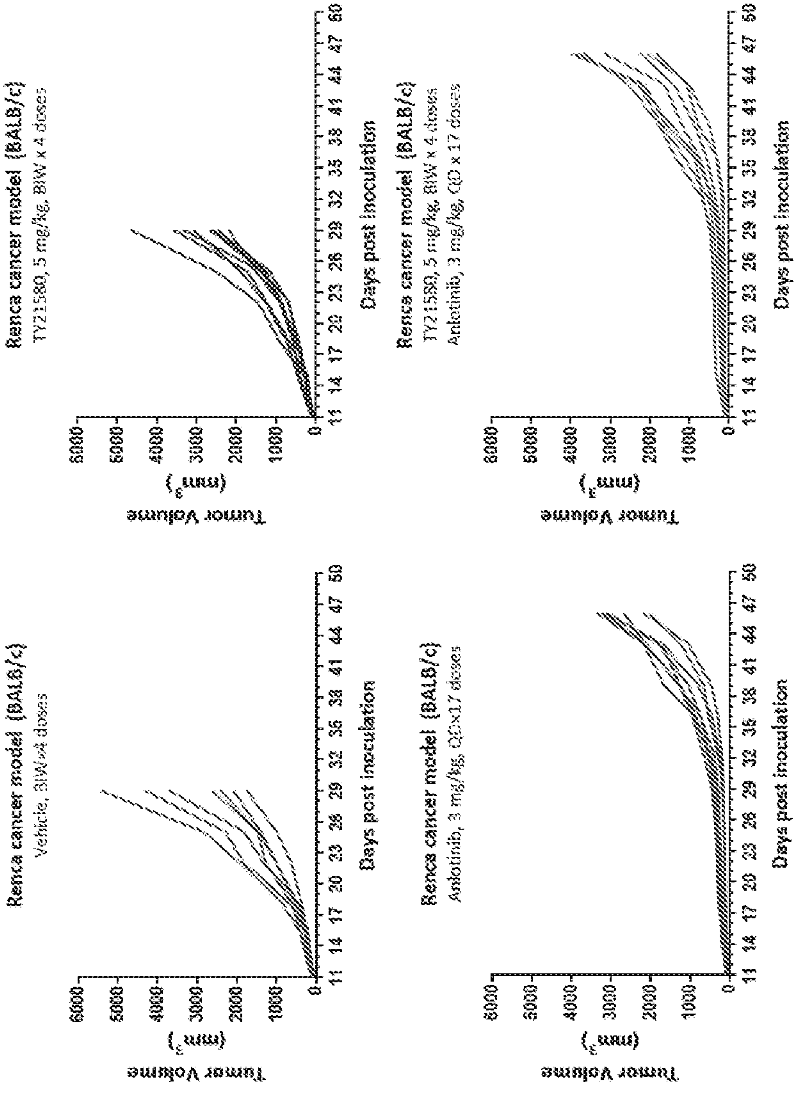

FIGS. 22A-22B provide the results of TY21580 administered in combination with Anlotinib in the Renca cancer model to assess in vivo antitumor efficacy of TY21580 and the VEGFR inhibitor Anlotinib combination treatment. Mice were inoculated subcutaneously with Renca murine kidney cancer cells. When the mean tumor volume reached 86 mm3, the tumor bearing mice were randomized into different treatment groups of eight mice each. Intraperitoneal administration of TY21580 at 5 mg/kg was initiated on a biweekly schedule for four doses. Anlotinib at 3 mg/kg was p.o. dosed daily for 17 doses. As shown in FIGS. 22A-22B, compared to the vehicle control group, 5 mg/kg TY21580 alone had no antitumor effect, whereas Anlotinib alone showed strong antitumor activity with TGI of 93% on Day 29. The combination of TY21580 with Anlotinib exhibited the same anti-tumor effect as Anlotinib single agent, suggesting that there was no synergy between these two agents in this tumor model.

Figure 23A:
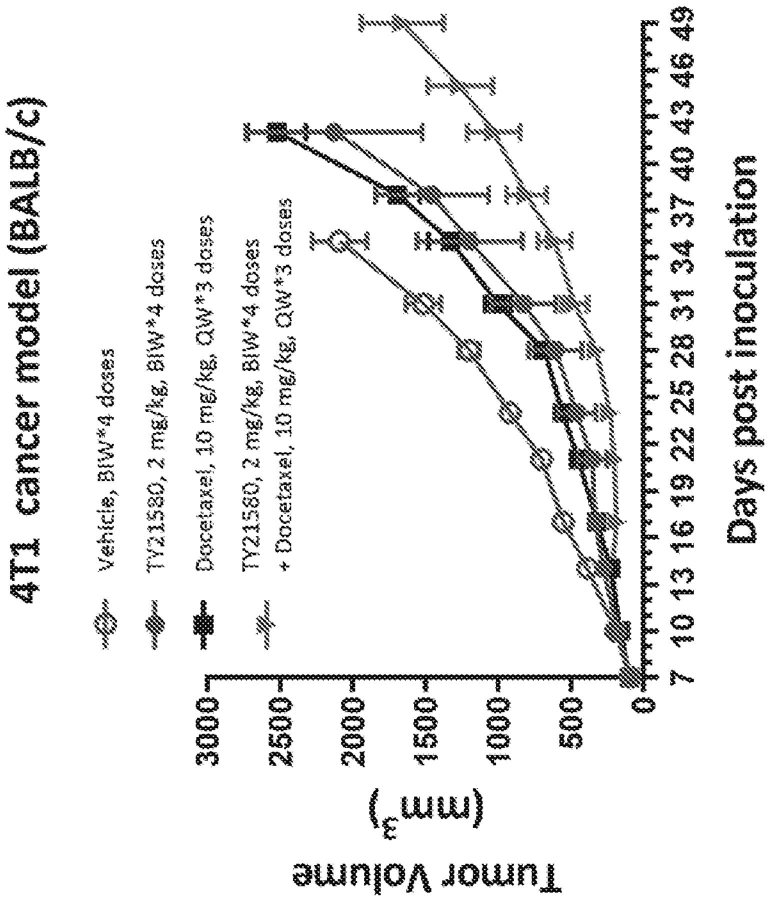
FIGS. 23A-23B show the effect of TY21580 administered in combination with Docetaxel in the 4T1 cancer model.
Figure 23B:
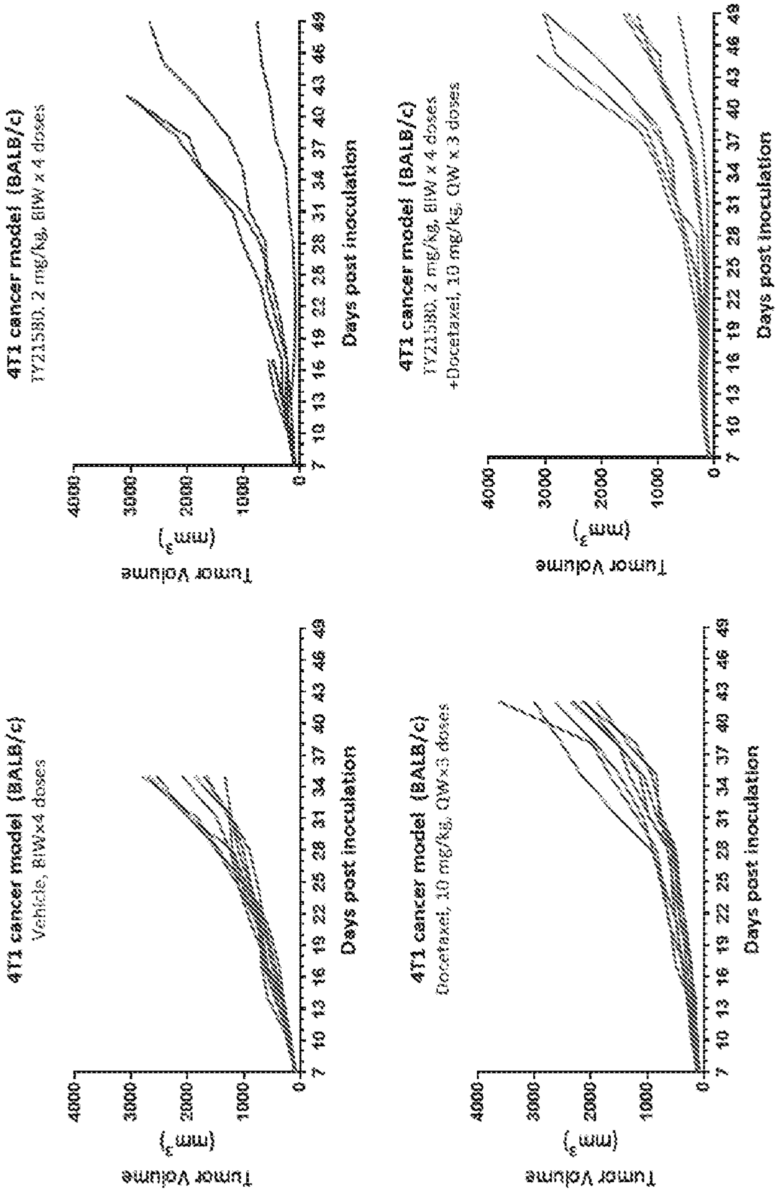

FIGS. 23A-23B provide the results of TY21580 administered in combination with Docetaxel in the 4T1 cancer model to assess in vivo antitumor efficacy of TY21580 and Docetaxel combination treatment. Dosing started when average tumor volume reached about 90 mm3 (n=8 per group). When the mean tumor volume reached 90 $mm^3$, the tumor bearing mice were randomized into different treatment groups of eight mice each. Intraperitoneal administration of TY21580 at 2 mg/kg was initiated on a biweekly schedule for four doses. Docetaxel at 10 mg/kg was i.v. dosed weekly for 3 doses. 4/8 mice died in TY21580 monotherapy group 2 weeks after the start of dosing, while only ⅛ mice died in the combination therapy group 6 weeks after the start of dosing. As shown in FIGS. 23A-23B, compared to the vehicle control group, both 2 mg/kg TY21580 or 10 mg/kg Docetaxel alone showed partial antitumor activity (TGI of 44.9% and 38.3% respectively on Day 35). Combination of TY21580 with Docetaxel exhibited further enhanced anti-tumor effect with TGI of 74%, suggesting that TY21580 could synergize with Docetaxel in tumor inhibition.

Figure 24A:
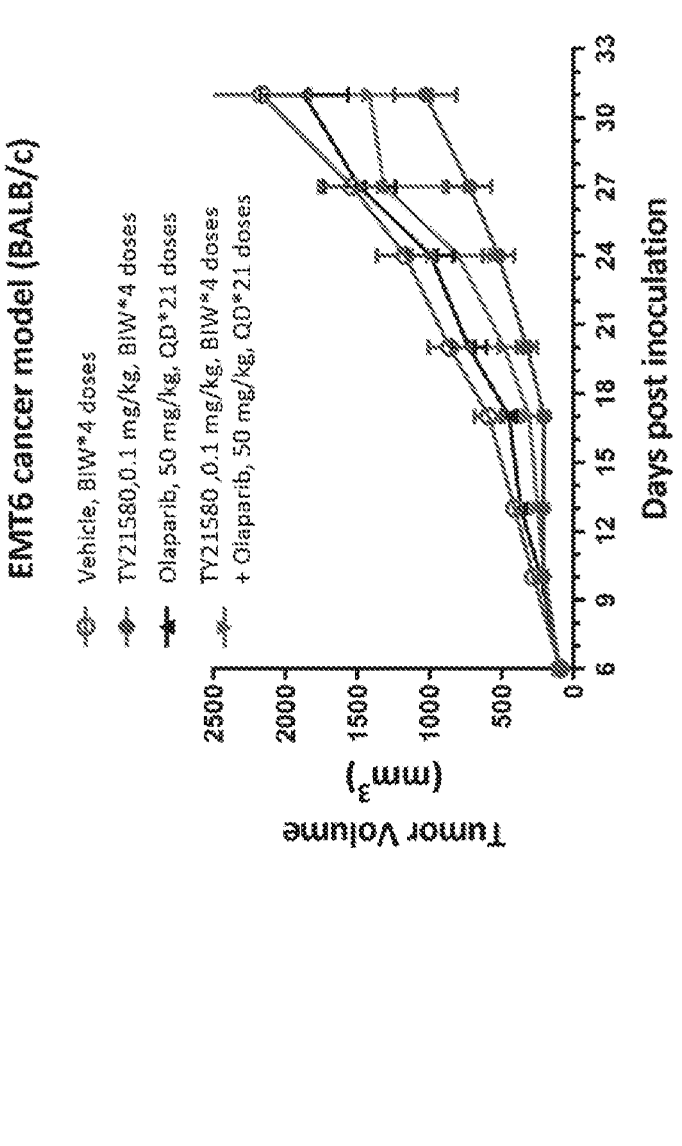
FIGS. 24A-24B show the effect of TY21580 administered in combination with Olaparib in the EMT6 cancer model.
Figure 24B:
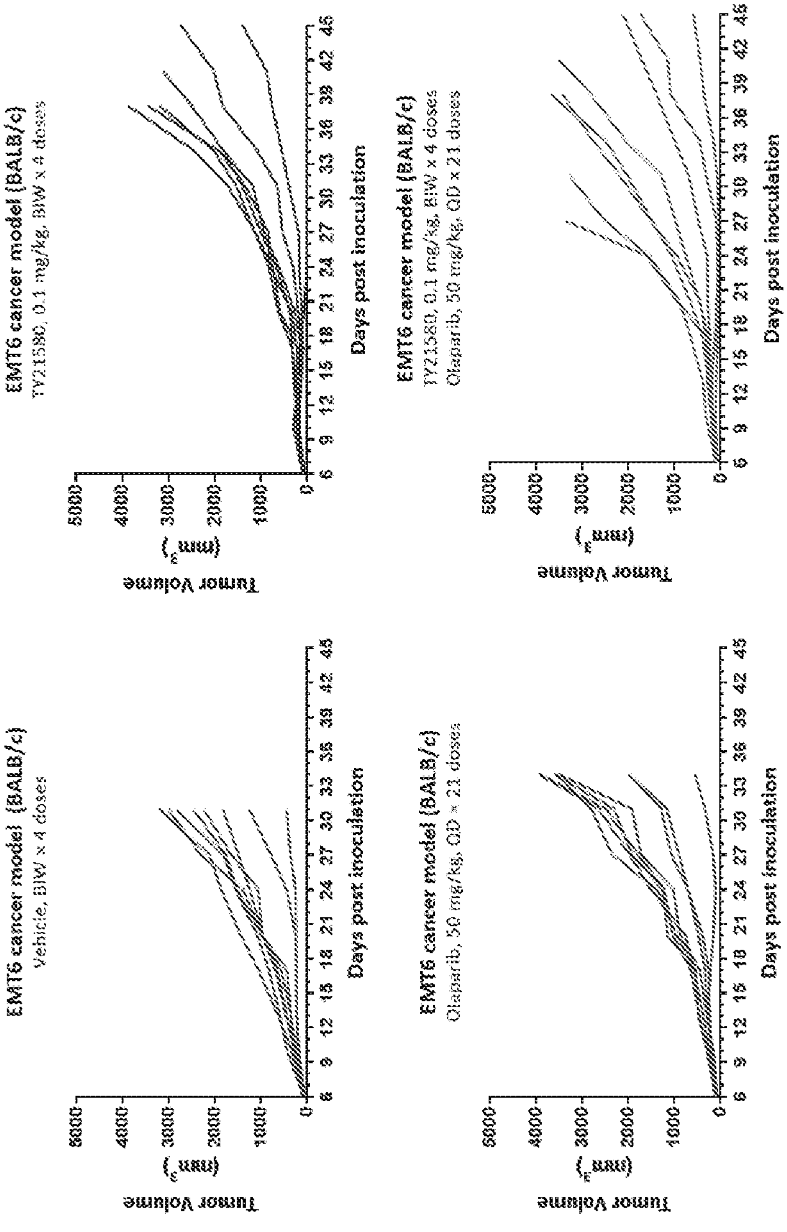

FIGS. 24A-24B provide the results of TY21580 administered in combination with Olaparib in the EMT6 cancer model to assess in vivo antitumor efficacy of TY21580 and PARP inhibitor Olaparib combination treatment. Mice were inoculated subcutaneously with EMT6 murine breast cancer cells. When the mean tumor volume reached 95 mm3, the tumor bearing mice were randomized into different treatment groups of eight mice each. Intraperitoneal administration of TY21580 at 0.1 mg/kg was initiated on a biweekly schedule. Olaparib at 50 mg/kg was p.o. dosed daily for 21 doses. As shown in FIGS. 24A-24B, compared to the vehicle control group, Olaparib alone had no significant antitumor effect, whereas 0.1 mg/kg TY21580 alone showed significant antitumor activity with Day 27 TGI of 56%. The combination of TY21580 with Olaparib exhibited reduced anti-tumor effect with TGI of 15.4%, suggesting that Olaparib may antagonize TY21580 activity in tumor inhibition.

Figure 25:
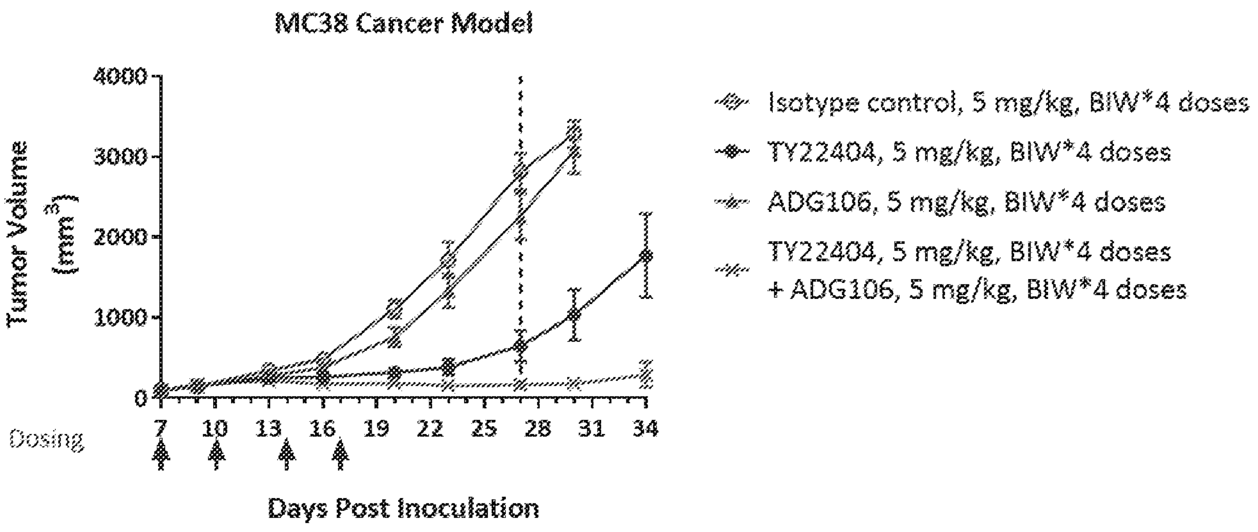
FIG. 25 show the effect of TY22404 administered in combination with ADG106 antibody in the MC38 cancer model.

FIG. 25 provides the results of TY22404 administered in combination with ADG106 antibody in the MC38 cancer model to assess in vivo antitumor efficacy of the combination treatment. Mice were inoculated subcutaneously with MC38 murine colon tumor cells. When the mean tumor volume reached 97 mm3, the tumor bearing mice were randomized into different treatment groups of eight mice each. Intraperitoneal administration of test antibodies was initiated on a biweekly schedule for four doses. Tumor growth inhibition (TGI) relative to the isotype control group was evaluated on Day 27 post tumor cell inoculation. As shown in FIG. 25, monotherapy of TY22404 at 5 mg/kg showed significant antitumor activity, with a TGI of 77%. whereas ADG106 alone at 5 mg/kg had no significant antitumor activity (TGI=21%). Combination of these two agents exhibited significantly enhanced anti-tumor effect, with mean TGI of 94% and 4 of the 8 mice complete tumor regression. The responses to combination therapies were superior to both agents alone and suggested that TY22404 could synergize with ADG106 in tumor inhibition.

Figure 26:
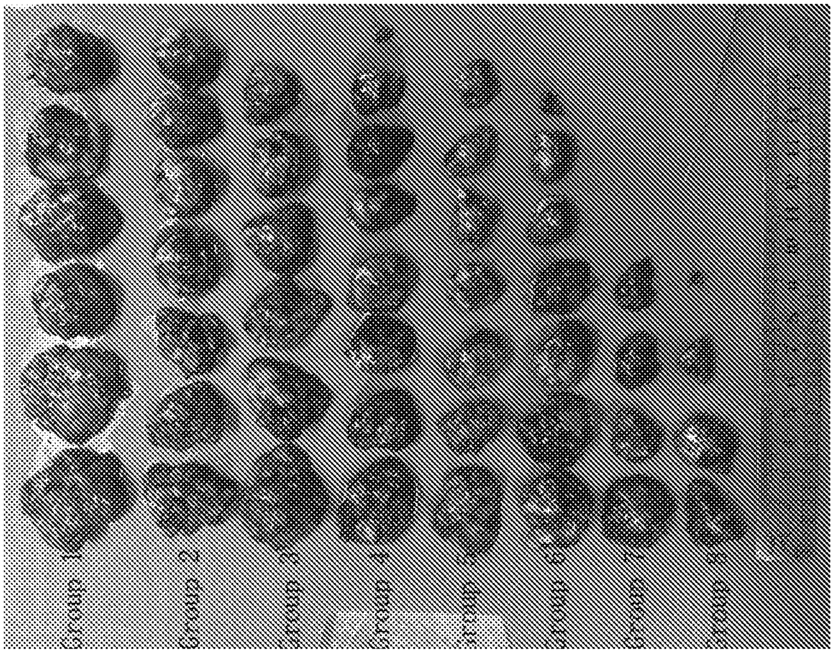
FIG. 26 shows the effect of TY21580 administered in combination with icaritin ("SNG162") and/or ADG106 in the syngeneic mouse B16F10 melanoma model.
Figure 26:
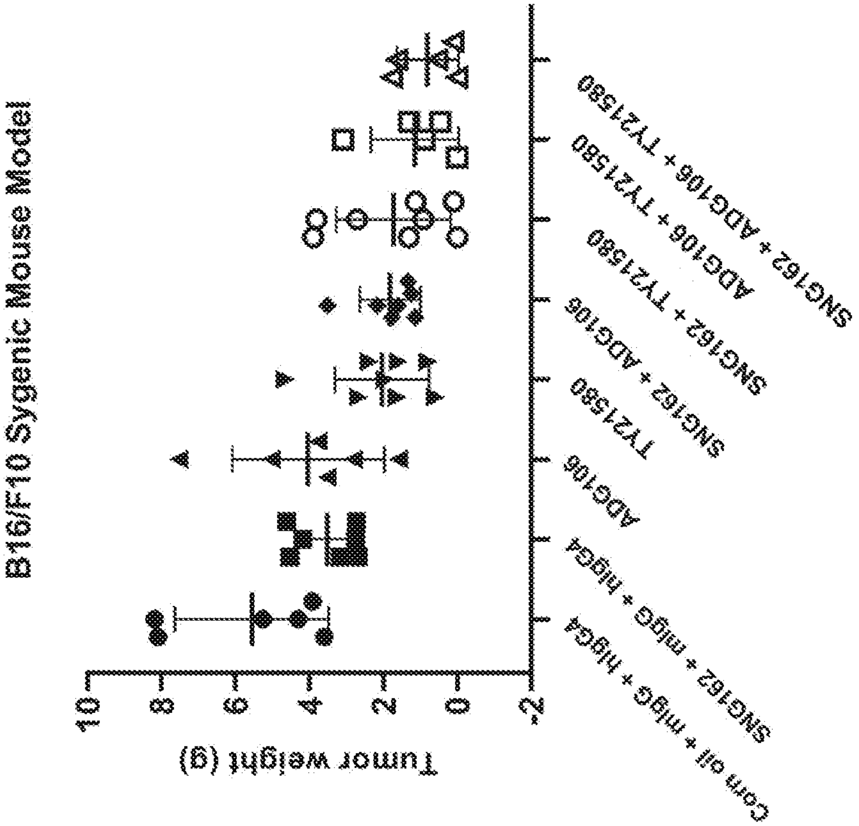

FIG. 26 provides the results of TY21580 administered in combination with icaritin ("SNG162") and/or ADG106 in the syngeneic mouse B16F10 melanoma model. BALB/c mice (n=8 per group) were inoculated subcutaneously with B16F10 murine melanoma cells. Treatment began at Day 6 post tumor inoculation. The mice were administrated with Ctrl (Corn oil+mIgG+hIgG4), TY21580 (5 mg/kg), ADG106 (5 mg/kg) and the combination of TY21580 and ADG106 by i.p. injection. The mice were administered with every three days (Q3D) for a total of six doses. TY21580 administered in combination with icaritin ("SNG162") and/or ADG106 were also tested in the syngeneic mouse B16F10 melanoma model. As shown in FIG. 26, ADG106 showed synergistic anti-tumor effect with TY21580 in this model. By the end of the experiment, there was no tumor in each of the three groups of SNG162+TY21580, ADG106+TY21580, and SNG162+ADG106+TY21580.

Example 3. TY22404 Activation and TY21580 vs TY22404 Pharmacokinetics

Figure 27:
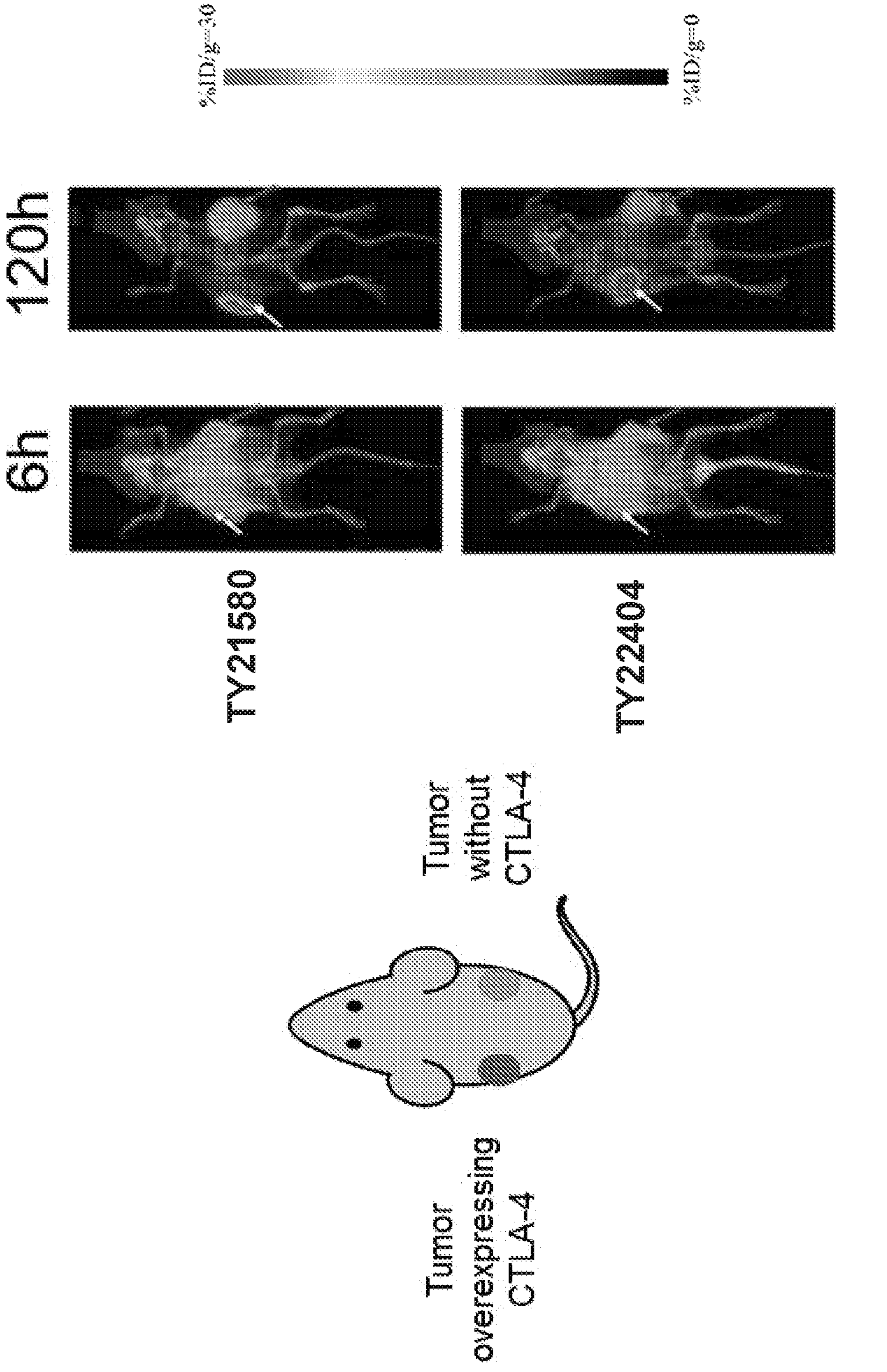
FIG. 27 shows in vivo imaging of TY22404 and TY21580 in mice bearing both CTLA4 negative and positive H22 tumors.

As shown in FIG. 27, BALB/c female mice were subcutaneously inoculated with murine H22 liver cancer tumor cells with or without human CTLA4 expression. As shown in the diagram in FIG. 27, H22 tumor cells with exogenously overexpressed CTLA4 and parental H22 tumor cells without CTLA4 expression were inoculated on the left and right flank of the mice, respectively. Both parental TY21580 and TY22404 mAb were 89Zr radio-labeled, and i.v. injected into the tumor-bearing mice through tail vein. PET/CT scan was conducted at different time points to image the signal distributions. The image results indicated that after 120 hours of mAb dosing, TY22404 was accumulated mainly to tumors with target CTLA4 expression, similar to the situation for the parental TY21580. These results suggested that TY22404 was activated in tumor microenvironment, which enabled the target binding.

Figure 28:
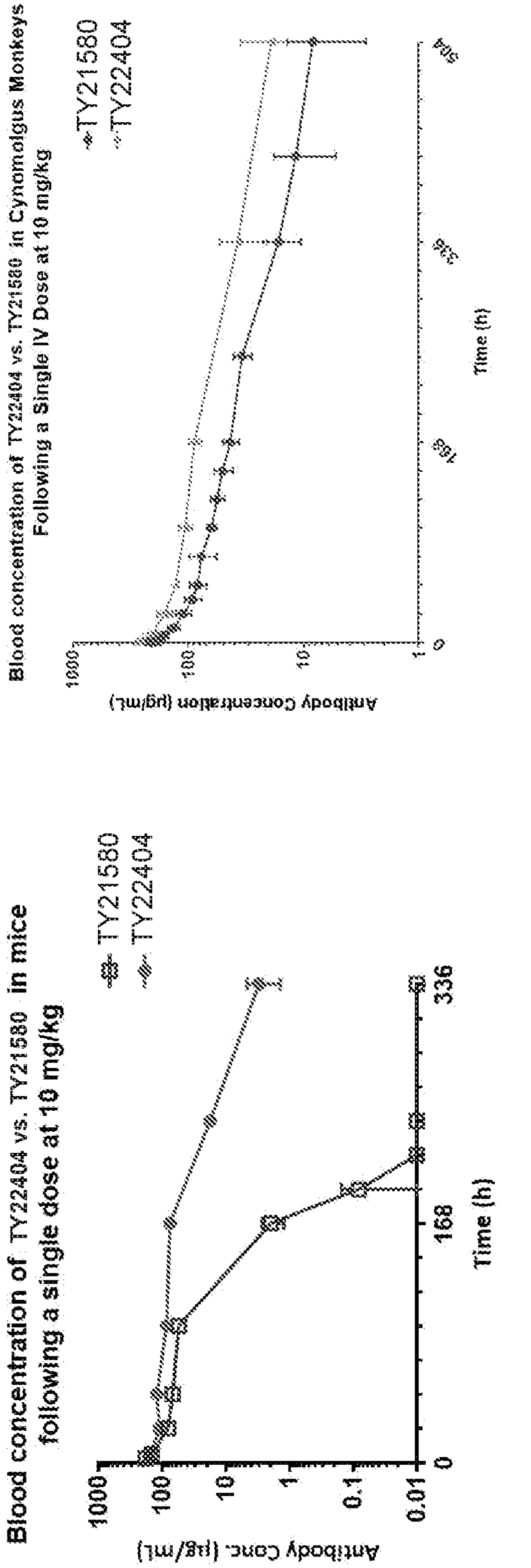
FIG. 28 shows pharmacokinetics of TY21580 vs TY22404 in mice (left) and cynomolgus monkeys (right).

As shown in FIG. 28, mice and cynomolgus monkeys were administered with a single dose of TY21580 or TY22404 at 10 mg/kg, respectively. Blood samples were collected at different time points following antibody dosing, and concentrations of test antibodies were measured. The mean concentrations of TY21580 or TY22404 at different time points were plotted against time. The results indicate that TY22404 exhibits extended half-life and higher systemic exposure than TY21580 in both mice and cynomolgus monkeys, consistent with the concept that SAFEbody protects antibody from binding to its targets in normal physiological conditions and results in reduced target mediated drug disposition (TMDD).

Example 4. Clinical Analysis of Anti-CTLA4 SAFEbody in Phase 1 Dose Escalation Study A Phase 1 dose escalation and cohort expansion study on anti-CTLA4 SAFEbody has been conducted in multiple sites in Australia and US. This was an open-label, multi-site phase 1 study in patients with advanced solid tumors who have failed multiple lines of prior therapies. anti-CTLA4 SAFEbody was administered once every 3 weeks until disease progression or unacceptable toxicity with 0.1 mg/kg, 0.3 mg/kg, 1 mg/kg, 3 mg/kg or 10 mg/kg.

The SAFEbody comprised the VH and VL sequences of TY21580 with masking and linker moieties comprising the sequences of SEQ ID Nos: 192 and 221, respectively (combined MM/LM sequence of EVGSYPNPSSDCVPYYYACAYSGR-SAGGGGTPLGLAGSGGS; SEQ ID NO: 200), at the N-terminus of the light chain. See SEQ ID Nos: 320 and 322 for the full heavy and light chains (including mask/linker), respectively.

Figure 29:
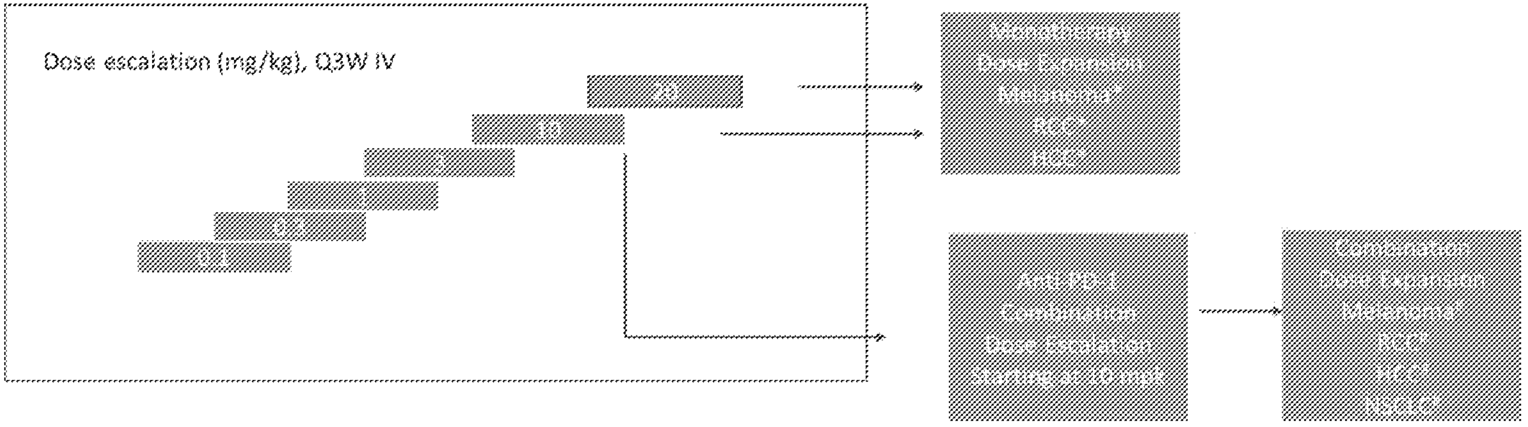
FIGS. 29 & 30 show the design of a Phase 1 dose escalation study examining anti-CTLA4 SAFEbody administration in human patients. Anti-CTLA4 SAFEbody was administered once every 3 weeks until disease progression or unacceptable toxicity with 0.1 mg/kg, 0.3 mg/kg, 1 mg/kg, 3 mg/kg or 10 mg/kg, with cohort expansion at 10 mpk recommended by SRC, and the combination with anti-PD1 for anti-CTLA4 SAFEbody at 6 mg/kg and the combination with ADG106 for anti-CTLA4 SAFEbody at 3 mg/kg in selected indications.
Figure 30:
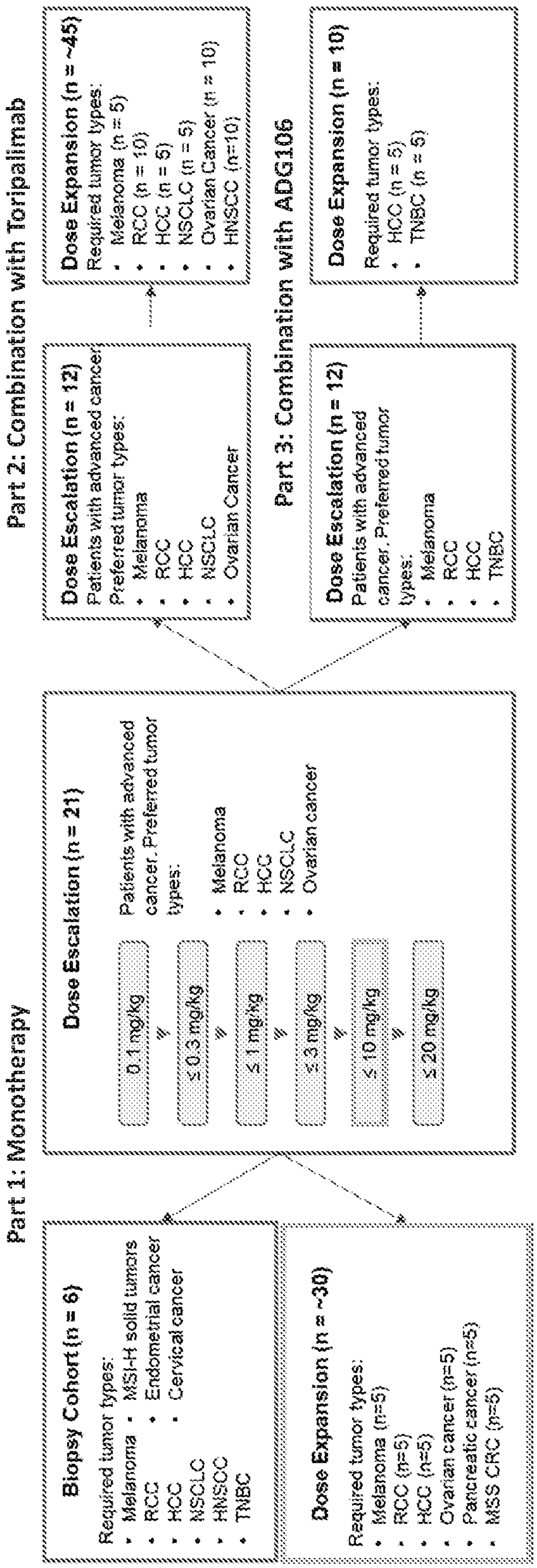

About 18 patients have been enrolled in dose escalation from 0.1 to 10 mg. No DLT has been observed up to 10 mg/kg for Q3W continuously with cohort expansion at 10 mpk recommended by SRC, and the combination with anti-PD1 for anti-CTLA4 SAFEbody at 6 mg/kg and the combination with ADG106 for anti-CTLA4 SAFEbody at 3 mg/kg in selected indications (FIGS. 29 & 30).

Patient demographic profiles, along with treatment history and indications, are shown in Table G.

TABLE G

Study patient characteristics

| Demographics and baseline parameters | All Patients (n = 13) |
|---|---|
| Age (Years) | |
| Median (Min, Max) | 64 (45, 84) |
| Sex | |
| Female | 8 |
| Male | 5 |
| Race | |
| White | 12 |
| Asian | 1 |
| African American | 0 |
| ECOG | |
| 0 | 8 |
| 1 | 5 |
| Number of Prior Systemic Regimens | |
| Median (Min, Max) | 2 (1, 8) |

TABLE G-continued

| Study patient characteristics | |
|---|---|
| Demographics and baseline parameters | All Patients (n = 13) |
| Cancer Types | |
| Ovarian cancer | 3 |
| Pancreatic cancer | 2 |
| Cholangiocarcinoma | 2 |
| Lung cancer | 2 |
| Breast cancer | 1 |
| Melanoma | 1 |
| Hepatocellular carcinoma | 1 |
| Glioblastoma | 1 |
| Dose Administered | |
| Median (Min, Max) | 2 (1, 7) |

Treatment-related safety profile is shown in FIG. 31. These data show that the anti-CTLA4 SAFEbody has a very robust safety profile up to 10 mpk, consistent with the preclinical observation.

Figure 32B:
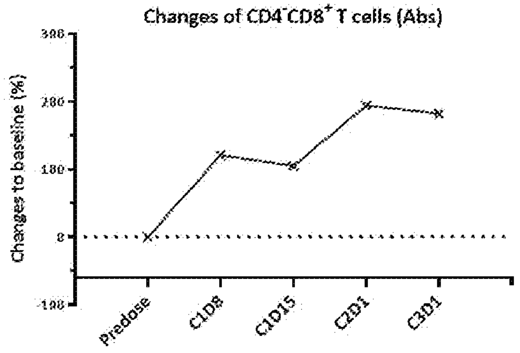

Two case studies were selected for two cold tumors. First, an ovarian cancer patient has had 5 lines of prior therapies (FIG. 32A). Upon enrolling in this study at 1 mpk, the patient showed continuous tumor shrinkage for each tumor assessment after every two cycles of anti-CTLA4 SAFE-body treatment. The targeted tumor lesions have shrunk from −13%, −19% to −22%, while the CA125 has dropped steadily from −18%, −67% to −77% consistent with the clinical benefit to the patient. Second, a UV melanoma patient who has failed ipilimumab plus nivolumab in prior therapies has shown-24% tumor shrinkage (FIG. 32B), which is supported by T cell activation after two cycles of anti-CTLA4 SAFEbody therapies. These observations were surprising for this cold tumor subtype, which has no effective therapy.

Example 5. Preliminary Biomarker Analysis of Anti-CTLA4 SAFEbody in Phase 1 Dose Escalation Study For preliminary biomarker assessment, peripheral blood and serum samples were collected from patients enrolled in the Phase I clinical trial described in Example 4 and assessed for exploratory biomarker studies. The studies included peripheral lymphocyte profiling by flow cytometry, analysis of serum levels of cytokines, soluble receptors/ligands and MMPs.

For cytokine analysis, serum was prepared from fresh blood collected from each patient at different timepoints (Cycle 1 Day 1 pre-dose, Cycle 1 Day 8, Cycle 1 Day 15, Cycle 2 Day 1 pre-dose, Cycle 3 Day 1 pre-dose, and Cycle 4 Day 1 pre-dose) according to standard protocol. The concentrations of a panel of proinflammatory cytokines (IFN-γ, TNF-α, IL-2, IL-6, and IL-10), which are early responders of immune activation, in serum were measured by a sensitive and quantitative MSD V-Plex assay (Cat. No. K151A9H) following the manufacturer's instructions.

Figure 33:
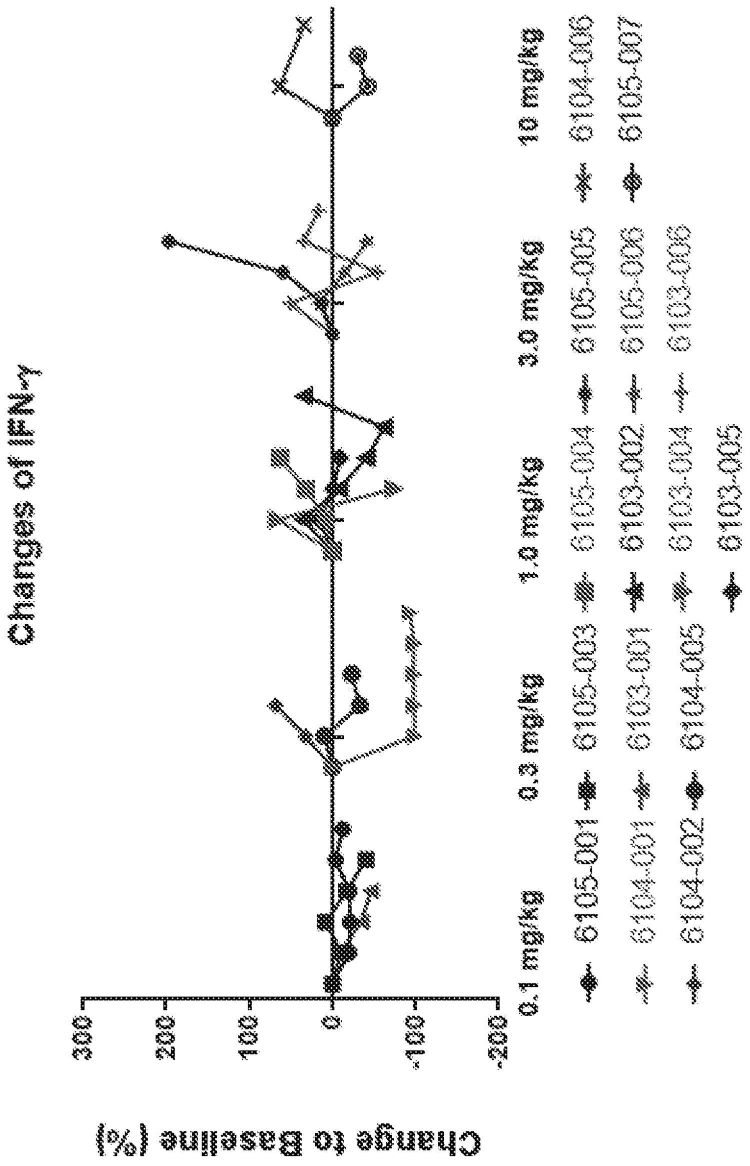
FIG. 33 shows dynamic changes of proinflammatory cytokine TNF-α in serum of cancer patients during the course of treatment (Cycle 1 Day 1 pre-dose).
Figure 34:
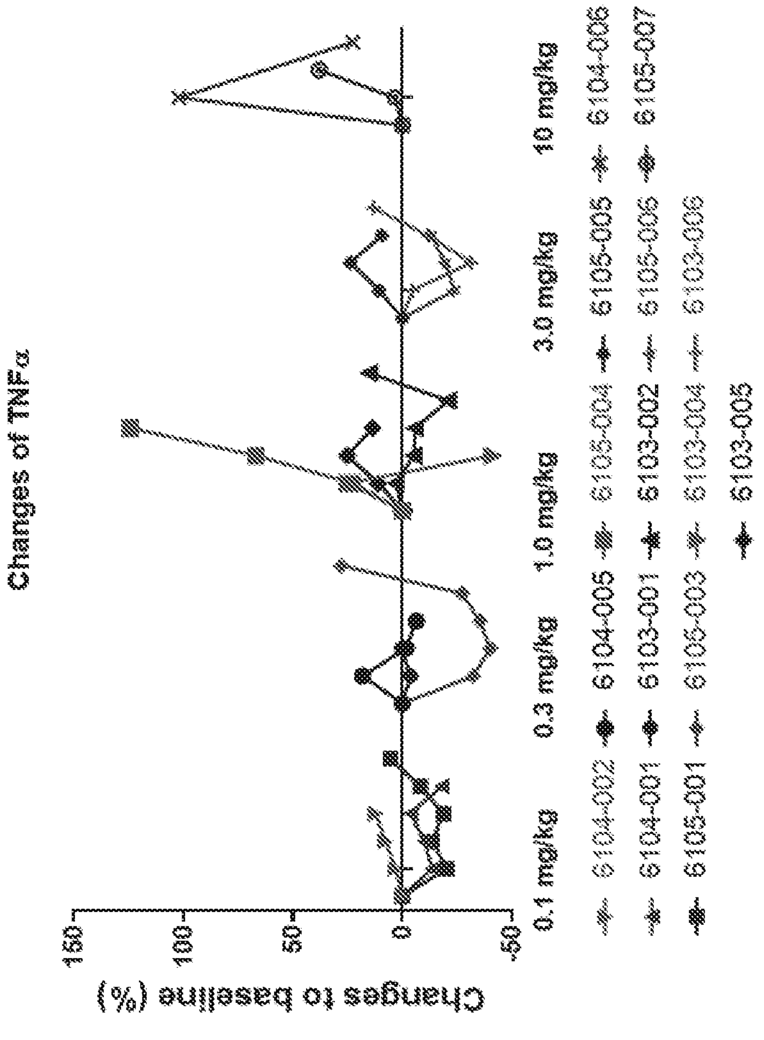
FIG. 34 shows show TNF-α levels over course of treatment, including absolute serum concentration (pg/mL.

The absolute concentrations and changes relative to base level (Cycle 1 Day 1 pre-dose) of IFN-γ and TNF-α over the treatment course were plotted as shown in FIG. 33 for IFN-Y and FIG. 34 for TNF-α. For patient 6105-005 with 3 mg/kg dose, IFN-γ abundance was increased significantly from Cycle 1 Day 8 to Cycle 2 Day 1. The level of IFN-γ in patient 6105-003 was abnormally high at C1D1 pre-dose and excluded from further analysis. The abundance of IFN-Y in patient 6105-005 dosed with 3 mg/kg TY22404 was increased significantly from C1D8 to C2D1. For patient 6105-004 with 1 mg/kg dose, TNF-α abundance showed a dramatic increase during treatment. Overall, transient increased levels of IFN-γ and/or TNF-α were observed in some patients after TY22404 treatment, indicative of immune activation.

Figure 35A:
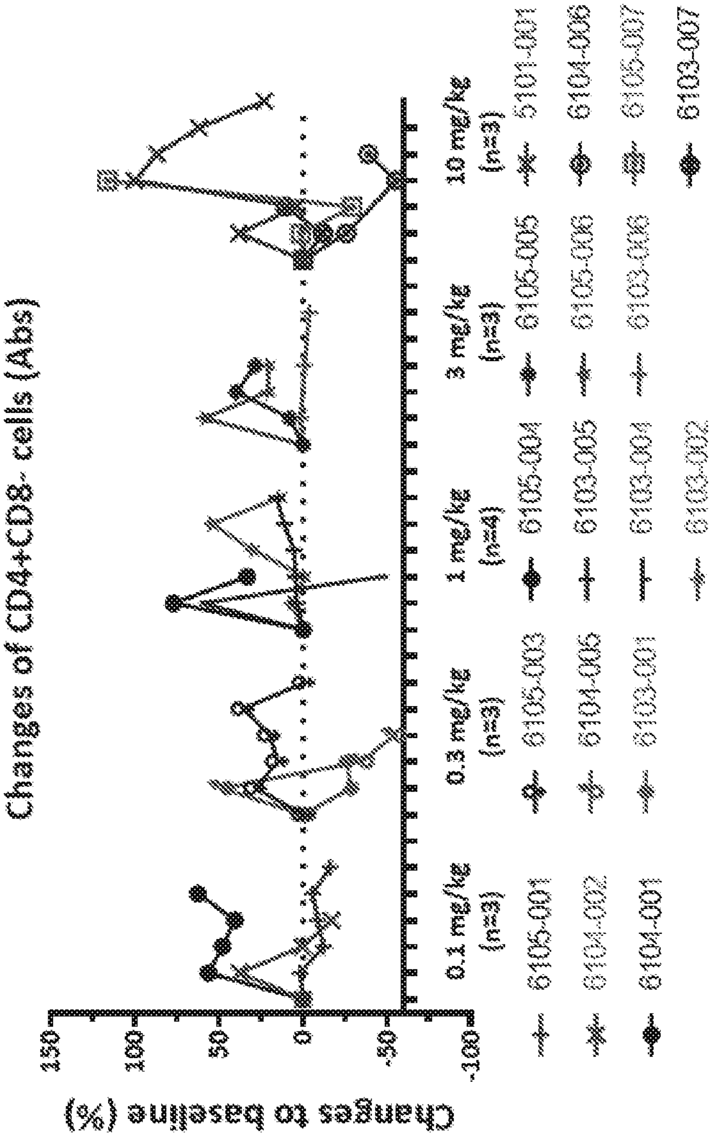
FIGS. 35A-35C show changes relative to base level (Cycle 1 Day 1 pre-dose) of absolute counts of immune cell sub-populations from peripheral blood samples of patients treated with anti-CTLA4 SAFEbody, including CD4+ Helper T cells (FIG. 35A), CD8+ Cytotoxic T cells (FIG. 35B), and NK cells (FIG. 35C).
Figure 35B:
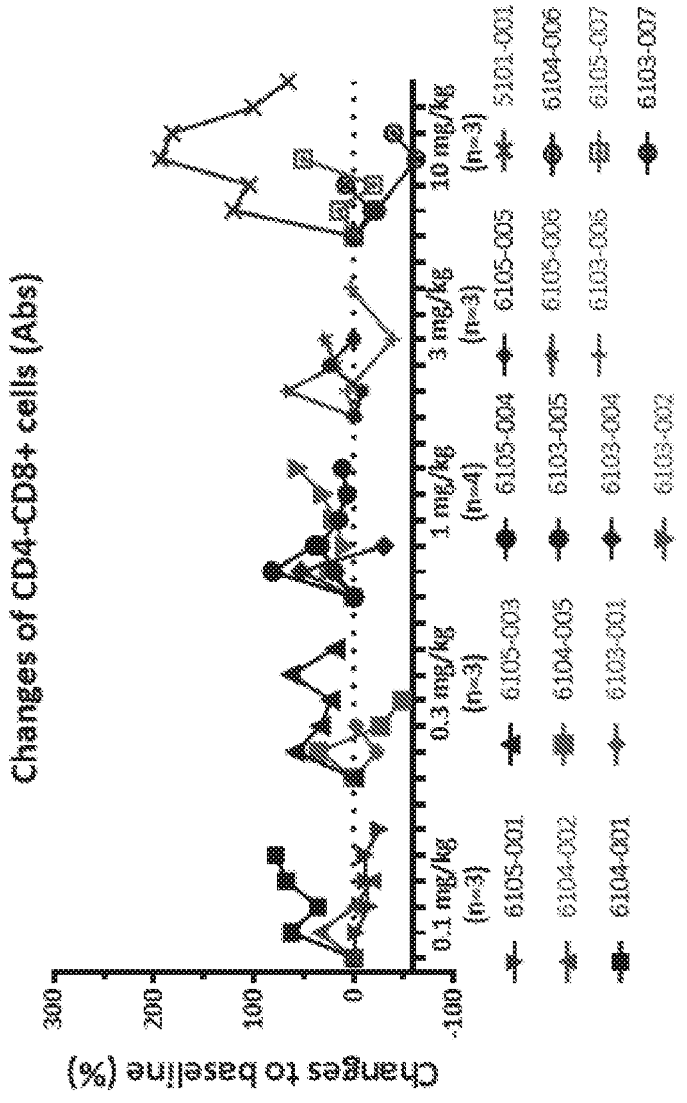
Figure 35C:
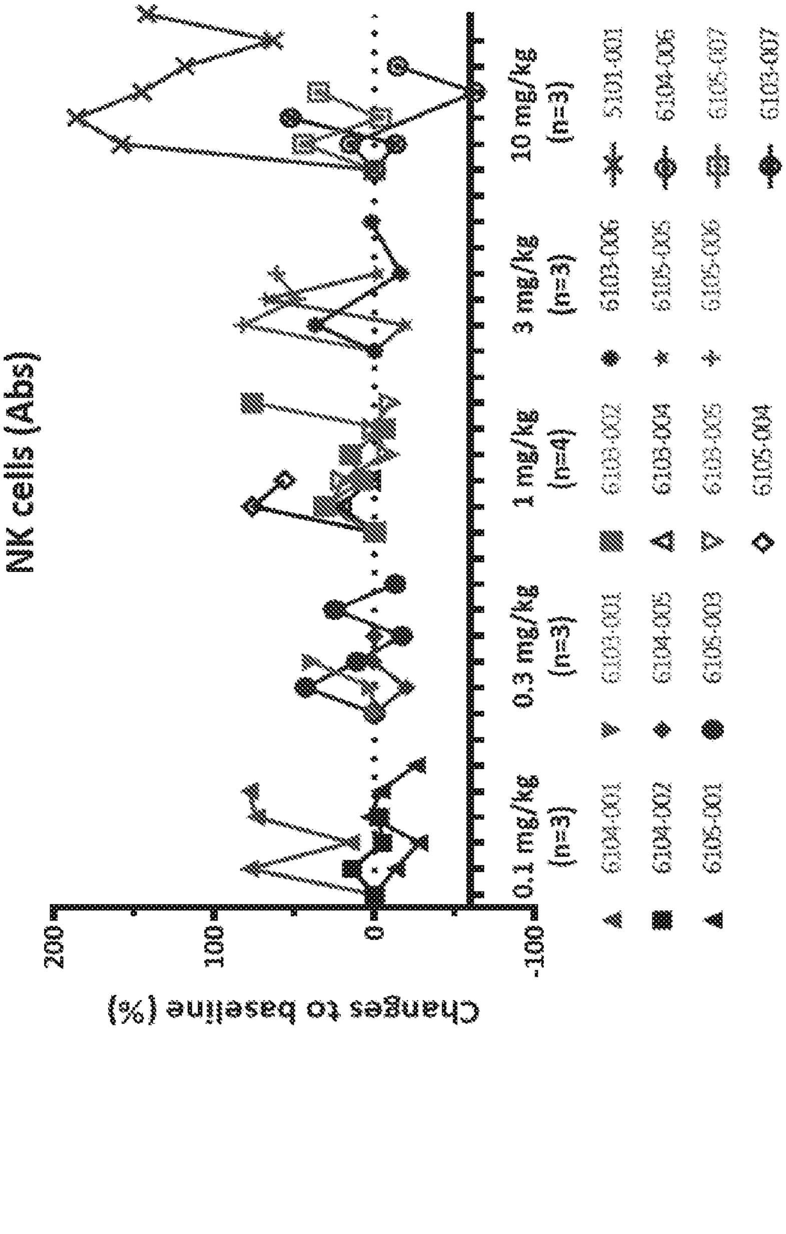

For immune cell profiling, fresh peripheral blood samples were collected from each patient at different time points (Cycle 1 Day 1 pre-dose, Cycle 1 Day 8, Cycle 1 Day 15, Cycle 2 Day 1 pre-dose, Cycle 3 Day 1 pre-dose, and Cycle 4 Day 1 pre-dose) according to standard protocol. The profile of immune cell sub-populations, including CD4+ Helper T cells, CD8+ Cytotoxic T cell, B cells, and NK cells, was determined by TBNK FACS panel. The changes relative to base level (Cycle 1 Day 1 pre-dose) of absolute counts in each sub-population over the treatment course were plotted as shown in FIGS. 35A-35C. Overall, transient increased CD4+, CD8+ T and NK cells were observed after TY22404 treatment in some patients. The increase of absolute counts and percentage of NK cells after treatment might be dose dependent.

Example 6. In Vivo Cleavage of TY22404 in Mouse H22 Tumor, Liver and Plasma

The vivo cleavage efficiency of TY22404 by urokinase-type plasminogen activator (uPA) or matrix metalloproteinase-9 (MMP9) in mouse H22 tumor, liver, and plasma was assessed by traditional Western blot (WB). In brief, the H22 tumor cells were maintained in vitro as a monolayer culture in RPMI-1640 medium supplemented with 10% fetal bovine serum at 37° C. in an atmosphere of 5% $CO_2$ in air. The cells growing in an exponential growth phase were harvested and counted for tumor inoculation. Each mouse (BALB/c) was inoculated subcutaneously at the right flank region with H22 tumor cells ($2\times10^6$) in 0.1 ml of PBS for tumor development. The BALB/c mice were randomly divided into 2 groups (N=3), based on the initial tumor volume (about 300 $mm^3$). Then mice in the study were treated with 5 mg/kg of TY22404 via intravenous bolus. At 24-h and 96-h after dosing, tumor, liver and plasma samples were collected from the two groups (3 mice each group), respectively, for subsequent WB analysis. The tissue samples were lysed in ice-cold RIPA Lysis Buffer (CST, 9806S), with protease inhibitor cocktail (Sigma, P8340) and the total tissue proteins were quantified by bicinchoninic (BCA) Kit (Shenggong, C503021-0500). Subsequently, the target antibodies were pulled-down and enriched with pre-treated protein A beads (GenScript, L00695). The prepared samples were loaded onto an 12% gradient gel for SDS-PAGE. The primary antibody was used with anti-human kappa light chain antibody (Abcam, ab134930; 1:5000 dilution), the second antibody was used with HRP-labelled mouse anti-rabbit IgG (H+L) (Jackson Immunoresearch, 211-035-109; 1:10000 dilution) and enhanced chemiluminescence (ECL) method was used for final signal detection. The mixture of the intact and cleaved TY22404 at 1:1 ratio was used as a standard control in the assay (labelled with STD).

Figure 36:
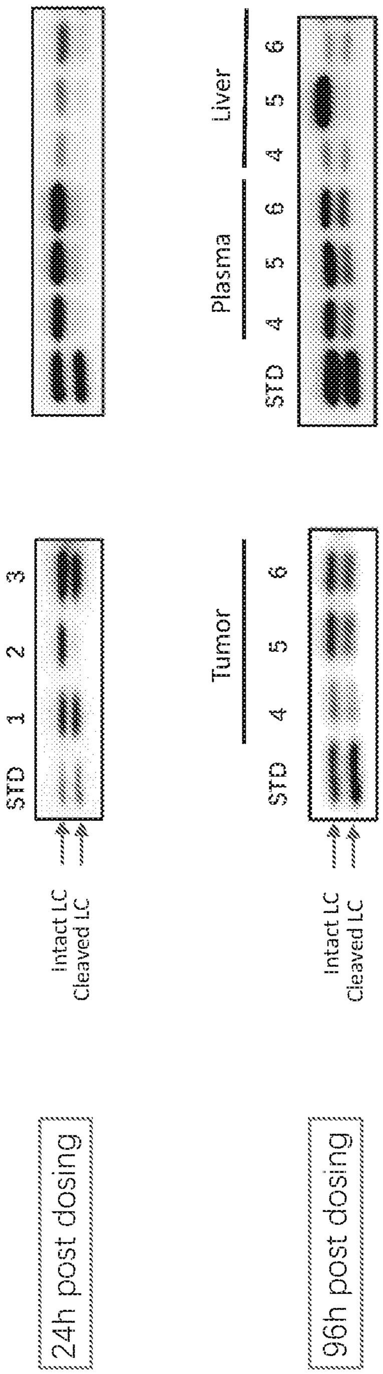
FIG. 36 shows the cleaved form, about half of total activatable anti-CTLA4 antibody TY22404, was detected in the tumors of 2/3 mice following bolus injection of TY22404, but not detected in the liver and plasma at the 24-h after dosing. However, at 96-h after dosing, the cleaved form of TY22404 was observed in all the samples including tumor, liver, and plasma from all the 3 mice (labelled with 4-6).

As shown in FIG. 36, the cleaved form, about half of total TY22404, was detected in the tumors of 2/3 mice (labelled with 1-3), but not detected in the liver and plasma at the 24-h after dosing. However, at 96-h after dosing, the cleaved form of TY22404 was observed in all the samples including tumor, liver, and plasma from all the 3 mice (labelled with 4-6).

Example 7. Dose Dependent Treg Depletion of TY22404 in CT26 Murine Colon Cancer Model BALB/c mice (n=10 per group, female, 8-9 weeks old) were inoculated subcutaneously with CT26 (SIBS) murine colon cancer cells. Treatment began at Day 9 post tumor inoculation when the average tumor volume reached about 150 $mm^3$. The mice were administrated with isotype Ctrl at 5 mg/kg and TY22404 at 5, 1 and 0.2 mg/kg by i.p. injection. The mice were administered with these antibodies at Day 9 and Day 12 and terminated at Day 14 for peripheral and tumor infiltrating lymphocytes analysis.

Figure 37:
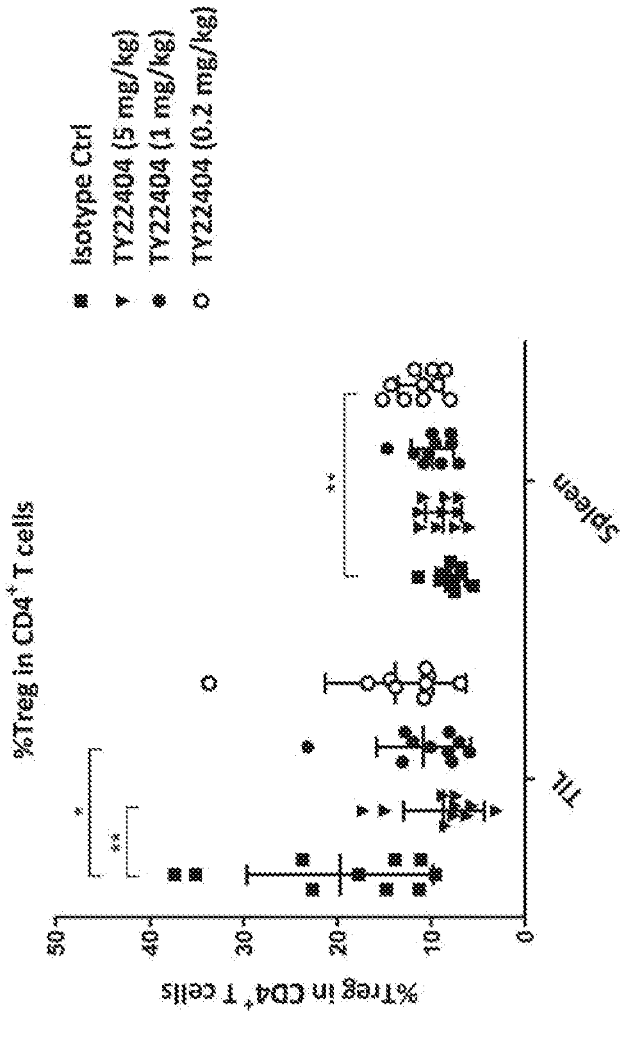
FIG. 37 shows that activatable anti-CTLA4 antibody TY22404 significantly reduced the percentage of Tregs in CD4+ T cells comparing with isotype Ctrl in tumor infiltrating lymphocytes (TILs) in a dose dependent manner. However, TY22404 did not reduce the percentage of Tregs in CD4+ T cells in peripheral lymphocytes in peripheral blood
Figure 38:
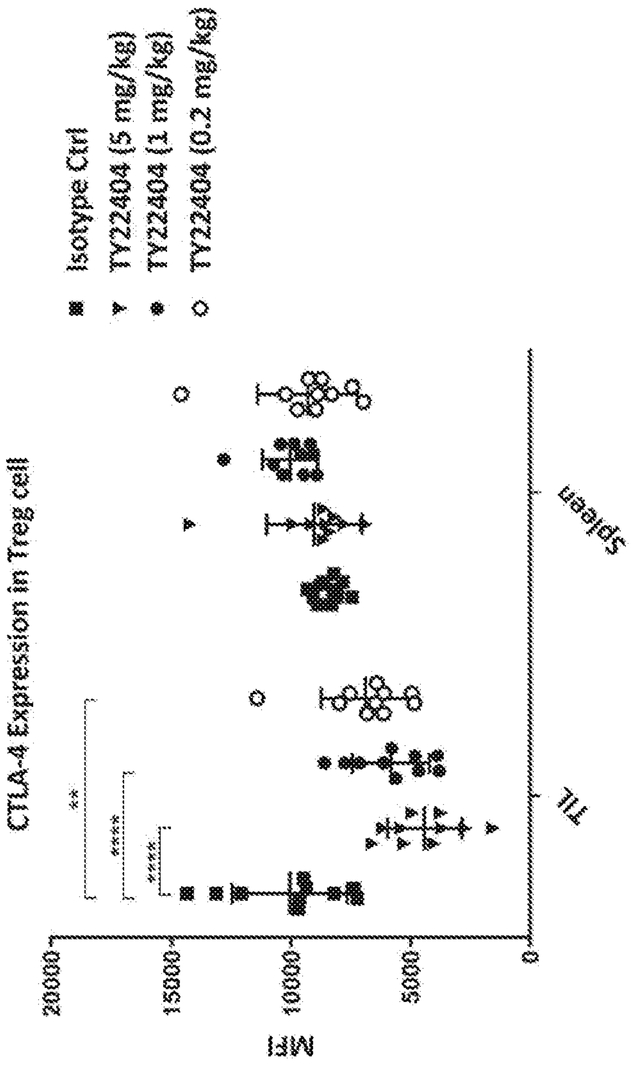
FIG. 38 shows that the CTLA-4 expression levels on Treg cells in TILs was significantly decreased after treated with TY22404 in a dose dependent manner. However, the CTLA-4 expression levels were not changed on peripheral Treg cells after treated with TY22404.

As shown in FIG. 37, TY22404 significantly reduced the percentage of Tregs in CD4+ T cells comparing with isotype Ctrl in TILs in a dose dependent manner. However, TY22404 did not reduce the percentage of Tregs in CD4+ T cells in peripheral lymphocytes in peripheral blood and spleen. As shown in FIG. 38, the CTLA-4 expression levels on $T_{reg}$ cells in TILs was significantly decreased after treated with TY22404 in a dose dependent manner. However, the CTLA-4 expression levels were not changed on peripheral $T_{reg}$ cells after treated with TY22404.

EXEMPLARY SEQUENCES

TABLE D anti-CTLA4 variable region polynucleotide sequences

| Ab name: | VH: | VL: |
|---|---|---|
| TY21585 | GAGGTTCAGCTGGTGGAGTCTGGCGGTGG<br>CCTGGTGCAGCCAGGGGGCTCACTCCGTTT<br>GTCCTGTGCAGCTTCCGGATTCACCTTCTCC<br>GACTACGCTATTCACTGGGTGCGTCAGGCC<br>CCGGGTAAGGGACTCGAGTGGATCGGTATC<br>ATCTCCCCATCTAGCGGTTCTACTAACTACG<br>CCCAGAAGTTCCAGGGTCGTGTGACTATAA<br>GTCGCGACAATTCGAAAAACACACTGTACC<br>TACAACTGAACAGCTTAAGAGCTGAGGAC<br>ACTGCCGTCTATTATTGCGCCAGAGACATTC<br>ACTCTGGTTCTTCTGGTTACTACTACGGTTT<br>CGACGTCTGGGGTCAAGGAACACTAGTCA<br>CCGTCTCCTCG<br>(SEQ ID NO: 108) | GATATCCAGTTGACCCAGTCCCCGAGTTC<br>CCTGTCCGCCTCTGTGGGCGATCGGGTCA<br>CCATCACCTGCCGTGCCTCTGAGTCTGTG<br>GACTTCTTCGGTATCTCTTTCCTGGCCTGG<br>TATCAACAGAAACCAGGAAAAGCTCCGA<br>AGCTTCTGATCTACGACGCCTCTAACCGT<br>GCCACCGGTATCCCATCTCGCTTCTCTGG<br>ATCCGGTTCCGGGACGGATTTCACTCTGA<br>CCATCAGCAGTCTGCAGCCGGAAGACTT<br>CGCAACTTATTACTGCCAGCACTACACCT<br>CTTCGCCACCAGTGTACACCTTCGGACAG<br>GGTACCAAGGTGGAGATCAAACGA<br>(SEQ ID NO: 121) |
| TY21586 | GAGGTTCAGCTGGTGGAGTCTGGCGGTGG<br>CCTGGTGCAGCCAGGGGGCTCACTCCGTTT<br>GTCCTGTGCAGCTTCCGGATACTCTATCACC<br>TCTGGTTACTACTGGGCCTGGATTCGTCAG<br>GCCCCGGGTAAGGGCCTCGAGTGGGTGTCT<br>TCCATCTCTGGTTCCGGTTCTACTACCTACT<br>ACGCCGACTCTGTCAAGGGCCGTTTCACTA<br>TAAGTCGCGACAATTCGAAAAACACACTGT<br>ACCTACAACTGAACAGCTTAAGAGCTGAG<br>GACACTGCCGTCTATTATTGCGCCAGAGAT<br>GGTTTCGGCTACTTCGACTACTGGGGTCAA<br>GGAACACTAGTCACCGTCTCCTCG<br>(SEQ ID NO: 109) | GATATCCAGTTGACCCAGTCCCCGAGTTC<br>CCTGTCCGCCTCTGTGGGCGATCGGGTCA<br>CCATCACCTGCTCTGCCTCTTCTAGCGTG<br>AGCTACGTGTACTGGTATCAACAGAAACC<br>AGGAAAAGCTCCGAAGCTTCTGATCTACG<br>ACGCCTCTTCTCTGGAATCTGGTGTGCCA<br>TCTCGCTTCTCTGGATCCGGTTCCGGGAC<br>GGATTTCACTCTGACCATCAGCAGTCTGC<br>AGCCGGAAGACTTCGCAACTTATTACTGC<br>GTGCAGGGTCTTCAGACCCCTTGGACCTT<br>CGGACAGGGTACCAAGGTGGAGATCAAA<br>CGA<br>(SEQ ID NO: 122) |
| TY21587 | GAGGTTCAGCTGGTGGAGTCTGGCGGTGG<br>CCTGGTGCAGCCAGGGGGCTCACTCCGTTT<br>GTCCTGTGCAGCTTCCGGATTCACCTTCTCC<br>GACTACGGTATTCACTGGGTGCGTCAGGCC<br>CCGGGTAAGGGCCTCGAGTGGATCGGTGA<br>AATCTACCACTCTGGTTCTACCTACTACTCT<br>CCATCTCTGAAGTCTCGTGTGACTATAAGTC<br>GCGACAATTCGAAAAACACACTGTACCTAC<br>AACTGAACAGCTTAAGAGCTGAGGACACT<br>GCCGTCTATTATTGCGCCAGAGACGTTGCC<br>CCTGGTTCTTCTGGTTACTACGACGGTTTCG<br>ACTTCTGGGGTCAAGGAACACTAGTCACCG<br>TCTCCTCG<br>(SEQ ID NO: 110) | GATATCCAGTTGACCCAGTCCCCGAGTTC<br>CCTGTCCGCCTCTGTGGGCGATCGGGTCA<br>CCATCACCTGCCGTGCCTCTCAGGGTATT<br>GGCTCTTCCCTGGCTTGGTATCAACAGAA<br>ACCAGGAAAAGCTCCGAAGCTTCTGATC<br>TACGACGCCTCTAACCGTGCCACCGGTAT<br>CCCATCTCGCTTCTCTGGATCCGGTTCCG<br>GGACGGATTTCACTCTGACCATCAGCAGT<br>CTGCAGCCGGAAGACTTCGCAACTTATTA<br>CTGCCAGCAGTACGACCAATGGCCACCTT<br>GGACCTTCGGACAGGGTACCAAGGTGGA<br>GATCAAACGA<br>(SEQ ID NO: 123) |
| TY21588 | GAGGTTCAGCTGGTGGAGTCTGGCGGTGG<br>CCTGGTGCAGCCAGGGGGCTCACTCCGTTT<br>GTCCTGTGCAGCTTCCGGATACTCTATCTCC<br>TCTGGTTACCACTGGGACTGGATTCGTCAG<br>GCCCCGGGTAAGGGCCTCGAGTGGGTGTCT<br>GGTATCTCTGGTTACGGTGGTTCTACCTACT<br>ACGCCGACTCTGTCAAGGGCCGTTTCACTA<br>TAAGTCGCGACAATTCGAAAAACACACTGT<br>ACCTACAACTGAACAGCTTAAGAGCTGAG<br>GACACTGCCGTCTATTATTGCGCCAGACAC<br>AGTTATTACGGTTCCGGTAATTTCGACTACT<br>GGGGTCAAGGAACACTAGTCACCGTCTCCT<br>CG<br>(SEQ ID NO: 111) | GATATCCAGTTGACCCAGTCCCCGAGTTC<br>CCTGTCCGCCTCTGTGGGCGATCGGGTCA<br>CCATCACCTGCCGTGCCTCTGAGTCTGTG<br>GACTTCTTCGGTAAGTCTTTCCTGCACTG<br>GTATCAACAGAAACCAGGAAAAGCTCCG<br>AAGCTTCTGATCTACGACGCCTCTAACCT<br>GGAAACCGGTGTGCCATCTCGCTTCTCTG<br>GATCCGGTTCCGGGACGGATTTCACTCTG<br>ACCATCAGCAGTCTGCAGCCGGAAGACT<br>TCGCAACTTATTACTGCCAGCAGTCCTAC<br>TCCTGGCCTCCGACCTTCGGACAGGGTAC<br>CAAGGTGGAGATCAAACGA<br>(SEQ ID NO: 124) |

TABLE D-continued anti-CTLA4 variable region polynucleotide sequences

| Ab name: | VH: | VL: |
|---|---|---|
| TY21589 | GAGGTTCAGCTGGTGGAGTCTGGCGGTGG<br>CCTGGTGCAGCCAGGGGGCTCACTCCGTTT<br>GTCCTGTGCAGCTTCCGGATTCACCTTCTCC<br>GACTACTGGATTCACTGGGTGCGTCAGGCC<br>CCGGGTAAGGGCCTCGAGTGGATCGGTTGG<br>ATCTCCCCATCTGGCGGTGGTACTAAGTAC<br>GCCCAGAAGTTCCAGGGTCGTGTGACTATA<br>AGTCGCGACAATTCGAAAAACACACTGTAC<br>CTACAACTGAACAGCTTAAGAGCTGAGGA<br>CACTGCCGTCTATTATTGCGCCAGAGGGGC<br>TTACGAATTTGACTACTGGGGTCAAGGAAC<br>ACTAGTCACCGTCTCCTCG<br>(SEQ ID NO: 112) | GATATCCAGTTGACCCAGTCCCCGAGTTC<br>CCTGTCCGCCTCTGTGGGCGATCGGGTCA<br>CCATCACCTGCCGTGCCTCTCAGTCTGTG<br>AGCAGCCGTTTCCTGGCCTGGTATCAACA<br>GAAACCAGGAAAAGCTCCGAAGCTTCTG<br>ATCTACGACGCCTCTAACCGTGCCACCGG<br>TATCCCATCTCGCTTCTCTGGATCCGGTTC<br>CGGGACGGATTTCACTCTGACCATCAGCA<br>GTCTGCAGCCGGAAGACTTCGCAACTTAT<br>TACTGCCAGCAGTCCTACCCCACCCCTCT<br>TACCTTCGGACAGGGTACCAAGGTGGAG<br>ATCAAACGA<br>(SEQ ID NO: 125) |
| TY21580 | GAGGTTCAGCTGGTGGAGTCTGGCGGTGG<br>CCTGGTGCAGCCAGGGGGCTCACTCCGTTT<br>GTCCTGTGCAGCTTCCGGATACTCTATCTCC<br>TCTGGTTACCACTGGAGCTGGATTCGTCAG<br>GCCCCGGGTAAGGGCCTCGAGTGGCTGGC<br>CCGGATCGACTGGGACGATGACAAGTACTA<br>CTCTACCTCTCTGAAGTCTCGTCTGACTATA<br>AGTCGCGACAATTCGAAAAACACACTGTAC<br>CTACAACTGAACAGCTTAAGAGCTGAGGA<br>CACTGCCGTCTATTATTGCGCCAGATCGTAC<br>GTGTACTTCGACTACTGGGGTCAAGGAACA<br>CTAGTCACCGTCTCCTCG<br>(SEQ ID NO: 113) | GATATCCAGTTGACCCAGTCCCCGAGTTC<br>CCTGTCCGCCTCTGTGGGCGATCGGGTCA<br>CCATCACCTGCCGTGCCTCTCAGTCTGTG<br>CGCGGCCGTTTCCTGGCCTGGTATCAACA<br>GAAACCAGGAAAAGCTCCGAAGCTTCTG<br>ATCTACGACGCCTCTAACCGTGCCACCGG<br>TATCCCATCTCGCTTCTCTGGATCCGGTTC<br>CGGGACGGATTTCACTCTGACCATCAGCA<br>GTCTGCAGCCGGAAGACTTCGCAACTTAT<br>TACTGCCAGCAGTCCTCCTCCTGGCCTCC<br>GACCTTCGGACAGGGTACCAAGGTGGAG<br>ATCAAACGA<br>(SEQ ID NO: 126) |
| TY21591 | GAGGTTCAGCTGGTGGAGTCTGGCGGTGG<br>CCTGGTGCAGCCAGGGGGCTCACTCCGTTT<br>GTCCTGTGCAGCTTCCGGATTCTCTCTGTCT<br>ACCGGCGGTGTGGCTGTGAGCTGGATTCGT<br>CAGGCCCCGGGTAAGGGCCTCGAGTGGAT<br>CGGTGAAATCTACCACTCTGGTTCTACCTAC<br>TACTCTCCATCTCTGAAGTCTCGTGTGACTA<br>TAAGTCGCGACAATTCGAAAAACACACTGT<br>ACCTACAACTGAACAGCTTAAGAGCTGAG<br>GACACTGCCGTCTATTATTGCGCCCGTCGTA<br>TCGCCACCGCTACTTACTTCGACTACTGGG<br>GTCAAGGAACACTAGTCACCGTCTCCTCG<br>(SEQ ID NO: 114) | GATATCCAGTTGACCCAGTCCCCGAGTTC<br>CCTGTCCGCCTCTGTGGGCGATCGGGTCA<br>CCATCACCTGCCGTGCCTCTCAGACCGTG<br>TTCTCTCGTTACCTGGCTTGGTATCAACA<br>GAAACCAGGAAAAGCTCCGAAGCTTCTG<br>ATCTACGACGCCTCTAACCGTGCCACCGG<br>TATCCCATCTCGCTTCTCTGGATCCGGTTC<br>CGGGACGGATTTCACTCTGACCATCAGCA<br>GTCTGCAGCCGGAAGACTTCGCAACTTAT<br>TACTGCCAGCAGTCCTACTACTGGCCACC<br>TTGGACCTTCGGACAGGGTACCAAGGTG<br>GAGATCAAACGA<br>(SEQ ID NO: 127) |
| TY21686 | GAGGTTCAGCTGGTGGAGTCTGGCGGTGG<br>CCTGGTGCAGCCAGGGGGCTCACTCCGTTT<br>GTCCTGTGCAGCTTCCGGATTCTCTCTGTCT<br>ACCGGCGGTGTGGCTGTGGGCTGGATTCGT<br>CAGGCCCCGGGTAAGGGCCTCGAGTGGGT<br>GTCTGCTATCTCTGGTTACGGTTCTACTACC<br>TACTACGCCGACTCTGTCAAGGGCCGTTTC<br>ACTATAAGTCGCGACAATTCGAAAAACACA<br>CTGTACCTACAACTGAACAGCTTAAGAGCT<br>GAGGACACTGCCGTCTATTATTGCGCCAGA<br>TTGCCATACTCCGCCTACGCTTTCGACTACT<br>GGGGTCAAGGAACACTAGTCACCGTCTCCT<br>CG<br>(SEQ ID NO: 115) | GATATCCAGTTGACCCAGTCCCCGAGTTC<br>CCTGTCCGCCTCTGTGGGCGATCGGGTCA<br>CCATCACCTGCCGTGCCTCTCAGGGTGTG<br>TCTTCTTACCTGGCCTGGTATCAACAGAA<br>ACCAGGAAAAGCTCCGAAGCTTCTGATC<br>TACGCCGCCTCTACCTTGCAGTCTGGTGT<br>GCCATCTCGCTTCTCTGGATCCGGTTCCG<br>GGACGGATTTCACTCTGACCATCAGCAGT<br>CTGCAGCCGGAAGACTTCGCAACTTACTA<br>CTGCCAGCACCACTACGGCACCCCACTG<br>ACCTTCGGTCAGGGTACCAAGGTGGAGA<br>TCAAACGA<br>(SEQ ID NO: 128) |
| TY21687 | GAGGTTCAGCTGGTGGAGTCTGGCGGTGG<br>CCTGGTGCAGCCAGGGGGCTCACTCCGTTT<br>GTCCTGTGCAGCTTCCGGATTCACCTTCTCC<br>GGCTACGCTATTCACTGGGTGCGTCAGGCC<br>CCGGGTAAGGGCCTCGAGTGGATCGGTATC<br>ATCTCCCCATCTGGCGGTGGTACTAAGTAC<br>GCCCAGAAGTTCCAGGGTCGTGTGACTATA<br>AGTCGCGACAATTCGAAAAACACACTGTAC<br>CTACAACTGAACAGCTTAAGAGCTGAGGA<br>CACTGCCGTCTATTATTGCGCCAGACACCC<br>ATTCGCCTACTGGGGTCAAGGAACACTAGT<br>CACCGTCTCCTCG<br>(SEQ ID NO: 116) | GATATCCAGTTGACCCAGTCCCCGAGTTC<br>CCTGTCCGCCTCTGTGGGCGATCGGGTCA<br>CCATCACCTGCCGTGCCTCTCAGTCTGTG<br>GACTTCTACGGTATCTCTTTCCTGGACTG<br>GTATCAACAGAAACCAGGAAAAGCTCCG<br>AAGCTTCTGATCTACGACGCCTCTAACCG<br>TGCCACCGGTATCCCATCTCGCTTCTCTGG<br>ATCCGGTTCCGGGACGGATTTCACTCTGA<br>CCATCAGCAGTCTGCAGCCGGAAGACTT<br>CGCAACTTATTACTGCCAGCAGTACGTCT<br>CTTCGCCACCAGAGTACACCTTCGGACAG<br>GGTACCAAGGTGGAGATCAAACGA<br>(SEQ ID NO: 129) |
| TY21689 | GAGGTTCAGCTGGTGGAGTCTGGCGGTGG<br>CCTGGTGCAGCCAGGGGGCTCACTCCGTTT<br>GTCCTGTGCAGCTTCCGGATACACCTTCTC<br>CGGCTACGGTATTCACTGGGTGCGTCAGGC<br>CCCGGGTAAGGGCCTCGAGTGGATCGGTG | GATATCCAGTTGACCCAGTCCCCGAGTTC<br>CCTGTCCGCCTCTGTGGGCGATCGGGTCA<br>CCATCACCTGCCGTGCCTCTCAGTCTGTG<br>GACTTCGACGGTTTCTCTTTCCTGCACTG<br>GTATCAACAGAAACCAGGAAAAGCTCCG |

TABLE D-continued

| anti-CTLA4 variable region polynucleotide sequences | | |
|---|---|---|
| Ab name: | VH: | VL: |
| | AAATCTACCACTCTGGTTCTACCTACTACTC TCCATCTCTGAAGTCTCGTGTGACTATAAGT CGCGACAATTCGAAAAACACACTGTACCTA CAACTGAACAGCTTAAGAGCTGAGGACAC TGCCGTCTATTATTGCGCCAGAAGAATTGAC GCCTTCGACATCTGGGGTCAAGGAACACTA GTCACCGTCTCCTCG (SEQ ID NO: 117) | AAGCTTCTGATCTACGACGCCTCTTCTCT GGAATCTGGTGTGCCATCTCGCTTCTCTG GATCCGGTTCCGGGACGGATTTCACTCTG ACCATCAGCAGTCTGCAGCCGGAAGACT TCGCAACTTATTACTGCCAGCAGCGTGAC TCCTGGCCTTACACCTTCGGACAGGGTAC CAAGGTGGAGATCAAACGA (SEQ ID NO: 130) |
| TY21680 | GAGGTTCAGCTGGTGGAGTCTGGCGGTGG CCTGGTGCAGCCAGGGGGCTCACTCCGTTT GTCCTGTGCAGCTTCCGGATACACCTTCTC CGGCTACGCTATTCACTGGGTGCGTCAGGC CCCGGGTAAGGGCCTCGAGTGGATCGGTAT CATCTCCCCATCTGGCGGTGGTACTAAGTAC GCCCAGAAGTTCCAGGGTCGTGTGACTATA AGTCGCGACAATTCGAAAAACACACTGTAC CTACAACTGAACAGCTTAAGAGCTGAGGA CACTGCCGTCTATTATTGCGCCAGACTCTAT GACGTTGCCTACTGGGGTCAAGGAACACTA GTCACCGTCTCCTCG (SEQ ID NO: 118) | GATATCCAGTTGACCCAGTCCCCGAGTTC CCTGTCCGCCTCTGTGGGCGATCGGGTCA CCATCACCTGCCGTGCCTCTCAGTCTGTG GACTTCCACGGTAAGTCTTTCCTGCACTG GTATCAACAGAAACCAGGAAAAGCTCCG AAGCTTCTGATCTACGACGCCTCTTCTCT GGAATCTGGTGTGCCATCTCGCTTCTCTG GATCCGGTTCCGGGACGGATTTCACTCTG ACCATCAGCAGTCTGCAGCCGGAAGACT TCGCAACTTATTACTGCGAGCAATCCCTG GAAGTCCCATTCACCTTCGGACAGGGTAC CAAGGTGGAGATCAAACGA (SEQ ID NO: 131) |
| TY21691 | GAGGTTCAGCTGGTGGAGTCTGGCGGTGG CCTGGTGCAGCCAGGGGGCTCACTCCGTTT GTCCTGTGCAGCTTCCGGATTCACCTTCTCC GACTACGCTATTCACTGGGTGCGTCAGGCC CCGGGTAAGGGCCTCGAGTGGATCGGTATC ATCTCCCCATCTGGCGGTTCTACTAAGTACG CCCAGAAGTTCCAGGGTCGTGTGACTATAA GTCGCGACAATTCGAAAAACACACTGTACC TACAACTGAACAGCTTAAGAGCTGAGGAC ACTGCCGTCTATTATTGCGCCAGACTCGGTT ACGGGTACTTCGACGTCTGGGGTCAAGGA ACACTAGTCACCGTCTCCTCG (SEQ ID NO: 119) | GATATCCAGTTGACCCAGTCCCCGAGTTC CCTGTCCGCCTCTGTGGGCGATCGGGTCA CCATCACCTGCCGTGCCTCTCAGTCTGTG GACTTCTACGGTATCTCTTTCCTGCACTGG TATCAACAGAAACCAGGAAAAGCTCCGA AGCTTCTGATCTACGACGCCTCTTCTCTG GAATCTGGTGTGCCATCTCGCTTCTCTGG ATCCGGTTCCGGGACGGATTTCACTCTGA CCATCAGCAGTCTGCAGCCGGAAGACTT CGCAACTTATTACTGCGTGCAGGCTCTTC AGTTGCCTCTTACCTTCGGACAGGGTACC AAGGTGGAGATCAAACGA (SEQ ID NO: 132) |
| TY21692 | GAGGTTCAGCTGGTGGAGTCTGGCGGTGG CCTGGTGCAGCCAGGGGGCTCACTCCGTTT GTCCTGTGCAGCTTCCGGATACTCTATCACC TCTGGTCACTACTGGAGCTGGATTCGTCAG GCCCCGGGTAAGGGCCTCGAGTGGATCGGT GACATCTCCCACTCTGGTTCTACCTACTACT CTCAATCTCTGAAGTCTCGTGTGACTATAAG TCGCGACAATTCGAAAAACACACTGTACCT ACAACTGAACAGCTTAAGAGCTGAGGACA CTGCCGTCTATTATTGCGCGCGTGGTAGTAG GACCGGCTACTTCGACTATTGGGGTCAAGG AACACTAGTCACCGTCTCCTCG (SEQ ID NO: 120) | GATATCCAGTTGACCCAGTCCCCGAGTTC CCTGTCCGCCTCTGTGGGCGATCGGGTCA CCATCACCTGCCGTGCCTCTCAGTCTATCT CTTCTTACCTGAACTGGTATCAACAGAAA CCAGGAAAAGCTCCGAAGCTTCTGATCTA CGACGCCTCTAACCTGGAAACCGGTGTG CCATCTCGCTTCTCTGGATCCGGTTCCGG GACGGATTTCACTCTGACCATCAGCAGTC TGCAGCCGGAAGACTTCGCAACTTACTAC TGCCAGCACCACTACGGCACCCCACTGA CCTTCGGTCAGGGTACCAAGGTGGAGATC AAACGA (SEQ ID NO: 133) |

TABLE E

| Antibody component sequences | | |
|---|---|---|
| Name: | Sequence: | Notes: |
| Mm formula | Formula (XVIII): $X_mCX_nCZ_o$ (SEQ ID NO: 134) | where m is from 3-10, n is from 3-10, and o is from 1-10, where each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P |
| MM formula | Formula (XIX): $Z_mCZ_nCZ_o$ (SEQ ID NO: 135) | where m is from 3-10, n is from 3-10, and o is from 1-10, wherein each Z is independently an amino acid selected from the group consisting of D, A, Y, S, T, N, I, L, F, V, H, and P |

TABLE E-continued

| Antibody component sequences | | |
|---|---|---|
| Name: | Sequence: | Notes: |
| MM formula | Formula (XX): $(NNK)_m$TGY$(NNK)_n$TGY$(NHC)_o$ (SEQ ID NO: 136) | wherein each N is independently A, G, T, or C, wherein each K is independently T or G, wherein each Y is independently T or C, and wherein each H is independently A, T, or C |
| MM formula | Formula (XXI): Z6CX6CZ2 (SEQ ID NO: 137) | where each X is independently an amino acid selected from the group consisting of A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P |
| MM formula | Formula (XXII): Z6CX8CZ2 (SEQ ID NO: 138) | where each X is independently an amino acid selected from the group consisting of A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P |
| MM formula | Formula (XXIII): (Z6)C(Z6)C(Z2) (SEQ ID NO: 139) | where each Z is independently an amino acid selected from the group consisting of D, A, Y, S, T, N, I, L, F, V, H, and P |
| MM formula | Formula (XXIV): (Z6)C(28)C(Z2) (SEQ ID NO: 140) | where each Z is independently an amino acid selected from the group consisting of D, A, Y, S, T, N, I, L, F, V, H, and P |
| CTLA4 MM1 | NFVADSCPDHPYPCSA (SEQ ID NO: 141) | |
| CTLA4 MM2 | IVHHSDCDAFYPYCDS (SEQ ID NO: 142) | |
| CTLA4 MM3 | YSAYPACDSHYPYCNS (SEQ ID NO: 143) | |
| CTLA4 MM4 | PNPSSDCVPYYYACAY (SEQ ID NO: 144) | |
| CTLA4 MM5 | YSAYPACDSHYPYCQS (SEQ ID NO: 145) | |
| CTLA4 MM6 | PQPSSDCVPYYYACAY (SEQ ID NO: 146) | |
| CTLA4 MM7 | PNPASDCVPYYYACAY (SEQ ID NO: 147) | |
| N-terminal sequence on masking moieties | EVGSY (SEQ ID NO: 148) | |
| Protease cleavage site | SGRSA (SEQ ID NO: 149) | |
| Protease cleavage site | PLGLAG (SEQ ID NO: 150) | |
| Protease cleavage site | ENLYFQG (SEQ ID NO: 151) | |
| MM + CM | Formula (XXV): EVGSY(Z6)C(Z6)C(Z2)SGRSA (SEQ ID NO: 152) | where each Z is independently an amino acid selected from D, A, Y, S, T, N, I, L, F, V, H, and P |
| MM + CM | Formula (XXVI): EVGSY(Z6)C(X6)C(Z2)SGRSA (SEQ ID NO: 153) | each X is independently an amino acid selected from A, C, D, E, F, G, H, I, K, L, M, N, P, Q, R, S, T, V, W, and Y, and |

TABLE E-continued

| Antibody component sequences | | |
|---|---|---|
| Name: | Sequence: | Notes: |
| | | where each Z is independently an amino acid selected from the group consisting of D, A, Y, S, T, N, I, L, F, V, H, and P |
| MM + CM | Formula (XXVII): EVGSY(Z6)C(Z8)C(Z2)SGRSA (SEQ ID NO: 154) | where each Z is independently an amino acid selected from D, A, Y, S, T, N, I, L, F, V, H, and P |
| MM + CM | Formula (XXVIII): EVGSY(Z6)C(X8)C(Z2)SGRSA (SEQ ID NO: 155) | where each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P |
| Linker | GGGGS (SEQ ID NO: 156) | |
| Linker | SGGS (SEQ ID NO: 157) | |
| Linker | GGSG (SEQ ID NO: 158) | |
| Linker | GGSGG (SEQ ID NO: 159) | |
| Linker | GSGSG (SEQ ID NO: 160) | |
| Linker | GSGGG (SEQ ID NO: 161) | |
| Linker | GGGSG (SEQ ID NO: 162) | |
| Linker | GSSSG (SEQ ID NO: 163) | |
| MM + CM + Linkers | Formula (XXIX): EVGSY$X_1X_2X_3X_4X_5X_6$C$X_7X_8X_9X_{10}X_{11}X_{12}X_{13}X_{14}$SGRSAGGGGTENLYFQGSGGS (SEQ ID NO: 164) | |
| BC2071 | EVGSYDALHYACPPDYYACYYSGRSAGGGGTENLYFQGSGGS (SEQ ID NO: 165) | |
| BC2072 | EVGSYNSYHAYCPHPLYPCTASGRSAGGGGTENLYFQGSGGS (SEQ ID NO: 166) | |
| BC2075 | EVGSYASSAVLCVTAYFSCNSSGRSAGGGGTENLYFQGSGGS (SEQ ID NO: 167) | |
| BC2078 | EVGSYNFVADSCPDHPYPCSASGRSAGGGGSPLGLAGSGGS (SEQ ID NO: 168) | |
| BC2078-alternate | EVGSYNFVADSCPDHPYPCSASGRSAGGGGTENLYFQGSGGS (SEQ ID NO: 169) | |
| BC2079 | EVGSYIVHHSDCDAFYPYCDSSGRSAGGGGSPLGLAGSGGS (SEQ ID NO: 170) | |
| BC2079-alternate | EVGSYIVHHSDCDAFYPYCDSSGRSAGGGGTENLYFQGSGGS (SEQ ID NO: 171) | |
| BC2081 | EVGSYYSAYPACDSHYPYCNSSGRSAGGGGSPLGLAGSGGS (SEQ ID NO: 172) | |
| BC2081-alternate | EVGSYYSAYPACDSHYPYCNSSGRSAGGGGTENLYFQGSGGS (SEQ ID NO: 173) | |
| BC2086 | EVGSYPNPSSDCVPYYYACAYSGRSAGGGGSPLGLAGSGGS (SEQ ID NO: 174) | |

TABLE E-continued

| Antibody component sequences | | |
|---|---|---|
| Name: | Sequence: | Notes: |
| BC2086-alternate | EVGSYPNPSSDCVPYYYACAYSGRSAGGGGTENLYFQGSGGS (SEQ ID NO: 175) | |
| TY22563 | EVGSYYSAYPACDSHYPYCQSSGRSAGGGGSPLGLAGSGGS (SEQ ID NO: 176) | |
| | EVGSYYSAYPACDSHYPYCNSAGRSAGGGGSPLGLAGSGGS (SEQ ID NO: 177) | |
| | EVGSYPQPSSDCVPYYYACAYSGRSAGGGGSPLGLAGSGGS (SEQ ID NO: 178) | |
| | EVGSYPNPASDCVPYYYACAYSGRSAGGGGSPLGLAGSGGS (SEQ ID NO: 179) | |
| Invariant cleavage sequence | SGRSAGGGGSPLGLAGSGGS, SEQ ID NO: 180 | |

TABLE F

| Further Antibody component sequences | | |
|---|---|---|
| SEQ ID NO: | Sequence: | Notes: |
| 181 | XmCPDHPYPCXX | For all of the sequences with Xs, m is from 2-10, and each X is independently an amino acid selected from the group consisting of A, C, D, E, F, G, H, I, K, L, M, N, P, Q, R, S, T, V, W, and Y |
| 182 | XmCDAFYPYCXX | For all of the sequences with Xs, m is from 2-10, and each X is independently an amino acid selected from the group consisting of A, C, D, E, F, G, H, I, K, L, M, N, P, Q, R, S, T, V, W, and Y |
| 183 | XmCDSHYPYCXX | For all of the sequences with Xs, m is from 2-10, and each X is independently an amino acid selected from the group consisting of A, C, D, E, F, G, H, I, K, L, M, N, P, Q, R, S, T, V, W, and Y |
| 184 | XmCVPYYYACXX | For all of the sequences with Xs, m is from 2-10, and each X is independently an amino acid selected from the group consisting of A, C, D, E, F, G, H, I, K, L, M, N, P, Q, R, S, T, V, W, and Y |
| 185 | Blank Sequence | |
| 186 | Blank Sequence | |
| 187 | Blank Sequence | |
| 188 | Blank Sequence | |
| 189 | EVGSYNFVADSCPDHPYPCSA | |
| 190 | EVGSYIVHHSDCDAFYPYCDS | |
| 191 | EVGSYYSAYPACDSHYPYCNS | |
| 192 | EVGSYPNPSSDCVPYYYACAY | |
| 193 | EVGSYYSAYPACDSHYPYCQS | |

TABLE F-continued

| Further Antibody component sequences | | |
|---|---|---|
| SEQ ID NO: | Sequence: | Notes: |
| 194 | Blank Sequence | |
| 195 | EVGSYPQPSSDCVPYYYACAY | |
| 196 | EVGSYPNPASDCVPYYYACAY | |
| 197 | EVGSYIVHHSDCDAFYPYCDSSGRSAGGGG TPLGLAGSGGS | |
| 198 | EVGHSDCDAFYPYCDSSGRSAGGGGTPLGL AGSGGS | |
| 199 | EDCDAFYPYCDSSGRSAGGGGTPLGLAGSG GS | |
| 200 | EVGSYPNPSSDCVPYYYACAYSGRSAGGG GTPLGLAGSGGS | |
| 201 | EVGSSDCVPYYYACAYSGRSAGGGGTPLG LAGSGGS | |
| 202 | EDCVPYYYACAYSGRSAGGGGTPLGLAGS GGS | |
| 203 | MHVAQPAVVLASSRGIASFVCEYASPGKAT EVRVTVLRQADSQVTEVCAATYMMGNELT FLDDSICTGTSSGNQVNLTIQGLRAMDTGL YICKVELMYPPPYYLGIGNGAQIYVIDPE | |
| 204 | MHVAQPAVVLASSRGIASFVCEYASPGKAT EVRVTVLRQADSQVTEVCAATYMMGNELT FLDDSICTGTSSGNQVNLTIQGLRAMDTGL YICKVELMYPPPYYLGIGNGTQIYVIDPE | |
| 205 | KAMHVAQPAVVLASSRGIASFVCEYASPGK ATEVRVTVLRQADSQVTEVCAATYMMGN ELTFICTGTSSGNQVNLTIQGLRAMDTGLYI CKVELMYPPPYYLGIGNGTQIYVIDP | |
| 206 | AMHVAQPAVVLASSRGIASFVCEYASPGKA TEVRVTVLRQADSQVTEVCAATYMMGNEL TFDSICTGTSSGNQVNLTIQGLRAMDTGLYI CKVELMYPPPYYLGIGNGTQIYVI | |
| 207 | KAMHVAQPAVVLASSRGIASFVCEYASPGK ATEVRVTVLRQADSQVTEVCAATYMMGN ELTFLDDSICTGTSSGNQVNLTIQGLRAMDT GLYICKVELMYPPPYYLGIGNGTQIYVIDPE | *Homo sapiens* |
| 208 | EAIQVTQPSVVLASSHGVASFPCEYSPSHNT DEVRVTVLRQTNDQMTEVCATTFTEKNTV GFLDYPFCSGTFNESRVNLTIQGLRAVDTGL YLCKVELMYPPPYFVGMGNGTQIYVIDPE | *Mus musculus* |
| 209 | EVGSYPNPSSDCVPYYYACAYSGRSAPLGL A | |
| 210 | EDCVPYYYACAYSGRSAPLGLA | |
| 211 | EDCVPYYYACAYSGRSA | |
| 212 | EDCVPYYYACAYPLGLA | |
| 213 | EDCVPYYYACAY | |
| 214 | EVGSSDCVPYYYACAY | |
| 215 | EDCDAFYPYCDS | |
| 216 | EVGHSDCDAFYPYCDS | |
| 217 | EV(Zn)C(X8)C(Z2)SGRSA | where each X is independently an amino acid selected from the group consisting of A, C, D, E, F, G, H, I, K, L, M, N, P, Q, R, S, T, V, W, and Y, wherein nis 1-1 land wherein each Z is independently an |

TABLE F-continued

| Further Antibody component sequences | | |
|---|---|---|
| SEQ ID NO: | Sequence: | Notes: |
| | | amino acid selected from the group consisting of D, A, Y, S, T, N, I, L, F, V, H, and P. |
| 218 | EDC(Z6)C(Z2)SGRSA | where each Z is independently an amino acid selected from D, A, Y, S, T, N, I, L, F, V, H, and P. |
| 219 | EDC(Z6)C(Z2)PLGLA | where each Z is independently an amino acid selected from D, A, Y, S, T, N, I, L, F, V, H, and P. |
| 220 | SGRSAGGGGTENLYFQGSGGS | |
| 221 | SGRSAGGGGTPLGLAGSGGS | |
| 222 | SGRSAPLGLA | |
| 223 | FSLSTGGVGVGWI | |
| 224 | LALIDWADDKYYSPSLKSRL | |
| 225 | ARGGSDTVIGDWFAY | |
| 226 | RASQSIGSYLA | |
| 227 | DASNLETGV | |
| 228 | YCQQGYYLWT | |
| 229 | EVQLVESGGGLVQPGGSLRLSCAASGFSLSTGGVGVGWIRQAPGKGLEWLALIDWADDKYYSPSLKSRLTISRDNSKNTLYLQLNSLRAEDTAVYYCARGGSDTVIGDWFAYWGQGTLVTVSS | |
| 230 | DIQLTQSPSSLSASVGDRVTITCRASQSIGSYLAWYQQKPGKAPKLLIYDASNLETGVPSRFSGSGSGTDFTLTISSLQPEDFATYYCQQGYYLWTFGQGTKVEIK | |

SEQ ID NO: 231 human CD137 amino acid sequence
MGNSCYNIVATLLLVLNFERTRSLQDPCSNCPAGTFCDNNRNQICSPCPPNSESSAGGQRTCDICRQCKGVFRTRKE
CSSTSNAECDCTPGFHCLGAGCSMCEQDCKQGQELTKKGCKDCCFGFNDQKRGICRPWTNCSLDGKSVLVNGTKER
DVVCGPSPADLSPGASSVTPPAPAREPGHSPQIISFFLALTSTALLFLLFFLTLRFSVVKRGRKKLLYIFKQPFMRP
VQTTQEEDGCSCRFPEEEEGGCEL

SEQ ID NO: 232 ADG106 HVR-H1
FSLSTGGVGVGWI

SEQ ID NO: 233 ADG106 HVR-H2
LALIDWADDKYYSPSLKSRL

SEQ ID NO: 234 ADG106 HVR-H3
ARGGSDTVIGDWFAY

SEQ ID NO: 235 ADG106 HVR-L1
RASQSIGSYLA

SEQ ID NO: 236 ADG106 HVR-L2
DASNLETGV

SEQ ID NO: 237 ADG106 HVR-L3
YCQQGYYLWT

SEQ ID NO: 238 ADG106 VH
EVQLVESGGGLVQPGGSLRLSCAASGFSLSTGGVGVGWIRQAPGKGLEWLALIDWADDKYYSPSLKSRLTISRDNSK
NTLYLQLNSLRAEDTAVYYCARGGSDTVIGDWFAYWGQGTLVTVSS

SEQ ID NO: 239 ADG106 VL
DIQLTQSPSSLSASVGDRVTITCRASQSIGSYLAWYQQKPGKAPKLLIYDASNLETGVPSRFSGSGSGTDFTLTISS
LQPEDFATYYCQQGYYLWTFGQGTKVEIKR

-continued

SEQ ID NO: 240 ADG106 Heavy Chain
EVQLVESGGGLVQPGGSLRLSCAASGFSLSTGGVGVGWIRQAPGKGLEWLALIDWADDKYYSPSLKSRLTISRDNSK
NTLYLQLNSLRAEDTAVYYCARGGSDTVIGDWFAYWGQGTLVTVSSASTKGPSVFPLAPCSRSTSESTAALGCLVKD
YFPEPVTVSWNSGALTSGVHTFPAVLQSSGLYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFNWYVDGVEVHNAKTKPREEQFNSTYRVVSV
LTVLHQDWLNGKEYKCKVSNKGLPSSIEKTISKAKGQPREPQVYTLPPSQEEMTKNQVSLTCLVKGFYPSDIAVEWE
SNGQPENNYKTIPPVLDSDGSFFLYSRLTVDKSRWQEGNVFSCSVMHEALHNHYTQKSLSLSLGK SEQ ID NO: 241 ADG106 Light Chain
DIQLTQSPSSLSASVGDRVTITCRASQSIGSYLAWYQQKPGKAPKLLIYDASNLETGVPSRFSGSGSGTDFTLTISS
LQPEDFATYYCQQGYYLWTFGQGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC

SEQ ID NO: 242 AG10059 HVR-H1
YSITSGHYWAWI

SEQ ID NO: 243 AG10059 HVR-H2
VSSISGYGSTTYYADSVKGRF

SEQ ID NO: 244 AG10059 HVR-H3
ARGGSDAVLGDWFAY

SEQ ID NO: 245 AG10059 HVR-L1
RASQGIGSFLA

SEQ ID NO: 246 AG10059 HVR-L2
DASNLETGV

SEQ ID NO: 247 AG10059 HVR-L3
YCQQGYYLWT

SEQ ID NO: 248 AG10059 VH
EVQLVESGGGLVQPGGSLRLSCAASGYSITSGHYWAWIRQAPGKGLEWVSSISGYGSTTYYADSVKGRFTISRDNSK
NTLYLQLNSLRAEDTAVYYCARGGSDAVLGDWFAYWGQGTLVTVSS

SEQ ID NO: 249 AG10059 VL
DIQLTQSPSSLSASVGDRVTITCRASQGIGSFLAWYQQKPGKAPKLLIYDASNLETGVPSRFSGSGSGTDFTLTISS
LQPEDFATYYCQQGYYLWTFGQGTKVEIKR

SEQ ID NO: 250 AG10059 Heavy chain
EVQLVESGGGLVQPGGSLRLSCAASGYSITSGHYWAWIRQAPGKGLEWVSSISGYGSTTYYADSVKGRFTISRDNSK
NTLYLQLNSLRAEDTAVYYCARGGSDAVLGDWFAYWGQGTLVTVSSASTKGPSVFPLAPCSRSTSESTAALGCLVKD
YFPEPVTVSWNSGALTSGVHTFPAVLQSSGLYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFNWYVDGVEVHNAKTKPREEQFNSTYRVVSV
LTVLHQDWLNGKEYKCKVSNKGLPSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHYTQKSLSLSLGK SEQ ID NO: 251 AG10059 Light chain
DIQLTQSPSSLSASVGDRVTITCRASQGIGSFLAWYQQKPGKAPKLLIYDASNLETGVPSRFSGSGSGTDFTLTISS
LQPEDFATYYCQQGYYLWTFGQGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC

SEQ ID NO: 252 AG10058 HVR-H1
FSLSTSGVGVGWI

SEQ ID NO: 253 AG10058 HVR-H2
LALIDWDDDKYYSPSLKSRL

SEQ ID NO: 254 AG10058 HVR-H3
ARGGSDTVLGDWFAY

SEQ ID NO: 255 AG10058 HVR-L1
RASQSVSPYLA

SEQ ID NO: 256 AG10058 HVR-L2
DASSLESGV

SEQ ID NO: 257 AG10058 HVR-L3
YCQQGYSLWT

SEQ ID NO: 258 AG10058 VH
EVQLVESGGGLVQPGGSLRLSCAASGFSLSTSGVGVGWIRQAPGKGLEWLALIDWDDDKYYSPSLKSRLTISRDNSK
NTLYLQLNSLRAEDTAVYYCARGGSDTVLGDWFAYWGQGTLVTVSS

SEQ ID NO: 259 AG10058 VL
DIQLTQSPSSLSASVGDRVTITCRASQSVSPYLAWYQQKPGKAPKLLIYDASSLESGVPSRFSGSGSGTDFTLTISS
LQPEDFATYYCQQGYSLWTFGQGTKVEIKR

-continued

SEQ ID NO: 260 AG10058 Heavy chain
EVQLVESGGGLVQPGGSLRLSCAASGFSLSTSGVGVGWIRQAPGKGLEWLALIDWDDDKYYSPSLKSRLTISRDNSK
NTLYLQLNSLRAEDTAVYYCARGGSDTVLGDWFAYWGQGTLVTVSSASTKGPSVFPLAPCSRSTSESTAALGCLVKD
YFPEPVTVSWNSGALTSGVHTFPAVLQSSGLYSLSSVVTVPSSSLGTKTYICNVDHKPSNTKVDKRVESKYGPPCPP
CPAPEFLGGPSVFLFPPKPKDTLMISRIPEVTCVVVDVSQEDPEVQFNWYVDGVEVHNAKTKPREEQFNSTYRVVSV
LTVLHQDWLNGKEYKCKVSNKGLPSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHYTQKSLSLSLGK SEQ ID NO: 261 AG10058 Light chain
DIQLTQSPSSLSASVGDRVTITCRASQSVSPYLAWYQQKPGKAPKLLIYDASSLESGVPSRFSGSGSGTDFTLTISS
LQPEDFATYYCQQGYSLWTFGQGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSENRGEC SEQ ID NO: 262 HVR-H1 Formula (I)
X1TFX2X3YX4IHWV, wherein X1 is F or Y, X2 is S or T, X3 is G, N, or S, and X4 is A, G, or W SEQ ID NO: 263 HVR-H1 Formula (II)
YSIX1SGX2X3WX4WI, wherein X1 is S or T, X2 is H or Y, X3 is H or Y, and X4 is A, D, G, N, S, or T SEQ ID NO: 264 HVR-H1 Formula (III)
FSLSTX1GVX2VX3WI, wherein X1 is G or S, X2 is A or G, and X3 is A, G, S, or T SEQ ID NO: 265 HVR-H2 Formula (IV)
LALIDWX1X2DKX3YSX4SLKSRL, wherein X1 is A, D, or Y, X2 is D or G, X3 is R, S, or Y, and X4 is P or T SEQ ID NO: 266 HVR-H2 Formula (V)
IGX1IYHSGX2TYYX3PSLKSRV, wherein X1 is D or E, X2 is N or S, and X3 is N or S SEQ ID NO: 267 HVR-H2 Formula (VI)
VSX1ISGX2GX3X4TYYADSVKGRF, wherein X1 is A, G, S, V, or Y, X2 is A, D, S, or Y, X3 is D, G, or S, and X4 is S or T SEQ ID NO: 268 HVR-H3 Formula (VII)
ARX1GX2X3X4VX5GDWFX6Y, wherein X1 is E or G, X2 is E or S, X3 is D or T, X4 is A, T, or V, X5 is A, I, L, T, or V, and X6 is A, D, or G SEQ ID NO: 269 HVR-LI Formula (VIII)
X1ASQX2X3X4X5X6X7X8, wherein X1 is Q or R, X2 is D, G, or S, X3 is I or V, X4 is G, R, S, or T, X5 is P, R, S, or T, X6 is A, D, F, S, V, or Y, X7 is L or V, and X8 is A, G, or N SEQ ID NO: 270 HVR-L2 Formula (IX)
X1ASX2X3X4X5GX6, wherein X1 is A or D, X2 is N, S, or T, X3 is L or R, X4 is A, E, or Q, X5 is S or T, and X6 is I or V SEQ ID NO: 271 HVR-L3 Formula (X)
YCQQX1YX2X3X4T, wherein X1 is A, G, S, or Y, X2 is Q, S, or Y, X3 is I, L, T, or Y, and X4 is I, S, V, or W SEQ ID NO: 272 HVR-L3 Formula (XI)
YCX1QX2X3X4X5PX6T, wherein X1 is E or Q, X2 is P, S, or Y, X3 is D, L, S, T, or Y, X4 is D, E, H, S, or T, X5 is D, L T, or W, and X6 is L, P, R, or V SEQ ID NO: 273 sCD137 amino acid sequence
LQDPCSNCPAGTFCDNNRNQICSPCPPNSFSSAGGQRTCDICRQCKGVFRTRKECSSTSNAECDCTPGFHCL
GAGCSMCEQDCKQGQELTKKGCKDCCFGTFNDQKRGICRPWTNCSLDGKSVLVNGTKERDVVCGPSPAD
LSPGASSVTPPAPAREPGHSPQ SEQ ID NO: 274 CD137L nucleic acid sequence
Atggaatacgcctctgacgcttcactggaccccgaagccccgtggcctcccgcgccccgcgctcgcgcctgccgcgtactgccttgggccctg
gtcgcggggctgctgctgctgctgctgctcgctgccgcctgcgccgtcttcctcgcctgcccctgggccgtgtccggggctcgcgcctcgccc
ggctccgcggccagcccgagactccgcgagggtcccgagctttcgcccgacgatcccgccggcctcttggacctgcggcagggcatgtttgcg
cagctggtggcccaaaatgttctgctgatcgatgggcccctgagctggtacagtgacccaggcctggcaggcgtgtccctgacgggggcctg
agctacaaagaggacacgaaggagctggtggtggccaaggctggagtctactatgtcttctttcaactagagctgcggcgcgtggtggccggc
gagggctcaggctccgtttcacttgcgctgcacctgcagccactgcgctctgctgctggggccgccgccctggctttgaccgtggacctgcca
cccgcctcctccgaggctcggaactcggccttcggtttccagggccgcttgctgcacctgagtgccggccagcgcctgggcgtccatcttcac
actgaggccagggcacgccatgcctggcagcttacccagggcgccacagtcttgggactcttccgggtgacccccgaaatcccagccggactc
ccttcaccgaggtcggaa SEQ ID NO: 275 CD137L amino acid sequence
MEYASDASLD PEAPWPPAPR ARACRVLPWA LVAGLLLLLL LAAACAVFLA
CPWAVSGARA SPGSAASPRL REGPELSPDD PAGLLDLRQG MFAQLVAQNV
LLIDGPLSWY SDPGLAGVSL TGGLSYKEDT KELVVAKAGV YYVFFQLELR
RVVAGEGSGS VSLALHLQPL RSAAGAAALA LTVDLPPASS EARNSAFGFQ
GRLLHLSAGQ RLGVHLHTEA RARHAWqLTQ GATVLGLFRV TPEIPAGLPS
PRSE -continued SEQ ID NO: 276 PD-L1 amino acid sequence
MRIFAVFIFMTYWHLLNAFTVTVPKDLYVVEYGSNMTIECKFPVEKQLDLAALIVYWEMEDKNIIQFVHGE
DLKVQHSSYRQRARLLKDQLSLGNAALQITDVKLQDAGVYRCMISYGGADYKRITVKVNAPYNKINQRIL
VVDPVTSEHELTCQAEGYPKAEVIWTSSDHQVLSGKTTTTNSKREEKLFNVTSTLRINTTTNEIFYCTFRRL
DPEENHTAELVIPELPLAHPPNERTHLVILGAILLCLGVALTFIFRLRKGRMMDVKKCGIQDTNSKKQSDTH
LEET SEQ ID NO: 277 Ki67 amino acid sequence
MWPTRRLVTIKRSGVDGPHFPLSLSTCLFGRGIECDIRIQLPVVSKQHCKIETHEQEAILANFSSTNPTQVNGSVID
EPVRLKHGDVITIIDRSFRYENESLQNGRKSTEFPRKIREQEPARRVSRSSFSSDPDEKAQDSKAYSKITEGKVSGN
PQVHIKNVKEDSTADDSKDSVAQGTTNVHSSEHAGRNGRNAADPISGDFKEISSVKLVSRYGELKSVPTTQCLDNSK
KNESPFWKLYESVKKELDVKSQKENVLQYCRKSGLQTDYATEKESADGLQGETQLLVSRKSRPKSGGSGHAVAEPAS
PEQELDQNKGKGRDVESVQTPSKAVGASFPLYEPAKMKTPVQYSQQQNSPQKHKNKDLYTTGRRESVNLGKSEGFKA
GDKTLTPRKLSTRNRTPAKVEDAADSATKPENLSSKIRGSIPTDVEVLPTETEIHNEPFLTLWLTQVERKIQKDSLS
KPEKLGTTAGQMCSGLPGLSSVDINNFGDSINESEGIPLKRRRVSFGGHLRPELFDENLPPNTPLKRGEAPTKRKSL
VMHTPPVLKKIIKEQPQPSGKQESGSEIHVEVKAQSLVISPPAPSPRKIPVASDQRRRSCKTAPASSSKSQTEVPKR
GGRKSGNLPSKRVSISRSQHDILQMICSKRRSGASEANLIVAKSWADVVKLGAKQTQTKVIKHGPQRSMNKRQRRPA
TPKKPVGEVHSQFSTGHANSPCTIIIGKAHTEKVHVPARPYRVLNNFISNQKMDFKEDLSGIAEMFKTPVKEQPQLT
STCHIAISNSENLLGKQFQGTDSGEEPLLPTSESFGGNVFFSAQNAAKQPSDKCSASPPLRRQCIRENGNVAKTPRN
TYKMTSLETKTSDTETEPSKTVSTANRSGRSTEFRNIQKLPVESKSEEINTEIVECILKRGQKATLLQQRREGEMKE
IERPFETYKENIELKENDEKMKAMKRSRTWGQKCAPMSDLIDLKSLPDTELMKDTARGQNLLQTQDHAKAPKSEKGK
ITKMPCQSLQPEPINTPTHTKQQLKASLGKVGVKEELLAVGKFTRTSGETTHTHREPAGDGKSIRTFKESPKQILDP
AARVTGMKKWPRTPKEEAQSLEDLAGFKELFQTPGPSEESMTDEKTTKIACKSPPPESVDTPTSTKQWPKRSLRKAD
VEEEFLALRKLIPSAGKAMLTPKPAGGDEKDIKAFMGTPVQKLDLAGTLPGSKRQLQTPKEKAQALEDLAGFKELFQ
TPGHTEELVAAGKTTKIPCDSPQSDPVDTPTSTKQRPKRSIRKADVEGELLACRNLMPSAGKAMHTPKPSVGEEKDI
IIFVGTPVQKLDLTENLTGSKRRPQTPKEEAQALEDLIGFKELFQTPGHTEEAVAAGKTTKMPCESSPPESADTPTS
TRRQPKTPLEKRDVQKELSALKKLTQTSGETTHTDKVPGGEDKSINAFRETAKQKLDPAASVTGSKRHPKTKEKAQP
LEDLAGLKELFQTPVCTDKPTTHEKTIKIACRSQPDPVDTPTSSKPQSKRSLRKVDVEEEFFALRKRTPSAGKAMHT
PKPAVSGEKNIYAFMGTPVQKLDLTENLTGSKRRLQTPKEKAQALEDLAGFKELFQTRGHTEESMINDKTAKVACKS
SQPDPDKNPASSKRRLKTSLGKVGVKEELLAVGKLTQTSGETTHTHTEPTGDGKSMKAFMESPKQILDSAASLTGSK
RQLRTPKGKSEVPEDLAGFIELFQTPSHTKESMTNEKTTKVSYRASQPDLVDTPTSSKPQPKRSLRKADTEEEFLAF
RKQTPSAGKAMHTPKPAVGEEKDINTFLGTPVQKLDQPGNLPGSNRRLQTRKEKAQALEELTGFRELFQTPCTDNPT
TDEKTTKKILCKSPQSDPADTPTNTKQRPKRSLKKADVEEEFLAFRKLTPSAGKAMHTPKAAVGEEKDINTFVGTPV
EKLDLLGNLPGSKRRPQTPKEKAKALEDLAGFKELFQTPGHTEESMTDDKITEVSCKSPQPDPVKIPTSSKQRLKIS
LGKVGVKEEVLPVGKLTQTSGKTTQTHRETAGDGKSIKAFKESAKQMLDPANYGTGMERWPRTPKEEAQSLEDLAGF
KELFQTPDHTEESTTDDKITKIACKSPPPESMDTPTSTRRRPKTPLGKRDIVEELSALKQLTQTTHIDKVPGDEDKG
INVFRETAKQKLDPAASVTGSKRQPRIPKGKAQPLEDLAGLKELFQTPICTDKPTTHEKTIKIACRSPQPDPVGTPT
IFKPQSKRSLRKADVEEESLALRKRIPSVGKAMDIPKPAGGDEKDMKAFMGTPVQKLDLPGNLPGSKRWPQTPKEKA
QALEDLAGFKELFQTPGTDKPTTDEKTTKIACKSPQPDPVDTPASTKQRPKRNLRKADVEEEFLALRKRTPSAGKAM
DTPKPAVSDEKNINTEVETPVQKLDLLGNLPGSKRQPQTPKEKAEALEDLVGFKELFQTPGHTEESMIDDKITEVSC
KSPQPESFKTSRSSKQRLKIPLVKVDMKEEPLAVSKLTRISGETTQTHTEPTGDSKSIKAFKESPKQILDPAASVTG
SRRQLRTRKEKARALEDLVDFKELFSAPGHTEESMTIDKNTKIPCKSPPPELIDTATSTKRCPKTRPRKEVKEELSA
VERLTQTSGQSTHTHKEPASGDEGIKVLKQRAKKKPNPVEEEPSRRRPRAPKEKAQPLEDLAGFTELSETSGHTQES
LTAGKATKIPCESPPLEVVDTTASTKRHLRTRVQKVQVKEEPSAVKFTQTSGETTDADKEPAGEDKGIKALKESAKQ
TPAPAASVIGSRRRPRAPRESAQAIEDLAGFKDPAAGHTEESMTDDKTTKIPCKSSPELEDTATSSKRRPRTRAQKV
EVKEELLAVGKLTQTSGETTHIDKEPVGEGKGTKAFKQPAKRKLDAEDVIGSRRQPRAPKEKAQPLEDLASFQELSQ
TPGHTEELANGAADSFTSAPKQTPDSGKPLKISRRVLRAPKVEPVGDVVSTRDPVKSQSKSNISLPPLPFKRGGGKD
GSVTGTKRLRCMPAPEEIVEELPASKKQRVAPRARGKSSEPVVIMKRSLRTSAKRIEPAEELNSNDMKINKEEHKLQ
DSVPENKGISLRSRRQNKTEAEQQITEVFVLAERIEINRNEKKPMKTSPEMDIQNPDDGARKPIPRDKVTENKRCLR
SARQNESSQPKVAEESGGQKSAKVLMQNQKGKGEAGNSDSMCLRSRKTKSQPAASTLESKSVQRVTRSVKRCAENPK
KAEDNVCVKKIRTRSHRDSEDI SEQ ID NO: 286 Atezolizumab (anti-PD-L1) HVR-H1
GFTFSDSWIH SEQ ID NO: 287 Atezolizumab HVR-H2
WISPYGGSTYYADSVKG SEQ ID NO: 288 Atezolizumab HVR-H3
RHWPGGFDY SEQ ID NO: 289 Atezolizumab HVR-L1
RASQDVSTAVA SEQ ID NO: 290 Atezolizumab HVR-L2
SASFLYS SEQ ID NO: 291 Atezolizumab HVR-L3
QQYLYHPAT SEQ ID NO: 292 Atezolizumab VH
EVQLVESGGGLVQPGGSLRLSCAASGFTFSDSWIHWVRQAPGKGLEWVAWISPYGGSTYYADSVKGRFTI
SADTSKNTAYLQMNSLRAEDTAVYYCARRHWPGGFDYWGQGTLVTVSS SEQ ID NO: 293 Atezolizumab VL
DIQMTQSPSSLSASVGDRVTITCRASQDVSTAVAWYQQKPGKAPKLLIYSASFLYSGVPSRFSGSGSGTDFT
LTISSLQPEDFATYYCQQYLYHPATFGQGTKVEIKRTV -continued

SEQ ID NO: 294 2E5 HVR-H1
TYYIS

SEQ ID NO: 295 2E5 HVR-H2
YINMGSGGTNYNEKFK

SEQ ID NO: 296 2E5 HVR-H3
IGYFDY

SEQ ID NO: 297 2E5 HVR-L1
RSSQSLLDSDGGTYLY

SEQ ID NO: 298 2E5 HVR-L2
LVSTLGS

SEQ ID NO: 299 2E5 HVR-L3
MQLTHWPYT

SEQ ID NO: 300 2ES VH
QVQLVQSGAEVKKPGSSVKVSCKASGFTFTTYYISWVRQAPGQGLEYLGYINMGSGGTNYNEKFKGRVTI
TADKSTSTAYMELSSLRSEDTAVYYCAIIGYFDYWGQGTMVTVSS

SEQ ID NO: 301 2E5 VL
DVVMTQSPLSLPVTLGQPASISCRSSQSLLDSDGGTYLYWFQQRPGQSPRRLIYLVSTLGSGVPDRFSGSGS
GTDFTLKISRVEAEDVGVYYCMQLTHWPYTFGQGTKLEIK

SEQ ID NO: 302 First epitope of anti-CD137L
MEYASDASLDPEAPWPPAPRARACRVLP

SEQ ID NO: 303 Second epitope of anti-CD137L
MEYASDASLDPEAPWPPAPRARA

SEQ ID NO: 304 TY23561 HVR-H1
FSLSTSGVGVSWI

SEQ ID NO: 305 TY23561 HVR-H2
LALIDWAGDKYYSPSLKSRL

SEQ ID NO: 306 TY23561 HVR-H3
ARYGYSSYALDY

SEQ ID NO: 307 TY23561 HVR-L1
RASQSVRGSYLA

SEQ ID NO: 308 TY23561 HVR-L2
AASTLQSGV

SEQ ID NO: 309 TY23561 HVR-L3
YCQQYSSLWT

SEQ ID NO: 310 TY23561 VH
EVQLVESGGGLVQPGGSLRLSCAASGFSLSTSGVGVSWIRQAPGKGLEWLALIDWAGDKYYSPSLKSRLTI
SRDNSKNTLYLQLNSLRAEDTAVYYCARYGYSSYALDYWGQGTLVTVSS

SEQ ID NO: 311 TY23561 VL
DIQLTQSPSSLSASVGDRVTITCRASQSVRGSYLAWYQQKPGKAPKLLIYAASTLQSGVPSRFSGSGSGTDF
TLTISSLQPEDFATYYCQQYSSLWTFGQGTKVEIKR

SEQ ID NO: 312 Toripalimab (anti-PD1) HVR-H1
DYEMH

SEQ ID NO: 313 Toripalimab HVR-H2
VIESETGGIAYNQKFKG

SEQ ID NO: 314 Toripalimab HVR-H3
EGITTVATTYYWYFDV

SEQ ID NO: 315 Toripalimab HVR-L1
RSSQSIVHSNGNTYLE

SEQ ID NO: 316 Toripalimab HVR-L2
KVSNRFS

SEQ ID NO: 317 Toripalimab HVR-L3
FQGSHVPLT

SEQ ID NO: 318 Toripalimab VH
QGQLVQSGAEVKKPGASVKVSCKASGYTFTDYEMHWVRQAPIHGLEWIGVIESETGGTAYNQKFKGRVTITADKSTS
TAYMELSSLRSEDTAVYYCAREGITTVATTYYWYFDVWGQGTTVTVSS -continued SEQ ID NO: 319 Toripalimab VL
DVVMTQSPLSLPVILGQPASISCRSSQSIVHSNGNTYLEWYLQKPGQSPQLLIYKVSNRFSGVPDRFSGSGSGTDET
LKISRVEAEDVGVYYCFQGSHVPLTFGQGTKLEIK SEQ ID NO: 320 anti-CTLA4 SAFEbody 2 full heavy chain (minus C-terminal lysine)
EVQLVESGGGLVQPGGSLRLSCAASGYSISSGYHWSWIRQAPGKGLEWLARIDWDDDKYYSTSLKSRLTISRDNSKN
TLYLQLNSLRAEDTAVYYCARSYVYFDYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKPREEQYNSTYRVVSVLIVL
HQDWLNGKEYKCKVSNKALPAPIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLSLSPG SEQ ID NO: 321 anti-CTLA4 SAFEbody 2 full heavy chain (with C-terminal lysine)
EVQLVESGGGLVQPGGSLRLSCAASGYSISSGYHWSWIRQAPGKGLEWLARIDWDDDKYYSTSLKSRLTISRDNSKN
TLYLQLNSLRAEDTAVYYCARSYVYFDYWGQGTLVTVSSASTKGPSVFPLAPSSKSTSGGTAALGCLVKDYFPEPVT
VSWNSGALISGVHIFPAVLQSSGLYSLSSVVTVPSSSIGTQTYICNVNHKPSNTKVDKKVEPKSCDKTHTCPPCPAP
ELLGGPSVFLFPPKPKDTLMISRIPEVTCVVVDVSHEDPEVKENWYVDGVEVHNAKTKPREEQYNSTYRVVSVLTVL
HQDWINGKEYKCKVSNKALPAPIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLSLSPGK SEQ ID NO: 322 anti-CTLA4 SAFEbody 2 full light chain with N-terminal masking moiety and linker
EVGSYPNPSSDCVPYYYACAYSGRSAGGGGTPLGLAGSGGSDIQLTQSPSSLSASVGDRVTITCRASQSVRGRFLAW
YQQKPGKAPKLLIYDASNRATGIPSRFSGSGSGTDFTLTISSLQPEDFATYYCQQSSSWPPTFGQGTKVEIKRTVAA
PSVFIFPPSDEQLKSGTASVVCLLNNFYPREAKVQWKVDNALQSGNSQESVTEQDSKDSTYSLSSTLTLSKADYEKH
KVYACEVTHQGLSSPVTKSFNRGEC SEQ ID NO: 323 anti-CTLA4 SAFEbody 1 full heavy chain (minus C-terminal lysine)
EVQLVESGGGLVQPGGSLRLSCAASGYSISSGYHWSWIRQAPGKGLEWLARIDWDDDKYYSTSLKSRLTISRDNSKN
TLYLQLNSLRAEDTAVYYCARSYVYFDYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLSLSPG SEQ ID NO: 324 anti-CTLA4 SAFEbody 1 full heavy chain (with C-terminal lysine)
EVQLVESGGGLVQPGGSLRLSCAASGYSISSGYHWSWIRQAPGKGLEWLARIDWDDDKYYSTSLKSRLTISRDNSKN
TLYLQLNSLRAEDTAVYYCARSYVYFDYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELIKNQVSLTCLVKGFYPSDIAVEWESNGQ
PENNYKTTPPVLDSDGSFFLYSKLTVDKSRWQQGNVFSCSVMHEALHNHYTQKSLSLSPGK SEQ ID NO: 325 anti-CTLA4 SAFEbody 1 full light chain with N-terminal masking moiety and linker
EVGSYNFVADSCPDHPYPCSASGRSAGGGGSPLGLAGSGGSDIQLTQSPSSLSASVGDRVTITCRASQSVRGRFLAW
YQQKPGKAPKLLIYDASNRATGIPSRFSGSGSGTDFTLTISSLQPEDFATYYCQQSSSWPPTFGQGTKVEIKRTVAA
PSVFIFPPSDEQLKSGTASVVCLLNNFYPREAKVQWKVDNALQSGNSQESVTEQDSKDSTYSLSSTLILSKADYEKH
KVYACEVTHQGLSSPVTKSENRGEC SEQ ID NO: 326 anti-CTLA4 SAFEbody 3 full heavy chain (minus C-terminal lysine)
EVQLVESGGGLVQPGGSLRLSCAASGYSISSGYHWSWIRQAPGKGLEWLARIDWDDDKYYSTSLKSRLTISRDNSKN
TLYLQLNSLRAEDTAVYYCARSYVYFDYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKKVEPKSCDKTHTCPPCPAP
ELLGGPSVFLFPPKPKDTLMISRIPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLSLSPG SEQ ID NO: 327 anti-CTLA4 SAFEbody 3 full heavy chain (with C-terminal lysine)
EVQLVESGGGLVQPGGSLRLSCAASGYSISSGYHWSWIRQAPGKGLEWLARIDWDDDKYYSTSLKSRLTISRDNSKN
TLYLQLNSLRAEDTAVYYCARSYVYFDYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPFVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLSLSPGK SEQ ID NO: 328 anti-CTLA4 SAFEbody 3 full light chain with N-terminal masking moiety and linker
EVGSYIVHHSDCDAFYPYCDSSGRSAGGGGSPLGLAGSGGSDIQLTQSPSSLSASVGDRVTITCRASQSVRGRFLAW
YQQKPGKAPKLLIYDASNRATGIPSRFSGSGSGTDFTLTISSLQPEDFATYYCQQSSSWPPTFGQGTKVEIKRTVAA
PSVFIFPPSDEQLKSGTASVVCLLNNFYPREAKVQWKVDNALQSGNSQESVTEQDSKDSTYSLSSTLTLSKADYEKH
KVYACEVTHQGLSSPVTKSENRGEC

What is claimed is:

1. A method of treating a solid tumor in a subject, comprising administering to the subject an effective amount of an activatable antibody, wherein the activatable antibody comprises:

a first polypeptide comprising, from N-terminus to C-terminus, a masking moiety (MM), a cleavable moiety (CM), and a target binding moiety (TBM), wherein the MM comprises an amino acid sequence set forth in SEQ ID NO: 192;

wherein the CM comprises at least a first cleavage site;

wherein:

a) the TBM comprises an antibody light chain variable region (VL), and the activatable antibody further comprises a second polypeptide comprising an antibody heavy chain variable region (VH);

b) the TBM comprises an antibody heavy chain variable region (VH), and the activatable antibody further comprises a second polypeptide comprising an antibody light chain variable region (VL);

c) the TBM comprises from the N-terminus to the C-terminus, an antibody light chain variable region (VL) and an antibody heavy chain variable region (VH); or d) the TBM comprises from the N-terminus to the C-terminus, an antibody heavy chain variable region (VH) and an antibody light chain variable region (VL);

wherein the VH comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45;

wherein the VL comprises an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75; and wherein the activatable antibody binds to human CTLA4 via the VH and VL when the CM is cleaved, wherein the subject is resistant to or has relapsed from a prior therapy, wherein the prior therapy is an inhibitor of CTLA4, PD-1, or a PD-1 ligand.

2. The method of claim 1, wherein the prior therapy is the inhibitor of CTLA4.

3. The method of claim 1, wherein the prior therapy is the inhibitor of PD-1.

4. The method of claim 1, wherein the prior therapy is the inhibitor of PD-1 ligand.

5. The method of claim 1, wherein the prior therapy is both the inhibitor of CTLA4 and the inhibitor of PD-1.

6. The method of claim 1, wherein the prior therapy is both the inhibitor of CTLA4 and the inhibitor of PD-1 ligand.

7. The method of claim 1, wherein the inhibitor of CTLA4 is an anti-CTLA4 antibody, the inhibitor of PD-1 is an anti-PD-1 antibody, or the inhibitor of PD-1 ligand is an anti-PD-1 ligand antibody.

8. The method of claim 7, wherein the anti-PD-1 antibody is pembrolizumab, nivolumab, or toripalimab.

9. The method of claim 7, wherein the anti-CTLA4 antibody is ipilimumab.

10. The method of claim 1, wherein the subject has failed the prior therapy within about 1 year, 6 months, 3 months or less.

11. The method of claim 1, wherein the VH variable region comprises an amino acid sequence having at least 90% sequence identity to the amino acid sequence of SEQ ID NO: 87, and the VL variable region comprises an amino acid sequence having at least 90% sequence identity to the amino acid sequence of SEQ ID NO: 100.

12. The method of claim 1, wherein:

the antibody heavy chain comprises the amino acid sequence of SEQ ID NO: 320 and the antibody light chain comprises the amino acid sequence of SEQ ID NO: 322.

13. The method of claim 1, wherein the activatable antibody comprises an amino acid sequence of SEQ ID NO: 200.

14. The method of claim 1, wherein the subject receives at least 4 cycles of treatment with the activatable antibody.

15. The method of claim 1, wherein the solid tumor is ovarian cancer, pancreatic cancer, cholangiocarcinoma, lung cancer, breast cancer, melanoma, hepatocellular carcinoma, glioblastoma, renal cell carcinoma, head and neck squamous cell carcinoma, or colorectal cancer.

16. The method of claim 1, wherein the solid tumor is a microsatellite instability high (MSI-H) or mismatch repair deficient (dMMR) cancer.

17. The method of claim 1, wherein the solid tumor has metastasized.

18. The method of claim 1, wherein the solid tumor is colorectal cancer.

* * * * *